US009017671B2

(12) United States Patent
Andya et al.

(10) Patent No.: US 9,017,671 B2
(45) Date of Patent: Apr. 28, 2015

(54) METHOD OF TREATING CANCER WITH A PHARMACEUTICAL FORMULATION COMPRISING A HER2 ANTIBODY

(71) Applicant: Genentech, Inc., South San Francisco, CA (US)

(72) Inventors: James Andya, Millbrae, CA (US); Shiang C. Gwee, Pacifica, CA (US); Jun Liu, Pacifica, CA (US); Ye Shen, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/660,114

(22) Filed: Oct. 25, 2012

(65) Prior Publication Data

US 2013/0071384 A1 Mar. 21, 2013

Related U.S. Application Data

(60) Division of application No. 12/554,194, filed on Sep. 4, 2009, now Pat. No. 8,372,396, which is a continuation of application No. 11/254,182, filed on Oct. 19, 2005, now abandoned.

(60) Provisional application No. 60/620,413, filed on Oct. 20, 2004.

(51) Int. Cl.
*A61K 39/395* (2006.01)
*C07K 16/28* (2006.01)
*C07K 16/32* (2006.01)

(52) U.S. Cl.
CPC ..... *A61K 39/39541* (2013.01); *A61K 39/39591* (2013.01); *C07K 16/2878* (2013.01); *C07K 16/32* (2013.01); *C07K 2317/24* (2013.01)

(58) Field of Classification Search
None
See application file for complete search history.

(56) References Cited

U.S. PATENT DOCUMENTS

| | | |
|---|---|---|
| 4,968,603 A | 11/1990 | Slamon et al. |
| 5,183,884 A | 2/1993 | Kraus et al. |
| 5,480,968 A | 1/1996 | Kraus et al. |
| 5,608,038 A | 3/1997 | Eibl et al. |
| 5,641,869 A | 6/1997 | Vandlen et al. |
| 5,648,237 A | 7/1997 | Carter |
| 5,677,171 A | 10/1997 | Hudziak et al. |
| 5,720,937 A | 2/1998 | Hudziak et al. |
| 5,720,954 A | 2/1998 | Hudziak et al. |
| 5,725,856 A | 3/1998 | Hudziak et al. |
| 5,763,223 A | 6/1998 | Wiley et al. |
| 5,770,195 A | 6/1998 | Hudziak et al. |
| 5,772,997 A | 6/1998 | Hudziak et al. |
| 5,783,186 A | 7/1998 | Arakawa et al. |
| 5,821,337 A | 10/1998 | Carter et al. |
| 5,824,311 A | 10/1998 | Greene et al. |
| 6,015,567 A | 1/2000 | Hudziak et al. |
| 6,030,945 A | 2/2000 | Ashkenazi |
| 6,054,297 A | 4/2000 | Carter et al. |
| 6,072,047 A | 6/2000 | Rauch et al. |
| 6,127,526 A | 10/2000 | Blank |
| 6,165,464 A | 12/2000 | Hudziak et al. |
| 6,171,586 B1 | 1/2001 | Lam et al. |
| 6,252,050 B1 | 6/2001 | Ashkenazi et al. |
| 6,252,055 B1 | 6/2001 | Relton |
| 6,267,958 B1 | 7/2001 | Andya et al. |
| 6,284,236 B1 | 9/2001 | Wiley et al. |
| 6,313,269 B1 | 11/2001 | Deen et al. |
| 6,333,169 B1 | 12/2001 | Hudziak et al. |
| 6,333,398 B1 | 12/2001 | Blank |
| 6,339,142 B1 | 1/2002 | Basey et al. |
| 6,342,369 B1 | 1/2002 | Ashkenazi |
| 6,342,383 B1 | 1/2002 | Perron et al. |
| 6,387,371 B1 | 5/2002 | Hudziak et al. |
| 6,399,063 B1 | 6/2002 | Hudziak et al. |
| 6,407,213 B1 | 6/2002 | Carter et al. |
| 6,417,335 B1 | 7/2002 | Basey et al. |
| 6,433,147 B1 | 8/2002 | Ni et al. |
| 6,461,823 B1 | 10/2002 | Ni et al. |
| 6,489,447 B1 | 12/2002 | Basey et al. |
| 6,569,642 B1 | 5/2003 | Rauch et al. |
| 6,573,043 B1 | 6/2003 | Cohen et al. |
| 6,627,196 B1 | 9/2003 | Baughman et al. |
| 6,632,979 B2 | 10/2003 | Erickson et al. |
| 6,639,055 B1 | 10/2003 | Carter et al. |
| 6,642,358 B1 | 11/2003 | Rauch et al. |
| 6,685,940 B2 | 2/2004 | Andya et al. |
| 6,719,971 B1 | 4/2004 | Carter et al. |
| 6,743,625 B2 | 6/2004 | Ni et al. |
| 6,746,668 B2 | 6/2004 | Ashkenazi |
| 6,797,814 B2 | 9/2004 | Blank |
| 6,800,738 B1 | 10/2004 | Carter et al. |
| 6,821,515 B1 | 11/2004 | Cleland et al. |

(Continued)

FOREIGN PATENT DOCUMENTS

| | | |
|---|---|---|
| EP | 0 599 274 A1 | 11/1993 |
| EP | 0 870 827 A2 | 10/1998 |

(Continued)

OTHER PUBLICATIONS

Cacace et al., "The Hofmeister series: salt and solvent effects on interfacial phenomena" Quarterly Reviews of Biophysics 30(3):241-277 (Aug. 1997).

(Continued)

*Primary Examiner* — Yunsoo Kim
(74) *Attorney, Agent, or Firm* — Wendy M. Lee

(57) ABSTRACT

The present application describes antibody formulations, including monoclonal antibodies formulated in histidine-acetate buffer, as well as a formulation comprising an antibody that binds to domain II of HER2 (for example, Pertuzumab), and a formulation comprising an antibody that binds to DR5 (for example, Apomab).

14 Claims, 34 Drawing Sheets

(56) References Cited

U.S. PATENT DOCUMENTS

| | | |
|---|---|---|
| 6,905,830 B2 | 6/2005 | Cohen et al. |
| 6,949,245 B1 | 9/2005 | Sliwkowski |
| 6,984,494 B2 | 1/2006 | Ralph |
| 7,018,809 B1 | 3/2006 | Carter |
| 7,041,292 B1 | 5/2006 | Sliwkowski |
| 7,060,268 B2 | 6/2006 | Andya et al. |
| 7,074,404 B2 | 7/2006 | Basey et al. |
| 7,097,840 B2 | 8/2006 | Erickson et al. |
| 7,129,051 B2 | 10/2006 | Cohen et al. |
| 7,279,287 B2 | 10/2007 | Ralph |
| 7,344,840 B2 | 3/2008 | Cohen et al. |
| 7,371,376 B1 | 5/2008 | Fendly |
| 7,371,379 B2 | 5/2008 | Baughman et al. |
| 7,435,797 B2 | 10/2008 | Lowman et al. |
| 7,449,184 B2 | 11/2008 | Allison et al. |
| 7,468,252 B2 | 12/2008 | Cohen et al. |
| 7,485,302 B2 | 2/2009 | Adams et al. |
| 7,485,704 B2 | 2/2009 | Fahrner et al. |
| 7,498,030 B2 | 3/2009 | Adams et al. |
| 7,501,122 B2 | 3/2009 | Adams et al. |
| 7,531,645 B2 | 5/2009 | Basey et al. |
| 7,537,931 B2 | 5/2009 | Adams et al. |
| 7,560,111 B2 | 7/2009 | Kao et al. |
| 7,575,748 B1 | 8/2009 | Erickson et al. |
| 7,618,631 B2 | 11/2009 | Sliwkowski |
| 7,674,589 B2 | 3/2010 | Cohen et al. |
| 7,682,609 B2 | 3/2010 | Andya et al. |
| 7,700,299 B2 | 4/2010 | Moecks et al. |
| 7,807,799 B2 | 10/2010 | Fahrner et al. |
| 7,811,773 B2 | 10/2010 | Ralph |
| 7,846,441 B1 | 12/2010 | Hellmann |
| 7,850,966 B2 | 12/2010 | Lowman et al. |
| 7,862,817 B2 | 1/2011 | Adams et al. |
| 7,879,325 B2 | 2/2011 | Kao et al. |
| 7,892,549 B2 | 2/2011 | Paton et al. |
| 7,919,254 B2 | 4/2011 | Cohen et al. |
| 7,981,418 B2 | 7/2011 | Amler et al. |
| 7,993,834 B2 | 8/2011 | Mass |
| 8,044,017 B2 | 10/2011 | Emery et al. |
| 8,075,890 B2 | 12/2011 | Carter et al. |
| 8,075,892 B2 | 12/2011 | Hellmann |
| 8,076,066 B2 | 12/2011 | Mass |
| 8,142,784 B2 | 3/2012 | Ebens, Jr. et al. |
| 8,163,287 B2 | 4/2012 | Sliwkowski et al. |
| 8,241,630 B2 | 8/2012 | Kao et al. |
| 8,247,397 B2 | 8/2012 | Belvin et al. |
| 8,309,087 B2 | 11/2012 | Hellmann |
| 8,333,964 B2 | 12/2012 | Agus |
| 8,337,856 B2 | 12/2012 | Blattler et al. |
| 8,372,396 B2 | 2/2013 | Andya et al. |
| 8,404,234 B2 | 3/2013 | Allison et al. |
| 8,425,908 B2 | 4/2013 | Hellmann |
| 8,440,402 B2 | 5/2013 | Mass |
| 8,529,901 B2 | 9/2013 | Hasmann et al. |
| 8,591,897 B2 | 11/2013 | Bryant |
| 8,592,152 B2 | 11/2013 | Mass |
| 8,597,654 B2 | 12/2013 | Bryant |
| 8,604,014 B2 | 12/2013 | Belvin et al. |
| 8,642,036 B2 | 2/2014 | Hellmann |
| 8,652,474 B2 | 2/2014 | Harris et al. |
| 8,652,479 B2 | 2/2014 | Ebens, Jr. et al. |
| 8,663,643 B2 | 3/2014 | Berry et al. |
| 8,691,232 B2 | 4/2014 | Derynck et al. |
| 8,710,196 B2 | 4/2014 | Emery et al. |
| 8,758,747 B2 | 6/2014 | Kallmeyer et al. |
| 2001/0010924 A1 | 8/2001 | Deen et al. |
| 2001/0014326 A1 | 8/2001 | Andya et al. |
| 2002/0001587 A1 | 1/2002 | Erickson et al. |
| 2002/0035736 A1 | 3/2002 | Erickson et al. |
| 2002/0045571 A1 | 4/2002 | Liu |
| 2002/0048785 A1 | 4/2002 | Holtzman |
| 2002/0072091 A1 | 6/2002 | Ni et al. |
| 2002/0090662 A1 | 7/2002 | Ralph |
| 2002/0098550 A1 | 7/2002 | Ni et al. |
| 2002/0160446 A1 | 10/2002 | Holtzman |
| 2003/0078388 A1 | 4/2003 | Basey et al. |
| 2003/0113316 A1 | 6/2003 | Kaisheva |
| 2003/0124119 A1 | 7/2003 | Yamazaki et al. |
| 2003/0125540 A1 | 7/2003 | Holtzman |
| 2003/0147884 A1 | 8/2003 | Paton et al. |
| 2003/0152987 A1 | 8/2003 | Cohen et al. |
| 2003/0190316 A1 | 10/2003 | Kakuta et al. |
| 2003/0202972 A1 | 10/2003 | Andya et al. |
| 2004/0037823 A9 | 2/2004 | Paton et al. |
| 2004/0082047 A1 | 4/2004 | Emery et al. |
| 2004/0106161 A1 | 6/2004 | Bossenmaier et al. |
| 2004/0170623 A1 | 9/2004 | Arvinte et al. |
| 2004/0191243 A1 | 9/2004 | Chen |
| 2004/0197324 A1 | 10/2004 | Shire et al. |
| 2004/0197326 A1 | 10/2004 | Fick et al. |
| 2004/0258685 A1 | 12/2004 | Brunetta et al. |
| 2005/0002928 A1 | 1/2005 | Hellmann |
| 2005/0063972 A1 | 3/2005 | Basey et al. |
| 2005/0100944 A1 | 5/2005 | Cohen et al. |
| 2005/0118163 A1 | 6/2005 | Mizushima et al. |
| 2005/0208043 A1 | 9/2005 | Adams et al. |
| 2005/0214278 A1 | 9/2005 | Kakuta et al. |
| 2005/0238640 A1 | 10/2005 | Sliwkowski |
| 2005/0244417 A1 | 11/2005 | Ashkenazi et al. |
| 2005/0244929 A1 | 11/2005 | Carter |
| 2005/0276812 A1 | 12/2005 | Ebens et al. |
| 2006/0013819 A1 | 1/2006 | Kelsey |
| 2006/0018899 A1 | 1/2006 | Kao et al. |
| 2006/0034840 A1 | 2/2006 | Agus |
| 2006/0034842 A1 | 2/2006 | Adams et al. |
| 2006/0046270 A1 | 3/2006 | Ralph |
| 2006/0067930 A1 | 3/2006 | Adams et al. |
| 2006/0073143 A1 | 4/2006 | Adams et al. |
| 2006/0083739 A1 | 4/2006 | Sliwkowski |
| 2006/0088523 A1 | 4/2006 | Andya et al. |
| 2006/0099201 A1 | 5/2006 | Andya et al. |
| 2006/0121044 A1 | 6/2006 | Amler et al. |
| 2006/0127395 A1 | 6/2006 | Arvinte et al. |
| 2006/0165702 A1 | 7/2006 | Allison et al. |
| 2006/0182739 A1 | 8/2006 | Basey et al. |
| 2006/0182740 A1 | 8/2006 | Yang et al. |
| 2006/0183150 A1 | 8/2006 | Cohen et al. |
| 2006/0188509 A1 | 8/2006 | Derynck et al. |
| 2006/0193854 A1 | 8/2006 | Adams et al. |
| 2006/0198843 A1 | 9/2006 | Adams et al. |
| 2006/0204505 A1 | 9/2006 | Sliwkowski et al. |
| 2006/0210561 A1 | 9/2006 | Baughman et al. |
| 2006/0212956 A1 | 9/2006 | Crocker et al. |
| 2006/0228745 A1 | 10/2006 | Mass |
| 2006/0275305 A1 | 12/2006 | Bryant |
| 2006/0275306 A1 | 12/2006 | Andya et al. |
| 2007/0009976 A1 | 1/2007 | Lenz et al. |
| 2007/0020261 A1 | 1/2007 | Sliwkowski et al. |
| 2007/0026001 A1 | 2/2007 | Ashkenazi et al. |
| 2007/0037228 A1 | 2/2007 | Moecks et al. |
| 2007/0166753 A1 | 7/2007 | Mass |
| 2007/0184055 A1 | 8/2007 | Sliwkowski |
| 2007/0202516 A1 | 8/2007 | Mass |
| 2007/0224203 A1 | 9/2007 | Friess et al. |
| 2007/0269429 A1 | 11/2007 | Kelsey et al. |
| 2007/0292419 A1 | 12/2007 | Hellmann |
| 2008/0038271 A1 | 2/2008 | Amler et al. |
| 2008/0050373 A1 | 2/2008 | Cohen |
| 2008/0050385 A1 | 2/2008 | Friess et al. |
| 2008/0050748 A1 | 2/2008 | Cohen et al. |
| 2008/0102069 A1 | 5/2008 | Friess et al. |
| 2008/0108096 A1 | 5/2008 | Ralph |
| 2008/0112957 A1 | 5/2008 | Fendly et al. |
| 2008/0112958 A1 | 5/2008 | Mass |
| 2008/0160026 A1 | 7/2008 | Ashkenazi et al. |
| 2008/0171040 A1 | 7/2008 | Ebens, et al. |
| 2008/0187533 A1 | 8/2008 | Hellmann |
| 2008/0226659 A1 | 9/2008 | Erickson et al. |
| 2008/0241146 A1 | 10/2008 | Ashkenazi et al. |
| 2008/0286280 A1 | 11/2008 | Kallmeyer et al. |
| 2008/0306247 A1 | 12/2008 | Mizushima et al. |
| 2008/0317753 A1 | 12/2008 | Amler et al. |
| 2009/0081223 A1 | 3/2009 | Allison et al. |
| 2009/0087432 A1 | 4/2009 | Sliwkowski |

(56) References Cited

U.S. PATENT DOCUMENTS

| | | |
|---|---|---|
| 2009/0098135 A1 | 4/2009 | Belvin et al. |
| 2009/0099344 A1 | 4/2009 | Fahrner et al. |
| 2009/0131639 A1 | 5/2009 | Kakuta et al. |
| 2009/0148402 A1 | 6/2009 | Brunetta et al. |
| 2009/0148435 A1 | 6/2009 | Lebreton et al. |
| 2009/0155259 A1 | 6/2009 | Derynck et al. |
| 2009/0155803 A1 | 6/2009 | Cohen et al. |
| 2009/0187007 A1 | 7/2009 | Lowman et al. |
| 2009/0202536 A1 | 8/2009 | Ebens et al. |
| 2009/0202546 A1 | 8/2009 | Harris et al. |
| 2009/0220492 A1 | 9/2009 | Basey et al. |
| 2009/0226455 A1 | 9/2009 | Filvaroff |
| 2009/0239236 A1 | 9/2009 | Mass |
| 2009/0285837 A1 | 11/2009 | Kao et al. |
| 2009/0291076 A1 | 11/2009 | Morichika et al. |
| 2009/0317387 A1 | 12/2009 | Paton et al. |
| 2010/0008975 A1 | 1/2010 | Amler et al. |
| 2010/0015157 A1 | 1/2010 | Andya et al. |
| 2010/0016556 A1 | 1/2010 | Carter et al. |
| 2010/0112603 A1 | 5/2010 | Moecks et al. |
| 2010/0120053 A1 | 5/2010 | Cohen et al. |
| 2010/0158899 A1 | 6/2010 | Andya et al. |
| 2010/0196363 A1 | 8/2010 | Vanhauwere et al. |
| 2010/0285010 A1 | 11/2010 | Friess et al. |
| 2010/0285011 A1 | 11/2010 | Morichika et al. |
| 2010/0298156 A1 | 11/2010 | Lee-Hoeflich et al. |
| 2011/0027190 A1 | 2/2011 | Hasmann et al. |
| 2011/0033460 A1 | 2/2011 | Fendly et al. |
| 2011/0044977 A1 | 2/2011 | Adler et al. |
| 2011/0064736 A1 | 3/2011 | Friess et al. |
| 2011/0064737 A1 | 3/2011 | Agus |
| 2011/0117096 A1 | 5/2011 | Bossenmaier et al. |
| 2011/0117097 A1 | 5/2011 | Kao et al. |
| 2011/0129464 A1 | 6/2011 | Adams et al. |
| 2011/0151454 A1 | 6/2011 | Lee-Hoeflich et al. |
| 2011/0159014 A1 | 6/2011 | Lowman et al. |
| 2011/0165157 A1 | 7/2011 | Derynck et al. |
| 2011/0223159 A1 | 9/2011 | Friess et al. |
| 2011/0223619 A1 | 9/2011 | Belvin et al. |
| 2011/0236383 A1 | 9/2011 | Andya et al. |
| 2011/0245103 A1 | 10/2011 | Amler et al. |
| 2011/0246399 A1 | 10/2011 | Amler et al. |
| 2011/0250194 A1 | 10/2011 | Hellmann |
| 2012/0003217 A1 | 1/2012 | Bryant |
| 2012/0034213 A1 | 2/2012 | Hellmann |
| 2012/0034609 A1 | 2/2012 | Mass |
| 2012/0065381 A1 | 3/2012 | Emery et al. |
| 2012/0093838 A1 | 4/2012 | Mass |
| 2012/0107302 A1 | 5/2012 | Berry et al. |
| 2012/0107391 A1 | 5/2012 | Kelsey |
| 2012/0121586 A1 | 5/2012 | Kiermaier et al. |
| 2012/0251530 A1 | 10/2012 | Sliwkowski et al. |
| 2013/0039909 A1 | 2/2013 | Amler et al. |
| 2013/0071384 A1 | 3/2013 | Andya et al. |
| 2013/0095172 A1 | 4/2013 | Alavattam et al. |
| 2013/0108620 A1 | 5/2013 | Blattler et al. |
| 2013/0142865 A1 | 6/2013 | Allison et al. |
| 2013/0149299 A1 | 6/2013 | Baughman et al. |
| 2013/0183292 A1 | 7/2013 | Friess et al. |
| 2013/0195845 A1 | 8/2013 | Fendly et al. |
| 2013/0195851 A1 | 8/2013 | Alavattam et al. |
| 2013/0209459 A1 | 8/2013 | Hellmann |
| 2013/0216532 A1 | 8/2013 | Adler et al. |
| 2013/0224185 A1 | 8/2013 | Andya et al. |
| 2013/0323180 A1 | 12/2013 | Hasmann et al. |
| 2013/0345217 A1 | 12/2013 | Belvin et al. |
| 2014/0018523 A1 | 1/2014 | Basey et al. |
| 2014/0044704 A1 | 2/2014 | Paton et al. |
| 2014/0044706 A1 | 2/2014 | Belvin et al. |
| 2014/0044709 A1 | 2/2014 | Klencke et al. |
| 2014/0079692 A1 | 3/2014 | Baughman et al. |
| 2014/0086940 A1 | 3/2014 | Bryant |
| 2014/0093458 A1 | 4/2014 | Dobosz et al. |
| 2014/0128580 A1 | 5/2014 | Ebens, Jr. et al. |
| 2014/0140993 A1 | 5/2014 | Ross et al. |
| 2014/0186343 A1 | 7/2014 | Harris et al. |
| 2014/0186347 A1 | 7/2014 | Derynck et al. |
| 2014/0186867 A1 | 7/2014 | Harris et al. |
| 2014/0212411 A1 | 7/2014 | Blattler et al. |
| 2014/0227255 A1 | 8/2014 | Bauss et al. |

FOREIGN PATENT DOCUMENTS

| | | |
|---|---|---|
| EP | 1 174 148 A1 | 1/2002 |
| EP | 2263691 | 12/2010 |
| WO | 94/00136 A1 | 1/1994 |
| WO | 94/22478 | 10/1994 |
| WO | 97/01633 A1 | 1/1997 |
| WO | 97/04801 | 2/1997 |
| WO | 97/04807 | 2/1997 |
| WO | 97/25428 A1 | 7/1997 |
| WO | 97/25428 R3 | 7/1997 |
| WO | 98/18921 A1 | 5/1998 |
| WO | 98/28426 A2 | 7/1998 |
| WO | 98/28426 A3 | 7/1998 |
| WO | 98/28426 R3 | 7/1998 |
| WO | 98/32856 | 7/1998 |
| WO | 98/35986 | 8/1998 |
| WO | 98/41629 | 9/1998 |
| WO | 98/46643 | 10/1998 |
| WO | 98/46751 A1 | 10/1998 |
| WO | 98/51793 | 11/1998 |
| WO | 98/56418 | 12/1998 |
| WO | 99/01556 | 1/1999 |
| WO | 99/02653 | 2/1999 |
| WO | 99/09165 | 2/1999 |
| WO | 99/11791 | 3/1999 |
| WO | 99/37684 | 7/1999 |
| WO | 00/73349 A1 | 7/2000 |
| WO | 00/66160 | 11/2000 |
| WO | 00/75191 A2 | 12/2000 |
| WO | 01/00238 A1 | 1/2001 |
| WO | 01/00245 A2 | 1/2001 |
| WO | 01/00245 A3 | 1/2001 |
| WO | 02/09755 A2 | 2/2002 |
| WO | 02/30463 | 4/2002 |
| WO | 02/096457 A2 | 12/2002 |
| WO | 02/097033 A2 | 12/2002 |
| WO | 03/009817 | 2/2003 |
| WO | 03/009817 A2 | 2/2003 |
| WO | 03/014294 | 2/2003 |
| WO | 03/037913 A2 | 5/2003 |
| WO | 03/038043 A2 | 5/2003 |
| WO | 03/039485 A2 | 5/2003 |
| WO | 03/042367 A2 | 5/2003 |
| WO | 03/066661 A2 | 8/2003 |
| WO | 03/105891 A2 | 12/2003 |
| WO | 03/105894 | 12/2003 |
| WO | 03/105894 A1 | 12/2003 |
| WO | 03/106644 | 12/2003 |
| WO | 03/106644 A2 | 12/2003 |
| WO | 2004/001007 | 12/2003 |
| WO | 2004/001007 A2 | 12/2003 |
| WO | 2004/004639 A2 | 1/2004 |
| WO | 2004/016286 A2 | 2/2004 |
| WO | 2004019861 A2 | 3/2004 |
| WO | 2004/066957 | 8/2004 |
| WO | 2004/071439 A2 | 8/2004 |
| WO | 2004/091658 A1 | 10/2004 |
| WO | 2006/017773 A1 | 2/2006 |
| WO | 2006/020935 A2 | 2/2006 |
| WO | 2006/044908 | 4/2006 |
| WO | 2011/146568 A1 | 11/2011 |
| WO | 2011/146568 A8 | 11/2011 |
| WO | 2012/120004 A1 | 9/2012 |
| WO | 2013/083810 A1 | 6/2013 |
| WO | 2004/083178 A1 | 6/2014 |

OTHER PUBLICATIONS

Aasland et al., "Expression of Oncogenes in Thyroid Tumours: Coexpression of c-erbB2/neu and c-erbB" Brit J Cancer 57(4):358-363 (1988).

(56) References Cited

OTHER PUBLICATIONS

Acetic Acid Properties, pp. 1-4 (2011) http://chemicalland21.com/petrochemical/acetic%20acid.htm.
Agus et al. et al., "Phase I clinical study of pertuzumab, a novel HER dimerization inhibitor, in patients with advanced cancer" J Clin Oncol 23(11):2534-2543 (Apr. 10, 2005).
Agus et al., "Clinical Activity in a Phase I Trial of HER2-Targeted rhuMAb 2C4 (pertuzumab) in Patients with Advanced Solid Malignancies" (Slides presented at the 2003 ASCO Annual Meeting) pp. 1-32 (2003).
Agus et al., "Efficacy and safety of single agent pertuzumab (rhuMAb 2C4), a HER dimerization inhibitor, in hormone refractory prostate cancer after failure of taxane-based therap" Journal of Clinical Oncology (Abstract 4624 from the 41st Annual Meeting of ASCO) 23(16S):408s (Jun. 1, 2005).
Agus et al., "Targeting ligand-activated ErbB2 signaling inhibits breast and prostate tumor growth" Cancer Cell 2(2):127-137 (Aug. 2002).
Agus et al., "Clinical Activity in a Phase I Trial of HER-2-Targeted rhuMAb 2C4 (pertuzumab) in Patients with Advanced Solid Malignancies (AST)" P AM Assoc Canc Res (Abstract No. 771), 22:192 (2003).
Agus, D. et al., "Efficacy and safety of single agent pertuzumab (rhuMAb 2C4), a HER dimerization inhibitor, in hormone refractory prostate cancer after failure of taxane-based therapy" (Poster 4624 from the 41st Annual Meeting of the American Society of Clinical Oncology) (May 15, 2005).
Amler et al., "Identification of a predictive expression pattern for phosphorylated HER2 as a potential diagnostic marker for pertuzumab (OMNITRAG) activity in ovarian cancer" (Poster 4497 presented at the Apr. 2006 American Association for Cancer Research Meeting) (Apr. 2006).
Arakawa et al. et al., "Protein-Solvent Interactions in Pharmaceutical Formulations" Pharm RES 8(3):285-291 ( 1991).
Armitage et al., "Molecular and Biological Characterization of a Murine Ligand for CD40" Nature 357(6373):80-82 (1992).
Artega, C. L. et al., "p185$^{c\text{-}erB\text{-}2}$ Signaling Enhances Ciplatin-induced Cytotoxicity in Human Breast Carcinoma Cells: Association Between on Oncogenic Receptor Tyrosine Kinase and Drug-induced DNA Repair" Cancer Res 54(14):3757-3765 (Jul. 15, 1994).
Ashkenazi and Dixit, "Apoptosis control by death and cecoy receptors" Curr Opin Cell Biol 11(2):255-260 ( 1999).
Ashkenazi and Dixit, "Death Receptors: Signaling and Modulation" Science 281:1305-1308 ( 1998).
Ashkenazi et al., "Safety and antitumor activity of recombinant soluble Apo2 ligand"Journal of Clinical Investigation 104(2):155-163 (1999).
Ashkenzai et al., "Targeting death and decoy receptors of the tumour-necrosis factor superfamily" Nature Reviews—Cancer 2:420-430 (2002).
Bacuc, S. C. et al., "Differentiation of Cultured Human Breast Cancer Cells (AU-565 and MCF-7) Assocaited With Loss of Cell Surface HER-2/neu Antigen"Mol Carcinogen 3(6):350-362 ( 1990).
Bacus, S. S. et al., "Tumor-inhibitory Monoclonal Antibodies to the HER-2/Neu Receptor Induces Differentiation of Human Breast Cancer Cells" Cancer Res 52(9):2580-2589 (May 1, 1992).
Barriuso Feijoo et al., "Anticuerpos contra el cancer" Rev. Clin. Exp. (Contains English abstract) 2004(12):649-654 (2004).
Baselga and Mendelsohn, "Receptor Blockade With Monoclonal Antibodies as Anti-Cancer Therapy" Pharmac. Ther. 64:127-154 (1994).
Baselga et al., "Phase II Study of Weekly Intravenous Recombinant Humanized Anti-p185$^{HER2}$ Monoclonal Antibody in Patients With HER2/neu-Overexpressing Metatatic Breast Cancer" J Clin Oncol 14(3):737-744 (Mar. 1996).
Bodmer et al., "Cysteine 230 is Essential for the Structure and Activity of the Cytotoxic Ligand TRAIL" Journal of Biological Chemistry 275:20632-20637 (2000).
Bodmer et al., "TRAIL receptor-2 signals apoptosis through FADD and caspase-8" Nature Cell Biology 2:241-243 (2000).
Borst et al., "Oncogene Alterations in Endometrial Carcinoma" Gynecol Oncol 38(3):364-366 (Sep. 1990).
Bossenmaier et al. et al., "Presence of HER2/HER3 heterodimers predicts antitumor effects of pertuzumab (OMNITARG) in different human xenograft models" P Am Assoc Canc Res (Abstract 5342), 45:1232 (Mar. 2004).
Breen, E.D. et al. et al., "Effect of Moisture on the Stability of a Lyophilized Humanized Monoclonal Antibody Formulation" Pharm Res 18(9):1345-1353 (Sep. 2001).
Browning et al., "Lymphotoxin β, a Novel Member of the TNF Family That Forms a Heteromeric Complex with Lymphotoxin on the Cell Surface" CELL 72:847-856 ( 1993).
Carraway and Cantley, "A Neu Acquaintance for ErbB3 and ErbB4: A Role for Receptor Heterodimerization in Growth Signaling" CELL 78:5-8 (Jul. 15, 1994).
Carraway et al., "Neuregulin-2, A New Ligand of ErbB3-ErbB4-Receptor Tyrosine Kinases" NATURE 387:512-516 (May 29, 1997).
Cha et al., "2.8 A Resolution Crystal Structure of Human TRAIL, a Cytokine with Selective Antitumor Activity" Immunity 11:253-261 (1999).
Chang et al., "Ligands for ERbB-Family Receptors Encoded by a Neuregulin-Like Gene" Nature 387:509-512 (May 29, 1997).
Chen et al., "Influence of histidine on the stability and physical properties of a fully human antibody in aqueous and solid forms" Pharmaceutical Reserach 20(12):1952-1960 (Dec. 2003).
Chicheportiche et al., "TWEAK, A New Secreted Ligand in the Tumor Necrosis Factor Family that Weakly Induces Apoposis" Journal of Biological Chemistry 272(51):32401-32410 (1997).
Chinnaiyan et al., "Combined effect of tumor necrosis factor-related apoptosis-inducing ligand and ionizing radiation in breast cancer therapy" Proc. Natl. Acad. Sci. 97:1754-1759 (2000).
Chuntharapai et al., "Isotype-dependent inhibition of tumor growth in vivo by monoclonal andibodies to death receptor 4" J. Immunol. 166:4891-4898 (2001).
Cleland et al. et al., "A specific molar ratio of stabilizer to protein is required for storage stability of a lyophilized monoclonal antibody" J Pharm Sci 90(3):310-321 (Mar. 2001).
Cleland et al. et al., "The Development of Stable Protein Formulations: A Close Look at Protein Aggregation, Deamidation, and Oxidation" Crit Rev Ther Drug 10(4):307-377 ( 1993).
Cohen et al., "Expression Pattern of the neu (NGL) Gene-Encoded Growth Factor Receptor Protein (p185$^{neu}$) in Normal and Transformed Epithelial Tissues of the Digestive Tract" Oncogene 4(1):81-88 (Jan. 1989).
Cortes et al., "Open label, randomized, phase II study of pertuzumab (P) in patients (pts) with metastatic breast cancer (MBC) with low expression of HER2" Journal of Clinical Oncology (Abstract 3068 from the 41st Annual Meeting of ASCO) 23(16s):208s (Jun. 1, 2005).
Cortes et al., "Open label, randomized, phase II study of pertuzumab (OMNITARG) in patients with metastic breast cancer (MBC) with low expression of HER2" (Poster 3068 from the 41st Annual Meeting of the American Society of Clinical Oncology (ASCO)) (May 15, 2005).
de Bono et al., "An open label, phase II, multicenter study to evaluate the efficacy and safety of pertuzumab in chemotherapy-naive patients with Hormone-Refractory Prostate Cancer (HRPC)" (Poster 4609 from the 41 st Annual Meeting of the American Society of Clinical Oncology (ASCO)) (May 15, 2005).
de Bono et al., "An open label, phase II, multicenter, study to evaluate the efficacy and safety of pertuzumab (P) in chemotherapy naive patients (pts) with Hormone Refractory Prostate Cancer (HRPC)" Journal of Clinical Oncology (Abstract 4609; 41st Annual Meeting of ASCO) 23(16S):405s (Jun. 1, 2005).
Dealrty et al., "DNA Fragmentation and Cytotoxicity Caused by Tumor Necrosis Factor is Enhanced by Interferon-γ" Eur J Immunol. 17:689-693 ( 1987).
Degli-Esposti et al., "The Novel Receptor TRAIL-R4 Induces NF-κB and Protects against TRAIL-Mediated Apoptosis, yet Retains and Incomplete Death Domain" Immunity 7:813-820 (1997).
Degli-Esposti et al., "Cloning and Characterization of TRAIL-R3, a Novel Member of the Emerging TRAIL Receptor Family" J Exp Med 186(7):1165-1170 ( 1997).

(56) References Cited

OTHER PUBLICATIONS

Drebin et al., "Down-Modulation of an Oncogene Protein Product and Reversion of the Transformed Phenotype by Monoclonal Antibodies" CELL 41(3):695-706 (Jul. 1985).
Drebin et al., "Monoclonal Antibodies Reactive With Distinct Domains of the neu Oncogene-Encoded p185 Molecule Exert Synergistic Anti-Tumor Effects In Vivo" Oncogene 2:273-277 (1988).
D'Souza and Taylor-Papadimitriou, "Overexpression of ERBB2 in human mammary epithelial cells signals inhibition of transcription of the E-cadherin gene" P Natl Acad Sci USA 91(15:7202-7206 (Jul. 1994).
Earp et al., "Heterodimerization and Functional Interaction Between EGF Receptor Family Members: A New Signaling Paradigm With Implications For Breast Cancer Research" Breast Cancer Res Treatment 35:115-132 (1995).
F. Hoffmann La-Roche Ltd., Pertuzumab combined with Herceptin and chemothereapy significantly extended the time people with HER2-positive metastatic breast cancer lived without their disease getting worse, pp. 1-3 (Media Release Jun. 15, 2011) http://www.roche.com/media/media_releases/med-cor-2011-07-15.htm.
Fendly et al., "Characterization of Murine Monoclonal Antibodies Reactive to Either the Human Epidermal Growth Factor or HER2/neu Gene Product" Cancer Res 50:1550-1558 (Mar. 1, 1990).
Friess et al., "Combination treatment with erlotinib and pertuzumab against human tumor xenografts is superior to monotherapy" Clinical Cancer Research 11(14):5300-5309 (Jul. 15, 2005).
Friess et al., "In vivo activity of recombinant humanized monoclonal antibody 2C4 in xenografts is independent of tumor type and degree of HER2 overexpression" European Journal of Cancer (Abstract 496 from the EORTIC-NCI-AACR conference in Frankfurt, Germany Nov. 19-22, 2002.) 38(Suppl. 7):S149 (2002).
Fukushige et al., "Localization of a Novel v-erbB-Related Gene, c-erbB-2, on Human Chromosome 17 and Its Amplification in a Gastric Cancer Cell Line" Mol Cell Biol 6(3):955-958 (Mar. 1986).
Gazitt, Y., "TRAIL is a potent inducer of apoptosis in myeloma cells derived from multiple myeloma patients and is not cytotoxic to hematopoietic stem cells" Leukemia 13:1817-1824 (1999).
Genentech, Inc., CLEOPATRA Protocol: A Study to Evaluate Pertuzumab + Trastuzumab + Docetaxel vs. Placebo + Trastuzumab + Docetaxel in Previously Untreated Her2-Positive Metastatic Breast Cancer (CLEOPATRA), pp. 1-4 (Jul. 28, 2010) http://clinicaltrials.gov/ct2/show/NCT00567190.
Gliniak and Le, "Tumor Necrosis Factor-related Apoptosis-inducing Ligand's Antitumor Activity in Vivo is Enhanced by the Chemoptherapeutic Agent CPT-11" Cancer Research 59:6153-6158 (1999).
Golstein, P., "Cell Death: TRAIL and its Receptors" Curr Biol 7:R750-R753 (1997).
Gordon et al., "Clinical activity of pertuzumab (rhuMab 2C4) in advanced, refractory or recurrent ovarian cancer and the role of HER2 activation status" (Poster #5051 from the 41st Annual Meeting of the American Society of Clinical Oncology (ASCO)) (May 15, 2005).
Gordon et al., "Clinical activity of pertuzumab (rhuMab 2C4) in advanced, refractory or recurrent ovarian cancer (OC), and the role of HER2 activation status" Journal of Clinical Oncology (Abstract #5051 from the 41st Annual Meeting of ASCO) 23(16S):467s (Jun. 1, 2005).
Griffith et al., "Functional Analysis of TRAIL Receptors Using Monoclonal Antibodies" The Journal of Immunology 162:2597-2605 (1999).
Griffith et al., "Monocyte-mediated Tumoricidal Activity via the Tumor Necrosis Factor-related Cytokine, TRAIL" Journal of Experimental Medicine 189:1343-1353 (1999).
Groenen et al., "Structure-Function Relationships for the EGF/TGF-α Family of Mitogens" Growth Factors 11:235-257 (1994).
Gruss and Dower, "Tumor Necrosis Factor Ligand Superfamily: Involvement in the Pathology of Malignant Lymphomas" Blood 85:3378-3404 (1995).

Gu et al., "Overexpression of her-2/neu in Human Prostate Cancer and Benign Hyperplasia" Cancer Lett 99:185-189 (1996).
Guerin et al., "Overexpression of Either c-myc or c-erbB-2/neu Proto-Oncogenes in Human Breast Carcinomas: Correlation with Poor Prognosis" Oncogene Res. 3:21-31 (1988).
Hahne et al., "APRIL, A New Ligand of the Tumor Necrosis Factor Family, Stimulates Tumor Cell Growth" J Exp Med 188(6):1185-1190 (Sep. 21, 1998).
Hancock, M. C. et al., "A Monoclonal Antibody Against the c-erbB-2 Protein Enhances the Cytotoxicity of cis-Diamminedichloroplatinum Against Human Breast and Ovarian Tumor Cell Lines" Cancer Res 51:4575-4580 (Sep. 1, 1991).
Harari et al., "Neuregulin-4: A Novel Growth Factor That Acts Through the ErbB-4 Receptor Tyrosine Kinase" Oncogene 18:2681-2689 (1999).
Harwerth, I. et al., "Monoclonal Antibodies Against the Extracellular Domain of the erbB-2 Receptor Function as Partial Ligand Agonists" J Biol Chem 267(21):15160-15167 (Jul. 25, 1992).
Hasmann et al., "Pertuzumab (Omnitarg) Potentiates Antitumor Effects on NSCLS Xenografts without Increasing Toxicity when Combined with Cytotoxic Chemotherapeutic Agents" American Association for Cancer Research (Abstract #B213; supplement to Clinical Cancer Research) 9(16) (Dec. 1, 2003).
HERCEPTIN® (trastuzumab) Prescribing Information, pp. 1-32 (Oct. 2010).
Holmes et al., "Identification of Heregulin, A Specific Activator of p185 $^{erbB2}$" Science 256:1205-1210 (May 22, 1992).
Hudziak et al., "p185$^{HER2}$ Monoclonal Antibody Has Antiproliferative Effects In Vitro and Sensitizes Human Breast Tumor Cells to Tumor Necrosis Factor" Molecular & Cellular Biology 9(3):1165-1172 (Mar. 1989).
Hylander et al., "An antibody to DR5 (TRAIL-Receptor 2) suppresses the growth of patient derived gastrointestinal tumors grown in SCID mice." (Abstract, 2d International Congress on Monoclonal Antibodies in Cancers, Aug. 29-Sep. 1, 2002, Banoff, Canada).
Hymowitz et al., "A unique zinc-binding site revealed by the high-resolution X-ray structure of homotrimeric Apo2L/TRAIL" Biochemistry 39(4):633-640 (2000).
Hymowitz et al., "Triggering Cell Death: The Crystal Structure of APo2L/TRAIL in a Complex with Death Receptor 5" Molecular Cell 4(4):563-571 (1999).
Ichikawa, K. et al., "Tumoricidal activity of a novel anti-human DR5 monoclonal antibody without hepatocyte cytotoxicity" Nature Med. 7(8):954-960 (2001).
James Andya's C.V., pp. 1-13 (2011).
Jo et al., "Apoptosis induced in normal human hepatocytes by tumor necrosis factor-related apoptosis-inducing ligand" Nature Medicine 6(5):564-567 (2000).
Johnsen et al., "Regulation of Apo-2 Ligand/TRAIL Expression in NK cells-Involvement in NK Cell-Mediated Cytoxicity" Cytokine 11:664-672 (1999).
Kasprzyk, P. G. et al., "Therapy of an Animal Model of Human Gastric Cancer Using a Combination of Anti-erbB-2 Monoclonal Antibodies" Cancer Res 52(10):2771-2776 (May 15, 1992).
Keane, et al., "Chemotherapy Augments TRAIL-induced Apoptosis in Breast Cell Lines" Cancer Research 59:734-741 (Feb. 1, 1999).
Kern et al., "p185 $^{neu}$ Expression in Human Lung Adenocarcinomas Predicts Shortened Survival" Cancer Res 50(16):5184-5191 (Aug. 15, 1990).
King et al., "Amplification of a Novel v-erbB-Related Gene in a Human Mammary Carcinoma" Science 229:974-976 (Sep. 1985).
Kischkel et al., "Apo2L/TRAIL-dependent recruitment of endogenous FADD and caspase-8 to death receptors 4 and 5"Immunity 12:611-620 (2000).
Klapper et al., "A Subclass of Tumor-Inhibitory Monoclonal Antibodies to ErbB-2/HER2 Blocks Crosstalk With Growth Factor Receptors" Oncogene 14:2099-2109 (1997).
Kotts et al., 'Differential growth inhibition of human carcinoma cells exposed to monoclonal antibodies directed against the extracellular domain of the HER2/ERBB2 protooncogene' In Vitro (Abstract #176) 26(3):59A (1990).
Kraus et al., "Isolation and characterization of ERBB3, a third member of the ERBB/epidermal growth factor reseptor family: Evidence

(56) References Cited

OTHER PUBLICATIONS for overexpression in a subset of human mammary tumors" P Natl Acad Sci USA 86:9193-9197 (Dec. 1989).
Kumar et al., "Regualtion of phosphorylation of the c-erbB-2/HER2 gene product by a monoclonal antibody and serum growth factor(s) in human mammary carcinoma cells" Mol Cell Biol 11(2):979-986 (Feb. 1991).
Lawrence et al., "Differential hepatocyte toxicity of recombinant Apo2L/TRAIL versions" Nature Medicine 7(4):383-385 (Apr. 2001).
Lee et al., "Transforming Growth Factor α: Expression, Regulation, and Biological Activities" Pharmacological Reviews 47(1):51-85 (Mar. 1995).
Lemke, G., "Neuregulins in Development" Molecular Cellular Neurosciences 7:247-262 ( 1996).
Levi et al., "The Influence of Heregulins on Human Schwann Cell Proliferation" J Neurosci 15(2):1329-1340 (Feb. 1995).
Lewis et al., "Differential Responses of Human Tumor Cell Lines to Anti-p185 $^{HER2}$ Monoclonal Antibodies" Cancer Immunol. Immunother. 37:255-263 (1993).
Lewis et al., "Growth regulation of human breast and ovarian tumor cells by heregulin: Evidence for the requirement of ErbB2 as a critical component in mediating heregulin responsiveness" Cancer Res 56:1457-1465 (Mar. 15, 1996).
Locksley et al., "The TNF and TNF Receptor Superfamilies: Integrating Mammalian Biology" Cell 104:487-501 (Feb. 23, 2001).
LUCENTIS® (ranibizumab injection) Prescribing Information, pp. 1-6 ( Jun. 2010).
MacFarlane et al., "Identification and Molecular Cloning of Two Novel Receptors for the Cytotoxic Ligand TRAIL" Journal of Biological Chemistry 272(41):25417-25420 (1997).
Maier, L. A. et al., "Requirements for the Internalization of a Murine Monoclonal Antibody Directed against the HER-2/neu Gene Product c-erbB-2" Cancer Res 51(19):5361-5369 (Oct. 1, 1991).
Mariani et al., "Interleukin 1β-converting Enzyme Related Proteases/Caspases Are Involved in TRAIL-induced Apoptosis of Myeloma and Leukemia Cells" Journal of Cell Biology 137:221-229 (1997).
Marsters et al., "A Novel Receptor for Apo2L/TRAIL Contains a Truncated Death Domain" Curr Biol 7:1003-1006 ( 1997).
Marsters et al., "Identification of Ligand for the Death-Domain-Containing Receptor Apo3" Curr Biol 8(9):525-528 ( 1998).
Masui et al., "Growth Inhibition of Human Tumor Cells in Athymic Mice by Anti-Epidermal Growth Factor Receptor Monoclonal Antibodies" Cancer Research 44(3):1002-1007 (Mar. 1984).
McCann et al., "c-erbB-2 Oncoprotein Expression Primary Human Tumors" Cancer 65(1):88-92 (Jan. 1, 1990).
McKenzie, S.J. et al., "Generation and Characterization of Monoclonal Antibodies Specific for the Human neu Oncogene Product, p185" Oncogene 4:543-548 ( 1989).
Mizutani et al., "Synergistic Cytotoxicity and Apoptosis by Apo-2 Ligand and Adriamycin against Bladder Cancer Cells" Clin. Cnacer Research 5:2605-2612 (1999).
Mongkolsapaya et al., "Cutting erdge: Lymphocyte Inhibitor of TRAIL (TNF-Related Apoptosis-Inducing Ligand): A New Receptor Protecting Lymphocytes From the Death Ligand TRAIL" J. Immunol. 160(1):3-6 (1998).
Mongkolsapaya et al., "Structure of the TRAIL-DR5 complex reveals mechanisms conferring specificity in apoptotic initiation" Nature Structural Biology 6(11):1048-1053 (Nov. 1999).
Moore et al., "BLyS: Member of the Tumor Necrosis Factor Family and B Lymphocyte Stimulator" Science 285(5425):260-263 ( 1999).
Morrissey et al., "Axon-Induced Mitogenesis of Human Schwann Cells Involves Heregulin and p185$^{erbB2}$" P Natl Acad Sci USA 92:1431-1435 (Feb. 1995).
Mukhopadhyay et al., "Identification and Characterization of a Novel Cytokine,Thank, a TNF Homologue That Activates Apoptosis, Nuclear Factor-κB, and c-Jun NH$_2$-Terminal Kinase" J Biol Chem 274:15978-15981 ( 1999).

Myers et al., "Biological Effects of Monoclonal Antireceptor Antibodies Reactive with neu Oncogene Product, p185neu" Method Enzymol 198:277-290 ( 1991).
Nagata, S., "Steering anti-cancer drugs away from the TRAIL" Nature Medicine 6(5):502-503 (May 2000).
Nahta, R. et al., "The HER-2-targeting antibodies trastuzumab and pertuzumab synergistically inhibit the survival of breast cancer cells" Cancer Res 64(7):2343-2346 (Apr. 1, 2004).
Pan et al., "TRUNDD, A New Member of the TRAIL Receptor Family That Antagonizes TRAIL Signalling" FEBS Letters 424(1-2):41-45 (1998).
Pan et al., "An Antagonist Decoy Receptor and a Death Domain-Containing Receptor for TRAIL" Science 277:815-818 (Aug. 1997).
Pan et al., "The Receptor for the Cytotoxic Ligand TRAIL" Science 276:111-113 (Apr. 4, 1997).
Park et al., "Amplification, Overexpression, and Rearrangement of the erbB-2 Protooncogene in Primary Human Stomach Carcinomas" Cancer Res 49(23):6605-6609 (Dec. 1, 1989).
Pietras et al., "Antibody to HER-2/neu receptor blocks DNA repair after cisplatin in human breast and ovarian cancer cells" Oncogene 9:1829-1838 ( 1994).
Pikal, M., "Freeze-Drying of Proteins, Part 2: Formulation Selection" Biopharm 3(9):26-30 ( 1990).
Pitti et al., "Induction of Apoptosis by Apo-2 Ligand, a New Member of the Tumor Necrosis Factor Cytokine Family" J Biol Chem 271:12687-12690 ( 1996).
Plowman et al., "Heregulin induces tyrosine phosphorylation of HER4/p180 $^{erbB4}$" nature 366:473-475 (Dec. 2, 1993).
Plowman et al., "Ligand-specific activation of HER4/p180 $^{erbB4}$, a fourth member of the epidermal growth factor receptor family" P Natl Acad Sci USA 90:1746-1750 (Mar. 1993).
Qin et al., "Avoiding premature apoptosis of normal epidermal cells" Nature medicine 7(4):385-386 (Apr. 2001).
Rieger et al., "APO2 ligand: a novel lethal weapon against malignant glimoa?" FEBS Letters 427:124-128 (1998).
Ross et al., "HER-2/neu Gene Amplification Status in Prostate Cancer by Fluorescence in Situ Hybridization" Hum Pathol 28(7):827-833 (Jul. 1997).
Ross et al., "Prognostic Significance of HER-2/neu Gene Amplification Status by Fluorescnce In Situ Hybridization of Prostate Carcinoma" Cancer 79(11):2162-2170 (Jun. 1, 1997).
Roth et al., "Locoreginal Apo2L/TRAIL Eradicates Intracranial Human Malignant Glioma Xenografts in Athymic Mice in the Absense of Neurotoxicity" Biochem. Biophys. Res. Comm 265:479-483 (1999).
Sadasivan et al., "Overexpression of Her-2/Neu May Be an Indicator of Poor Prognosis in Prostatc Cancer" J Urol 150:126-131 (Jul. 1993).
Salvesen & Dixit, "Caspases: intracellular signaling of proteolysis" Cell 91:443-446 (1997).
Sarup et al., "Characterization of an anti-P185$^{HER2}$ monoclonal antibody that stimulates receptor function and Inhibits tumor cell growth" Growth Regulat 1:72-82 ( 1991).
Schaefer et al., "γ-Heregulin: A novel heregulin isoform that is an autocrine growth factor for the human breast cancer cell line, MDA-MB-175" Oncogene 15:1385-1394 ( 1997).
Schernerman e tal., "Using a risk assessment process to determine criticality of product quality attributes" Quality by Design for Biopharmaceuticals, A.S. Rathore and R. Mhatre, New Jersey:John Wiley & Sons, Inc., Chapter 4, pp. 53-84 (2009).
Schmid et al., "DNA Fragmentation: Manifestation of Target Cell Destruct. Mediated by Cytotoxic T-cell Lines, Lymphotoxin-Secreting Helper T-cell Clones, and Cell-Free Lymphotoxin-Containing Supernatant" P Natl Acad Sci USA 83:1881-1885 ( 1986).
Schneider et al., "Characterization of Two Receptors for TRAIL" FEBS Letters 416:329-334 (1997).
Schneider et al., "BAFF, A Novel Ligand of the Tumor Necrosis Factor Family, Stimulates B Cell Growth" J Exp Med 189:1747-1756 ( 1999).
Scott et al., "p185$^{HER2}$ signal transduction in breast cancer cells" J Biol Chem 266(22):14300-14305 (Aug. 5, 1991).

(56) References Cited

OTHER PUBLICATIONS

Screaton et al., "TRICK2, A New Alternatively Spliced Receptor that Transduces the Cytotoxic Signal From TRAIL" Current Biology 7:693-696 (1997).
Shawver, L. K. et al., "Ligand-Like Effects Induced by Anti-c-erbB-2 Antibodies Do Not Correlate with and Are Not Required for Growth Inhibition of Human Carcinoma Cells" Cancer Res 54(5):1367-1373 (Mar. 1, 1994).
Shepard et al., "Monoclonal antibody therapy of human cancer: Taking the HER2 protooncogene to the clinic" J Clin Immunol 11(3):117-127 (1991).
Sheridan et al., "Control of TRAIL-Induced Apoptosis by a Family of Signaling and Decoy Receptors" Science 277:818-821 (1997).
Shu et al., "TALL-1 is a Novel Member of the TNF Family that is Down-Regulated by Mitogens" J Leukocyte Biol 65:680-683 (1999).
Sigam-Aldrich, BioUltra Reagents, Biological Buffers, pp. 1-12 (2011) http://www.sigmaaldrich.com/life-science/metabolomics/bioultra-reagents/biological-buffers.html.
Slamon et al., "Human breast cancer: Correlation of relapse and survival with amplification of the HER-2/neu oncogene" Science 235:177-182 (Jan. 9, 1987).
Slamon et al., "Studies of the HER-2/neu proto-oncogene in human breast and ovarian cancer" Science 244:707-712 (May 12, 1989).
Sliwkowski et al., "Coexpression of erbB2 and erbB3 Proteins Reconstitutes a High Affinity Receptor for Heregulin" J Biol Chem 269(20):14661-14665 (May 20, 1994).
Song et al., "Tumor Necrosis Factor-related Apoptosis-inducing Ligand (TRAIL) Is an Inhibitor of Autoimmune Inflammation and Cell Cycle Progression" Journal of Experimental Medicine 1991(7):1095-1103 (2000).
Sprick et al., "FADD/MORT1 and Caspase-8 Are Recruited to TRAIL Receptors 1 and 2 and Are Essential Apoptosis Mediated by TRAIL Receptor 2" Immunity 12:599-609 (2000).
Stancovski et al., "Mechanistic Aspects of the Opposing Effects of Monoclonal Antibodies to the ERBB2 Receptor on Tumor Growth" Proc. Natl. Acad. Sci. USA 88(19):8691-8695 (Oct. 1, 1991).
SYNAGIS® (palivizumab) Prescribing Information, pp. 1-2 (Apr. 2011).
Tagliabue, E. et al., "Selection of Monoclonal Antibodies Which Induce Internalization and Phosphorylation of p185$^{HER2}$ and Growth Inhibition of Cells With HER2/NEU Gene Amplification" Int J Cancer 47(6):933-937 (Apr. 1, 1991).
Thomas and Hersey, "TNF-Related Apoptosis-Inducing Ligand (TRAIL) Iduces Apoptosis in Fas Ligand-Resistant Melanoma Cells and Mediates CD4 T Cell Killing of Target Cells" J. Immunol. 161:2195-2200 (1998).
Vitetta and Uhr, "Monoclonal antibodies as agonists: An expanded role for their use in cancer therapy" Cancer Res 54(20):5301-5309 (Oct. 15, 1994).
Walczak et al., "TRAIL-R2: A Novel Apoptosis-Mediating Receptor for TRAIL" EMBO Journal 16(17):5386-5397 (1997).
Walczak et al., "Tumoricidal activity of tumor necrosis factor-related apoptosis-inducing ligand in vivo" Nature Med. 5:157-163 (1999).
Wallach Cytokine Reference "TNF Ligand and TNF/NGF Receptor Families" Academic Press,:377-411 (2000).
Weiner et al., "Expressing of the neu Gene-encoded Protein (P185$^{neu}$) in Human Non-Small Cell Carcinomas of the Lung" Cancer Res 50(2):421-425 (Jan. 15, 1990).
Wiley et al., "Identification and Characterization of a New Member of the TNF Family that Induces Apoptosis" Immunity 3:673-682 (1995).
Williams et al., "Expression of c-erbB-2 in Human Pancreatic Adenocarcinomas" Pathobiology 59(1):46-52 (1991).
Wu et al., "Apoptosis Induced By an Anti-Epidermal Growth Receptor Monoclonal Antibody in a Human Colorectal Carcinoma Cell Line and Its Delay By Insulin" Journal of Clinical Investigation 95(4):1897-1905 (Apr. 1995).
Wu et al., "KILLER/DR5 is a DNA Damage-Inducible p53-Regulated Death Receptor Gene" Nature Genetics 17:141-143 (1997).
XOLAIR® (omalizumab) prescribing Information, pp. 1-18 (Jul. 2010).
Xu et al., "Antibody-Induced Growth Inhibition is Mediated Through Immunochemically and Functionally Distinct Epitopes on the Extracellular Domain of the c-erbB-2 (HER-2/neu) Gene Product p185" Int J Cencer 53(3):401-408 (Feb. 1, 1993).
Yokota et al., "Amplification of c-erbB-2 Oncogene in Human Adenocarcinomas in Vivo" Lancet 1(8484):765-767 (Apr. 5, 1986).
Yonemura et al., "Evalution of Immunoreactivity for erbB-2 Protein as a Marker of Poor Short Term Prognosis in Gastric Cancer" Cencer Res 51(3):1034-1038 (Feb. 1, 1991).
Yu et al., "Tumor Necrosis Factor-related Apoptosis-inducing Ligand-mediated Apoptosis in Androgen-independent Prostate Cancer Cells" Cancer Research 60:2384-2389 (2000).
Zhang et al., "Neuregulin-3 (NRG3): A novel neural tissue-enriched protein that binds and activates ErbB4" P Natl Acad Sci USA 94:9562-9567 (Sep. 22, 1997).
Zhau et al., "Amplification and Expression of the c-erb B-2/neu Proto-Oncogene in Human Bladder Cancer" Mol Carcinogen 3(5):254-257 (1990).
Genentech, Inc., 'Genentech reports additional data from biooncology pipeline at ASCO' (press release), pp. 1-2 (Jun. 1, 2003).
Declaration of James Andya with Exhibits A-L, pp. 1-200 (executed Oct. 6, 2011).
Declaration of Jun Liu, Ph.D. with Figures 1-9 (filed in EP Patent 1,802,344 Opposition), pp. 1-16 (Feb. 27, 2014).
HERCEPTIN® (trastuzumab) Full Prescribing Information, pp. 1-32 (revised Nov. 2013).
Lam et al., "Antioxidants for Prevention of Methionine Oxidation in Recombinant Monoclonal Antibody HER2" Journal of Pharmaceutical Sciences 86(11):1250-1255 (Nov. 1997).
LUCENTIS® (ranibizumab injection) Full Prescribing Information, pp. 1-9 (revised Feb. 2013).
Nema et al., Encyclopedia of Pharmaceutical Technology "Excipients—their role in parenteral dosage forms" Swarbrick, J. and Boylan, J.,Marcel Dekker, Inc., vol. 3:1164-1187 (2002).
PERJETA® (pertuzumab) Full Prescribing Information, pp. 1-24 (revised Sep. 2013).
Pramanick et al., "Excipient selection in parenteral formulation development" Pharma Times 45(3):65-77 (Mar. 2013).
Sigma Chemical Company, Biochemicals, organic compounds and diagnostic reagents (cover page included), St. Louis, MO:Sigma Chemical Co.,:1-9; 544-545 (1996).
SYNAGIS® (palivizumab) Full Prescribing Information, pp. 1-15 (revised Apr. 2012).
Wataha et al., "Elemental release from dental casting alloys into biological media with and without protein" Dental Materials 17(5):409-414 (Sep. 2001).
Yamasaki et al., "Differential scanning calorimetris studies on bovine serum albumin: II. Effects of neutral salts and urea" Int. J. Biol. Macromol. 13(6):322-328 (Dec. 1991).
Zhou et al., "Biologics formulation factors affecting metal leachables from stainless steel" AAPS PharmSciTech 12(1):411-421 (Mar. 2011).

Variable Light

```
                 10              20              30              40
2C4     DTVMTQSHKIMSTSVGDRVSITC [KASQDVSIGVA] WYQQRP
        **       ****  *                            *
574     DIQMTQSPSSLSASVGDRVTITC [KASQDVSIGVA] WYQQKP
                                       *    * hum κI  DIQMTQSPSSLSASVGDRVTITC [RASQSISNYLA] WYQQKP 50              60              70              80
2C4     GQSPKLLIY [SASYRYT] GVPDRFTGSGSGTDFTFTISSVQA
         **                       *  *          *    * *
574     GKAPKLLIY [SASYRYT] GVPSRFSGSGSGTDFTLTISSLQP
                   * ***** hum κI  GKAPKLLIY [AASSLES] GVPSRFSGSGSGTDFTLTISSLQP 90             100
2C4     EDLAVYYC [QQYYIYPYT] FGGGTKLEIK (SEQ ID NO:1)
          * *                  *    *
574     EDFATYYC [QQYYIYPYT] FGQGTKVEIK (SEQ ID NO:3)
                  *** * hum κI  EDFATYYC [QQYNSLPWT] FGQGTKVEIK (SEQ ID NO:5)
```

FIG. 2A

Variable Heavy

```
                 10              20                30              40
2C4     EVQLQQSGPELVKPGTSVKISCKAS [GFTFTDYTMD] WVKQS
           **        **    * ***  *                   * *
574     EVQLVESGGGLVQPGGSLRLSCAAS [GFTFTDYTMD] WVRQA
                                   ** * * hum III EVQLVESGGGLVQPGGSLRLSCAAS [GFTFSSYAMS] WVRQA 50    a        60              70              80
2C4     HGKSLEWIG [DVNPNSGGSIYNQRFKG] KASLTVDRSSRIVYM
        * *    **                      *** *      **** *
574     PGKGLEWVA [DVNPNSGGSIYNQRFKG] RFTLSVDRSKNTLYL
                   **** * ****              * * * hum III PGKGLEWVA [VISGDGGSTYYADSVKG] RFTISRDNSKNTLYL abc     90     100ab           110
2C4     ELRSLTFEDTAVYYCAR [NLGPSFYFDY] WGQGTTLTVSS (SEQ ID NO:2)
        ***   **                                **
574     QMNSLRAEDTAVYYCAR [NLGPSFYFDY] WGQGTLVTVSS (SEQ ID NO:4)
                           ******** hum III QMNSLRAEDTAVYYCAR [GRVGYSLYDY] WGQGTLVTVSS (SEQ ID NO:6)
```

FIG. 2B

Amino Acid Sequence for Pertuzumab Light Chain

```
1         10        20        30        40        50        60
|         |         |         |         |         |         |
DIQMTQSPSSLSASVGDRVTITCKASQDVSIGVAWYQQKPGKAPKLLIYSASYRYTGVPS 70        80        90        100       110       120
          |         |         |         |         |         |
RFSGSGSGTDFTLTISSLQPEDFATYYCQQYYIYPYTFGQGTKVEIKRTVAAPSVFIFPP 130       140       150       160       170       180
          |         |         |         |         |         |
SDEQLKSGTASVVCLLNNFYPREAKVQWKVDNALQSGNSQESVTEQDSKDSTYSLSSTLT 190       200       210
          |         |         |
LSKADYEKHKVYACEVTHQGLSSPVTKSFNRGEC
```

FIG. 3A

Amino Acid Sequence for Pertuzumab Heavy Chain

```
1         10        20        30        40        50        60
|         |         |         |         |         |         |
EVQLVESGGGLVQPGGSLRLSCAASGFTFTDYTMDWVRQAPGKGLEWVADVNPNSGGSIY 70        80        90        100       110       120
          |         |         |         |         |         |
NQRFKGRFTLSVDRSKNTLYLQMNSLRAEDTAVYYCARNLGPSFYFDYWGQGTLVTVSSA 130       140       150       160       170       180
          |         |         |         |         |         |
STKGPSVFPLAPSSKSTSGGTAALGCLVKDYFPEPVTVSWNSGALTSGVHTFPAVLQSSG 190       200       210       220       230       240
          |         |         |         |         |         |
LYSLSSVVTVPSSSLGTQTYICNVNHKPSNTKVDKKVEPKSCDKTHTCPPCPAPELLGGP 250       260       270       280       290       300
          |         |         |         |         |         *|
SVFLFPPKPKDTLMISRTPEVTCVVVDVSHEDPEVKFNWYVDGVEVHNAKTKPREEQYNS 310       320       330       340       350       360
          |         |         |         |         |         |
TYRVVSVLTVLHQDWLNGKEYKCKVSNKALPAPIEKTISKAKGQPREPQVYTLPPSREEM 370       380       390       400       410       420
          |         |         |         |         |         |
TKNQVSLTCLVKGFYPSDIAVEWESNGQPENNYKTTPPVLDSDGSFFLYSKLTVDKSRWQ 430       440       448
          |         |         ||
QGNVFSCSVMHEALHNHYTQKSLSLSPG
```

FIG. 3B

```
1                                              15                              30                              45
M  G  W  S  C  I  I  F  L  F  L  V  A  T  A  T  G  V  H  S  D  I  Q  M  T  Q  S  P  S  S  L  S  A  S  V  G  D  R  V  T  I  T  C  K  A  S
46                                             60                              75                              90
Q  D  V  S  I  G  V  A  W  Y  Q  Q  K  P  G  K  A  P  K  L  L  I  Y  S  A  S  Y  R  Y  T  G  V  P  S  R  F  S  G  S  G  S  G  T  D  F
91                                             105                             120                             135
T  L  T  I  S  S  L  Q  P  E  D  F  A  T  Y  Y  C  Q  Q  Y  Y  I  Y  P  Y  T  F  G  Q  G  T  K  V  E  I  K  R  T  V  A  A  P  S  V  F
136                                            150                             165                             180
I  F  P  P  S  D  E  Q  L  K  S  G  T  A  S  V  V  C  L  L  N  N  F  Y  P  R  E  A  K  V  Q  W  K  V  D  N  A  L  Q  S  G  N  S  Q  E
181                                            195                             210                             225
S  V  T  E  Q  D  S  K  D  S  T  Y  S  L  S  S  T  L  T  L  S  K  A  D  Y  E  K  H  K  V  Y  A  C  E  V  T  H  Q  G  L  S  S  P  V  T
226                        233
K  S  F  N  R  G  E  C    (SEQ ID NO. 17)
```

*FIG. 4A*

```
1   M G W S C I I L F L V A T A T G V H S E V Q L V E S G G G L V Q P G G S L R L S C A A S G         45
46  F T F T D Y T M D W V R Q A P G K G L E W V A D V N P N S G G S I Y N Q R F K G R F T L S         90
91  V D R S K N T L Y L Q M N S L R A E D T A V Y Y C A R N L G P S F Y F D Y W G Q G T L V T        135
136 V S S A S T K G P S V F P L A P S S K S T S G G T A A L G C L V K D Y F P E P V T V S W N        180
181 S G A L T S G V H T F P A V L Q S S G L Y S L S S V V T V P S S S L G T Q T Y I C N V N H        225
226 K P S N T K V D K K V E P K S C D K T H T C P P C P A P E L L G G P S V F L F P P K P K D        270
271 T L M I S R T P E V T C V V V D V S H E D P E V K F N W Y V D G V E V H N A K T K P R E E        315
316 Q Y N S T Y R V V S V L T V L H Q D W L N G K E Y K C K V S N K A L P A P I E K T I S K A        360
361 K G Q P R E P Q V Y T L P P S R E E M T K N Q V S L T C L V K G F Y P S D I A V E W E S N        405
406 G Q P E N N Y K T T P P V L D S D G S F F L Y S K L T V D K S R W Q Q G N V F S C S V M H        450
451 E A L H N H Y T Q K S L S L S P G    (SEQ ID NO. 18)
```

FIG. 4B

| Trastuzumab<br>Herceptin | Pertuzumab<br>Omnitarg |
|---|---|
| 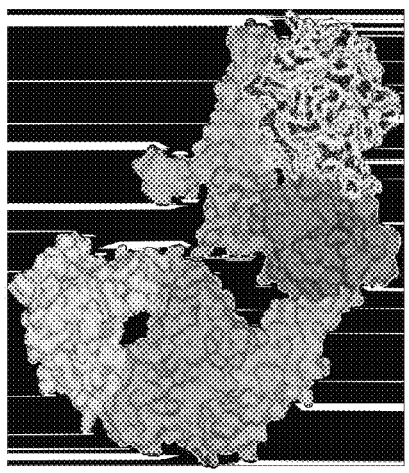 | 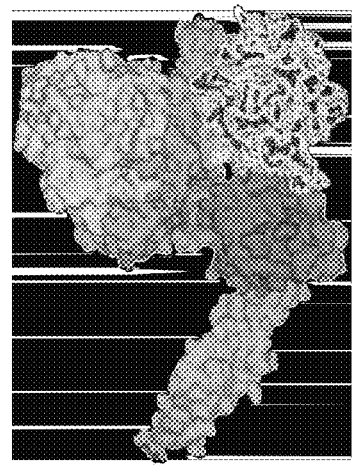 |
| • Binds in IV near JM. | • Binds in II at dimerization interface |
| • Protects against receptor shedding | • Does not prevent receptor shedding |
| • Moderately affects receptor down-modulation | • Moderately affects receptor down-modulation |
| • Slight effect on HER2's role as a coreceptor | • Major effect on HER2's role as a coreceptor |

*FIG. 7*

Light Chain

```
1                           15                          30                          45
DIQMTQSPSSLSASVGDRVTITCRASQDVNTAVAWYQQKPGKAPK
46                          60                          75                          90
LLIYSASFLYSGVPSRFSGSRSGTDFTLTISSLQPEDFATYYCQQ
91                          105                         120                         135
HYTTPPTFGQGTKVEIKRTVAAPSVFIFPPSDEQLKSGTASVVCL
136                         150                         165                         180
LNNFYPREAKVQWKVDNALQSGNSQESVTEQDSKDSTYSLSSTLT
181                         195                         210     214
LSKADYEKHKVYACEVTHQGLSSPVTKSFNRGEC
```

FIG. 14A

Heavy Chain

```
1                         15                        30                        45
EVQLVESGGGLVQPGGSLRLSCAASGFNIKDTYIHWVRQAPGKGL
46                        60                        75                        90
EWVARIYPTNGYTRYADSVKGRFTISADTSKNTAYLQMNSLRAED
91                        105                       120                       135
TAVYYCSRWGGDGFYAMDYWGQGTLVTVSSASTKGPSVFPLAPSS
136                       150                       165                       180
KSTSGGTAALGCLVKDYFPEPVTVSWNSGALTSGVHTFPAVLQSS
181                       195                       210                       225
GLYSLSSVVTVPSSSLGTQTYICNVNHKPSNTKVDKKVEPKSCDK
226                       240                       255                       270
THTCPPCPAPELLGGPSVFLFPPKPKDTLMISRTPEVTCVVVDVS
271                       285                       300                       315
HEDPEVKFNWYVDGVEVHNAKTKPREEQYNSTYRVVSVLTVLHQD
316                       330                       345                       360
WLNGKEYKCKVSNKALPAPIEKTISKAKGQPREPQVYTLPPSREE
361                       375                       390                       405
MTKNQVSLTCLVKGFYPSDIAVEWESNGQPENNYKTTPPVLDSDG
406                       420                       435                       449
SFFLYSKLTVDKSRWQQGNVFSCSVMHEALHNHYTQKSLSLSPG
```

*FIG. 14B*

```
  1 V H S D I Q M T Q S P S S L S A S V G D R V T I T C K A S Q D V S I G V A W Y Q Q K P G K
 46 A P K L L I Y S A S Y R Y T G V P S R F S G S G S G T D F T L T I S S L Q P E D F A T Y Y
 91 C Q Q Y Y I Y P Y T F G Q G T K V E I K R T V A A P S V F I F P P S D E Q L K S G T A S V
136 V C L L N N F Y P R E A K V Q W K V D N A L Q S G N S Q E S V T E Q D S K D S T Y S L S S
181 T L T L S K A D Y E K H K V Y A C E V T H Q G L S S P V T K S F N R G E C   (SEQ ID NO. 23)
```

*FIG. 15A*

```
  1 EVQLVESGGG LVQPGGSLRL SCAASGFTFT DYTMDWVRQA PGKGL       45
 46 EWVADVNPNS GGSIYNQRFK GRFTLSVDRS KNTLYLQMNS LRAED       90
 91 TAVYYCARNL GPSFYFDYWG QGTLVTVSSA STKGPSVFPL APSSK      135
136 STSGGTAALG CLVKDYFPEP VTVSWNSGAL TSGVHTFPAV LQSSG      180
181 LYSLSSVVTV PSSSLGTQTY ICNVNHKPSN TKVDKKVEPK SCDKT      225
226 HTCPPCPAPE LLGGPSVFLF PPKPKDTLMI SRTPEVTCVV VDVSH      270
271 EDPEVKFNWY VDGVEVHNAK TKPREEQYNS TYRVVSVLTV LHQDW      315
316 LNGKEYKCKV SNKALPAPIE KTISKAKGQP REPQVYTLPP SREEM      360
361 TKNQVSLTCL VKGFYPSDIA VEWESNGQPE NNYKTTPPVL DSDGS      405
406 FFLYSKLTVD KSRWQQGNVF SCSVMHEALH NHYTQKSLSL SPGK       449

(SEQ ID NO. 24)
```

Oligosaccharide Structures Commonly Observed in IgG Antibodies

| Structures | Abbreviation | Mass |
|---|---|---|
| Manα(1→6)<br>　　　＼<br>　　　　Manα(1→6)<br>　　　　　　　＼<br>Manα(1→3)／　　Manβ(1→4)GlcNAcβ(1→4)GlcNAc- | Man5 | 1235 |
| 　　　　　　　　　　　　　　　Fucα(1→6)<br>　　　　　　　　　　　　　　　　｜<br>GlcNAcβ(1→2){ Manα(1→6)<br>　　　　　　　　Manα(1→3) }Manβ(1→4)GlcNAcβ(1→4)GlcNAc- | G-1 | 1260 |
| GlcNAcβ(1→2)Manα(1→6)<br>　　　　　　　　　　　　＼<br>GlcNAcβ(1→2)Manα(1→3)／Manβ(1→4)GlcNAcβ(1→4)GlcNAc- | G0-F | 1317 |
| Manα(1→6)<br>　　　＼<br>　　　　Manα(1→6)<br>　　　　　　　＼<br>Manα(1→3)／　　Manβ(1→4)GlcNAcβ(1→4)GlcNAc-<br>Manα(1→2)Manα(1→3)／ | Man6 | 1398 |

Oligosaccharide Structures Commonly Observed in IgG Antibodies

| Structures | Abbreviation | Mass |
|---|---|---|
| Galβ(1→4)GlcNAcβ(1→2)Manα(1→6)\Manβ(1→4)GlcNAcβ(1→4)GlcNAc- with Fucα(1→6) on GlcNAc; Manα(1→3)/ | G1-1 | 1423 |
| GlcNAcβ(1→2)Manα(1→6)\Manβ(1→4)GlcNAcβ(1→4)GlcNAc- with Fucα(1→6); GlcNAcβ(1→2)Manα(1→3)/ | G0 | 1463 |
| GlcNAcβ(1→2)Manα(1→6)\Manβ(1→4)GlcNAcβ(1→4)GlcNAc- with Fucα(1→6); Galβ(1→4)GlcNAcβ(1→2)Manα(1→3)/ | G1 (1-6) | 1626 |
| Galβ(1→4)GlcNAcβ(1→2)Manα(1→6)\Manβ(1→4)GlcNAcβ(1→4)GlcNAc- with Fucα(1→6); GlcNAcβ(1→2)Manα(1→3)/ | G1 (1-3) | 1626 |
| Galβ(1→4)GlcNAcβ(1→2)Manα(1→6)\Manβ(1→4)GlcNAcβ(1→4)GlcNAc- with Fucα(1→6); Galβ(1→4)GlcNAcβ(1→2)Manα(1→3)/ | G2 | 1788 |

Masses shown in this figure correspond to the (M+Na)⁺ values.

FIG. 16B

Anti-IgE Antibodies: Light Chain (V_L and C_L Domains)

```
              10          20          30          40          50          60          70          80
E25     DIQLTQSPSS LSASVGDRVT ITC[RASQSVD YDGDSYMN]WY QQKPGKAPKL LIY[AASYLES] GVPSRFSGSG SGTDFTLTIS
E26     DIQLTQSPSS LSASVGDRVT ITC[RASKPVD YDGDSYLN]WY QQKPGKAPKL LIY[AASYLES] GVPSRFSGSG SGTDFTLTIS
HAE1    DIQLTQSPSS LSASVGDRVT ITC[RASKPVD GEGDSYLN]WY QQKPGKAPKL LIY[AASYLES] GVPSRFSGSG SGTDFTLTIS
Hu-901  DIQLTQSPGT LSISEGERAT LSC RASQSIG TNIH----- WY QQKPGQAPRL LIK YASESIS GIPSRFSGSG SGTDFTLTIS 90         100         110         C_L starts
E25     SLQPEDFATY YC[QQSHEDPY T]FGQGTKVEI KRT VAAPSVFIFPPSDEQLKSGTASVVCLLNNFYPREAKVQWKVDNALQSGNSQESVTEQD
E26     SLQPEDFATY YC[QQSHEDPY T]FGQGTKVEI KRT VAAPSVFIFPPSDEQLKSGTASVVCLLNNFYPREAKVQWKVDNALQSGNSQESVTEQD
HAE1    SLQPEDFATY YC[QQSHEDPY T]FGQGTKVEI KRT VAAPSVFIFPPSDEQLKSGTASVVCLLNNFYPREAKVQWKVDNALQSGNSQESVTEQD
Hu-901  RLEPEDFAMY YC QQSDSWPI T FGQGTKVEI T       VAAPSVFIFPPSDEQLKSGTASVVCLLNNFYPREAKVQWKVDNALQSGNSQESVTEQD E25     SKDSTYSLSSTLTLSKADYEKHKVYACEVTHQGLSSPVTKSFNRGEC  SEQ ID NO.: 37
E26     SKDSTYSLSSTLTLSKADYEKHKVYACEVTHQGLSSPVTKSFNRGEC  SEQ ID NO.: 38
HAE1    SKDSTYSLSSTLTLSKADYEKHKVYACEVTHQGLSSPVTKSFNRGEC  SEQ ID NO.: 39
Hu-901  SKDSTYSLSSTLTLSKADYEKHKVYACEVTHQGLSSPVTKSFNRGEC  SEQ ID NO.: 40
```

FIG. 17A

Anti-IgE Antibodies: Heavy Chain (V$_H$ and C$_H$ Domains)

```
              10         20         30         40        50  a       60         70         80         90
E25     EVQLVESGGG LVQPGGSLRL SCAVSGYSIT S[GYSMNW]IRQ APGKGLEWVA [SITYDGSTNY NPSVKG]RITI SRDDSKNTFY LQMNSLRAED
E26     EVQLVESGGG LVQPGGSLRL SCAVSGYSIT S[GYSMNW]IRQ APGKGLEWVA [SITYDGSTNY NPSVKG]RITI SRDDSKNTFY LQMNSLRAED
HAE1    EVQLVESGGG LVQPGGSLRL SCAVSGYSIT S[GYSMNW]IRQ APGKGLEWVA [SIKYSGETKY NPSVKG]RITI SRDDSKNTFY LQMNSLRAED
Hu-901  QVQLVQSGAE VKKPGASVKV SCKASGYTF- S MWLEW VRQ APGQGLEWIG EISPGTFTTNY NEKFKA RATF TADTSTNTAY MELSSLRSED 100       110ab       120 C_H starts
E25     TAVYYCAR[GS HYFGHMHFAV] WGQGTLVTVSS ASTKGPSVFPLAPSSKSTSGGTAALGCLVKDYFPEPVTVSWNSGALTSGVHTFPAVLQSSGLYSLSS
E26     TAVYYCAR[GS HYFGHMHFAV] WGQGTLVTVSS ASTKGPSVFPLAPSSKSTSGGTAALGCLVKDYFPEPVTVSWNSGALTSGVHTFPAVLQSSGLYSLSS
HAE1    TAVYYCAR[ES HFSGSNYDYFDY] WGQGTLVTVSS ASTKGPSVFPLAPSSKSTSGGTAALGCLVKDYFPEPVTVSWNSGALTSGVHTFPAVLQSSGLYSLSS
Hu-901  TAVYYCAR ES HFSGSNYDYFDY  WGQGTLVTVSS ASTKGPSVFPLAPSSKSTSGGTAALGCLVKDYFPEPVTVSWNSGALTSGVHTFPAVLQSSGLYSLSS E25     VVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVE
E26     VVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVE
HAE1    VVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVE
Hu-901  VVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVE E25     VHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWE
E26     VHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWE
HAE1    VHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWE
Hu-901  VHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWE E25     SNGQPENNYKTTPPVLDSDGSFFLYSKLTVDKSRWQQGNVFSCSVMHEALHNHYTQKSLSLSPGK    SEQ ID NO.: 41
E26     SNGQPENNYKTTPPVLDSDGSFFLYSKLTVDKSRWQQGNVFSCSVMHEALHNHYTQKSLSLSPGK    SEQ ID NO.: 42
HAE1    SNGQPENNYKTTPPVLDSDGSFFLYSKLTVDKSRWQQGNVFSCSVMHEALHNHYTQKSLSLSPGK    SEQ ID NO.: 43
Hu-901  SNGQPENNYKTTPPVLDSDGSFFLYSKLTVDKSRWQQGNVFSCSVMHEALHNHYTQKSLSLSPGK    SEQ ID NO.: 44
```

FIG. 17B

Sequence Alignment of Variable Light Domains

```
           |————FR1————|      CDR1         |—
              10        20      30               40
2H7        QIVLSQSPAILSASPGEKVTMTC  [RASSSVS-YMH]   WYQQKP
           * ***       **     * **
hu2H7.v16  DIQMTQSPSSLSASVGDRVTITC  [RASSSVS-YMH]   WYQQKP
                                    * * * **
hum kI     DIQMTQSPSSLSASVGDRVTITC  [RASQSISNYLA]   WYQQKP —FR2—|     CDR2      |————FR3———
                     50           60       70         80
2H7        GSSPKPWIY  [APSNLAS]  GVPARFSGSGSGTSYSLTISRVEA
           **     *              *         ***    ****
hu2H7.v16  GKAPKPLIY  [APSNLAS]  GVPSRFSGSGSGTDFTLTISSLQP
                *     * * *
hum kI     GKAPKLLIY  [AASSLES]  GVPSRFSGSGSGTDFTLTISSLQP —|   CDR3       |—FR4—|
                         90          100
2H7        EDAATYYC  [QQWSFNPPT]  FGAGTKLELKR
              *                   *   * *
hu2H7.v16  EDFATYYC  [QQWSFNPPT]  FGQGTKVEIKR
                     **** *
hum kI     EDFATYYC  [QQYNSLPWT]  FGQGTKVEIKR
```

*FIG. 18A*

Sequence Alignment of Variable Heavy Domains

```
           |————FR1————|      CDR1          |—
              10        20      30               40
2H7        QAYLQQSGAELVRPGASVKMSCKAS  [GYTFTSYNMH]   WVKQT
           *** **   **    *   * ***   *                * *
hu2H7.v16  EVQLVESGGGLVQPGGSLRLSCAAS  [GYTFTSYNMH]   WVRQA
                                       * *   * *
hum III    EVQLVESGGGLVQPGGSLRLSCAAS  [GFTFSSYAMS]   WVRQA —FR2—|       CDR2           |————FR3———
                      50    a    60         70         80
2H7        PRQGLEWIG  [AIYPGNGDTSYNQKFKG]  KATLTVDKSSSTAYM
           **      *                       ** **    ** * *
hu2H7.v16  PGKGLEWVG  [AIYPGNGDTSYNQKFKG]  RFTISVDKSKNTLYL
                *     * **** * * ****                 * *
hum III    PGKGLEWVA  [VISGDGGSTYYADSVKG]  RFTISRDNSKNTLYL —|    CDR3          |—FR4—|
                    abc      90    100abcde       110
2H7        QLSSLTSEDSAVYFCAR  [VVYYSNSYWYFDV]  WGTGTTVTVSS
           **  **      *  *                    *
hu2H7.v16  QMNSLRAEDTAVYYCAR  [VVYYSNSYWYFDV]  WGQGTLVTVSS
                             ******* *** *
hum III    QMNSLRAEDTAVYYCAR  [GRVGYSLY---DY]  WGQGTLVTVSS
```

*FIG. 18B*

Anti-VEGF Antibody Variable Domain Sequences anti-VEGF variable light sequence:

DIQMTQTTSSLSASLGDRVIISCSASQDISNYLNWYQQKPDGTVKVLIYFTSSLHSGVPSRFSGS
GSGTDYSLTISNLEPEDIATYYCQQYSTVPWTFGGGTKLEIK
(SEQ ID NO: 31)

anti-VEGF variable heavy sequence of:

EIQLVQSGPELKQPGETVRISCKASGYTFTNYGMNWVKQAPGKGLKWMGWINTYTGEPTYAADFK
RRFTFSLETSASTAYLQISNLKNDDTATYFCAKYPHYYGSSHWYFDVWGAGTTVTVSS
(SEQ ID NO: 32)

anti-VEGF antibody variable light sequence:

DIQMTQSPSSLSASVGDRVTITCSASQDISNYLNWYQQKPGKAPKVLIYFTSSLHSGVPSRFSGS
GSGTDFTLTISSLQPEDFATYYCQQYSTVPWTFGQGTKVEIK
(SEQ ID NO: 33)

anti-VEGF antibody variable heavy sequence:

EVQLVESGGGLVQPGGSLRLSCAASGYTFTNYGMNWVRQAPGKGLEWVGWINTYTGEPTYAADFK
RRFTFSLDTSKSTAYLQMNSLRAEDTAVYYCAKYPHYYGSSHWYFDVWGQGTLVTVSS
(SEQ ID NO: 34)

anti-VEGF antibody variable light sequence:

DIQLTQSPSSLSASVGDRVTITCSASQDISNYLNWYQQKPGKAPKVLIYFTSSLHSGVPSRFSGS
GSGTDFTLTISSLQPEDFATYYCQQYSTVPWTFGQGTKVEIK
(SEQ ID NO: 35)

anti-VEGF antibody variable heavy sequence:

EVQLVESGGGLVQPGGSLRLSCAASGYDFTHYGMNWVRQAPGKGLEWVGWINTYTGEPTYAADFK
RRFTFSLDTSKSTAYLQMNSLRAEDTAVYYCAKYPYYYGTSHWYFDVWGQGTLVTVSS
(SEQ ID NO: 36)

FIG. 19

```
  1 TTTCCTCACTGACTATAAAGAATAGAGAAGGAAGGGCTTCAGTGACCGGCTGCCTGGCTGACTACAGCAGTCAGACTCTGACAGGATC

1 ATGGCTATGATGAGGTCCAGGGGGGACCCTGGGACACAGACCTGCCTGATCGTGATCTTCACAGTCTTCCTGCAGTCTCTCTGT
  1 MetAlaMetMetGluValGlnGlyProSerLeuGlyGlnThrProAlaAspLeuIleValIleValIlePheThrValLeuLeuGlnSerLeuCys

181 GTGGCTGTAACTTACGTGTACTTACCAACGAGCTGAAGCAGATGCAGGACAAGTACTCCAAAAGTGGCATTGCTTGTTCTTAAAAGAA
 31 ValAlaValThrTyrValTyrPheThrAsnGluLysGlnMetGlnAspLysTyrSerGlyIleAlaCysPheLeuLysGlu

271 GATGACAGTTATTGGGACCCCAATGACGAAGAGAGTATGAACAGCCCCTGCTGGCAAGTCAAGTGGCAACTCCGTCAGCTCGTTAGAAAG
 61 AspAspSerTyrTrpAspProAsnAspGluGluSerMetAsnSerProCysTrpGlnValLysTrpGlnLeuArgGlnLeuValArgLys

361 ATGATTTTGAGAACCTCTGAGGAAACCATTTCTACAGTTCAAGAAAAGCAACAAATATTCTCCCTAGTGAGAGAAAGAGGTCCNCAG
 91 MetIleLeuArgThrSerGluGluThrIleSerThrValGlnGluLysGlnGlnIleSerProLeuValArgGluArgGlyProGln

451 AGAGTAGCAGCTCACATAACTGGGACCAGAGGAAGAACAACATTGTCTTCTCCAAACTCCAAGAATGAAAAGGCTCTGGGCCGCAAA
121 ArgValAlaAlaHisIleThrGlyThrArgGlySerAsnThrLeuSerSerProAsnSerLysAsnGluLysAlaLeuGlyArgLys

541 ATAAACTCCTGGGAATCATCAAGGAGTGGGCATTCATTCCTGAGGAGGAATGGTGTCATCCATGAAGGG
151 IleAsnSerTrpGluSerSerArgSerGlyHisSerPheLeuSerAsnLeuHisLeuArgAsnGlyGluLeuValIleHisGluLysGly

631 TTTTACTACATCTATTCCAAACATACTTTCGATTCTTTGAGGAGGAAATAAAAGAAAACACAAAGAACGACAAACAAATGGTCCAATATATT
181 PheTyrTyrIleTyrSerGlnThrPheArgPheGluGluGluIleLysGluAsnThrLysAsnAspLysGlnMetValGlnTyrIle

721 TACAAATACACAAGTTATCCTGACCCTATATTGTTGATGAAAAGTGCTAAAAGTGCTGGTCTAAAGATGCAGAAATATGGACTCTAT
211 TyrLysTyrThrSerTyrProAspProIleLeuLeuMetLysSerAlaArgAsnSerCysTrpSerLysAspAlaGluTyrGlyLeuTyr

811 TCCATCTATCAAGGGGAATATTTGAGCTTAAGGAAAATGACAGAATTTTGTTTCTGTAACAAATGAGCACTTGATAGACATGGACCAT
241 SerIleTyrGlnGlyGluTyrLeuSerLeuArgLysLysMetThrGluPheCysPheCysAsnLysHisLeuIleAspMetAspHis

901 GAAGCCAGTTTTTCGGGCCTTTTAGTGGCTAACTGACCCTGGAAGAAAAAGCAATAACCTCAAAGTGACTATTCAGTTTCAGGAT
271 GluAlaSerPhePheGlyAlaPheLeuValGlyStp

991 GATACACTATGAAGATGTTTCAAAAATCTGACCAAAACAAACAAACAGAAA
```

```
901  GGTCCCTGAG CAGGAAATGG AAGTCCAGGA GCCAGCAGAG CCAACAGGTG TCAACATGTT GTCCCCCGGG GAGTCAGAGC ATCTGCTGA  ACCGGCAGAA
     CCAGGGACTC GTCCTTACC  TTCAGGTCCT CGGTCGTCTC GGTTGTCCAC AGTTGTACAA CAGGGGGCCC CTCAGTCTCG TAGACGACCT TGGCCGTCTT
255  ValProGlu  GlnGluMetG luValGlnGl uProAlaGlu ProThrGlyV alAsnMetLe uSerProGly GluSerGluH isLeuLeuGl uProAlaGlu

1001 GCTGAAAGGT CTCAGAGGAG GAGGCTGCTG GTTCCAGCAA ATGAAGGTGA TCCCACTGAG ACTCTGAGAC AGTGCTTGCA TGACTTGTGC GACTTGGTGC
     CGACTTTCCA GAGTCTCCTC CTCCGACGAC CAAGGTCGTT TACTTCCACT AGGGTGACTC TGAGACTCTG TCACGAACGT ACTGAACGT  CTGAACCACG
288  AlaGluArgS erGlnArgAr gArgLeuLeu ValProAlaA snGluGlyAs pProThrGlu ThrLeuArgG lnCysPheAs pAspPheAla AspLeuValPro

1101 CCTTTGACTC CTGGGAGCCG CTCATGAGGA AGTTGGGCCT GAGATAAAGG TGGCTAAAGC ACTCTGAGAC GGCCACAGGG ACACCTGTA
     GGAAACTGAG GACCCTCGGC GAGTACTCCT TCAACCCGGA GTACTGTTA  CTCTATTTCC ACCGATTTCG ACTCCGTGC  CCGGTGTCC  TGTGGAACAT
322  PheAspSe   rTrpGluPro LeuMetArgL ysLeuGlyLe uMetAspAsn GluIleLysV alAlaLysAl aGluAlaAla GlyHisArgA spThrLeuTyr

1201 CACGATGCTG ATAAAGTGGG TCAACAAAAC CGGGCGAGAT GCCTCTGTCC ACACCCTGCT GGATGCCTTG GAGACGCTGG GAGAGAGACT TGCCAAGCAG
     GTGCTACGAC TATTTCACCC AGTTGTTTTG GCCCGCTCTA CGGAGACAGG TGTGGGACGA CCTACGGAAC CTCGCGACC  CTCTCTGA   ACGGTTCGTC
355  ThrMetLeu  IleLysTrpV alAsnLysTh rGlyArgAsp AlaSerValH isThrLeuLe uAspAlaLeu GluThrLeuG lyGluArgLe uAlaLysGln

1301 AAGATTGAGG ACCACTGTT  GAGCTCTGGA AAGTTCATGT ATCTAGAAGG TAATGCAGAC TCTGCCWTGT CCTAAGTGTG ATTCTCTTCA GGAAGTGAGA
     TTCTAACTCC TGGTGAACAA CTCGAGACCT TTCAAGTACA TAGATCTTCC ATTACGTCTG AGACGGAACA GGATTCACAC TAAGAGAAGT CCTTCACTCT
388  LysIleGluA spHisLeuLe uSerSerGly LysPheMetT yrLeuGluGl yAsnAlaAsp SerAlaXaaS erOC*

1401 CCTTCCCTGG TTTACCTTTT TTCTGAAAA  AGCCCAACTG GACTCCAGTC TCCACATGCT AGTAGGAAAG TGCCACAATT GTCACATGAC CGGTACTGGA AGAAACTCTC
     GGAAGGGACC AAATGGAAAA AAGACCTTTT TCGGGTTGAC CTGAGGTCAG AGGTGTACGA TCATCCTTTC ACGGTGTTAA CAGTGTACTG GCCATGACCT TCTTTGAGAG

1501 CCATCCAACA TCACCCAGTG GATGGAACAT CCTGTAACTT TTCACTGCAC TTGTTTTCAC TGGGATGTCA TTGTTTTCAC AGCACTTTTT TATGGAAAT  CTATGGAAAT
     GGTAGGTTGT AGTGGGTCAC CTACCTTGTA GGACATTGAA AAGTGACGTG AACCGTAATA ACCCTACCAA AACAAAAGTG ACTTACACTA TTATTCCTGT GATACCTTTA

1601 GTCTGGATCA TTCCGTTTGT GCGTACTTTG AGATTTTGGT TGGGATGTCA TTGTTTTCAC AGCACTTTTT TATCCTAATG TAAATGCTTT ATTTATTTAT
     CAGACCTAGT AAGGCAAACA CGCATGAAAC TCTAAACCAA ACCCTACAGT AACAAAAGTG TCGTGAAAAA ATAGGATTAC ATTACGAAA  TAAATAAATA

1701 TTGGGCTACA TTGTAAGATC CATCTACAAA AAAAAAAAAG GGCGGCCGCG ACTCTAGAGT CGACCTTGCA GCCATGGCC
     AACCCGATGT AACATTCTAG GTAGATGTTT TTTTTTTTTC CCGCCGGCGC TGAGATCTCA GCTGGACGTC TTCGAACCGG CGGTACCGG
```

FIG. 25B

```
ATG GAA CAA CGG GGA CAG AAC GCC CCG GCC GCT TCG GGG GCC CGG AAA    48
Met Glu Gln Arg Gly Gln Asn Ala Pro Ala Ala Ser Gly Ala Arg Lys
 1               5                  10                 15

AGG CAC GGC CCA GGA CCC AGG GAG GCG CGG GGA GCC AGG CCT GGG CCC    96
Arg His Gly Pro Gly Pro Arg Glu Ala Arg Gly Ala Arg Pro Gly Pro
                20                  25                 30

CGG GTC CCC AAG ACC CTT GTG CTC GTT GTC GCC GCG GTC CTG CTG TTG   144
Arg Val Pro Lys Thr Leu Val Leu Val Val Ala Ala Val Leu Leu Leu
             35                  40                 45

GTC TCA GCT GAG TCT GCT CTG ATC ACC CAA CAA GAC CTA GCT CCC CAG   192
Val Ser Ala Glu Ser Ala Leu Ile Thr Gln Gln Asp Leu Ala Pro Gln
         50                  55                 60

CAG AGA GCG GCC CCA CAA CAA AAG AGG TCC AGC CCC TCA GAG GGA TTG   240
Gln Arg Ala Ala Pro Gln Gln Lys Arg Ser Ser Pro Ser Glu Gly Leu
 65              70                  75                 80

TGT CCA CCT GGA CAC CAT ATC TCA GAA GAC GGT AGA GAT TGC ATC TCC   288
Cys Pro Pro Gly His His Ile Ser Glu Asp Gly Arg Asp Cys Ile Ser
                 85                  90                 95

TGC AAA TAT GGA CAG GAC TAT AGC ACT CAC TGG AAT GAC CTC CTT TTC   336
Cys Lys Tyr Gly Gln Asp Tyr Ser Thr His Trp Asn Asp Leu Leu Phe
                100                 105                110

TGC TTG CGC TGC ACC AGG TGT GAT TCA GGT GAA GTG GAG CTA AGT CCG   384
Cys Leu Arg Cys Thr Arg Cys Asp Ser Gly Glu Val Glu Leu Ser Pro
            115                 120                125

TGC ACC ACG ACC AGA AAC ACA GTG TGT CAG TGC GAA GAA GGC ACC TTC   432
Cys Thr Thr Thr Arg Asn Thr Val Cys Gln Cys Glu Glu Gly Thr Phe
    130                 135                 140

CGG GAA GAA GAT TCT CCT GAG ATG TGC CGG AAG TGC CGC ACA GGG TGT   480
Arg Glu Glu Asp Ser Pro Glu Met Cys Arg Lys Cys Arg Thr Gly Cys
145                 150                 155                160

CCC AGA GGG ATG GTC AAG GTC GGT GAT TGT ACA CCC TGG AGT GAC ATC   528
Pro Arg Gly Met Val Lys Val Gly Asp Cys Thr Pro Trp Ser Asp Ile
                165                 170                175

GAA TGT GTC CAC AAA GAA TCA GGT ACA AAG CAC AGT GGG GAA GCC CCA   576
Glu Cys Val His Lys Glu Ser Gly Thr Lys His Ser Gly Glu Ala Pro
                180                 185                190

GCT GTG GAG GAG ACG GTG ACC TCC AGC CCA GGG ACT CCT GCC TCT CCC   624
Ala Val Glu Glu Thr Val Thr Ser Ser Pro Gly Thr Pro Ala Ser Pro
            195                 200                205

TGT TCT CTC TCA GGC ATC ATC ATA GGA GTC ACA GTT GCA GCC GTA GTC   672
Cys Ser Leu Ser Gly Ile Ile Ile Gly Val Thr Val Ala Ala Val Val
            210                 215                220
```

*FIG. 26A*

```
TTG ATT GTG GCT GTG TTT GTT TGC AAG TCT TTA CTG TGG AAG AAA GTC    720
Leu Ile Val Ala Val Phe Val Cys Lys Ser Leu Leu Trp Lys Lys Val
225                 230                 235                 240

CTT CCT TAC CTG AAA GGC ATC TGC TCA GGT GGT GGT GGG GAC CCT GAG    768
Leu Pro Tyr Leu Lys Gly Ile Cys Ser Gly Gly Gly Gly Asp Pro Glu
                245                 250                 255

CGT GTG GAC AGA AGC TCA CAA CGA CCT GGG GCT GAG GAC AAT GTC CTC    816
Arg Val Asp Arg Ser Ser Gln Arg Pro Gly Ala Glu Asp Asn Val Leu
                260                 265                 270

AAT GAG ATC GTG AGT ATC TTG CAG CCC ACC CAG GTC CCT GAG CAG GAA    864
Asn Glu Ile Val Ser Ile Leu Gln Pro Thr Gln Val Pro Glu Gln Glu
            275                 280                 285

ATG GAA GTC CAG GAG CCA GCA GAG CCA ACA GGT GTC AAC ATG TTG TCC    912
Met Glu Val Gln Glu Pro Ala Glu Pro Thr Gly Val Asn Met Leu Ser
290                 295                 300

CCC GGG GAG TCA GAG CAT CTG CTG GAA CCG GCA GAA GCT GAA AGG TCT    960
Pro Gly Glu Ser Glu His Leu Leu Glu Pro Ala Glu Ala Glu Arg Ser
305                 310                 315                 320

CAG AGG AGG AGG CTG CTG GTT CCA GCA AAT GAA GGT GAT CCC ACT GAG   1008
Gln Arg Arg Arg Leu Leu Val Pro Ala Asn Glu Gly Asp Pro Thr Glu
                325                 330                 335

ACT CTG AGA CAG TGC TTC GAT GAC TTT GCA GAC TTG GTG CCC TTT GAC   1056
Thr Leu Arg Gln Cys Phe Asp Asp Phe Ala Asp Leu Val Pro Phe Asp
                340                 345                 350

TCC TGG GAG CCG CTC ATG AGG AAG TTG GGC CTC ATG GAC AAT GAG ATA   1104
Ser Trp Glu Pro Leu Met Arg Lys Leu Gly Leu Met Asp Asn Glu Ile
            355                 360                 365

AAG GTG GCT AAA GCT GAG GCA GCG GGC CAC AGG GAC ACC TTG TAC ACG   1152
Lys Val Ala Lys Ala Glu Ala Ala Gly His Arg Asp Thr Leu Tyr Thr
        370                 375                 380

ATG CTG ATA AAG TGG GTC AAC AAA ACC GGG CGA GAT GCC TCT GTC CAC   1200
Met Leu Ile Lys Trp Val Asn Lys Thr Gly Arg Asp Ala Ser Val His
385                 390                 395                 400

ACC CTG CTG GAT GCC TTG GAG ACG CTG GGA GAG AGA CTT GCC AAG CAG   1248
Thr Leu Leu Asp Ala Leu Glu Thr Leu Gly Glu Arg Leu Ala Lys Gln
                405                 410                 415

AAG ATT GAG GAC CAC TTG TTG AGC TCT GGA AAG TTC ATG TAT CTA GAA   1296
Lys Ile Glu Asp His Leu Leu Ser Ser Gly Lys Phe Met Tyr Leu Glu
                420                 425                 430

GGT AAT GCA GAC TCT GCC ATG TCC TAA                               1323
Gly Asn Ala Asp Ser Ala Met Ser  *
                435                 440
```

*FIG. 26B*

EVQLVQSGGGVERPGGSLRLSCAASGFTFDDYAMSWVRQAPGKGLEWVSGINWQGGSTGY
ADSVKGRVTISRDNAKNSLYLQMNSLRAEDTAVYYCAKILGAGRGWYFDYWGKGTTVTVS
SASTKGPSVFPLAPSSKSTSGGTAALGCLVKDYFPEPVTVSWNSGALTSGVHTFPAVLQS
SGLYSLSSVVTVPSSSLGTQTYICNVNHKPSNTKVDKKVEPKSCDKTHTCPPCPAPELLG
GPSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSRE
EMTKNQVSLTCLVKGFYPSDIAVEWESNGQPENNYKTTPPVLDSDGSFFLYSKLTVDKSR
WQQGNVFSCSVMHEALHNHYTQKSLSLSPGK

<451 residues; 0 stop; molecular weight: 49167.50

FIG. 27

SELTQDPAVSVALGQTVRITCSGDSLRSYYASWYQQKPGQAPVLVIYGANNRPSGIPDRF
SGSSSGNTASLTITGAQAEDEADYYCNSADSSGNHVVFGGGTKLTVLGQPKAAPSVTLFP
PSSEELQANKATLVCLISDFYPGAVTVAWKADSSPVKAGVETTTPSKQSNNKYAASSYLS
LTPEQWKSHKSYSCQVTHEGSTVEKTVAPTECS

<213 residues; 0 stop; molecular weight: 22400.70

FIG. 28

Alignment, 16ES and Apomab 7.3 Heavy Chains

```
16E2         1   EVQLVQSGGGVERPGGSLRLSCAASGFTFDDYGMSW
                                                *
Apomab7.3    1   EVQLVQSGGGVERPGGSLRLSCAASGFTFDDYAMSW 16E2        37   VRQAPGKGLEWVSGINWNGGSTGYADSVKGRVTISRDNAKNSLYLQMNSL
                                 *
Apomab7.3   37   VRQAPGKGLEWVSGINWQGGSTGYADSVKGRVTISRDNAKNSLYLQMNSL 16E2        87   RAEDTAVYYCAKILGAGRGWYFDLWGKGTTVTVSSASTKGPSVFPLAPSS
                                      *
Apomab7.3   87   RAEDTAVYYCAKILGAGRGWYFDYWGKGTTVTVSSASTKGPSVFPLAPSS 16E2       137   KSTSGGTAALGCLVKDYFPEPVTVSWNSGALTSGVHTFPAVLQSSGLYSL
Apomab7.3  137   KSTSGGTAALGCLVKDYFPEPVTVSWNSGALTSGVHTFPAVLQSSGLYSL 16E2       187   SSVVTVPSSSLGTQTYICNVNHKPSNTKVDKKVEPKSCDKTHTCPPCPAP
Apomab7.3  187   SSVVTVPSSSLGTQTYICNVNHKPSNTKVDKKVEPKSCDKTHTCPPCPAP 16E2       237   ELLGGPSVFLFPPKPKDTLMISRTPEVTCVVVDVSHEDPEVKFNWYVDGV
Apomab7.3  237   ELLGGPSVFLFPPKPKDTLMISRTPEVTCVVVDVSHEDPEVKFNWYVDGV 16E2       287   EVHNAKTKPREEQYNSTYRVVSVLTVLHQDWLNGKEYKCKVSNKALPAPI
Apomab7.3  287   EVHNAKTKPREEQYNSTYRVVSVLTVLHQDWLNGKEYKCKVSNKALPAPI 16E2       337   EKTISKAKGQPREPQVYTLPPSREEMTKNQVSLTCLVKGFYPSDIAVEWE
Apomab7.3  337   EKTISKAKGQPREPQVYTLPPSREEMTKNQVSLTCLVKGFYPSDIAVEWE 16E2       387   SNGQPENNYKTTPPVLDSDGSFFLYSKLTVDKSRWQQGNVFSCSVMHEAL
Apomab7.3  387   SNGQPENNYKTTPPVLDSDGSFFLYSKLTVDKSRWQQGNVFSCSVMHEAL 16E2.huIgG1 437  HNHYTQKSLSLSPGK
Apomab7.3   437  HNHYTQKSLSLSPGK
```

*FIG. 29*

Alignment, 16E2 and Apomab 7.3 Light Chains

```
16E2        1   SELTQDPAVSVALGQTVRITCQGDSLRSYYASWYQQKPGQAPVLVIYGKN
                                *                                *
Apomab7.3   1   SELTQDPAVSVALGQTVRITCSGDSLRSYYASWYQQKPGQAPVLVIYGAN 16E2       51   NRPSGIPDRFSGSSSGNTASLTITGAQAEDEADYYCNSRDSSGNHVVFGG
                                                      *
Apomab7.3  51   NRPSGIPDRFSGSSSGNTASLTITGAQAEDEADYYCNSADSSGNHVVFGG

16E2      101   GTKLTVLGQPKAAPSVTLFPPSSEELQANKATLVCLISDFYPGAVTVAWK

Apomab7.3 101   GTKLTVLGQPKAAPSVTLFPPSSEELQANKATLVCLISDFYPGAVTVAWK

16E2      151   ADSSPVKAGVETTTPSKQSNNKYAASSYLSLTPEQWKSHKSYSCQVTHEG

Apomab7.3 151   ADSSPVKAGVETTTPSKQSNNKYAASSYLSLTPEQWKSHKSYSCQVTHEG

16E2      201   STVEKTVAPTECS

Apomab7.3 201   STVEKTVAPTECS
```

FIG. 30

Apomab Variable Heavy Domain Sequence

CDR H1
EVQLVQSGGGVERPGGSLRLSCAASGFTFDDYAMWVRQAPGKGLEWV

CDR H2
SGINWQGGSTGYADSVKGRVTISRDNAKNSLYLQMNSLRAEDTAVYYCAK

CDR H3
ILGAGRGWYFDYWGKGTTVTVSSASTKGP

FIG. 31A

Apomab Variable Light Domain Sequence

CDR L1
SELTQDPAVSVALGQTVRITCSGDSLRSYYASWYQQKPGQAPVLVIY

CDR L2                                  CDRL3
GANNRPSGIPDRFSGSSSGNTASLTITGAQAEDEADYYCNSADSSGNHVV

FGGGTKLTVLG

FIG. 31B

Light Chain Alignment

```
                 1                                              32
hu2H7.v16        DIQMTQSPSSLSASVGDRVTITCRASSSVSYMHWYQQKPGKAPKPLIYAP
                 *************************** *********************
hu2H7.v511       DIQMTQSPSSLSASVGDRVTITCRASSSVSYLHWYQQKPGKAPKPLIYAP 52
hu2H7.v16        SNLASGVPSRFSGSGSGTDFTLTISSLQPEDFATYYCQQWSFNPPTFGQG
                 ****************************************.********
hu2H7.v511       SNLASGVPSRFSGSGSGTDFTLTISSLQPEDFATYYCQQWAFNPPTFGQG 102
hu2H7.v16        TKVEIKRTVAAPSVFIFPPSDEQLKSGTASVVCLLNNFYPREAKVQWKVD
                 **************************************************
hu2H7.v511       TKVEIKRTVAAPSVFIFPPSDEQLKSGTASVVCLLNNFYPREAKVQWKVD 152
hu2H7.v16        NALQSGNSQESVTEQDSKDSTYSLSSTLTLSKADYEKHKVYACEVTHQGL
                 **************************************************
hu2H7.v511       NALQSGNSQESVTEQDSKDSTYSLSSTLTLSKADYEKHKVYACEVTHQGL 202       214
hu2H7.v16        SSPVTKSFNRGEC
                 *************
hu2H7.v511       SSPVTKSFNRGEC
```

*FIG. 32*

Heavy Chain Alignment

```
             1
hu2H7.v16    EVQLVESGGGLVQPGGSLRLSCAASGYTFTSYNMHW
             ***********************************
hu2H7.v511   EVQLVESGGGLVQPGGSLRLSCAASGYTFTSYNMHW 37              52a                            82abc
hu2H7.v16    VRQAPGKGLEWVGAIYPGNGDTSYNQKFKGRFTISVDKSKNTLYLQMNSL
             ******************* *****************************
hu2H7.v511   VRQAPGKGLEWVGAIYPGNGATSYNQKFKGRFTISVDKSKNTLYLQMNSL 83            100abcde           113
hu2H7.v16    RAEDTAVYYCARVVYYSNSYWYFDVWGQGTLVTVSS
             ****************   *****************
hu2H7.v511   RAEDTAVYYCARVVYYSYRYWYFDVWGQGTLVTVSS 118
hu2H7.v16    ASTKGPSVFPLAPS
             **************
hu2H7.v511   ASTKGPSVFPLAPS 132
hu2H7.v16    SKSTSGGTAALGCLVKDYFPEPVTVSWNSGALTSGVHTFPAVLQSSGLYS
             **************************************************
hu2H7.v511   SKSTSGGTAALGCLVKDYFPEPVTVSWNSGALTSGVHTFPAVLQSSGLYS 182
hu2H7.v16    LSSVVTVPSSSLGTQTYICNVNHKPSNTKVDKKVEPKSCDKTHTCPPCPA
             **************************************************
hu2H7.v511   LSSVVTVPSSSLGTQTYICNVNHKPSNTKVDKKVEPKSCDKTHTCPPCPA 232
hu2H7.v16    PELLGGPSVFLFPPKPKDTLMISRTPEVTCVVVDVSHEDPEVKFNWYVDG
             **************************************************
hu2H7.v511   PELLGGPSVFLFPPKPKDTLMISRTPEVTCVVVDVSHEDPEVKFNWYVDG 282
hu2H7.v16    VEVHNAKTKPREEQYNSTYRVVSVLTVLHQDWLNGKEYKCKVSNKALPAP
             ***************** ****************************** *****
hu2H7.v511   VEVHNAKTKPREEQYNATYRVVSVLTVLHQDWLNGKEYKCKVSNAALPAP 332
hu2H7.v16    IEKTISKAKGQPREPQVYTLPPSREEMTKNQVSLTCLVKGFYPSDIAVEW
             *   **********************************************
hu2H7.v511   IAATISKAKGQPREPQVYTLPPSREEMTKNQVSLTCLVKGFYPSDIAVEW 382
hu2H7.v16    ESNGQPENNYKTTPPVLDSDGSFFLYSKLTVDKSRWQQGNVFSCSVMHEA
             **************************************************
hu2H7.v511   ESNGQPENNYKTTPPVLDSDGSFFLYSKLTVDKSRWQQGNVFSCSVMHEA 432        447
hu2H7.v16    LHNHYTQKSLSLSPGK
             ****************
hu2H7.v511   LHNHYTQKSLSLSPGK
```

*FIG. 33*

METHOD OF TREATING CANCER WITH A PHARMACEUTICAL FORMULATION COMPRISING A HER2 ANTIBODY

This is a divisional application which claims priority under 35 USC §120 to continuation application Ser. No. 12/554,194, filed Sep. 4, 2009, which claims priority to non-provisional application Ser. No. 11/254,182 filed Oct. 19, 2005 (now abandoned), which claims priority under 35 USC §119 to provisional application 60/620,413 filed Oct. 20, 2004, the entire disclosures of which are hereby incorporated by reference.

FIELD OF THE INVENTION

The present invention concerns antibody formulations, including monoclonal antibodies formulated in histidine-acetate buffer, as well as a formulation comprising an antibody that binds to domain II of HER2 (for example, Pertuzumab), and a formulation comprising an antibody that binds to DR5 (for example, Apomab).

BACKGROUND OF THE INVENTION

In the past ten years, advances in biotechnology have made it possible to produce a variety of proteins for pharmaceutical applications using recombinant DNA techniques. Because proteins are larger and more complex than traditional organic and inorganic drugs (i.e. possessing multiple functional groups in addition to complex three-dimensional structures), the formulation of such proteins poses special problems. For a protein to remain biologically active, a formulation must preserve intact the conformational integrity of at least a core sequence of the protein's amino acids while at the same time protecting the protein's multiple functional groups from degradation. Degradation pathways for proteins can involve chemical instability (i.e. any process which involves modification of the protein by bond formation or cleavage resulting in a new chemical entity) or physical instability (i.e. changes in the higher order structure of the protein). Chemical instability can result from deamidation, racemization, hydrolysis, oxidation, beta elimination or disulfide exchange. Physical instability can result from denaturation, aggregation, precipitation or adsorption, for example. The three most common protein degradation pathways are protein aggregation, deamidation and oxidation. Cleland et al. *Critical Reviews in Therapeutic Drug Carrier Systems* 10(4): 307-377 (1993).

Antibody Formulations

Included in the proteins used for pharmaceutical applications are antibodies. An example of an antibody useful for therapy is an antibody which binds to the HER2 antigen, such as Pertuzumab.

U.S. Pat. No. 6,339,142 describes a HER2 antibody composition comprising a mixture of anti-HER2 antibody and one or more acidic variants thereof, wherein the amount of the acidic variant(s) is less than about 25%. Trastuzumab is an exemplified HER2 antibody.

U.S. Pat. Nos. 6,267,958 and 6,685,940 (Andya et al.) describe lyophilized antibody formulations, including HER2 and IgE antibody formulations. WO97/04807 and US 2004/0197326A1 (Fick et al.) describe methods for treating allergic asthma with an IgE antibody. WO99/01556 (Lowman et al.) relates to IgE antibody with aspartyl residues prone to isomerization, and improved variants thereof. US 2002/0045571 (Liu et al.) provides reduced viscosity concentrated protein formulations, exemplified by humanized IgE antibody formulations, rhuMAb E25 and E26. WO 02/096457 and US 2004/0170623 (Arvinte et al.) describes stable liquid formulations comprising anti-IgE antibody E25. See, also, US 2004/0197324 A1 (Liu and Shire) concerning high concentration anti-IgE formulation.

U.S. Pat. No. 6,171,586 (Lam et al.) describes stable aqueous antibody formulations. A F(ab')2 rhuMAb CD18 antibody was formulated in sodium acetate and histidine-HCl buffers. The preferred formulation for rhuMAb CD18 was 10 mM sodium acetate, 8% trehalose, 0.01% TWEEN 20™, pH 5.0. Acetate (pH 5.0) formulations of rhuMAb CD20 stored at 40° C. for one month demonstrated greater stability than those samples formulated in histidine (pH 5.0 or 6.0).

US 2003/0190316 (Kakuta et al.) concerns formulated antibody hPM-1, a humanized IL-6 receptor antibody. Monomer loss was the greatest in sodium citrate (pH 6.7), followed by sodium phosphate (pH 6.8), Tris-HCl (pH 7.2), histidine-HCl (pH 7.2) and glycine (pH 7.6) in descending order. The effect of phosphate-Na (pH 6.5), phosphate-His (pH 6.0 or 6.5), His-HCl (pH 6.5), and phosphate-Na (pH 6.0) on the stability of hPM-1 was assessed.

WO 2004/071439 (Burke et al.) state that impurities arose in a natalizumab (anti-alpha4 integrin humanized monoclonal antibody) formulation from the degradation of polysorbate 80, apparently through an oxidation reaction involving metal ions and hisitidine. Thus, a phosphate buffer was selected.

WO 2000/066160 (English language counterpart EP 1 174 148A1) (Okada et al.) refers to a formulation of a humanized C4G1 antibody which binds to a fibrinogen receptor of a human platelet membrane glycoprotein GPIIb/IIIa, in a sodium phosphate or sodium citrate buffer.

WO 2004/019861 (Johnson et al.) concerns CDP870, a pegylated anti-TNFα Fab fragment, formulated at 200 mg/ml in 50 mM sodium acetate (pH 5.5) and 125 mM sodium chloride.

WO 2004/004639 (Nesta, P.) refers to a formulation for huC242-DM1, a tumor-activated immunotoxin, in a 50 mM succinic acid buffer (pH 6.0) and sucrose (5% w/v).

WO 03/039485 (Kaisheva et al.) found that Daclizumab (a humanized IL-2 receptor antibody) had the highest stability in sodium succinate buffer at pH 6.0, and rapidly lost potency in histidine as the buffer oxidized.

WO 2004/001007 concerns a CD80 monoclonal antibody in a histidine HCl, sodium acetate or sodium citrate buffer.

U.S. Pat. No. 6,252,055 (Relton, J.) refers to anti-CD4 and anti-CD23 antibodies formulated in maleate, succinate, sodium acetate or phosphate buffers, with phosphate being identified as the preferred buffer.

U.S. Pat. No. 5,608,038 (Eibl et al.) refers to highly concentrated polyclonal immunoglobulin preparations with immunoglobulin, glucose or sucrose, and sodium chloride therein.

WO 03/015894 (Oliver et al.) refers to an aqueous formulation of 100 mg/mL SYNAGIS®, 25 mM histidine-HCl, 1.6 mM glycine, pH 6.0, and a lyophilized SYNAGIS® which when formulated (before lyophilization) contains 25 mM histidine, 1.6 mM glycine and 3% w/v mannitol at pH 6.0.

US 2004/0191243 A1 (Chen et al.) reports formulation of ABX-IL8, a human IgG2 antibody.

US 2003/0113316 A1 (Kaisheva et al.) refers to a lyophilized anti-IL2 receptor antibody formulation.

HER2 Antibodies

The HER family of receptor tyrosine kinases are important mediators of cell growth, differentiation and survival. The receptor family includes four distinct members including epidermal growth factor receptor (EGFR, ErbB1, or HER1), HER2 (ErbB2 or p185$^{neu}$), HER3 (ErbB3) and HER4 (ErbB4 or tyro2).

EGFR, encoded by the erbB1 gene, has been causally implicated in human malignancy. In particular, increased expression of EGFR has been observed in breast, bladder, lung, head, neck and stomach cancer as well as glioblastomas. Increased EGFR receptor expression is often associated with increased production of the EGFR ligand, transforming growth factor alpha(TGF-α), by the same tumor cells resulting in receptor activation by an autocrine stimulatory pathway. Baselga and Mendelsohn *Pharmac. Ther.* 64:127-154 (1994). Monoclonal antibodies directed against the EGFR or its ligands, TGF-α and EGF, have been evaluated as therapeutic agents in the treatment of such malignancies. See, e.g., Baselga and Mendelsohn., supra; Masui et al. *Cancer Research* 44:1002-1007 (1984); and Wu et al. *J. Clin. Invest.* 95:1897-1905 (1995).

The second member of the HER family, p185$^{neu}$, was originally identified as the product of the transforming gene from neuroblastomas of chemically treated rats. The activated form of the neu proto-oncogene results from a point mutation (valine to glutamic acid) in the transmembrane region of the encoded protein. Amplification of the human homolog of neu is observed in breast and ovarian cancers and correlates with a poor prognosis (Slamon et al., *Science*, 235:177-182 (1987); Slamon et al., *Science*, 244:707-712 (1989); and U.S. Pat. No. 4,968,603). To date, no point mutation analogous to that in the neu proto-oncogene has been reported for human tumors. Overexpression of HER2 (frequently but not uniformly due to gene amplification) has also been observed in other carcinomas including carcinomas of the stomach, endometrium, salivary gland, lung, kidney, colon, thyroid, pancreas and bladder. See, among others, King et al., *Science,* 229:974 (1985); Yokota et al., *Lancet:* 1:765-767 (1986); Fukushige et al., *Mol Cell Biol.,* 6:955-958 (1986); Guerin et al., *Oncogene Res.,* 3:21-31 (1988); Cohen et al., *Oncogene,* 4:81-88 (1989); Yonemura et al., *Cancer Res.,* 51:1034 (1991); Borst et al., *Gynecol. Oncol.,* 38:364 (1990); Weiner et al., *Cancer Res.,* 50:421-425 (1990); Kern et al., *Cancer Res.,* 50:5184 (1990); Park et al., *Cancer Res.,* 49:6605 (1989); Zhau et al., *Mol. Carcinog.,* 3:254-257 (1990); Aasland et al. *Br. J. Cancer* 57:358-363 (1988); Williams et al. *Pathobiology* 59:46-52 (1991); and McCann et al., *Cancer,* 65:88-92 (1990). HER2 may be overexpressed in prostate cancer (Gu et al. *Cancer Lett.* 99:185-9 (1996); Ross et al. *Hum. Pathol.* 28:827-33 (1997); Ross et al. *Cancer* 79:2162-70 (1997); and Sadasivan et al. *J. Urol.* 150:126-31 (1993)).

Antibodies directed against the rat p185$^{neu}$ and human HER2 protein products have been described. Drebin and colleagues have raised antibodies against the rat neu gene product, p185$^{neu}$ See, for example, Drebin et al., *Cell* 41:695-706 (1985); Myers et al., *Meth. Enzym.* 198:277-290 (1991); and WO94/22478. Drebin et al. *Oncogene* 2:273-277 (1988) report that mixtures of antibodies reactive with two distinct regions of p185$^{neu}$ result in synergistic anti-tumor effects on neu-transformed NIH-3T3 cells implanted into nude mice. See also U.S. Pat. No. 5,824,311 issued Oct. 20, 1998.

Hudziak et al., *Mol. Cell. Biol.* 9(3):1165-1172 (1989) describe the generation of a panel of HER2 antibodies which were characterized using the human breast tumor cell line SK-BR-3. Relative cell proliferation of the SK-BR-3 cells following exposure to the antibodies was determined by crystal violet staining of the monolayers after 72 hours. Using this assay, maximum inhibition was obtained with the antibody called 4D5 which inhibited cellular proliferation by 56%. Other antibodies in the panel reduced cellular proliferation to a lesser extent in this assay. The antibody 4D5 was further found to sensitize HER2-overexpressing breast tumor cell lines to the cytotoxic effects of TNF-α. See also U.S. Pat. No. 5,677,171 issued Oct. 14, 1997. The HER2 antibodies discussed in Hudziak et al. are further characterized in Fendly et al. *Cancer Research* 50:1550-1558 (1990); Kotts et al. *In Vitro* 26(3):59A (1990); Sarup et al. *Growth Regulation* 1:72-82 (1991); Shepard et al. *J. Clin. Immunol.* 11(3):117-127 (1991); Kumar et al. *Mol. Cell. Biol.* 11(2):979-986 (1991); Lewis et al. *Cancer Immunol. Immunother.* 37:255-263 (1993); Pietras et al. *Oncogene* 9:1829-1838 (1994); Vitetta et al. *Cancer Research* 54:5301-5309 (1994); Sliwkowski et al. *J. Biol. Chem.* 269(20):14661-14665 (1994); Scott et al. *J. Biol. Chem.* 266:14300-5 (1991); D'souza et al. *Proc. Natl. Acad. Sci.* 91:7202-7206 (1994); Lewis et al. *Cancer Research* 56:1457-1465 (1996); and Schaefer et al. *Oncogene* 15:1385-1394 (1997).

A recombinant humanized version of the murine HER2 antibody 4D5 (huMAb4D5-8, rhuMAb HER2, Trastuzumab or HERCEPTIN®; U.S. Pat. No. 5,821,337) is clinically active in patients with HER2-overexpressing metastatic breast cancers that have received extensive prior anti-cancer therapy (Baselga et al., *J. Clin. Oncol.* 14:737-744 (1996)). Trastuzumab received marketing approval from the Food and Drug Administration Sep. 25, 1998 for the treatment of patients with metastatic breast cancer whose tumors overexpress the HER2 protein.

Other HER2 antibodies with various properties have been described in Tagliabue et al. *Int. J. Cancer* 47:933-937 (1991); McKenzie et al. *Oncogene* 4:543-548 (1989); Maier et al. *Cancer Res.* 51:5361-5369 (1991); Bacus et al. *Molecular Carcinogenesis* 3:350-362 (1990); Stancovski et al. *PNAS (USA)* 88:8691-8695 (1991); Bacus et al. *Cancer Research* 52:2580-2589 (1992); Xu et al. *Int. J. Cancer* 53:401-408 (1993); WO94/00136; Kasprzyk et al. *Cancer Research* 52:2771-2776 (1992); Hancock et al. *Cancer Res.* 51:4575-4580 (1991); Shawver et al. *Cancer Res.* 54:1367-1373 (1994); Arteaga et al. *Cancer Res.* 54:3758-3765 (1994); Harwerth et al. *J. Biol. Chem.* 267:15160-15167 (1992); U.S. Pat. No. 5,783,186; and Klapper et al. *Oncogene* 14:2099-2109 (1997).

Homology screening has resulted in the identification of two other HER receptor family members; HER3 (U.S. Pat. Nos. 5,183,884 and 5,480,968 as well as Kraus et al. *PNAS (USA)* 86:9193-9197 (1989)) and HER4 (EP Pat Appin No 599,274; Plowman et al., *Proc. Natl. Acad. Sci. USA,* 90:1746-1750 (1993); and Plowman et al., *Nature,* 366:473-475 (1993)). Both of these receptors display increased expression on at least some breast cancer cell lines.

The HER receptors are generally found in various combinations in cells and heterodimerization is thought to increase the diversity of cellular responses to a variety of HER ligands (Earp et al. *Breast Cancer Research and Treatment* 35: 115-132 (1995)). EGFR is bound by six different ligands; epidermal growth factor (EGF), transforming growth factor alpha (TGF-α), amphiregulin, heparin binding epidermal growth factor (HB-EGF), betacellulin and epiregulin (Groenen et al. *Growth Factors* 11:235-257 (1994)). A family of heregulin proteins resulting from alternative splicing of a single gene are ligands for HER3 and HER4. The heregulin family includes alpha, beta and gamma heregulins (Holmes et al., *Science,* 256:1205-1210 (1992); U.S. Pat. No. 5,641,869; and Schaefer et al. *Oncogene* 15:1385-1394 (1997)); neu differentiation factors (NDFs), glial growth factors (GGFs); acetylcholine receptor inducing activity (ARIA); and sensory and motor neuron derived factor (SMDF). For a review, see Groenen et al. *Growth Factors* 11:235-257 (1994); Lemke, G. *Molec. & Cell. Neurosci.* 7:247-262 (1996) and Lee et al. *Pharm. Rev.* 47:51-85 (1995). Recently three additional HER ligands were identified; neuregulin-2 (NRG-2) which is reported to bind either HER3 or HER4 (Chang et al. *Nature* 387 509-512 (1997); and Carraway et al. *Nature* 387:512-516 (1997)); neuregulin-3 which binds HER4 (Zhang et al. *PNAS (USA)* 94(18):9562-7 (1997)); and neuregulin-4 which binds HER4 (Harari et al. *Oncogene* 18:2681-89 (1999)) HB-EGF, betacellulin and epiregulin also bind to HER4.

While EGF and TGFα a do not bind HER2, EGF stimulates EGFR and HER2 to form a heterodimer, which activates EGFR and results in transphosphorylation of HER2 in the heterodimer. Dimerization and/or transphosphorylation appears to activate the HER2 tyrosine kinase. See Earp et al., supra. Likewise, when HER3 is co-expressed with HER2, an active signaling complex is formed and antibodies directed against HER2 are capable of disrupting this complex (Sliwkowski et al., *J. Biol. Chem.*, 269(20):14661-14665 (1994)). Additionally, the affinity of HER3 for heregulin (HRG) is increased to a higher affinity state when co-expressed with HER2. See also, Levi et al., *Journal of Neuroscience* 15: 1329-1340 (1995); Morrissey et al., *Proc. Natl. Acad. Sci. USA* 92: 1431-1435 (1995); and Lewis et al., *Cancer Res.*, 56:1457-1465 (1996) with respect to the HER2-HER3 protein complex. HER4, like HER3, forms an active signaling complex with HER2 (Carraway and Cantley, *Cell* 78:5-8 (1994)).

To target the HER signaling pathway, rhuMAb 2C4 (Pertuzumab) was developed as a humanized antibody that inhibits the dimerization of HER2 with other HER receptors, thereby inhibiting ligand-driven phosphorylation and activation, and downstream activation of the RAS and AKT pathways. In a phase I trial of Pertuzumab as a single agent for treating solid tumors, 3 subjects with advanced ovarian cancer were treated with Pertuzumab. One had a durable partial response, and an additional subject had stable disease for 15 weeks Agus et al. *Proc Am Soc Clin Oncol* 22: 192, Abstract 771 (2003).

DR5 Antibodies

Various ligands and receptors belonging to the tumor necrosis factor (TNF) superfamily have been identified in the art. Included among such ligands are tumor necrosis factor-alpha ("TNF-alpha"), tumor necrosis factor-beta ("TNF-beta" or "lymphotoxin-alpha"), lymphotoxin-beta ("LT-beta"), CD30 ligand, CD27 ligand, CD40 ligand, OX-40 ligand, 4-1BB ligand, LIGHT, Apo-1 ligand (also referred to as Fas ligand or CD95 ligand), Apo-2 ligand (also referred to as Apo2L or TRAIL), Apo-3 ligand (also referred to as TWEAK), APRIL, OPG ligand (also referred to as RANK ligand, ODF, or TRANCE), and TALL-1 (also referred to as BlyS, BAFF or THANK) (See, e.g., Ashkenazi, *Nature Review*, 2:420-430 (2002); Ashkenazi and Dixit, *Science*, 281:1305-1308 (1998); Ashkenazi and Dixit, *Curr. Opin. Cell Biol.*, 11:255-260 (1999); Golstein, *Curr. Biol.*, 7:R750-R753 (1997) Wallach, *Cytokine Reference*, Academic Press, 2000, pages 377-411; Locksley et al., *Cell*, 104:487-501 (2001); Gruss and Dower, *Blood*, 85:3378-3404 (1995); Schmid et al., *Proc. Natl. Acad. Sci.*, 83:1881 (1986); Dealtry et al., *Eur. J. Immunol.*, 17:689 (1987); Pitti et al., *J. Biol. Chem.*, 271:12687-12690 (1996); Wiley et al., *Immunity*, 3:673-682 (1995); Browning et al., *Cell*, 72:847-856 (1993); Armitage et al. *Nature*, 357:80-82 (1992), WO 97/01633 published Jan. 16, 1997; WO 97/25428 published Jul. 17, 1997; Marsters et al., *Curr. Biol.*, 8:525-528 (1998); Chicheportiche et al., *Biol. Chem.*, 272:32401-32410 (1997); Hahne et al., *J. Exp. Med.*, 188:1185-1190 (1998); WO98/28426 published Jul. 2, 1998; WO98/46751 published Oct. 22, 1998; WO/98/18921 published May 7, 1998; Moore et al., *Science*, 285:260-263 (1999); Shu et al., *J. Leukocyte Biol.*, 65:680 (1999); Schneider et al., *J. Exp. Med.*, 189:1747-1756 (1999); Mukhopadhyay et al., *J. Biol. Chem.*, 274:15978-15981 (1999)).

Induction of various cellular responses mediated by such TNF family ligands is typically initiated by their binding to specific cell receptors. Some, but not all, TNF family ligands bind to, and induce various biological activity through, cell surface "death receptors" to activate caspases, or enzymes that carry out the cell death or apoptosis pathway (Salvesen et al., *Cell*, 91:443-446 (1997)). Included among the members of the TNF receptor superfamily identified to date are TNFR1, TNFR2, TACI, GITR, CD27, OX-40, CD30, CD40, HVEM, Fas (also referred to as Apo-1 or CD95), DR4 (also referred to as TRAIL-R1), DR5 (also referred to as Apo-2 or TRAIL-R2), DcR1, DcR2, osteoprotegerin (OPG), RANK and Apo-3 (also referred to as DR3 or TRAMP).

Most of these TNF receptor family members share the typical structure of cell surface receptors including extracellular, transmembrane and intracellular regions, while others are found naturally as soluble proteins lacking a transmembrane and intracellular domain. The extracellular portion of typical TNFRs contains a repetitive amino acid sequence pattern of multiple cysteine-rich domains (CRDs), starting from the NH$_2$-terminus.

The ligand referred to as Apo-2L or TRAIL was identified several years ago as a member of the TNF family of cytokines. (see, e.g., Wiley et al., *Immunity*, 3:673-682 (1995); Pitti et al., *J. Biol. Chem.*, 271:12687-12690 (1996); WO 97/01633; WO 97/25428; U.S. Pat. No. 5,763,223 issued Jun. 9, 1998; U.S. Pat. No. 6,284,236 issued Sep. 4, 2001). The full-length native sequence human Apo2L/TRAIL polypeptide is a 281 amino acid long, Type II transmembrane protein. Some cells can produce a natural soluble form of the polypeptide, through enzymatic cleavage of the polypeptide's extracellular region (Mariani et al., *J. Cell. Biol.*, 137:221-229 (1997)). Crystallographic studies of soluble forms of Apo2L/TRAIL reveal a homotrimeric structure similar to the structures of TNF and other related proteins (Hymowitz et al., *Molec. Cell*, 4:563-571 (1999); Cha et al., *Immunity*, 11:253-261 (1999); Mongkolsapaya et al., *Nature Structural Biology*, 6:1048 (1999); Hymowitz et al., *Biochemistry*, 39:633-640 (2000)). Apo2L/TRAIL, unlike other TNF family members however, was found to have a unique structural feature in that three cysteine residues (at position 230 of each subunit in the homotrimer) together coordinate a zinc atom, and that the zinc binding is important for trimer stability and biological activity. (Hymowitz et al., supra; Bodmer et al., *J. Biol. Chem.*, 275:20632-20637 (2000)).

It has been reported in the literature that Apo2L/TRAIL may play a role in immune system modulation, including autoimmune diseases such as rheumatoid arthritis (see, e.g., Thomas et al., *J. Immunol.*, 161:2195-2200 (1998); Johnsen et al., *Cytokine*, 11:664-672 (1999); Griffith et al., *J. Exp. Med.*, 189:1343-1353 (1999); Song et al., *J. Exp. Med.*, 191: 1095-1103 (2000)).

Soluble forms of Apo2L/TRAIL have also been reported to induce apoptosis in a variety of cancer cells, including colon, lung, breast, prostate, bladder, kidney, ovarian and brain tumors, as well as melanoma, leukemia, and multiple myeloma (see, e.g., Wiley et al., supra; Pitti et al., supra; U.S. Pat. No. 6,030,945 issued Feb. 29, 2000; U.S. Pat. No. 6,746, 668 issued Jun. 8, 2004; Rieger et al., *FEBS Letters*, 427:124-

128 (1998); Ashkenazi et al., *J. Clin. Invest.*, 104:155-162 (1999); Walczak et al., *Nature Med.*, 5:157-163 (1999); Keane et al., *Cancer Research*, 59:734-741 (1999); Mizutani et al., *Clin. Cancer Res.*, 5:2605-2612 (1999); Gazitt, *Leukemia*, 13:1817-1824 (1999); Yu et al., *Cancer Res.*, 60:2384-2389 (2000); Chinnaiyan et al., *Proc. Natl. Acad. Sci.*, 97:1754-1759 (2000)). In vivo studies in murine tumor models further suggest that Apo2L/TRAIL, alone or in combination with chemotherapy or radiation therapy, can exert substantial anti-tumor effects (see, e.g., Ashkenazi et al., supra; Walzcak et al., supra; Gliniak et al., *Cancer Res.*, 59:6153-6158 (1999); Chinnaiyan et al., supra; Roth et al., *Biochem. Biophys. Res. Comm.*, 265:479-483 (1999); PCT Application US/00/15512; PCT Application US/01/23691). In contrast to many types of cancer cells, most normal human cell types appear to be resistant to apoptosis induction by certain recombinant forms of Apo2L/TRAIL (Ashkenazi et al., supra; Walzcak et al., supra). Jo et al. has reported that a polyhistidine-tagged soluble form of Apo2L/TRAIL induced apoptosis in vitro in normal isolated human, but not non-human, hepatocytes (Jo et al., *Nature Med.*, 6:564-567 (2000); see also, Nagata, *Nature Med.*, 6:502-503 (2000)). It is believed that certain recombinant Apo2L/TRAIL preparations may vary in terms of biochemical properties and biological activities on diseased versus normal cells, depending, for example, on the presence or absence of a tag molecule, zinc content, and % trimer content (See, Lawrence et al., *Nature Med.*, Letter to the Editor, 7:383-385 (2001); Qin et al., *Nature Med.*, Letter to the Editor, 7:385-386 (2001)).

Apo2L/TRAIL has been found to bind at least five different receptors. At least two of the receptors which bind Apo2L/TRAIL contain a functional, cytoplasmic death domain. One such receptor has been referred to as "DR4" (and alternatively as TR4 or TRAIL-R1) (Pan et al., *Science*, 276:111-113 (1997); see also WO98/32856 published Jul. 30, 1998; WO99/37684 published Jul. 29, 1999; WO 00/73349 published Dec. 7, 2000; U.S. Pat. No. 6,433,147 issued Aug. 13, 2002; U.S. Pat. No. 6,461,823 issued Oct. 8, 2002, and U.S. Pat. No. 6,342,383 issued Jan. 29, 2002).

Another such receptor for Apo2L/TRAIL has been referred to as DR5 (it has also been alternatively referred to as Apo-2; TRAIL-R or TRAIL-R2, TR6, Tango-63, hAPO8, TRICK2 or KILLER) (see, e.g., Sheridan et al., *Science*, 277:818-821 (1997), Pan et al., *Science*, 277:815-818 (1997), WO98/51793 published Nov. 19, 1998; WO98/41629 published Sep. 24, 1998; Screaton et al., *Curr. Biol.*, 7:693-696 (1997); Walczak et al., *EMBO J.*, 16:5386-5387 (1997); Wu et al., *Nature Genetics*, 17:141-143 (1997); WO98/35986 published Aug. 20, 1998; EP870,827 published Oct. 14, 1998; WO98/46643 published Oct. 22, 1998; WO99/02653 published Jan. 21, 1999; WO99/09165 published Feb. 25, 1999; WO99/11791 published Mar. 11, 1999; US 2002/0072091 published Aug. 13, 2002; US 2002/0098550 published Dec. 7, 2001; U.S. Pat. No. 6,313,269 issued Dec. 6, 2001; US 2001/0010924 published Aug. 2, 2001; US 2003/0125540 published Jul. 3, 2003; US 2002/0160446 published Oct. 31, 2002, US 2002/0048785 published Apr. 25, 2002; U.S. Pat. No. 6,342,369 issued February, 2002; U.S. Pat. No. 6,569,642 issued May 27, 2003, U.S. Pat. No. 6,072,047 issued Jun. 6, 2000, U.S. Pat. No. 6,642,358 issued Nov. 4, 2003; U.S. Pat. No. 6,743,625 issued Jun. 1, 2004). Like DR4, DR5 is reported to contain a cytoplasmic death domain and be capable of signaling apoptosis upon ligand binding (or upon binding a molecule, such as an agonist antibody, which mimics the activity of the ligand). The crystal structure of the complex formed between Apo-2L/TRAIL and DR5 is described in Hymowitz et al., *Molecular Cell*, 4:563-571 (1999).

Upon ligand binding, both DR4 and DR5 can trigger apoptosis independently by recruiting and activating the apoptosis initiator, caspase-8, through the death-domain-containing adaptor molecule referred to as FADD/Mort1 (Kischkel et al., *Immunity*, 12:611-620 (2000); Sprick et al., *Immunity*, 12:599-609 (2000); Bodmer et al., *Nature Cell Biol.*, 2:241-243 (2000)).

Apo2L/TRAIL has been reported to also bind those receptors referred to as DcR1, DcR2 and OPG, which believed to function as inhibitors, rather than transducers of signaling (see., e.g., DcR1 (also referred to as TRID, LIT or TRAIL-R3) (Pan et al., *Science*, 276:111-113 (1997); Sheridan et al., *Science*, 277:818-821 (1997); MacFarlane et al., *J. Biol. Chem.*, 272:25417-25420 (1997); Schneider et al., *FEBS Letters*, 416:329-334 (1997); Degli-Esposti et al., *J. Exp. Med.*, 186:1165-1170 (1997); and Mongkolsapaya et al., *J. Immunol.*, 160:3-6 (1998)); DcR2 (also called TRUNDD or TRAIL-R4) (Marsters et al., *Curr. Biol.*, 7:1003-1006 (1997); Pan et al., *FEBS Letters*, 424:41-45 (1998); Degli-Esposti et al., *Immunity*, 7:813-820 (1997)), and OPG. In contrast to DR4 and DR5, the DcR1 and DcR2 receptors do not signal apoptosis.

Certain antibodies which bind to the DR4 and/or DR5 receptors have been reported in the literature. For example, anti-DR4 antibodies directed to the DR4 receptor and having agonistic or apoptotic activity in certain mammalian cells are described in, e.g., WO 99/37684 published Jul. 29, 1999; WO 00/73349 published Jul. 12, 2000; WO 03/066661 published Aug. 14, 2003. See, also, e.g., Griffith et al., *J. Immunol.*, 162:2597-2605 (1999); Chuntharapai et al., *J. Immunol.*, 166: 4891-4898 (2001); WO 02/097033 published Dec. 2, 2002; WO 03/042367 published May 22, 2003; WO 03/038043 published May 8, 2003; WO03/037913 published May 8, 2003. Certain anti-DR5 antibodies have likewise been described, see, e.g., WO 98/51793 published Nov. 8, 1998; Griffith et al., *J. Immunol.*, 162:2597-2605 (1999); Ichikawa et al., *Nature Med.*, 7:954-960 (2001); Hylander et al., "An Antibody to DR5 (TRAIL-Receptor 2) Suppresses the Growth of Patient Derived Gastrointestinal Tumors Grown in SCID mice", Abstract, 2d International Congress on Monoclonal Antibodies in Cancers, Aug. 29-Sep. 1, 2002, Banff, Alberta, Canada; WO 03/038043 published May 8, 2003; WO 03/037913 published May 8, 2003. In addition, certain antibodies having cross-reactivity to both DR4 and DR5 receptors have been described (see, e.g., U.S. Pat. No. 6,252,050 issued Jun. 26, 2001).

SUMMARY OF THE INVENTION

The invention herein relates, at least in part, to the identification of histidine-acetate, pH 5.5 to 6.5, as a particularly useful buffer for formulating monoclonal antibodies, especially full length IgG1 antibodies which are susceptible to deamidation and/or aggregation. The formulation retards degradation of the antibody product therein.

Thus, in a first aspect, the invention concerns a stable pharmaceutical formulation comprising a monoclonal antibody in histidine-acetate buffer, pH 5.5 to 6.5. The monoclonal antibody preferably binds an antigen selected from the group consisting of HER2, CD20, DR5, BR3, IgE, and VEGF.

In addition, the invention concerns a method of treating a disease or disorder in a subject comprising administering the formulation to a subject in an amount effective to treat the disease or disorder.

In another aspect, the invention concerns a pharmaceutical formulation comprising: (a) a full length IgG1 antibody susceptible to deamidation or aggregation in an amount from about 10 mg/mL to about 250 mg/mL; (b) histidine-acetate buffer, pH 5.5 to 6.5; (c) saccharide selected from the group consisting of trehalose and sucrose, in an amount from about 60 mM to about 250 mM; and (d) polysorbate 20 in an amount from about 0.01% to about 0.1%.

The invention also provides a method for reducing deamidation or aggregation of a therapeutic monoclonal antibody, comprising formulating the antibody in a histidine-acetate buffer, pH 5.5 to 6.5.

In yet a further aspect, the invention concerns a pharmaceutical formulation comprising an antibody that binds to domain II of HER2 in a histidine buffer at a pH from about 5.5 to about 6.5, a saccharide and a surfactant.

The invention also relates to a pharmaceutical formulation comprising Pertuzumab in an amount from about 20 mg/mL to about 40 mg/mL, histidine-acetate buffer, sucrose, and polysorbate 20, wherein the pH of the formulation is from about 5.5 to about 6.5.

The invention also pertains to a pharmaceutical formulation comprising a DR5 antibody in a histidine buffer at a pH from about 5.5 to about 6.5, a saccharide, and a surfactant.

In another aspect, the invention concerns a pharmaceutical formulation comprising Apomab in an amount from about 10 mg/mL to about 30 mg/mL, histidine-acetate buffer, trehalose, and polysorbate 20, wherein the pH of the formulation is from about 5.5 to about 6.5.

In yet another aspect, the invention provides a method of treating cancer in a subject, comprising administering the pharmaceutical formulation to the subject in an amount effective to treat the cancer.

The invention also concerns a vial with a stopper pierceable by a syringe or a stainless steel tank comprising the formulation inside the vial or tank, optionally in frozen form.

Moreover, the invention provides a method of making a pharmaceutical formulation comprising: (a) preparing the monoclonal antibody formulation; and (b) evaluating physical stability, chemical stability, or biological activity of the monoclonal antibody in the formulation.

BRIEF DESCRIPTION OF THE DRAWINGS

FIGS. 2A and 2B depict alignments of the amino acid sequences of the variable light ($V_L$) (FIG. 2A) and variable heavy ($V_H$) (FIG. 2B) domains of murine monoclonal antibody 2C4 (SEQ ID Nos. 1 and 2, respectively); $V_L$ and $V_H$ domains of humanized 2C4 version 574 (SEQ ID Nos. 3 and 4, respectively), and human $V_L$ and $V_H$ consensus frameworks (hum κ1, light kappa subgroup I; humIII, heavy subgroup III) (SEQ ID Nos. 5 and 6, respectively). Asterisks identify differences between humanized 2C4 version 574 and murine monoclonal antibody 2C4 or between humanized 2C4 version 574 and the human framework. Complementarity Determining Regions (CDRs) are in brackets.

FIGS. 3A and 3B show the amino acid sequences of Pertuzumab light chain and heavy chain (SEQ ID Nos. 15 and 16, respectively). CDRs are shown in bold. Calculated molecular mass of the light chain and heavy chain are 23,526.22 Da and 49,216.56 Da (cysteines in reduced form). The carbohydrate moiety is attached to Asn 299 of the heavy chain.

FIGS. 4A and 4B show the amino acid sequences of Pertuzumab light and heavy chain, each including an intact amino terminal signal peptide sequence (SEQ ID Nos. 17 and 18, respectively).

FIG. 7 compares activities of Trastuzumab and Pertuzumab.

FIGS. 14A and 14B show the amino acid sequences of Trastuzumab light chain (SEQ ID No. 13) and heavy chain (SEQ ID No. 14).

FIGS. 15A and 15B depict a variant Pertuzumab light chain sequence (SEQ ID No. 23) and a variant Pertuzumab heavy chain sequence (SEQ ID No. 24).

FIGS. 16A and 16B show oligosaccharide structures commonly observed in IgG antibodies.

FIGS. 17A and 17B show the sequences of the light and heavy chains (SEQ ID Nos. 37-44) of specific anti-IgE antibodies E25, E26, HAE1 and Hu-901. In FIG. 17A, the variable light domain ends with the residues VEIK, residue 111. In FIG. 17B, the variable heavy domain ends with the residues VTVSS, around residue 120.

FIG. 18A is a sequence alignment comparing the amino acid sequences of the variable light domain ($V_L$) of each of murine 2H7 (SEQ ID No. 25), humanized 2H7v16 variant (SEQ ID No. 26), and the human kappa light chain subgroup I (SEQ ID No. 27). The CDRs of $V_L$ of 2H7 and hu2H7v16 are as follows: CDR1 (SEQ ID No. 57), CDR2 (SEQ ID No. 58), and CDR3 (SEQ ID No. 59).

FIG. 18B is a sequence alignment comparing the amino acid sequences of the variable heavy domain ($V_H$) of each of murine 2H7 (SEQ ID No. 28), humanized 2H7v16 variant (SEQ ID No. 29), and the human consensus sequence of the heavy chain subgroup III (SEQ ID No. 30). The CDRs of $V_H$ of 2H7 and hu2H7v16 are as follows: CDR1 (SEQ ID No. 60), CDR2 (SEQ ID No. 61), and CDR3 (SEQ ID No. 62).

In FIG. 18A and FIG. 18B, the CDR1, CDR2 and CDR3 in each chain are enclosed within brackets, flanked by the framework regions, FR1-FR4, as indicated. 2H7 refers to murine 2H7 antibody. The asterisks in between two rows of sequences indicate the positions that are different between the two sequences. Residue numbering is according to Kabat et al. *Sequences of Immunological Interest,* 5th Ed. Public Health Service, National Institutes of Health, Bethesda, Md. (1991), with insertions shown as a, b, c, d, and e.

FIG. 19 depicts variable domain sequences of three different VEGF antibodies with SEQ ID Nos. 31-36.

FIG. 24 shows the nucleotide sequence of human Apo-2 ligand cDNA (SEQ ID No. 45) and its derived amino acid sequence (SEQ ID No. 46). The "N" at nucleotide position 447 (in SEQ ID No. 45) is used to indicate the nucleotide base may be a "T" or "G".

FIGS. 25A and 25B show the 411 amino acid sequence of human DR5 receptor (SEQ ID No. 47) as published in WO 98/51793 on Nov. 19, 1998, and the encoding nucleotide sequence (SEQ ID No. 48).

FIGS. 26A and 26B show the 440 amino acid sequence of human DR5 receptor (SEQ ID No. 49) and the encoding nucleotide sequence (SEQ ID No. 50), as also published in WO 98/35986 on Aug. 20, 1998.

FIG. 27 shows the Apomab 7.3 heavy chain amino acid sequence (SEQ ID No. 51).

FIG. 28 shows the Apomab 7.3 light chain amino acid sequence (SEQ ID No. 52).

FIG. 29 shows the alignment of 16E2 heavy chain (SEQ ID No. 53) and Apomab 7.3 heavy chain (SEQ ID No. 51) amino acid sequences.

FIG. 30 shows the alignment of 16E2 light chain (SEQ ID No. 54) and Apomab 7.3 light chain (SEQ ID No. 52) amino acid sequences.

FIGS. 31A and 31B depict the variable heavy amino acid sequence (FIG. 31A; SEQ ID No. 55) and variable light amino acid sequence (FIG. 31B; SEQ ID No. 56) of Apomab 7.3. CDR residues are identified in bold.

FIG. 32 shows an alignment of the mature 2H7v16 and 2H7v511 light chains (SEQ ID Nos. 63 and 64, respectively). Sequences shown with Kabat variable domain residue numbering and Eu constant domain residue numbering.

FIG. 33 shows an alignment of the mature 2H7v16 and 2H7v511 heavy chains (SEQ ID Nos. 65 and 66, respectively). Sequences shown with Kabat variable domain residue numbering and Eu constant domain residue numbering.

DETAILED DESCRIPTION OF THE PREFERRED EMBODIMENTS

I. Definitions

Figure 1:
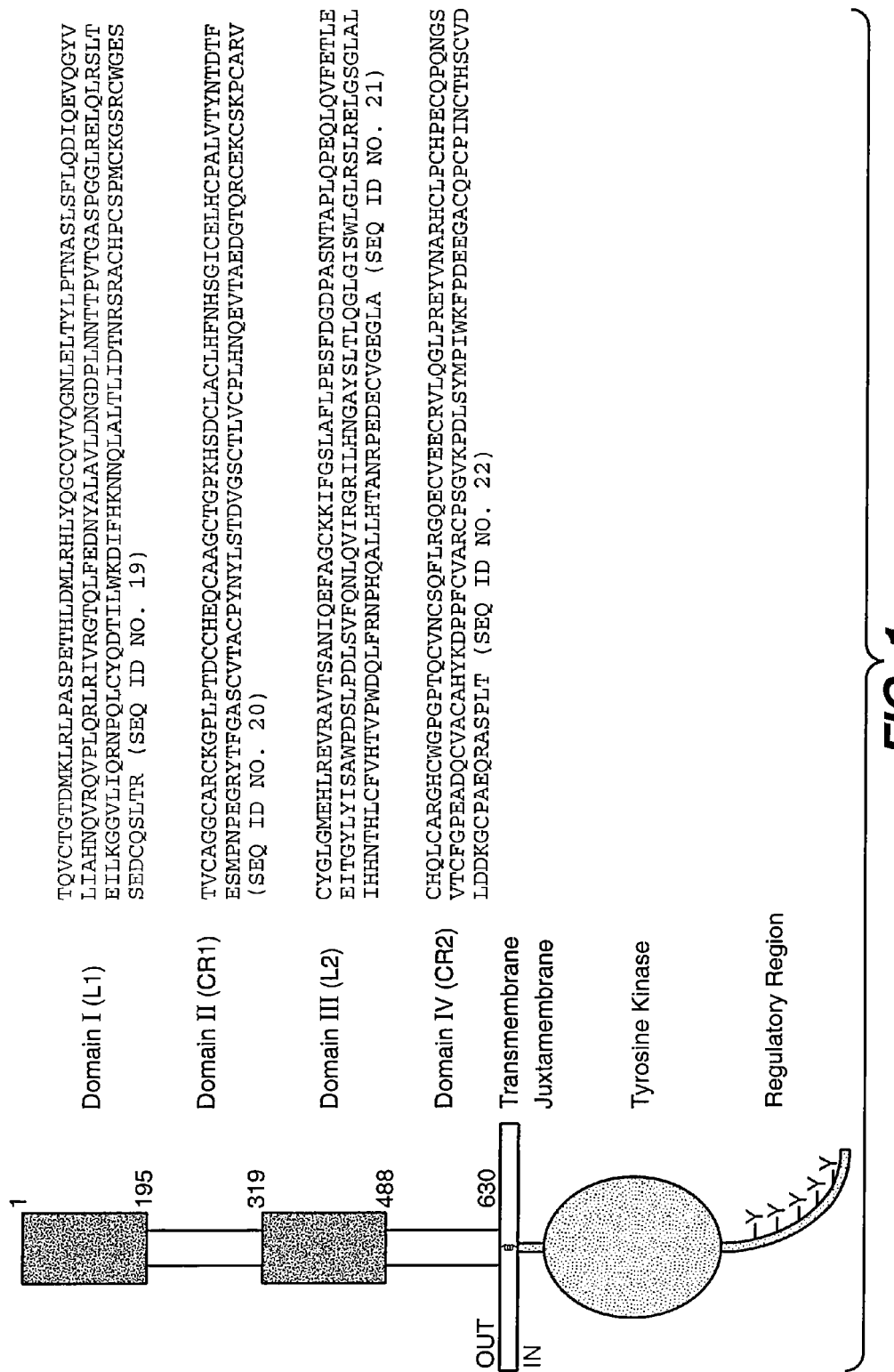
FIG. 1 depicts Domains I-IV (SEQ ID Nos.19-22, respectively) of the extracellular domain of HER2.

The term "pharmaceutical formulation" refers to a preparation which is in such form as to permit the biological activity of the active ingredient to be effective, and which contains no additional components which are unacceptably toxic to a subject to which the formulation would be administered. Such formulations are sterile.

A "sterile" formulation is aseptic or free from all living microorganisms and their spores.

Herein, a "frozen" formulation is one at a temperature below 0° C. Generally, the frozen formulation is not freeze-dried, nor is it subjected to prior, or subsequent, lyophilization. Preferably, the frozen formulation comprises frozen drug substance for storage (in stainless steel tank) or frozen drug product (in final vial configuration).

A "stable" formulation is one in which the protein therein essentially retains its physical stability and/or chemical stability and/or biological activity upon storage. Preferably, the formulation essentially retains its physical and chemical stability, as well as its biological activity upon storage. The storage period is generally selected based on the intended shelf-life of the formulation. Various analytical techniques for measuring protein stability are available in the art and are reviewed in *Peptide and Protein. Drug Delivery,* 247-301, Vincent Lee Ed., Marcel Dekker, Inc., New York, N.Y., Pubs. (1991) and Jones, A. *Adv. Drug Delivery Rev.* 10: 29-90 (1993), for example. Stability can be measured at a selected temperature for a selected time period. Preferably, the formulation is stable at about 40° C. for at least about 2-4 weeks, and/or stable at about 5.0 and/or 15° C. for at least 3 months, and/or stable at about −20° C. for at least 3 months or at least 1 year. Furthermore, the formulation is preferably stable following freezing (to, e.g., −70° C.) and thawing of the formulation, for example following 1, 2 or 3 cycles of freezing and thawing. Stability can be evaluated qualitatively and/or quantitatively in a variety of different ways, including evaluation of aggregate formation (for example using size exclusion chromatography, by measuring turbidity, and/or by visual inspection); by assessing charge heterogeneity using cation exchange chromatography or capillary zone electrophoresis; amino-terminal or carboxy-terminal sequence analysis; mass spectrometric analysis; SDS-PAGE analysis to compare reduced and intact antibody; peptide map (for example tryptic or LYS-C) analysis; evaluating biological activity or antigen binding function of the antibody; etc. Instability may involve any one or more of: aggregation, deamidation (e.g. Asn deamidation), oxidation (e.g. Met oxidation), isomerization (e.g. Asp isomeriation), clipping/hydrolysis/fragmentation (e.g. hinge region fragmentation), succinimide formation, unpaired cysteine(s), N-terminal extension, C-terminal processing, glycosylation differences, etc.

A "deamidated" monoclonal antibody herein is one in which one or more asparagine residue thereof has been derivitized, e.g. to an aspartic acid or an iso-aspartic acid.

An antibody which is "susceptible to deamidation" is one comprising one or more residue which has been found to be prone to deamidate.

An antibody which is "susceptible to aggregation" is one which has been found to aggregate with other antibody molecule(s), especially upon freezing and/or agitation.

An antibody which is "susceptible to fragmentation" is one which has been found to be cleaved into two or more fragments, for example at a hinge region thereof.

By "reducing deamidation, aggregation, or fragmentation" is intended preventing or decreasing the amount of deamidation, aggregation, or fragmentation relative to the monoclonal antibody formulated at a different pH or in a different buffer.

Herein, "biological activity" of a monoclonal antibody refers to the ability of the antibody to bind to antigen and result in a measurable biological response which can be measured in vitro or in vivo. Such activity may be antagonistic (for example where the antibody is a HER2 antibody) or agonistic (for instance where the antibody binds DR5). In the case of Pertuzumab, in one embodiment, the biological activity refers to the ability of the formulated antibody to inhibit proliferation of the human breast cancer cell line MDA-MB-175-VII. Where the antibody is Apomab, the biological activity can refer, for example, to the ability of the formulated antibody to kill colon carcinoma, Colo205, cells.

By "isotonic" is meant that the formulation of interest has essentially the same osmotic pressure as human blood. Isotonic formulations will generally have an osmotic pressure from about 250 to 350 mOsm. Isotonicity can be measured using a vapor pressure or ice-freezing type osmometer, for example.

As used herein, "buffer" refers to a buffered solution that resists changes in pH by the action of its acid-base conjugate components. The buffer of this invention preferably has a pH in the range from about 5.0 to about 7.0, preferably from about 5.5 to about 6.5, for example from about 5.8 to about 6.2, and most preferably has a pH of about 6.0. Examples of buffers that will control the pH in this range include acetate, succinate, succinate, gluconate, histidine, citrate, glycylglycine and other organic acid buffers. The preferred buffer herein is a histidine buffer.

A "histidine buffer" is a buffer comprising histidine ions. Examples of histidine buffers include histidine chloride, histidine acetate, histidine phosphate, histidine sulfate. The preferred histidine buffer identified in the examples herein was found to be histidine acetate. In the preferred embodiment, the histidine acetate buffer is prepared by titrating L-histidine (free base, solid) with acetic acid (liquid). Preferably, the histidine buffer or histidine-acetate buffer is at pH 5.5 to 6.5, preferably pH 5.8 to 6.2.

A "saccharide" herein comprises the general composition (CH2O)n and derivatives thereof, including monosaccharides, disaccharides, trisaccharides, polysaccharides, sugar alcohols, reducing sugars, nonreducing sugars, etc. Examples of saccharides herein include glucose, sucrose, trehalose, lactose, fructose, maltose, dextran, glycerin, dextran, erythritol, glycerol, arabitol, sylitol, sorbitol, mannitol, mellibiose, melezitose, raffinose, mannotriose, stachyose, maltose, lactulose, maltulose, glucitol, maltitol, lactitol, iso-maltulose, etc. The preferred saccharide herein is a nonreducing disaccharide, such as trehalose or sucrose.

Herein, a "surfactant" refers to a surface-active agent, preferably a nonionic surfactant. Examples of surfactants herein include polysorbate (for example, polysorbate 20 and, polysorbate 80); poloxamer (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.); polyethyl glycol, polypropyl glycol, and copolymers of ethylene and propylene glycol (e.g. Pluronics, PF68 etc); etc. The preferred surfactant herein is polysorbate 20.

A "HER receptor" is a receptor protein tyrosine kinase which belongs to the HER receptor family and includes EGFR, HER2, HER3 and HER4 receptors and other members of this family to be identified in the future. The HER receptor will generally comprise an extracellular domain, which may bind an HER ligand; a lipophilic transmembrane domain; a conserved intracellular tyrosine kinase domain; and a carboxyl-terminal signaling domain harboring several tyrosine residues which can be phosphorylated. Preferably the HER receptor is native sequence human HER receptor.

The extracellular domain of HER2 comprises four domains, Domain I (amino acid residues from about 1-195), Domain II (amino acid residues from about 196-320), Domain III (amino acid residues from about 321-488), and Domain IV (amino acid residues from about 489-632) (residue numbering without signal peptide). See Garrett et al. *Mol. Cell.* 11: 495-505 (2003), Cho et al. *Nature* 421: 756-760 (2003), Franklin et al. *Cancer Cell* 5:317-328 (2004), or Plowman et al. *Proc. Natl. Acad. Sci.* 90:1746-1750 (1993). See also FIG. 1 herein.

The terms "ErbB1," "HER1", "epidermal growth factor receptor" and "EGFR" are used interchangeably herein and refer to EGFR as disclosed, for example, in Carpenter et al. *Ann. Rev. Biochem.* 56:881-914 (1987), including naturally occurring mutant forms thereof (e.g. a deletion mutant EGFR as in Humphrey et al. *PNAS (USA)* 87:4207-4211 (1990)). erbB1 refers to the gene encoding the EGFR protein product.

The expressions "ErbB2" and "HER2" are used interchangeably herein and refer to human HER2 protein described, for example, in Semba et al., *PNAS (USA)* 82:6497-6501 (1985) and Yamamoto et al. *Nature* 319:230-234 (1986) (Genebank accession number X03363). The term "erbB2" refers to the gene encoding human ErbB2 and "neu" refers to the gene encoding rat p185$^{neu}$. Preferred HER2 is native sequence human HER2.

"ErbB3" and "HER3" refer to the receptor polypeptide as disclosed, for example, in U.S. Pat. Nos. 5,183,884 and 5,480,968 as well as Kraus et al. *PNAS (USA)* 86:9193-9197 (1989).

The terms "ErbB4" and "HER4" herein refer to the receptor polypeptide as disclosed, for example, in EP Pat Appin No 599,274; Plowman et al., *Proc. Natl. Acad. Sci. USA,* 90:1746-1750 (1993); and Plowman et al., *Nature,* 366:473-475 (1993), including isoforms thereof, e.g., as disclosed in WO99/19488, published Apr. 22, 1999.

By "HER ligand" is meant a polypeptide which binds to and/or activates a HER receptor. The HER ligand of particular interest herein is a native sequence human HER ligand such as epidermal growth factor (EGF) (Savage et al., *J. Biol. Chem.* 247:7612-7621 (1972)); transforming growth factor alpha (TGF-α) (Marquardt et al., *Science* 223:1079-1082 (1984)); amphiregulin also known as schwanoma or keratinocyte autocrine growth factor (Shoyab et al. *Science* 243:1074-1076 (1989); Kimura et al. *Nature* 348:257-260 (1990); and Cook et al. *Mol. Cell. Biol.* 11:2547-2557 (1991)); betacellulin (Shing et al., *Science* 259:1604-1607 (1993); and Sasada et al. *Biochem. Biophys. Res. Commun.* 190:1173 (1993)); heparin-binding epidermal growth factor (HB-EGF) (Higashiyama et al., *Science* 251:936-939 (1991)); epiregulin (Toyoda et al., *J. Biol. Chem.* 270:7495-7500 (1995); and Komurasaki et al. *Oncogene* 15:2841-2848 (1997)); a heregulin (see below); neuregulin-2 (NRG-2) (Carraway et al., *Nature* 387:512-516 (1997)); neuregulin-3 (NRG-3) (Zhang et al., *Proc. Natl. Acad. Sci.* 94:9562-9567 (1997)); neuregulin-4 (NRG-4) (Harari et al. *Oncogene* 18:2681-89 (1999)) or cripto (CR-1) (Kannan et al. *J. Biol. Chem.* 272(6):3330-3335 (1997)). HER ligands which bind EGFR include EGF, TGF-α, amphiregulin, betacellulin, HB-EGF and epiregulin. HER ligands which bind HER3 include heregulins. HER ligands capable of binding HER4 include betacellulin, epiregulin, HB-EGF, NRG-2, NRG-3, NRG-4 and heregulins.

"Heregulin" (HRG) when used herein refers to a polypeptide encoded by the heregulin gene product as disclosed in U.S. Pat. No. 5,641,869 or Marchionni et al., *Nature,* 362: 312-318 (1993). Examples of heregulins include heregulin-α, heregulin-β1, heregulin-β2 and heregulin-133 (Holmes et al., *Science,* 256:1205-1210 (1992); and U.S. Pat. No. 5,641, 869); neu differentiation factor (NDF) (Peles et al. *Cell* 69: 205-216 (1992)); acetylcholine receptor-inducing activity (ARIA) (Falls et al. *Cell* 72:801-815 (1993)); glial growth factors (GGFs) (Marchionni et al., *Nature,* 362:312-318 (1993)); sensory and motor neuron derived factor (SMDF) (Ho et al. *J. Biol. Chem.* 270:14523-14532 (1995)); γ-heregulin (Schaefer et al. *Oncogene* 15:1385-1394 (1997)). The term includes biologically active fragments and/or amino acid sequence variants of a native sequence HRG polypeptide, such as an EGF-like domain fragment thereof (e.g. HRGβ1$_{177-244}$).

A "HER dimer" herein is a noncovalently associated dimer comprising at least two different HER receptors. Such complexes may form when a cell expressing two or more HER receptors is exposed to an HER ligand and can be isolated by immunoprecipitation and analyzed by SDS-PAGE as described in Sliwkowski et al., *J. Biol. Chem.*, 269(20): 14661-14665 (1994), for example. Examples of such HER dimers include EGFR-HER2, HER2-HER3 and HER3-HER4 heterodimers. Moreover, the HER dimer may comprise two or more HER2 receptors combined with a different HER receptor, such as HER3, HER4 or EGFR. Other proteins, such as a cytokine receptor subunit (e.g. gp130) may be associated with the dimer.

A "heterodimeric binding site" on HER2, refers to a region in the extracellular domain of HER2 that contacts, or interfaces with, a region in the extracellular domain of EGFR, HER3 or HER4 upon formation of a dimer therewith. The region is found in Domain II of HER2. Franklin et al. Cancer Cell 5:317-328 (2004).

"HER activation" or "HER2 activation" refers to activation, or phosphorylation, of any one or more HER receptors, or HER2 receptors. Generally, HER activation results in signal transduction (e.g. that caused by an intracellular kinase domain of a HER receptor phosphorylating tyrosine residues in the HER receptor or a substrate polypeptide). HER activation may be mediated by HER ligand binding to a HER dimer comprising the HER receptor of interest. HER ligand binding to a HER dimer may activate a kinase domain of one or more of the HER receptors in the dimer and thereby results in phosphorylation of tyrosine residues in one or more of the HER receptors and/or phosphorylation of tyrosine residues in additional substrate polypeptides(s), such as Akt or MAPK intracellular kinases.

The term "antibody" herein is used in the broadest sense and specifically covers full length monoclonal antibodies, polyclonal antibodies, multispecific antibodies (e.g. bispecific antibodies) formed from at least two full length antibodies, and antibody fragments, so long as they exhibit the desired biological activity.

The term "monoclonal antibody" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. In addition to their specificity, the monoclonal antibodies are advantageous in that they are uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature*, 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature*, 352:624-628 (1991) and Marks et al., *J. Mol. Biol.*, 222:581-597 (1991), for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA,* 81:6851-6855 (1984)). Chimeric antibodies of interest herein include "primatized" antibodies comprising variable domain antigen-binding sequences derived from a non-human primate (e.g. Old World Monkey, Ape etc) and human constant region sequences.

"Antibody fragments" comprise a portion of a full length antibody, preferably comprising the antigen-binding or variable region thereof. Examples of antibody fragments include Fab, Fab', F(ab')$_2$, and Fv fragments; diabodies; linear antibodies; single-chain antibody molecules; and multispecific antibodies formed from antibody fragment(s).

A "full length antibody" is one which comprises an antigen-binding variable region as well as a light chain constant domain (CO and heavy chain constant domains, $C_H1$, $C_H2$ and $C_H3$. The constant domains may be native sequence constant domains (e.g. human native sequence constant domains) or amino acid sequence variants thereof. Preferably, the full length antibody has one or more effector functions.

The term "main species antibody" herein refers to the antibody structure in a composition which is the quantitatively predominant antibody molecule in the composition. In one embodiment, the main species antibody is a HER2 antibody, such as an antibody that binds to Domain II of HER2, antibody that inhibits HER dimerization more effectively than Trastuzumab, and/or an antibody which binds to a heterodimeric binding site of HER2. The preferred embodiment herein of a main species HER2 antibody is one comprising the variable light and variable heavy amino acid sequences in SEQ ID Nos. 3 and 4, and most preferably comprising the light chain and heavy chain amino acid sequences in SEQ ID Nos. 15 and 16 (Pertuzumab).

An "amino acid sequence variant" antibody herein is an antibody with an amino acid sequence which differs from a main species antibody. Ordinarily, amino acid sequence variants will possess at least about 70% homology with the main species antibody, and preferably, they will be at least about 80%, more preferably at least about 90% homologous with the main species antibody. The amino acid sequence variants possess substitutions, deletions, and/or additions at certain positions within or adjacent to the amino acid sequence of the main species antibody. Examples of amino acid sequence variants herein include acidic variant (e.g. deamidated antibody variant), basic variant, the antibody with an amino-terminal leader extension (e.g. VHS-) on one or two light chains thereof, antibody with a C-terminal lysine residue on one or two heavy chains thereof, etc, and includes combinations of variations to the amino acid sequences of heavy and/or light chains. The antibody variant of particular interest herein is the antibody comprising an amino-terminal leader extension on one or two light chains thereof, optionally further comprising other amino acid sequence and/or glycosylation differences relative to the main species antibody.

A "therapeutic monoclonal antibody" is an antibody used for therapy of a human subject. Therapeutic monoclonal antibodies disclosed herein include: HER2 antibodies for cancer and various non-malignant diseases or disorders; CD20 or BR3 antibodies for therapy of B cell malignancies, autoimmune diseases, graft rejection, or blocking an immune response to a foreign antigen; IgE antibodies for therapy of an IgE-mediated disorder; DR5 or VEGF antibodies for cancer therapy.

A "glycosylation variant" antibody herein is an antibody with one or more carbohydrate moeities attached thereto which differ from one or more carbohydrate moieties attached to a main species antibody. Examples of glycosylation variants herein include antibody with a G1 or G2 oligosaccharide structure, instead a G0 oligosaccharide structure, attached to an Fc region thereof, antibody with one or two carbohydrate moieties attached to one or two light chains thereof, antibody with no carbohydrate attached to one or two heavy chains of the antibody, etc, and combinations of glycosylation alterations.

Where the antibody has an Fc region, an oligosaccharide structure such as that shown in FIG. 16 herein may be attached to one or two heavy chains of the antibody, e.g. at residue 299 (298, Eu numbering of residues). For Pertuzumab, G0 was the predominant oligosaccharide structure, with other oligosaccharide structures such as G0-F, G-1, Man5, Man6, G1-1, G1(1-6), G1(1-3) and G2 being found in lesser amounts in the Pertuzumab composition.

Unless indicated otherwise, a "G1 oligosaccharide structure" herein includes G-1, G1-1, G1(1-6) and G1(1-3) structures.

An "amino-terminal leader extension" herein refers to one or more amino acid residues of the amino-terminal leader sequence that are present at the amino-terminus of any one or more heavy or light chains of an antibody. An exemplary amino-terminal leader extension comprises or consists of three amino acid residues, VHS, present on one or both light chains of an antibody variant.

"Homology" is defined as the percentage of residues in the amino acid sequence variant that are identical after aligning the sequences and introducing gaps, if necessary, to achieve the maximum percent homology. Methods and computer programs for the alignment are well known in the art. One such computer program is "Align 2", authored by Genentech, Inc., which was filed with user documentation in the United States Copyright Office, Washington, D.C. 20559, on Dec. 10, 1991.

Antibody "effector functions" refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; down regulation of cell surface receptors (e.g. B cell receptor; BCR), etc.

Depending on the amino acid sequence of the constant domain of their heavy chains, full length antibodies can be assigned to different "classes". There are five major classes of full length antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called $\alpha$, $\delta$, $\epsilon$, $\gamma$, and $\mu$, respectively. The subunit structures and three-dimensional configurations of different classes of immunoglobulins are well known.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells in summarized is Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS (USA)* 95:652-656 (1998).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g. from blood or PBMCs as described herein.

The terms "Fc receptor" or "FcR" are used to describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and Fcγ RBI subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daëron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

"Complement dependent cytotoxicity" or "CDC" refers to the ability of a molecule to lyse a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods* 202:163 (1996), may be performed.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end. The constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the n-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest,* 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest,* 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). "Framework Region" or "FR" residues are those variable domain residues other than the hypervariable region residues as herein defined.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-binding sites and is still capable of cross-linking antigen.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. $F(ab')_2$ antibody fragments originally were produced as pairs of Fab' fragments which have hinge cysteines between them. Other chemical couplings of antibody fragments are also known.

The "light chains" of antibodies from any vertebrate species can be assigned to one of two clearly distinct types, called kappa (κ) and lambda (λ), based on the amino acid sequences of their constant domains.

"Single-chain Fv" or "scFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the scFv to form the desired structure for antigen binding. For a review of scFv see Plückthun in *The Pharmacology of Monoclonal Antibodies,* vol. 113, Rosenburg and Moore eds., Springer-Verlag, New York, pp. 269-315 (1994). HER2 antibody scFv fragments are described in WO93/16185; U.S. Pat. No. 5,571,894; and U.S. Pat. No. 5,587,458.

The term "diabodies" refers to small antibody fragments with two antigen-binding sites, which fragments comprise a variable heavy domain ($V_H$) connected to a variable light domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA,* 90:6444-6448 (1993).

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fe), typically that of a human immunoglobulin. For further details, see Jones et al., *Nature* 321:522-525 (1986); Riechmann et al., *Nature* 332:323-329 (1988); and Presta, *Curr. Op, Struct. Biol.* 2:593-596 (1992).

Humanized HER2 antibodies include huMAb4D5-1, huMAb4D5-2, huMAb4D5-3, huMAb4D5-4, huMAb4D5-5, huMAb4D5-6, huMAb4D5-7 and huMAb4D5-8 or Trastuzumab (HERCEPTIN®) as described in Table 3 of U.S. Pat. No. 5,821,337 expressly incorporated herein by reference; humanized 520C9 (WO93/21319) and humanized 2C4 antibodies as described herein.

For the purposes herein, "Trastuzumab," "HERCEPTIN®," and "huMAb4D5-8" refer to an antibody comprising the light and heavy chain amino acid sequences in SEQ ID NOS. 13 and 14, respectively.

Herein, "Pertuzumab" and "rhuMAb 2C4" refer to an antibody comprising the variable light and variable heavy amino acid sequences in SEQ ID Nos. 3 and 4, respectfully. Where Pertuzumab is a full length antibody, it preferably comprises the light chain and heavy chain amino acid sequences in SEQ ID NOS. 15 and 16, respectively.

A "naked antibody" is an antibody (as herein defined) that is not conjugated to a heterologous molecule, such as a cytotoxic moiety or radiolabel.

An "affinity matured" antibody is one with one or more alterations in one or more hypervariable regions thereof which result an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of CDR and/or framework residues is described by: Barbas et al. *Proc Nat. Acad. Sci, USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

An "agonist antibody" is an antibody which binds to and activates a receptor. Generally, the receptor activation capability of the agonist antibody will be at least qualitatively similar (and may be essentially quantitatively similar) to a native agonist ligand of the receptor. An example of an agonist antibody is one which binds to a receptor in the TNF receptor superfamily, such as DR5, and induces apoptosis of cells expressing the TNF receptor (e.g. DR5). Assays for determining induction of apoptosis are described in WO98/51793 and WO99/37684, both of which are expressly incorporated herein by reference.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

A HER2 antibody which "inhibits HER dimerization more effectively than Trastuzumab" is one which reduces or eliminates HER dimers more effectively (for example at least about 2-fold more effectively) than Trastuzumab. Preferably, such an antibody inhibits HER2 dimerization at least about as effectively as an antibody selected from the group consisting of murine monoclonal antibody 2C4, a Fab fragment of murine monoclonal antibody 2C4, Pertuzumab, and a Fab fragment of Pertuzumab. One can evaluate HER dimerization inhibition by studying HER dimers directly, or by evaluating HER activation, or downstream signaling, which results from HER dimerization, and/or by evaluating the antibody-HER2 binding site, etc. Assays for screening for antibodies with the ability to inhibit HER dimerization more effectively than Trastuzumab are described in Agus et al. *Cancer Cell* 2: 127-137 (2002) and WO01/00245 (Adams et al.). By way of example only, one may assay for inhibition of HER dimerization by assessing, for example, inhibition of HER dimer formation (see, e.g., FIG. 1A-B of Agus et al. *Cancer Cell* 2: 127-137 (2002); and WO01/00245); reduction in HER ligand activation of cells which express HER dimers (WO01/00245 and FIG. 2A-B of Agus et al. *Cancer Cell* 2: 127-137 (2002), for example); blocking of HER ligand binding to cells which express HER dimers (WO01/00245, and FIG. 2E of Agus et al. *Cancer Cell* 2: 127-137 (2002), for example); cell growth inhibition of cancer cells (e.g. MCF7, MDA-MD-134, ZR-75-1, MD-MB-175, T-47D cells) which express HER dimers in the presence (or absence) of HER ligand (WO01/00245 and FIGS. 3A-D of Agus et al. *Cancer Cell* 2: 127-137 (2002), for instance); inhibition of downstream signaling (for instance, inhibition of HRG-dependent AKT phosphorylation or inhibition of HRG- or TGFα-dependent MAPK phosphorylation) (see, WO01/00245, and FIG. 2C-D of Agus et al. *Cancer Cell* 2: 127-137 (2002), for example). One may also assess whether the antibody inhibits HER dimerization by studying the antibody-HER2 binding site, for instance, by evaluating a structure or model, such as a crystal structure, of the antibody bound to HER2 (See, for example, Franklin et al. *Cancer Cell* 5:317-328 (2004)).

The HER2 antibody may "inhibit HRG-dependent AKT phosphorylation" and/or inhibit "HRG- or TGFα-dependent MAPK phosphorylation" more effectively (for instance at least 2-fold more effectively) than Trastuzumab (see Agus et al. *Cancer Cell* 2: 127-137 (2002) and WO01/00245, by way of example).

The HER2 antibody may be one which does "not inhibit HER2 ectodomain cleavage" (Molina et al. *Cancer Res.* 61:4744-4749 (2001).

A HER2 antibody that "binds to a heterodimeric binding site" of HER2, binds to residues in domain II (and optionally also binds to residues in other of the domains of the HER2 extracellular domain, such as domains I and III), and can sterically hinder, at least to some extent, formation of a HER2-EGFR, HER2-HER3, or HER2-HER4 heterodimer. Franklin et al. *Cancer Cell* 5:317-328 (2004) characterize the HER2-Pertuzumab crystal structure, deposited with the RCSB Protein Data Bank (ID Code IS78), illustrating an exemplary antibody that binds to the heterodimeric binding site of HER2.

An antibody that "binds to domain II" of HER2 binds to residues in domain II and optionally residues in other domain(s) of HER2, such as domains I and III. Preferably the antibody that binds to domain II binds to the junction between domains I, II and III of HER2.

A "growth inhibitory agent" when used herein refers to a compound or composition which inhibits growth of a cell, especially a HER expressing cancer cell either in vitro or in vivo. Thus, the growth inhibitory agent may be one which significantly reduces the percentage of HER expressing cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13.

Examples of "growth inhibitory" antibodies are those which bind to HER2 and inhibit the growth of cancer cells overexpressing HER2. Preferred growth inhibitory HER2 antibodies inhibit growth of SK-BR-3 breast tumor cells in cell culture by greater than 20%, and preferably greater than 50% (e.g. from about 50% to about 100%) at an antibody concentration of about 0.5 to 30 μg/ml, where the growth inhibition is determined six days after exposure of the SK-BR-3 cells to the antibody (see U.S. Pat. No. 5,677,171 issued Oct. 14, 1997). The SK-BR-3 cell growth inhibition assay is described in more detail in that patent and hereinbelow. The preferred growth inhibitory antibody is a humanized variant of murine monoclonal antibody 4D5, e.g., Trastuzumab.

An antibody which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is usually one which expresses the antigen to which the antibody binds. Preferably the cell is a tumor cell. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody which induces apoptosis is one which results in about 2 to 50 fold, preferably about 5 to 50 fold, and most preferably about 10 to 50 fold, induction of annexin binding relative to untreated cell in an annexin binding assay using cells that express an antigen to which the antibody binds. Examples of antibodies that induce apoptosis are HER2 antibodies 7C2 and 7F3, and certain DR5 antibodies.

The "epitope 2C4" is the region in the extracellular domain of HER2 to which the antibody 2C4 binds. In order to screen for antibodies which bind to the 2C4 epitope, a routine cross-blocking assay such as that described in *Antibodies, A Laboratory Manual*, Cold Spring Harbor Laboratory, Ed Harlow and David Lane (1988), can be performed. Alternatively, epitope mapping can be performed to assess whether the antibody binds to the 2C4 epitope of HER2. Epitope 2C4 comprises residues from domain II in the extracellular domain of HER2. 2C4 and Pertuzumab bind to the extracellular domain of HER2 at the junction of domains I, II and III. Franklin et al. *Cancer Cell* 5:317-328 (2004).

The "epitope 4D5" is the region in the extracellular domain of HER2 to which the antibody 4D5 (ATCC CRL 10463) and Trastuzumab bind. This epitope is close to the transmembrane domain of HER2, and within Domain IV of HER2. To screen for antibodies which bind to the 4D5 epitope, a routine cross-blocking assay such as that described in *Antibodies, A Laboratory Manual*, Cold Spring Harbor Laboratory, Ed Harlow and David Lane (1988), can be performed. Alternatively, epitope mapping can be performed to assess whether the antibody binds to the 4D5 epitope of HER2 (e.g. any one or more residues in the region from about residue 529 to about residue 625, inclusive, of HER2).

The "epitope 7C2/7F3" is the region at the amino terminus, within Domain I, of the extracellular domain of HER2 to which the 7C2 and/or 7F3 antibodies (each deposited with the ATCC, see below) bind. To screen for antibodies which bind to the 7C2/7F3 epitope, a routine cross-blocking assay such as that described in *Antibodies, A Laboratory Manual*, Cold Spring Harbor Laboratory, Ed Harlow and David Lane (1988), can be performed. Alternatively, epitope mapping can be performed to establish whether the antibody binds to the 7C2/7F3 epitope on HER2 (e.g. any one or more of residues in the region from about residue 22 to about residue 53 of HER2).

"Treatment" refers to both therapeutic treatment and prophylactic or preventative measures. Those in need of treatment include those already with the disease as well as those in which the disease is to be prevented. Hence, the patient to be treated herein may have been diagnosed as having the disease or may be predisposed or susceptible to the disease.

The terms "cancer" and "cancerous" refer to or describe the physiological condition in mammals that is typically characterized by unregulated cell growth. Examples of cancer include, but are not limited to, carcinoma, lymphoma, blastoma (including medulloblastoma and retinoblastoma), sarcoma (including liposarcoma and synovial cell sarcoma), neuroendocrine tumors (including carcinoid tumors, gastrinoma, and islet cell cancer), mesothelioma, schwannoma (including acoustic neuroma), meningioma, adenocarcinoma, melanoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophagael cancer, tumors of the biliary tract, as well as head and neck cancer.

The term "effective amount" refers to an amount of a drug effective to a disease in the patient. Where the disease is cancer, the effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. The effective amount may extend progression free survival, result in an objective response (including a partial response, PR, or complete response, CR), increase overall survival time, and/or improve one or more symptoms of cancer.

A "HER2-expressing cancer" is one comprising cells which have HER2 protein present at their cell surface.

A cancer which "overexpresses" a HER receptor is one which has significantly higher levels of a HER receptor, such as HER2, at the cell surface thereof, compared to a noncancerous cell of the same tissue type. Such overexpression may be caused by gene amplification or by increased transcription or translation. HER receptor overexpression may be determined in a diagnostic or prognostic assay by evaluating increased levels of the HER protein present on the surface of a cell (e.g. via an immunohistochemistry assay; IHC). Alternatively, or additionally, one may measure levels of HER-encoding nucleic acid in the cell, e.g. via fluorescent in situ hybridization (FISH; see WO98/45479 published October, 1998), southern blotting, or polymerase chain reaction (PCR) techniques, such as real time quantitative PCR(RT-PCR). One may also study HER receptor overexpression by measuring shed antigen (e.g., HER extracellular domain) in a biological fluid such as serum (see, e.g., U.S. Pat. No. 4,933, 294 issued Jun. 12, 1990; WO91/05264 published Apr. 18, 1991; U.S. Pat. No. 5,401,638 issued Mar. 28, 1995; and Sias et al. *J. Immunol. Methods* 132: 73-80 (1990)). Aside from the above assays, various in vivo assays are available to the skilled practitioner. For example, one may expose cells within the body of the patient to an antibody which is optionally labeled with a detectable label, e.g. a radioactive isotope, and binding of the antibody to cells in the patient can be evaluated, e.g. by external scanning for radioactivity or by analyzing a biopsy taken from a patient previously exposed to the antibody.

Conversely, a cancer which "does not overexpress HER2 receptor" is one which does not express higher than normal levels of HER2 receptor compared to a noncancerous cell of the same tissue type.

A cancer which "overexpresses" a HER ligand is one which produces significantly higher levels of that ligand compared to a noncancerous cell of the same tissue type. Such overexpression may be caused by gene amplification or by increased transcription or translation. Overexpression of the HER ligand may be determined diagnostically by evaluating levels of the ligand (or nucleic acid encoding it) in the patient, e.g. in a tumor biopsy or by various diagnostic assays such as the IHC, FISH, southern blotting, PCR or in vivo assays described above.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

A "chemotherapeutic agent" is a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaI1 and calicheamicin omegaI1 (see, e.g., *Agnew, Chem. Intl. Ed. Engl.,* 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chloranbucil; 6-thioguanine; mercaptopurine; methotrexate; platinum agents such as cisplatin, oxaliplatin, and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovovin; novantrone; edatrexate; daunomycin; aminopterin; ibandronate; topoisomerase inhibitor RFS 2000; difluoromethylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (Pfizer); perifosine, COX-2 inhibitor (e.g. celecoxib or etoricoxib), proteosome inhibitor (e.g. PS341); bortezomib (VELCADE®); CCI-779; tipifarnib (R11577); orafenib, ABT510; Bcl-2 inhibitor such as oblimersen sodium (GENA- SENSE®); pixantrone; EGFR inhibitors (see definition below); tyrosine kinase inhibitors (see definition below); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate or inhibit hormone action on tumors such as anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and nonsteroidal aromatase inhibitors such as anastrazole (ARIMIDEX®), letrozole (FEMARA®) and aminoglutethimide, and other aromatase inhibitors including vorozole (RIVISOR®), megestrol acetate (MEGASE®), fadrozole, imidazole; lutenizing hormone-releasing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor down-regulators (ERDs); anti-androgens such as flutamide, nilutamide and bicalutamide; testolactone; and pharmaceutically acceptable salts, acids or derivatives of any of the above; as well as combinations of two or more of the above.

As used herein, the term "EGFR-targeted drug" refers to a therapeutic agent that binds to EGFR and, optionally, inhibits EGFR activation. Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF (see WO98/50433, Abgenix).

The anti-EGFR antibody may be conjugated with a cytotoxic agent, thus generating an immunoconjugate (see, e.g., EP659,439A2, Merck Patent GmbH). Examples of small molecules that bind to EGFR include ZD1839 or Gefitinib (IRESSA™; Astra Zeneca), CP-358774 or Erlotinib HCL (TARCEVA™; Genentech/OSI) and AG1478, AG1571 (SU 5271; Sugen).

A "tyrosine kinase inhibitor" is a molecule which inhibits to some extent tyrosine kinase activity of a tyrosine kinase such as a HER receptor. Examples of such inhibitors include the EGFR-targeted drugs noted in the preceding paragraph as well as small molecule HER2 tyrosine kinase inhibitor such as TAK165 available from Takeda, dual-HER inhibitors such as EKB-569 (available from Wyeth) which preferentially binds EGFR but inhibits both HER2 & EGFR-overexpressing cells, GW572016 (available from Glaxo) an oral HER2 and EGFR tyrosine kinase inhibitor, and PKI-166 (available from Novartis); pan-HER inhibitors such as canertinib (CI-1033; Pharmacia); Raf-1 inhibitors such as antisense agent ISIS-5132 available from ISIS Pharmaceuticals which inhibits Raf-1 signaling; non-HER targeted TK inhibitors such as Imatinib mesylate (Gleevac™) available from Glaxo; MAPK extracellular regulated kinase I inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis(4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804,396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); Imatinib mesylate (Gleevac; Novartis); PKI 166 (Novartis); GW2016 (Glaxo SmithKline); CI-1033 (Pfizer); EKB-569 (Wyeth); Semaxinib (Sugen); ZD6474 (AstraZeneca); PTK-787 (Novartis/Schering AG); INC-1C11 (Imclone); or as described in any of the following patent publications: U.S. Pat. No. 5,804,396; WO99/09016 (American Cyanimid); WO98/43960 (American Cyanamid); WO97/38983 (Warner Lambert); WO99/06378 (Warner Lambert); WO99/06396 (Warner Lambert); WO96/30347 (Pfizer, Inc); WO96/33978 (Zeneca); WO96/3397 (Zeneca); and WO96/33980 (Zeneca).

An "anti-angiogenic agent" refers to a compound which blocks, or interferes with to some degree, the development of blood vessels. The anti-angiogenic factor may, for instance, be a small molecule or antibody that binds to a growth factor or growth factor receptor involved in promoting angiogenesis. The preferred anti-angiogenic factor herein is an antibody that binds to Vascular Endothelial Growth Factor (VEGF), such as Bevacizumab (AVASTIN®).

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-$\alpha$ and -$\beta$; mullerian-inhibiting substance; mouse gonadotropin-associated peptide; inhibin; activin; vascular endothelial growth factor; integrin; thrombopoietin (TPO); nerve growth factors such as NGF-$\beta$; platelet-growth factor; transforming growth factors (TGFs) such as TGF-$\alpha$ and TGF-$\beta$; insulin-like growth factor-I and -II; erythropoietin (EPO); osteoinductive factors; interferons such as interferon-$\alpha$, -$\beta$, and -$\gamma$; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1$\alpha$, IL-2, IL-3, IL-4, IL-5, IL-6, IL-7, IL-8, IL-9, IL-10, IL-11, IL-12; a tumor necrosis factor such as TNF-$\alpha$ or TNF-$\beta$; and other polypeptide factors including LIF and kit ligand (KL). As used herein, the term cytokine includes proteins from natural sources or from recombinant cell culture and biologically active equivalents of the native sequence cytokines.

The antibody which is formulated is preferably essentially pure and desirably essentially homogeneous (i.e. free from contaminating proteins etc). "Essentially pure" antibody means a composition comprising at least about 90% by weight of the antibody, based on total weight of the composition, preferably at least about 95% by weight. "Essentially homogeneous" antibody means a composition comprising at least about 99% by weight of antibody, based on total weight of the composition.

A "B-cell surface marker" or "B-cell surface antigen" herein is an antigen expressed on the surface of a B cell that can be targeted with an antibody that binds thereto. Exemplary B-cell surface markers include the CD10, CD19, CD20, CD21, CD22, CD23, CD24, CD37, CD40, CD53, CD72, CD73, CD74, CDw75, CDw76, CD77, CDw78, CD79a, CD79b, CD80, CD81, CD82, CD83, CDw84, CD85 and CD86 leukocyte surface markers (for descriptions, see The Leukocyte Antigen Facts Book, $2^{nd}$ Edition. 1997, ed. Barclay et al. Academic Press, Harcourt Brace & Co., New York). Other B-cell surface markers include RP105, FcRH2, B-cell CR2, CCR6, P2x5, HLA-DOB, CXCR5, FCER2, BR3, Btig, NAG14, SLGC16270, FcRH1, IRTA2, ATWD578, FcRH3, IRTA1, FcRH6, BCMA, and 239287. The B-cell surface marker of particular interest herein is preferentially expressed on B cells compared to other non-B-cell tissues of a mammal and may be expressed on both precursor B cells and mature B cells. The preferred B-cell surface marker herein is CD20 or BR3.

The "CD20" antigen, or "CD20," is an about 35-kDa, non-glycosylated phosphoprotein found on the surface of greater than 90% of B cells from peripheral blood or lymphoid organs. CD20 is present on both normal B cells as well as malignant B cells, but is not expressed on stem cells. Other names for CD20 in the literature include "B-lymphocyte-restricted antigen" and "Bp35". The CD20 antigen is described in Clark et al. Proc. Natl. Acad. Sci. (USA) 82:1766 (1985), for example.

Figure 5:
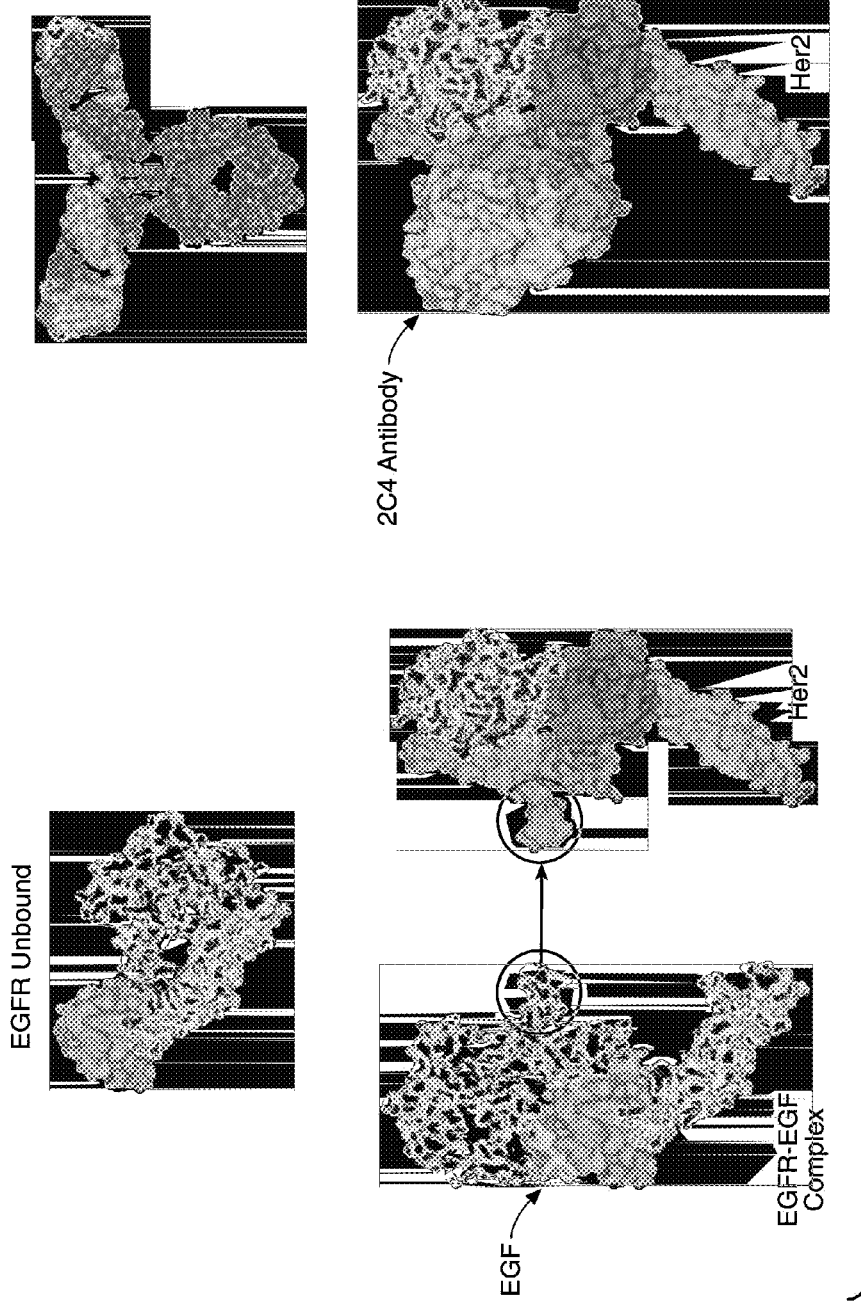
FIG. 5 depicts, schematically, binding of 2C4 at the heterodimeric binding site of HER2, thereby preventing heterodimerization with activated EGFR or HER3.
Figure 6:
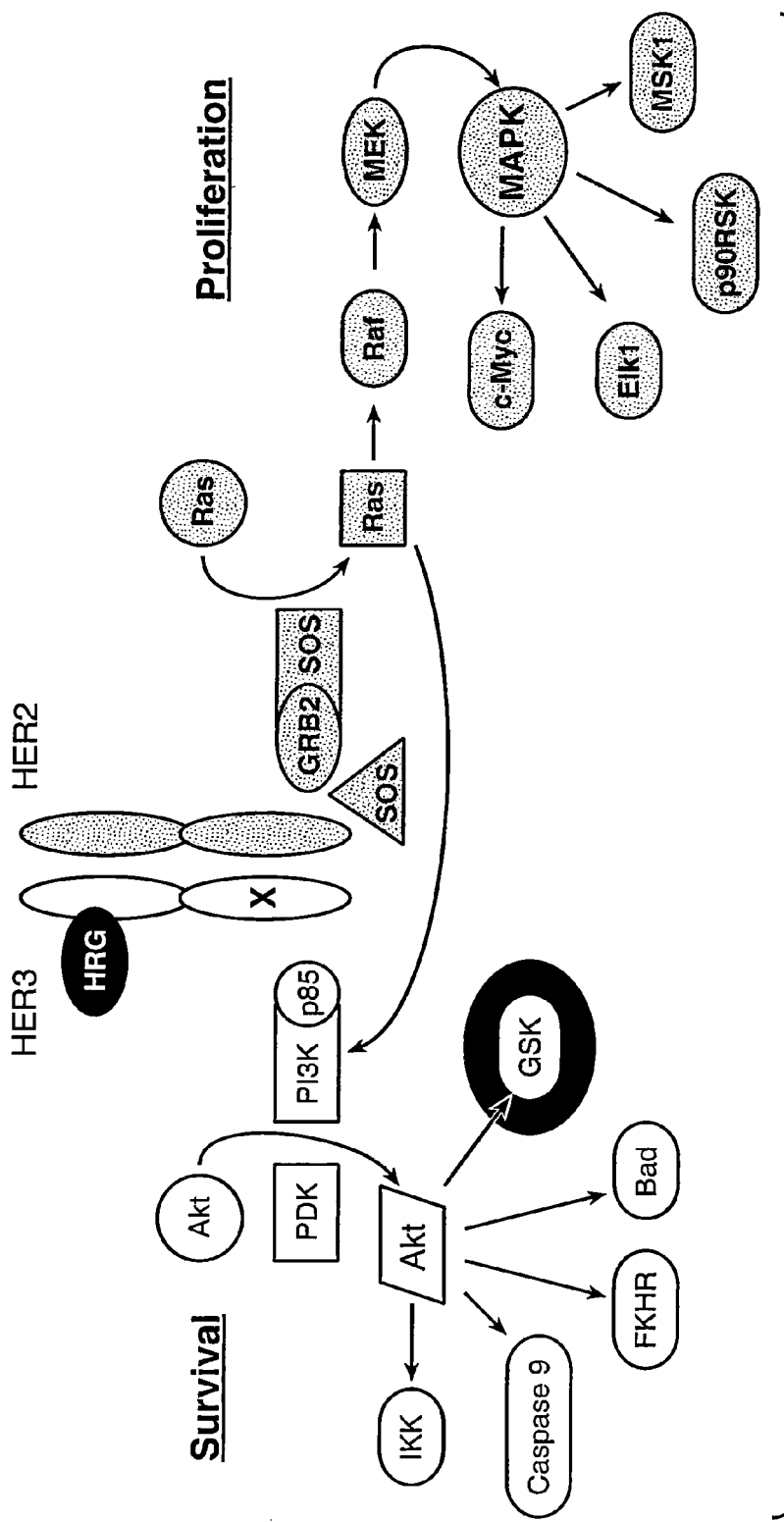
FIG. 6 depicts coupling of HER2/HER3 to the MAPK and Akt pathways.

Purely for the purposes herein, "humanized 2H7" refers to a humanized variant of the 2H7 antibody whose CDR sequences are disclosed in U.S. Pat. No. 5,500,362 (FIGS. 5 and 6), expressly incorporated herein by reference. Examples of humanized 2H7 antibodies herein include the variants described in WO2004/056312, also expressly incorporated herein by reference, as well as other variants, including, but not limited to: 2H7v16, 2H7v31, 2H7v73, 2H7v75, 2H7v96, 2H7v114, 2H7v115, 2H7v116, 2H7v138, 2H7v477, 2H7v375, etc.

In one embodiment, the humanized 2H7 antibody comprises one, two, three, four, five or six of the following CDR sequences:

CDR L1 sequence RASSSVSYXH wherein X is M or L (SEQ ID No. 67), for example SEQ ID No. 57 (FIG. 18A),
CDR L2 sequence of SEQ ID No. 58 (FIG. 18A),
CDR L3 sequence QQWXFNPPT wherein X is S or A (SEQ ID No. 68), for example SEQ ID No. 59 (FIG. 18A),
CDR H1 sequence of SEQ ID No. 60 (FIG. 18B),
CDR H2 sequence of AIYPGNGXTSYNQKFKG wherein X is D or A (SEQ ID No. 69), for example SEQ ID No. 61 (FIG. 18B), and
CDR H3 sequence of VVYYSXXYWYFDV wherein the X at position 6 is N, A, Y, W or D, and the X at position 7 is S or R (SEQ ID No. 70), for example SEQ ID No. 62 (FIG. 18B).

The CDR sequences above are generally present within human variable light and variable heavy framework sequences, such as substantially the human consensus FR residues of human light chain kappa subgroup I ($V_L \kappa I$), and substantially the human consensus FR residues of human heavy chain subgroup III ($V_H III$). See also WO 2004/056312 (Lowman et al.).

The variable heavy region may be joined to a human IgG chain constant region, wherein the region may be, for example, IgG1 or IgG3, including native sequence and variant constant regions.

In a preferred embodiment, such antibody comprises the variable heavy domain sequence of SEQ ID No. 29 (v16, as shown in FIG. 18B), optionally also comprising the variable light domain sequence of SEQ ID No. 26 (v16, as shown in FIG. 18A), which optionally comprises one or more amino acid substitution(s) at positions 56, 100, and/or 100a, e.g. D56A, N100A or N100Y, and/or S100aR in the variable heavy domain and one or more amino acid substitution(s) at positions 32 and/or 92, e.g. M32L and/or S92A, in the variable light domain. Preferably, the antibody is an intact antibody comprising the light chain amino acid sequences of SEQ ID Nos. 63 or 64, and heavy chain amino acid sequences of SEQ ID No. 65, 66, 71 or 72.

A preferred humanized 2H7 antibody is ocrelizumab (Genentech).

The antibody herein may further comprise at least one amino acid substitution in the Fc region that improves ADCC activity, such as one wherein the amino acid substitutions are at positions 298, 333, and 334, preferably S298A, E333A, and K334A, using Eu numbering of heavy chain residues. See also U.S. Pat. No. 6,737,056B1, Presta.

Any of these antibodies may comprise at least one substitution in the Fc region that improves FcRn binding or serum half-life, for example a substitution at heavy chain position 434, such as N434W. See also U.S. Pat. No. 6,737,056B1, Presta.

Any of these antibodies may further comprise at least one amino acid substitution in the Fc region that increases CDC activity, for example, comprising at least a substitution at position 326, preferably K326A or K326W. See also U.S. Pat. No. 6,528,624B1 (Idusogie et al.).

Some preferred humanized 2H7 variants are those comprising the variable light domain of SEQ ID No. 26 and the variable heavy domain of SEQ ID No. 29, including those with or without substitutions in an Fc region (if present), and those comprising a variable heavy domain with alteration N100A; or D56A and N100A; or D56A, N100Y, and S100aR; in SEQ ID No. 29 and a variable light domain with alteration M32L; or S92A; or M32L and S92A; in SEQ ID No. 26.

M34 in the variable heavy chain of 2H7v16 has been identified as a potential source of antibody stability and is another potential candidate for substitution.

In a summary of some various preferred embodiments of the invention, the variable region of variants based on 2H7v16 comprise the amino acid sequences of v16 except at the positions of amino acid substitutions that are indicated in the Table below. Unless otherwise indicated, the 2H7 variants will have the same light chain as that of v16.

Exemplary Humanized 2H7 Antibody Variants

| 2H7 Version | Heavy chain ($V_H$) changes | Light chain ($V_L$) changes | Fc changes |
| --- | --- | --- | --- |
| 16 for reference | — | — | — |
| 31 | — | — | S298A, E333A, K334A |

Exemplary Humanized 2H7 Antibody Variants

| 2H7 Version | Heavy chain (V_H) changes | Light chain (V_L) changes | Fc changes |
|---|---|---|---|
| 73 | N100A | M32L | |
| 75 | N100A | M32L | S298A, E333A, K334A |
| 96 | D56A, N100A | S92A | |
| 114 | D56A, N100A | M32L, S92A | S298A, E333A, K334A |
| 115 | D56A, N100A | M32L, S92A | S298A, E333A, K334A, E356D, M358L |
| 116 | D56A, N100A | M32L, S92A | S298A, K334A, K322A |
| 138 | D56A, N100A | M32L, S92A | S298A, E333A, K334A, K326A |
| 477 | D56A, N100A | M32L, S92A | S298A, E333A, K334A, K326A, N434W |
| 375 | — | — | K334L |
| 588 | — | — | S298A, E333A, K334A, K326A |
| 511 | D56A, N100Y, S100aR | M32L, S92A | S298A, E333A, K334A, K326A |

One preferred humanized 2H7 comprises 2H7v16 variable light domain sequence:

```
                                        (SEQ ID No. 26)
DIQMTQSPSSLSASVGDRVTITCRASSSVSYMHWYQQKPGKAPKPLIYAP

SNLASGVPSRFSGSGSGTDFTLTISSLQPEDFATYYCQQWSFNPPTFGQG

TKVEIKR;
``` and 2H7v16 variable heavy domain sequence:

```
                                        (SEQ ID No. 29)
EVQLVESGGGLVQPGGSLRLSCAASGYTFTSYNMHWVRQAPGKGLEWVGA

IYPGNGDTSYNQKFKGRFTISVDKSKNTLYLQMNSLRAEDTAVYYCARVV

YYSNSYWYFDVWGQGTLVTVSS.
```

Where the humanized 2H7v16 antibody is an intact antibody, it may comprise the light chain amino acid sequence:

```
                                        (SEQ ID No. 63)
DIQMTQSPSSLSASVGDRVTITCRASSSVSYMHWYQQKPGKAPKPLIYAP

SNLASGVPSRFSGSGSGTDFTLTISSLQPEDFATYYCQQWSFNPPTFGQG

TKVEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC;
``` and the heavy chain amino acid sequence of SEQ ID No. 65 or:

```
                                        (SEQ ID No. 71)
EVQLVESGGGLVQPGGSLRLSCAASGYTFTSYNMHWVRQAPGKGLEWVGA

IYPGNGDTSYNQKFKGRFTISVDKSKNTLYLQMNSLRAEDTAVYYCARVV

YYSNSYWYFDVWGQGTLVTVSSASTKGPSVFPLAPSSKSTSGGTAALGCL

VKDYFPEPVTVSWNSGALTSGVHTFPAVLQSSGLYSLSSVVTVPSSSLGT

QTYICNVNHKPSNTKVDKKVEPKSCDKTHTCPPCPAPELLGGPSVFLFPP

KPKDTLMISRTPEVTCVVVDVSHEDPEVKFNWYVDGVEVHNAKTKPREEQ

YNSTYRCCSVLTVLHQDWLNGKEYKCKVSNKALPAPIEKTISKAKGQPRE

PQVYTLPPSREEMTKNQVSLTCLVKGFYPSDIAVEWESNGQPENNYKTTP

PVLDSDGSFFLYSKLTVDKSRWQQGNVFSCSVMHEALHNHYTQKSLSLSP

G.
```

Another preferred humanized 2H7 antibody comprises 2H7v511 variable light domain sequence:

```
                                        (SEQ ID No. 73)
DIQMTQSPSSLSASVGDRVTITCRASSSVSYLHWYQQKPGKAPKPLIYAP

SNLASGVPSRFSGSGSGTDFTLTISSLQPEDFATYYCQQWAFNPPTFGQG

TKVEIKR
``` and 2H7v511 variable heavy domain sequence:

```
                                        (SEQ ID No. 74)
EVQLVESGGGLVQPGGSLRLSCAASGYTFTSYNMHWVRQAPGKGLEWVGA

IYPGNGATSYNQKFKGRFTISVDKSKNTLYLQMNSLRAEDTAVYYCARVV

YYSYRYWYFDVWGQGTLVTVSS.
```

Where the humanized 2H7v511 antibody is an intact antibody, it may comprise the light chain amino acid sequence:

```
                                        (SEQ ID No. 64)
DIQMTQSPSSLSASVGDRVTITCRASSSVSYLHWYQQKPGKAPKPLIYAP

SNLASGVPSRFSGSGSGTDFTLTISSLQPEDFATYYCQQWAFNPPTFGQG

TKVEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC
``` and the heavy chain amino acid sequence of SEQ ID No. 66 or:

```
                                        (SEQ ID No. 72)
EVQLVESGGGLVQPGGSLRLSCAASGYTFTSYNMHWVRQAPGKGLEWVGA

IYPGNGATSYNQKFKGRFTISVDKSKNTLYLQMNSLRAEDTAVYYCARVV

YYSYRYWYFDVWGQGTLVTVSSASTKGPSVFPLAPSSKSTSGGTAALGCL

VKDYFPEPVTVSWNSGALTSGVHTFPAVLQSSGLYSLSSVVTVPSSSLGT

QTYICNVNHKPSNTKVDKKVEPKSCDKTHTCPPCPAPELLGGPSVFLFPP

KPKDTLMISRTPEVTCVVVDVSHEDPEVKFNWYVDGVEVHNAKTKPREEQ

YNATYRVVSVLTVLHQDWLNGKEYKCKVSNAALPAPIAATISKAKGQPRE

PQVYTLPPSREEMTKNQVSLTCLVKGFYPSDIAVEWESNGQPENNYKTTP

PVLDSDGSFFLYSKLTVDKSRWQQGNVFSCSVMHEALHNHYTQKSLSLSP

G.
```

A "B-cell malignancy" herein includes non-Hodgkin's lymphoma (NHL), including low grade/follicular NHL, small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, mantle cell lymphoma, AIDS-related lymphoma, and Waldenstrom's Macroglobulinemia; leukemia, including acute lymphoblastic leukemia (ALL), chronic lymphocytic leukemia (CLL), Hairy cell leukemia and chronic myeloblastic leukemia; and other hematologic malignancies. Such malignancies may be treated with antibodies directed against B-cell surface markers, such as CD20.

Figure 11:
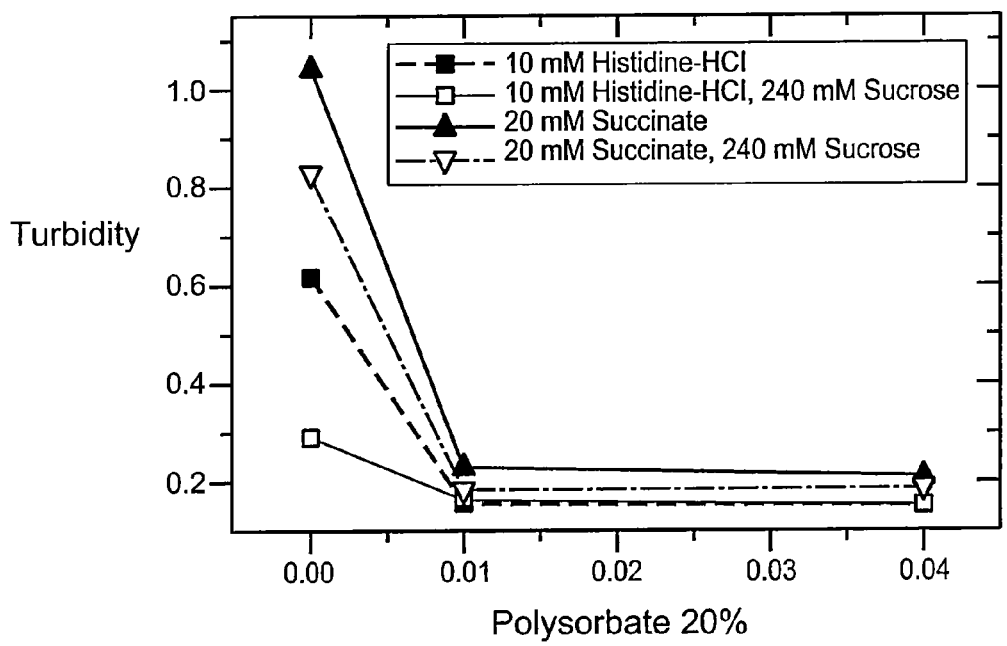
FIG. 11 is from an agitation study of Pertuzumab liquid formulations.

The term "non-Hodgkin's lymphoma" or "NHL", as used herein, refers to a cancer of the lymphatic system other than Hodgkin's lymphomas. Hodgkin's lymphomas can generally be distinguished from non-Hodgkin's lymphomas by the presence of Reed-Sternberg cells in Hodgkin's lymphomas and the absence of said cells in non-Hodgkin's lymphomas. Examples of non-Hodgkin's lymphomas encompassed by the term as used herein include any that would be identified as such by one skilled in the art (e.g., an oncologist or pathologist) in accordance with classification schemes known in the art, such as the Revised European-American Lymphoma (REAL) scheme as described in Color Atlas of Clinical Hematology, Third Edition; A. Victor Hoffbrand and John E. Pettit (eds.) (Harcourt Publishers Limited 2000) (see, in particular FIG. 11.57, 11.58 and/or 11.59). More specific examples include, but are not limited to, relapsed or refractory NHL, front line low grade NHL, Stage III/IV NHL, chemotherapy resistant NHL, precursor B lymphoblastic leukemia and/or lymphoma, small lymphocytic lymphoma, B cell chronic lymphacytic leukemia and/or prolymphocytic leukemia and/or small lymphocytic lymphoma, B-cell prolymphocytic lymphoma, immunocytoma and/or lymphoplasmacytic lymphoma, marginal zone B cell lymphoma, splenic marginal zone lymphoma, extranodal marginal zone—MALT lymphoma, nodal marginal zone lymphoma, hairy cell leukemia, plasmacytoma and/or plasma cell myeloma, low grade/follicular lymphoma, intermediate grade/follicular NHL, mantle cell lymphoma, follicle center lymphoma (follicular), intermediate grade diffuse NHL, diffuse large B-cell lymphoma, aggressive NHL (including aggressive front-line NHL and aggressive relapsed NHL), NHL relapsing after or refractory to autologous stem cell transplantation, primary mediastinal large B-cell lymphoma, primary effusion lymphoma, high grade immunoblastic NHL, high grade lymphoblastic NHL, high grade small non-cleaved cell NHL, bulky disease NHL, Burkitt's lymphoma, precursor (peripheral) T-cell lymphoblastic leukemia and/or lymphoma, adult T-cell lymphoma and/or leukemia, T cell chronic lymphocytic leukemia and/or prolymphacytic leukemia, large granular lymphocytic leukemia, mycosis fungoides and/or Sezary syndrome, extranodal natural killer/T-cell (nasal type) lymphoma, enteropathy type T-cell lymphoma, hepatosplenic T-cell lymphoma, subcutaneous panniculitis like T-cell lymphoma, skin (cutaneous) lymphomas, anaplastic large cell lymphoma, angiocentric lymphoma, intestinal T cell lymphoma, peripheral T-cell (not otherwise specified) lymphoma and angioimmunoblastic T-cell lymphoma.

An "autoimmune disease" herein is a disease or disorder arising from and directed against an individual's own tissues or a co-segregate or manifestation thereof or resulting condition therefrom. Examples of autoimmune diseases or disorders include, but are not limited to arthritis (rheumatoid arthritis, juvenile-onset rheumatoid arthritis, osteoarthritis, psoriatic arthritis, and ankylosing spondylitis), psoriasis, dermatitis including atopic dermatitis, chronic idiopathic urticaria, including chronic autoimmune urticaria, polymyositis/dermatomyositis, toxic epidermal necrolysis, scleroderma (including systemic scleroderma), sclerosis such as progressive systemic sclerosis, inflammatory bowel disease (IBD) (for example, Crohn's disease, ulcerative colitis, autoimmune inflammatory bowel disease), pyoderma gangrenosum, erythema nodosum, primary sclerosing cholangitis, episcleritis), respiratory distress syndrome, including adult respiratory distress syndrome (ARDS), meningitis, IgE-mediated diseases such as anaphylaxis and allergic and atopic rhinitis, encephalitis such as Rasmussen's encephalitis, uveitis or autoimmune uveitis, colitis such as microscopic colitis and collagenous colitis, glomerulonephritis (GN) such as membranous GN (membranous nephropathy), idiopathic membranous GN, membranous proliferative GN (MPGN), including Type I and Type II, and rapidly progressive GN, allergic conditions, allergic reaction, eczema, asthma, conditions involving infiltration of T cells and chronic inflammatory responses, atherosclerosis, autoimmune myocarditis, leukocyte adhesion deficiency, systemic lupus erythematosus (SLE) such as cutaneous SLE, subacute cutaneous lupus erythematosus, lupus (including nephritis, cerebritis, pediatric, non-renal, discoid, alopecia), juvenile onset (Type I) diabetes mellitus, including pediatric insulin-dependent diabetes mellitus (IDDM), adult onset diabetes mellitus (Type II diabetes), multiple sclerosis (MS) such as spino-optical MS, immune responses associated with acute and delayed hypersensitivity mediated by cytokines and T-lymphocytes, tuberculosis, sarcoidosis, granulomatosis including lymphomatoid granulomatosis, Wegener's granulomatosis, agranulocytosis, vasculitis (including large vessel vasculitis (including polymyalgia rheumatica and giant cell (Takayasu's) arteritis), medium vessel vasculitis (including Kawasaki's disease and polyarteritis nodosa), CNS vasculitis, systemic necrotizing vasculitis, and ANCA-associated vasculitis, such as Churg-Strauss vasculitis or syndrome (CSS)), temporal arteritis, aplastic anemia, Coombs positive anemia, Diamond Blackfan anemia, hemolytic anemia or immune hemolytic anemia including autoimmune hemolytic anemia (AIHA), pernicious anemia, pure red cell aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome, antigen-antibody complex mediated diseases, anti-glomerular basement membrane disease, anti-phospholipid antibody syndrome, allergic neuritis, Bechet's or Behcet's disease, Castleman's syndrome, Goodpasture's syndrome, Reynaud's syndrome, Sjogren's syndrome, Stevens-Johnson syndrome, pemphigoid such as pemphigoid bullous, pemphigus (including vulgaris, foliaceus, and pemphigus mucus-membrane pemphigoid), autoimmune polyendocrinopathies, Reiter's disease, immune complex nephritis, chronic neuropathy such as IgM polyneuropathies or IgM-mediated neuropathy, thrombocytopenia (as developed by myocardial infarction patients, for example), including thrombotic thrombocytopenic purpura (TTP) and autoimmune or immune-mediated thrombocytopenia such as idiopathic thrombocytopenic purpura (ITP) including chronic or acute ITP, autoimmune disease of the testis and ovary including autoimune orchitis and oophoritis, primary hypothyroidism, hypoparathyroidism, autoimmune endocrine diseases including thyroiditis such as autoimmune thyroiditis, chronic thyroiditis (Hashimoto's thyroiditis), or subacute thyroiditis, autoimmune thyroid disease, idiopathic hypothyroidism, Addison's disease, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis, myasthenia gravis, cerebellar degeneration, limbic and/or brainstem encephalitis, neuromyotonia, opsoclonus or opsoclonus myoclonus syndrome (OMS), and sensory neuropathy, Sheehan's syndrome, autoimmune hepatitis, chronic hepatitis, lupoid hepatitis, chronic active hepatitis or autoimmune chronic active hepatitis, lymphoid interstitial pneumonitis, bronchiolitis obliterans (non-transplant) vs NSIP, Guillain-Barré syndrome, Berger's disease (IgA nephropathy), primary biliary cirrhosis, celiac sprue (gluten enteropathy), refractory sprue, dermatitis herpetiformis, cryoglobulinemia, amylotrophic lateral sclerosis (ALS; Lou Gehrig's disease), coronary artery disease, autoimmune inner ear disease (AIED) or autoimmune hearing loss, opsoclonus myoclonus syndrome (OMS), polychondritis such as refractory polychondritis, pulmonary alveolar proteinosis, amyloidosis, giant cell hepatitis, scleritis, a non-cancerous lymphocytosis, a primary lymphocytosis, which includes monoclonal B cell lymphocytosis (e.g., benign monoclonal gammopathy and monoclonal garnmopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal segmental glomerulosclerosis (FSGS), endocrine ophthalmopathy, uveoretinitis, autoimmune hepatological disorder, fibromyalgia, multiple endocrine failure, Schmidt's syndrome, adrenalitis, gastric atrophy, presenile dementia, demyelinating diseases, Dressler's syndrome, alopecia arcata, CREST syndrome (calcinosis, Raynaud's phenomenon, esophageal dysmotility, sclerodactyl), and telangiectasia), male and female autoimmune infertility, ankylosing spondolytis, mixed connective tissue disease, Chagas' disease, rheumatic fever, recurrent abortion, farmer's lung, erythema multiforme, post-cardiotomy syndrome, Cushing's syndrome, bird-fancier's lung, Alport's syndrome, alveolitis such as allergic alveolitis and fibrosing alveolitis, interstitial lung disease, transfusion reaction, leprosy, malaria, leishmaniasis, kypanosomiasis, schistosomiasis, ascariasis, aspergillosis, Sampter's syndrome, Caplan's syndrome, dengue, endocarditis, endomyocardial fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, or Fuch's cyclitis, Henoch-Schonlein purpura, human immunodeficiency virus (HIV) infection, echovirus infection, cardiomyopathy, Alzheimer's disease, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, and giant cell polymyalgia.

The "tumor necrosis factor receptor superfamily" or "TNF receptor superfamily" herein refers to receptor polypeptides bound by cytokines in the TNF family. Generally, these receptors are Type I transmembrane receptors with one or more cysteine rich repeat sequences in their extracellular domain. The TNF receptor superfamily may be further subdivided into (1) death receptors; (2) decoy receptors; and (3) signaling receptors that lack death domains. The "death receptors" contain in their cytoplasmic or intracellular region a "death domain", i.e., a region or sequence which acts to transduce signals in the cell which can result in apoptosis or in induction of certain genes. The "decoy receptors" lack a functional death domain and are incapable of transducing signals which result in apoptosis. Examples of cytokines in the TNF gene family include Tumor Necrosis Factor-alpha (TNF-alpha), Tumor Necrosis Factor-beta (TNF-beta or lymphotoxin), CD30 ligand, CD27 ligand, CD40 ligand, OX-40 ligand, 4-1BB ligand, Apo-1 ligand (also referred to as Fas ligand or CD95 ligand), Apo-2 ligand (also referred to as TRAIL), Apo-3 ligand (also referred to as TWEAK), osteoprotegerin (OPG), APRIL, RANK ligand (also referred to as TRANCE), and TALL-1 (also referred to as BlyS, BAFF or THANK). Examples of receptors in the TNF receptor superfamily include: type 1 Tumor Necrosis Factor Receptor (TNFR1), type 2 Tumor Necrosis Factor Receptor (TNFR2), p75 Nerve Growth Factor receptor (NGFR), the B cell surface antigen CD40, the T cell antigen OX-40, Apo-1 receptor (also called Fas or CD95), Apo-3 receptor (also called DR3, swl-1, TRAMP and LARD), the receptor called "Transmembrane Activator and CAML-Interactor" or "TACI", BCMA protein, DR4, DR5 (alternatively referred to as Apo-2; TRAIL-R2, TR6, Tango-63, hAPO8, TRICK2 or KILLER), DR6, DcR1 (also referred to as TRID, LIT or TRAIL-R3), DcR2 (also called TRAIL-R4 or TRUNDD), OPG, DcR3 (also called TR6 or M68), CAR1, HVEM (also called ATAR or TR2), GITR, ZTNFR-5, NTR-1, TNFL1, CD30, Lymphotoxin beta receptor (LTBr), 4-1BB receptor and TR9 (EP988, 371A1).

The terms "Apo-2 ligand", "Apo-2L", "Apo2L", Apo-2 ligand/TRAIL" and "TRAIL" are used herein interchangeably to refer to a polypeptide sequence which includes amino acid residues 114-281, inclusive, 95-281, inclusive, residues 92-281, inclusive, residues 91-281, inclusive, residues 41-281, inclusive, residues 39-281, inclusive, residues 15-281, inclusive, or residues 1-281, inclusive, of the amino acid sequence shown in FIG. 24 (SEQ ID No. 46), as well as biologically active fragments, deletional, insertional, and/or substitutional variants of the above sequences. In one embodiment, the polypeptide sequence comprises residues 114-281 of FIG. 24 (SEQ ID No. 46). Optionally, the polypeptide sequence comprises residues 92-281 or residues 91-281 of FIG. 24 (SEQ ID No. 46). The Apo-2L polypeptides may be encoded by the native nucleotide sequence shown in FIG. 24 (SEQ ID No. 45). Optionally, the codon which encodes residue Pro119 (FIG. 24; SEQ ID No. 45) may be "CCT" or "CCG". Optionally, the fragments or variants are biologically active and have at least about 80% amino acid sequence identity, or at least about 90% sequence identity, or at least 95%, 96%, 97%, 98%, or 99% sequence identity with any one of the above sequences. The definition encompasses substitutional variants of Apo-2 ligand in which at least one of its native amino acids are substituted by another amino acid such as an alanine residue. The definition also encompasses a native sequence Apo-2 ligand isolated from an Apo-2 ligand source or prepared by recombinant and/or synthetic methods. The Apo-2 ligand of the invention includes the polypeptides referred to as Apo-2 ligand or TRAIL disclosed in WO97/01633 published Jan. 16, 1997, WO97/25428 published Jul. 17, 1997, WO99/36535 published Jul. 22, 1999, WO 01/00832 published Jan. 4, 2001, WO02/09755 published Feb. 7, 2002, WO 00/75191 published Dec. 14, 2000, and U.S. Pat. No. 6,030,945 issued Feb. 29, 2000. The terms are used to refer generally to forms of the Apo-2 ligand which include monomer, dimer, trimer, hexamer or hight oligomer forms of the polypeptide. All numbering of amino acid residues referred to in the Apo-2L sequence use the numbering according to FIG. 24 (SEQ ID No. 46), unless specifically stated otherwise.

"Apo-2 ligand receptor" includes the receptors referred to in the art as "DR4" and "DR5." Pan et al. have described the TNF receptor family member referred to as "DR4" (Pan et al., Science, 276:111-113 (1997); see also WO98/32856 published Jul. 30, 1998; WO 99/37684 published Jul. 29, 1999; WO 00/73349 published Dec. 7, 2000; U.S. Pat. No. 6,433, 147 issued Aug. 13, 2002; U.S. Pat. No. 6,461,823 issued Oct. 8, 2002, and U.S. Pat. No. 6,342,383 issued Jan. 29, 2002). Sheridan et al., Science, 277:818-821 (1997) and Pan et al.,

*Science*, 277:815-818 (1997) described another receptor for Apo2L/TRAIL (see also, WO98/51793 published Nov. 19, 1998; WO98/41629 published Sep. 24, 1998). This receptor is referred to as DR5 (the receptor has also been alternatively referred to as Apo-2; TRAIL-R, TR6, Tango-63, hAPO8, TRICK2 or KILLER; Screaton et al., *Curr. Biol.*, 7:693-696 (1997); Walczak et al., *EMBO J.*, 16:5386-5387 (1997); Wu et al., *Nature Genetics*, 17:141-143 (1997); WO98/35986 published Aug. 20, 1998; EP870,827 published Oct. 14, 1998; WO98/46643 published Oct. 22, 1998; WO99/02653 published Jan. 21, 1999; WO99/09165 published Feb. 25, 1999; WO99/11791 published Mar. 11, 1999; US 2002/0072091 published Aug. 13, 2002; US 2002/0098550 published Dec. 7, 2001; U.S. Pat. No. 6,313,269 issued Dec. 6, 2001; US 2001/0010924 published Aug. 2, 2001; US 2003/01255540 published Jul. 3, 2003; US 2002/0160446 published Oct. 31, 2002, US 2002/0048785 published Apr. 25, 2002; U.S. Pat. No. 6,569,642 issued May 27, 2003, U.S. Pat. No. 6,072,047 issued Jun. 6, 2000, U.S. Pat. No. 6,642,358 issued Nov. 4, 2003). As described above, other receptors for Apo-2L include DcR1, DcR2, and OPG. The term "Apo-2L receptor" when used herein encompasses native sequence receptor and receptor variants. These terms encompass Apo-2L receptor expressed in a variety of mammals, including humans. Apo-2L receptor may be endogenously expressed as occurs naturally in a variety of human tissue lineages, or may be expressed by recombinant or synthetic methods. A "native sequence Apo-2L receptor" comprises a polypeptide having the same amino acid sequence as an Apo-2L receptor derived from nature. Thus, a native sequence Apo-2L receptor can have the amino acid sequence of naturally-occurring Apo-2L receptor from any mammal, including humans. Such native sequence Apo-2L receptor can be isolated from nature or can be produced by recombinant or synthetic means. The term "native sequence Apo-2L receptor" specifically encompasses naturally-occurring truncated or secreted forms of the receptor (e.g., a soluble form containing, for instance, an extracellular domain sequence), naturally-occurring variant forms (e.g., alternatively spliced forms) and naturally-occurring allelic variants. Receptor variants may include fragments or deletion mutants of the native sequence Apo-2L receptor. FIGS. 25A-C show the 411 amino acid sequence of human DR5 receptor, along with its nucleotide sequence (SEQ ID Nos. 47 and 48) as published in WO 98/51793 on Nov. 19, 1998. A transcriptional splice variant of human DR5 receptor is known in the art. This splice variant encodes the 440 amino acid sequence of human DR5 receptor as shown in FIGS. 26A-C, along with its nucleotide sequence (SEQ ID Nos. 49 and 50), and as published in WO 98/35986 on Aug. 20, 1998.

"Death receptor antibody" is used herein to refer generally to antibody or antibodies directed to a receptor in the tumor necrosis factor receptor superfamily and containing a death domain capable of signalling apoptosis, and such antibodies include DR5 antibody and DR4 antibody.

"DR5 receptor antibody", "DR5 antibody", or "anti-DR5 antibody" is used in a broad sense to refer to antibodies that bind to at least one form of a DR5 receptor or extracellular domain thereof. Optionally the DR5 antibody is fused or linked to a heterologous sequence or molecule. Preferably the heterologous sequence allows or assists the antibody to form higher order or oligomeric complexes. Optionally, the DR5 antibody binds to DR5 receptor but does not bind or cross-react with any additional Apo-2L receptor (e.g. DR4, DcR1, or DcR2). Optionally the antibody is an agonist of DR5 signalling activity.

Optionally, the DR5 antibody of the invention binds to a DR5 receptor at a concentration range of about 0.1 nM to about 20 mM as measured in a BIAcore binding assay. Optionally, the DR5 antibodies of the invention exhibit an IC50 value of about 0.6 nM to about 18 mM as measured in a BIAcore binding assay.

Purely for the purposes herein, the term "Apomab" refers to an agonist antibody which binds to DR5 and comprises the variable heavy and variable light amino acid sequences of SEQ ID Nos. 55 and 56. Preferably Apomab comprises the heavy and light chains of SEQ ID Nos. 51 and 52, respectively.

II. Production of Antibodies

Techniques for producing antibodies which can be formulated according to the present invention follow.

(I) Antigen Selection and Preparation

Preferably, the antigen to which the antibody binds is a biologically important glycoprotein and administration of the antibody to a mammal suffering from a disease or disorder can result in a therapeutic benefit in that mammal. However, antibodies directed against nonpolypeptide antigens (such as tumor-associated glycolipid antigens; see U.S. Pat. No. 5,091,178) are also contemplated.

Where the antigen is a polypeptide, it may be a transmembrane molecule (e.g. receptor) or ligand such as a growth factor. Exemplary antigens include molecules such as renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, 5, or -6 (NT-3, NT-4, NT-5, or NT-6), or a nerve growth factor such as NGF-b; platelet-derived growth factor (PDGF); fibroblast growth factor such as aFGF and bFGF; epidermal growth factor (EGF); transforming growth factor (TGF) such as TGF-alpha and TGF-beta, including TGF-b1, TGF-b2, TGF-b3, TGF-b4, or TGF-b5; a tumor necrosis factor (TNF) such as TNF-alpha or TNF-beta; insulin-like growth factor-I and -II (IGF-I and IGF-II); des(1-3)-IGF-I (brain IGF-I), insulin-like growth factor binding proteins; CD proteins such as CD3, CD4, CD8, CD19, CD20, CD22 and CD40; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1, IL-2, IL-3, IL-4, IL-5, IL-6, IL-7, IL-8, IL-9 and IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as HER2, HER3 or HER4 receptor; and fragments of any of the above-listed polypeptides.

Exemplary molecular targets for antibodies encompassed by the present invention include CD proteins such as CD3, CD4, CD8, CD19, CD20, CD22, CD34 and CD40; members of the ErbB receptor family such as the EGF receptor, HER2, HER3 or HER4 receptor; B cell surface antigens, such as CD20 or BR3; a member of the tumor necrosis receptor superfamily, including DR5; prostate stem cell antigen (PSCA); cell adhesion molecules such as LFA-1, Mac1, p150.95, VLA-4, ICAM-1, VCAM, alpha4/beta7 integrin, and alphav/beta3 integrin including either alpha or beta subunits thereof (e.g. anti-CD11a, anti-CD18 or anti-CD11b antibodies); growth factors such as VEGF as well as receptors therefor; tissue factor (TF); a tumor necrosis factor (TNF) such as TNF-alpha or TNF-beta, alpha interferon (alpha-IFN); an interleukin, such as IL-8; IgE; blood group antigens; flk2/flt3 receptor; obesity (OB) receptor; mp1 receptor; CTLA-4; protein C etc.

Soluble antigens or fragments thereof, optionally conjugated to other molecules, can be used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule. Other antigens and forms thereof useful for preparing antibodies will be apparent to those in the art.

For production of HER2 antibodies, the HER2 antigen to be used for production thereof may be, e.g., a soluble form of the extracellular domain of HER2 or a portion thereof, containing the desired epitope. Alternatively, cells expressing HER2 at their cell surface (e.g. NIH-3T3 cells transformed to overexpress HER2; or a carcinoma cell line such as SK-BR-3 cells, see Stancovski et al. *PNAS* (*USA*) 88:8691-8695 (1991)) can be used to generate antibodies.

(ii) Monoclonal Antibodies

Monoclonal antibodies are obtained from a population of substantially homogeneous antibodies, i.e., the individual antibodies comprising the population are identical and/or bind the same epitope, except for possible variants that may arise during production of the monoclonal antibody. Thus, the modifier "monoclonal" indicates the character of the antibody as not being a mixture of discrete antibodies.

For example, the monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); and Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional antibody purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., *Curr. Opinion in Immunol.*, 5:256-262 (1993) and Plückthun, *Immunol. Revs.*, 130: 151-188 (1992).

In a further embodiment, monoclonal antibodies or antibody fragments can be isolated from antibody phage libraries generated using the techniques described in McCafferty et al., *Nature*, 348:552-554 (1990). Clackson et al., *Nature*, 352: 624-628 (1991) and Marks et al., *J. Mol. Biol.*, 222:581-597 (1991) describe the isolation of murine and human antibodies, respectively, using phage libraries. Subsequent publications describe the production of high affinity (nM range)

human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.*, 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy chain and light chain constant domains in place of the homologous murine sequences (U.S. Pat. No. 4,816,567; and Morrison, et al., *Proc. Natl. Acad. Sci. USA*, 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

(iii) Humanized Antibodies

Methods for humanizing non-human antibodies have been described in the art. Preferably, a humanized antibody has one or more amino acid residues introduced into it from a source which is non-human. These non-human amino acid residues are often referred to as "import" residues, which are typically taken from an import" variable domain. Humanization can be essentially performed following the method of Winter and co-workers (Jones et al., *Nature*, 321:522-525 (1986); Riechmann et al., *Nature*, 332:323-327 (1988); Verhoeyen et al., *Science*, 239:1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework region (FR) for the humanized antibody (Sims et al., *J. Immunol.*, 151:2296 (1993); Chothia et al., *J. Mol. Biol.*, 196:901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

WO 01/00245 describes production of exemplary humanized HER2 antibodies which bind HER2 and block ligand activation of a HER receptor. The humanized antibody of particular interest herein blocks EGF, TGF-α and/or HRG mediated activation of MAPK essentially as effectively as murine monoclonal antibody 2C4 (or a Fab fragment thereof) and/or binds HER2 essentially as effectively as murine monoclonal antibody 2C4 (or a Fab fragment thereof). The humanized antibody herein may, for example, comprise nonhuman hypervariable region residues incorporated into a human variable heavy domain and may further comprise a framework region (FR) substitution at a position selected from the group consisting of 69H, 71H and 73H utilizing the variable domain numbering system set forth in Kabat et al., *Sequences of Proteins of Immunological Interest*, 5th Ed. Public Health Service, National Institutes of Health, Bethesda, Md. (1991). In one embodiment, the humanized antibody comprises FR substitutions at two or all of positions 69H, 71H and 73H.

An exemplary humanized antibody of interest herein comprises variable heavy domain complementarity determining residues GFTFTDYTMX, where X is preferably D or S (SEQ ID No. 7); DVNPNSGGSIYNQRFKG (SEQ ID No. 8); and/or NLGPSFYFDY (SEQ ID No. 9), optionally comprising amino acid modifications of those CDR residues, e.g. where the modifications essentially maintain or improve affinity of the antibody. For example, the antibody variant of interest may have from about one to about seven or about five amino acid substitutions in the above variable heavy CDR sequences. Such antibody variants may be prepared by affinity maturation, e.g., as described below. The most preferred humanized antibody comprises the variable heavy domain amino acid sequence in SEQ ID No. 4.

The humanized antibody may comprise variable light domain complementarity determining residues KASQD-VSIGVA (SEQ ID No. 10); SASYXXX, where the X as position 5 is preferably R or L, wherein the X at position 6 is preferably Y or E, and the X as position 7 is preferably T or S (SEQ ID No. 11); and/or QQYYIYPYT (SEQ ID No. 12), e.g. in addition to those variable heavy domain CDR residues in the preceding paragraph. Such humanized antibodies optionally comprise amino acid modifications of the above CDR residues, e.g. where the modifications essentially maintain or improve affinity of the antibody. For example, the antibody variant of interest may have from about one to about seven or about five amino acid substitutions in the above variable light CDR sequences. Such antibody variants may be prepared by affinity maturation, e.g., as described below. The most preferred humanized antibody comprises the variable light domain amino acid sequence in SEQ ID No. 3.

The present application also contemplates affinity matured antibodies which bind HER2 and block ligand activation of a HER receptor. The parent antibody may be a human antibody or a humanized antibody, e.g., one comprising the variable light and/or heavy sequences of SEQ ID Nos. 3 and 4, respectively (i.e. variant 574). The affinity matured antibody preferably binds to HER2 receptor with an affinity superior to that of murine 2C4 or variant 574 (e.g. from about two or about four fold, to about 100 fold or about 1000 fold improved affinity, e.g. as assessed using a HER2-extracellular domain (ECD) ELISA). Exemplary variable heavy CDR residues for substitution include H28, H30, H34, H35, H64, H96, H99, or combinations of two or more (e.g. two, three, four, five, six, or seven of these residues). Examples of variable light CDR residues for alteration include L28, L50, L53, L56, L91, L92, L93, L94, L96, L97 or combinations of two or more (e.g. two to three, four, five or up to about ten of these residues).

Various forms of the humanized antibody or affinity matured antibody are contemplated. For example, the humanized antibody or affinity matured antibody may be an antibody fragment, such as a Fab, which is optionally conjugated with one or more cytotoxic agent(s) in order to generate an immunoconjugate. Alternatively, the humanized antibody or affinity matured antibody may be an full length antibody, such as an full length IgG1 antibody.

(iv) Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255-258 (1993); Bruggermann et al., *Year in Immuno.*, 7:33 (1993); and U.S. Pat. Nos. 5,591,669, 5,589,369 and 5,545,807.

Alternatively, phage display technology (McCafferty et al., *Nature* 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g., Johnson, Kevin S, and Chiswell, David J., *Current Opinion in Structural Biology* 3:564-571 (1993). Several sources of V-gene segments can be used for phage display. Clackson et al., *Nature*, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

Human HER2 antibodies are described in U.S. Pat. No. 5,772,997 issued Jun. 30, 1998 and WO 97/00271 published Jan. 3, 1997.

(v) Antibody Fragments

Various techniques have been developed for the production of antibody fragments. Traditionally, these fragments were derived via proteolytic digestion of full length antibodies (see, e.g., Morimoto et al., *Journal of Biochemical and Biophysical Methods* 24:107-117 (1992); and Brennan et al., *Science,* 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10:163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. Nos. 5,571,894; and 5,587,458. The antibody fragment may also be a "linear antibody", e.g., as described in U.S. Pat. No. 5,641,870 for example. Such linear antibody fragments may be monospecific or bispecific.

(vi) Bispecific Antibodies

Bispecific antibodies are antibodies that have binding specificities for at least two different epitopes. Exemplary bispecific antibodies may bind to two different epitopes of the HER2 protein. Other such antibodies may combine a HER2 binding site with binding site(s) for EGFR, HER3 and/or HER4. Alternatively, a HER2 arm may be combined with an arm which binds to a triggering molecule on a leukocyte such as a T-cell receptor molecule (e.g. CD2 or CD3), or Fc receptors for IgG (FcγR), such as FcγRI (CD64), FcγRII (CD32) and FcγRIII (CD16) so as to focus cellular defense mechanisms to the HER2-expressing cell. Bispecific antibodies may also be used to localize cytotoxic agents to cells which express HER2. These antibodies possess a HER2-binding arm and an arm which binds the cytotoxic agent (e.g. saporin, anti-interferon-α, vinca alkaloid, ricin A chain, methotrexate or radioactive isotope hapten). Bispecific antibodies can be prepared as full length antibodies or antibody fragments (e.g. F(ab')$_2$ bispecific antibodies).

WO 96/16673 describes a bispecific HER2/FcγRIII antibody and U.S. Pat. No. 5,837,234 discloses a bispecific HER2/FcγRI antibody IDM1 (Osidem). A bispecific HER2/Fcα antibody is shown in WO98/02463. U.S. Pat. No. 5,821,337 teaches a bispecific HER2/CD3 antibody. MDX-210 is a bispecific HER2-FcγRIII Ab.

Methods for making bispecific antibodies are known in the art. Traditional production of full length bispecific antibodies is based on the coexpression of two immunoglobulin heavy chain-light chain pairs, where the two chains have different specificities (Millstein et al., *Nature,* 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.,* 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein full length antibodies are proteolytically cleaved to generate $F(ab')_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217-225 (1992) describe the production of a fully humanized bispecific antibody $F(ab')_2$ molecule. Each Fab' fragment was separately secreted from *E. coli* and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147: 60 (1991).

(vii) Other Amino Acid Sequence Modifications

Amino acid sequence modification(s) of the antibodies described herein are contemplated. For example, it may be desirable to improve the binding affinity and/or other biological properties of the antibody. Amino acid sequence variants of the Antibody are prepared by introducing appropriate nucleotide changes into the Antibody nucleic acid, or by peptide synthesis. Such modifications include, for example, deletions from, and/or insertions into and/or substitutions of, residues within the amino acid sequences of the Antibody. Any combination of deletion, insertion, and substitution is made to arrive at the final construct, provided that the final construct possesses the desired characteristics. The amino acid changes also may alter post-translational processes of the Antibody, such as changing the number or position of glycosylation sites.

A useful method for identification of certain residues or regions of the Antibody that are preferred locations for mutagenesis is called "alanine scanning mutagenesis" as described by Cunningham and Wells *Science,* 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed Antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include a Antibody with an N-terminal methionyl residue or the antibody fused to a cytotoxic polypeptide. Other insertional variants of the Antibody molecule include the fusion to the N- or C-terminus of the Antibody to an enzyme (e.g. for ADEPT) or a polypeptide which increases the serum half-life of the antibody.

Another type of variant is an amino acid substitution variant. These variants have at least one amino acid residue in the Antibody molecule replaced by a different residue. The sites of greatest interest for substitutional mutagenesis include the hypervariable regions, but FR or Fc region alterations are also contemplated. Conservative substitutions are shown in Table 1 under the heading of "preferred substitutions". If such substitutions result in a change in biological activity, then more substantial changes, denominated "exemplary substitutions" in Table 1, or as further described below in reference to amino acid classes, may be introduced and the products screened.

TABLE 1

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, in *Biochemistry*, second ed., pp. 73-75, Worth Publishers, New York (1975)):

(1) non-polar: Ala (A), Val (V), Leu (L), Ile (I), Pro (P), Phe (F), Trp (W), Met (M)
(2) uncharged polar: Gly (G), Ser (S), Thr (T), Cys (C), Tyr (Y), Asn (N), Gln (Q)
(3) acidic: Asp (D), Glu (E)
(4) basic: Lys (K), Arg (R), His(H)

Alternatively, naturally occurring residues may be divided into groups based on common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

Any cysteine residue not involved in maintaining the proper conformation of the Antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and its antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Where the antibody comprises an Fc region, the carbohydrate attached thereto may be altered. For example, antibodies with a mature carbohydrate structure that lacks fucose attached to an Fc region of the antibody are described in US Pat Appl No US 2003/0157108 A1, Presta, L. See also US 2004/0093621 A1 (Kyowa Hakko Kogyo Co., Ltd). Antibodies with a bisecting N-acetylglucosamine (GlcNAc) in the carbohydrate attached to an Fc region of the antibody are referenced in WO03/011878, Jean-Mairet et al. and U.S. Pat. No. 6,602,684, Umana et al. Antibodies with at least one galactose residue in the oligosaccharide attached to an Fc region of the antibody are reported in WO97/30087, Patel et al. See, also, WO98/58964 (Raju, S.) and WO99/22764 (Raju, S.) concerning antibodies with altered carbohydrate attached to the Fc region thereof. Antibody compositions comprising main species antibody with such carbohydrate structures attached to the Fc region are contemplated herein.

Nucleic acid molecules encoding amino acid sequence variants of the Antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

(viii) Screening for Antibodies with the Desired Properties

Techniques for generating antibodies have been described above. One may further select antibodies with certain biological characteristics, as desired.

To identify an antibody which blocks ligand activation of a HER receptor, the ability of the antibody to block HER ligand binding to cells expressing the HER receptor (e.g. in conjugation with another HER receptor with which the HER receptor of interest forms a HER hetero-oligomer) may be determined. For example, cells naturally expressing, or transfected to express, HER receptors of the HER hetero-oligomer may be incubated with the antibody and then exposed to labeled HER ligand. The ability of the HER2 antibody to block ligand binding to the HER receptor in the HER hetero-oligomer may then be evaluated.

For example, inhibition of HRG binding to MCF7 breast tumor cell lines by HER2 antibodies may be performed using monolayer MCF7 cultures on ice in a 24-well-plate format essentially as described in WO01/00245. HER2 monoclonal antibodies may be added to each well and incubated for 30 minutes. $^{125}$I-labeled rHRGβ1$_{177\text{-}224}$ (25 pm) may then be added, and the incubation may be continued for 4 to 16 hours. Dose response curves may be prepared and an IC$_{50}$ value may be calculated for the antibody of interest. In one embodiment, the antibody which blocks ligand activation of an HER receptor will have an IC$_{50}$ for inhibiting HRG binding to MCF7 cells in this assay of about 50 nM or less, more preferably 10 nM or less. Where the antibody is an antibody fragment such as a Fab fragment, the IC$_{50}$ for inhibiting HRG binding to MCF7 cells in this assay may, for example, be about 100 nM or less, more preferably 50 nM or less.

Alternatively, or additionally, the ability of the HER2 antibody to block HER ligand-stimulated tyrosine phosphorylation of a HER receptor present in a HER hetero-oligomer may be assessed. For example, cells endogenously expressing the HER receptors or transfected to expressed them may be incubated with the antibody and then assayed for HER ligand-dependent tyrosine phosphorylation activity using an anti-phosphotyrosine monoclonal (which is optionally conjugated with a detectable label). The kinase receptor activation assay described in U.S. Pat. No. 5,766,863 is also available for determining HER receptor activation and blocking of that activity by an antibody.

In one embodiment, one may screen for an antibody which inhibits HRG stimulation of p180 tyrosine phosphorylation in MCF7 cells essentially as described in WO01/00245. For example, the MCF7 cells may be plated in 24-well plates and monoclonal antibodies to HER2 may be added to each well and incubated for 30 minutes at room temperature; then rHRGβ1$_{177\text{-}244}$ may be added to each well to a final concentration of 0.2 nM, and the incubation may be continued for 8 minutes. Media may be aspirated from each well, and reactions may be stopped by the addition of 100 μl of SDS sample buffer (5% SDS, 25 mM DTT, and 25 mM Tris-HCl, pH 6.8). Each sample (25 μl) may be electrophoresed on a 4-12% gradient gel (Novex) and then electrophoretically transferred to polyvinylidene difluoride membrane. Antiphosphotyrosine (at 1 μg/ml) immunoblots may be developed, and the intensity of the predominant reactive band at M$_r$ ~180,000 may be quantified by reflectance densitometry. The antibody selected will preferably significantly inhibit HRG stimulation of p180 tyrosine phosphorylation to about 0-35% of control in this assay. A dose-response curve for inhibition of HRG stimulation of p180 tyrosine phosphorylation as determined by reflectance densitometry may be prepared and an IC$_{50}$ for the antibody of interest may be calculated. In one embodiment, the antibody which blocks ligand activation of a HER receptor will have an IC$_{50}$ for inhibiting HRG stimulation of p180 tyrosine phosphorylation in this assay of about 50 nM or less, more preferably 10 nM or less. Where the antibody is an antibody fragment such as a Fab fragment, the IC$_{50}$ for inhibiting HRG stimulation of p180 tyrosine phosphorylation in this assay may, for example, be about 100 nM or less, more preferably 50 nM or less.

One may also assess the growth inhibitory effects of the antibody on MDA-MB-175 cells, e.g, essentially as described in Schaefer et al. Oncogene 15:1385-1394 (1997). According to this assay, MDA-MB-175 cells may treated with a HER2 monoclonal antibody (10 μg/mL) for 4 days and stained with crystal violet. Incubation with a HER2 antibody may show a growth inhibitory effect on this cell line similar to that displayed by monoclonal antibody 2C4. In a further embodiment, exogenous HRG will not significantly reverse this inhibition. Preferably, the antibody will be able to inhibit cell proliferation of MDA-MB-175 cells to a greater extent than monoclonal antibody 4D5 (and optionally to a greater extent than monoclonal antibody 7F3), both in the presence and absence of exogenous HRG.

In one embodiment, the HER2 antibody of interest may block heregulin dependent association of HER2 with HER3 in both MCF7 and SK-BR-3 cells as determined in a co-immunoprecipitation experiment such as that described in WO01/00245 substantially more effectively than monoclonal antibody 4D5, and preferably substantially more effectively than monoclonal antibody 7F3.

To identify growth inhibitory HER2 antibodies, one may screen for antibodies which inhibit the growth of cancer cells which overexpress HER2. In one embodiment, the growth inhibitory antibody of choice is able to inhibit growth of SK-BR-3 cells in cell culture by about 20-100% and preferably by about 50-100% at an antibody concentration of about 0.5 to 30 µg/ml. To identify such antibodies, the SK-BR-3 assay described in U.S. Pat. No. 5,677,171 can be performed. According to this assay, SK-BR-3 cells are grown in a 1:1 mixture of F12 and DMEM medium supplemented with 10% fetal bovine serum, glutamine and penicillin streptomycin. The SK-BR-3 cells are plated at 20,000 cells in a 35 mm cell culture dish (2 mls/35 mm dish). 0.5 to 30 µg/ml of the HER2 antibody is added per dish. After six days, the number of cells, compared to untreated cells are counted using an electronic COULTER™ cell counter. Those antibodies which inhibit growth of the SK-BR-3 cells by about 20-100% or about 50-100% may be selected as growth inhibitory antibodies. See U.S. Pat. No. 5,677,171 for assays for screening for growth inhibitory antibodies, such as 4D5 and 3E8.

In order to select for HER2 antibodies which induce apoptosis, an annexin binding assay using BT474 cells is available. The BT474 cells are cultured and seeded in dishes as discussed in the preceding paragraph. The medium is then removed and replaced with fresh medium alone or medium containing 10 µg/ml of the monoclonal antibody. Following a three day incubation period, monolayers are washed with PBS and detached by trypsinization. Cells are then centrifuged, resuspended in $Ca^{2+}$ binding buffer and aliquoted into tubes as discussed above for the cell death assay. Tubes then receive labeled annexin (e.g. annexin V-FTIC) (1 µg/ml). Samples may be analyzed using a FACSCAN™ flow cytometer and FACSCONVERT™ CellQuest software (Becton Dickinson). Those antibodies which induce statistically significant levels of annexin binding relative to control are selected as apoptosis-inducing antibodies. In addition to the annexin binding assay, a DNA staining assay using BT474 cells is available. In order to perform this assay, BT474 cells which have been treated with the antibody of interest as described in the preceding two paragraphs are incubated with 9 µg/ml HOECHST 33342™ for 2 hr at 37° C., then analyzed on an EPICS ELITE™ flow cytometer (Coulter Corporation) using MODFIT LT™ software (Verity Software House). Antibodies which induce a change in the percentage of apoptotic cells which is 2 fold or greater (and preferably 3 fold or greater) than untreated cells (up to 100% apoptotic cells) may be selected as pro-apoptotic antibodies using this assay. See WO98/17797 for assays for screening for HER2 antibodies which induce apoptosis, such as 7C2 and 7F3.

To screen for antibodies which bind to an epitope on HER2 bound by an antibody of interest, a routine cross-blocking assay such as that described in *Antibodies, A Laboratory Manual*, Cold Spring Harbor Laboratory, Ed Harlow and David Lane (1988), can be performed to assess whether the antibody cross-blocks binding of an antibody, such as 2C4 or Pertuzumab, to HER2. Alternatively, or additionally, epitope mapping can be performed by methods known in the art and/or one can study the antibody-HER2 structure (Franklin et al. *Cancer Cell* 5:317-328 (2004)) to see what domain(s) of HER2 is/are bound by the antibody.

(ix) Immunoconjugates

The invention also pertains to immunoconjugates comprising an antibody conjugated to a cytotoxic agent such as a chemotherapeutic agent, toxin (e.g. a small molecule toxin or an enzymatically active toxin of bacterial, fungal, plant or animal origin, including fragments and/or variants thereof), or a radioactive isotope (i.e., a radioconjugate).

Chemotherapeutic agents useful in the generation of such immunoconjugates have been described above. Conjugates of an antibody and one or more small molecule toxins, such as a calicheamicin, a maytansine (U.S. Pat. No. 5,208,020), a trichothene, and CC1065 are also contemplated herein.

In one preferred embodiment of the invention, the antibody is conjugated to one or more maytansine molecules (e.g. about 1 to about 10 maytansine molecules per antibody molecule). Maytansine may, for example, be converted to May-SS-Me which may be reduced to May-SH3 and reacted with modified antibody (Chari et al. *Cancer Research* 52: 127-131 (1992)) to generate a maytansinoid-antibody immunoconjugate.

Another immunoconjugate of interest comprises a HER2 antibody conjugated to one or more calicheamicin molecules. The calicheamicin family of antibiotics are capable of producing double-stranded DNA breaks at sub-picomolar concentrations. Structural analogues of calicheamicin which may be used include, but are not limited to, $\gamma_1^1$, $\alpha_2^1$, $\alpha_3^1$, N-acetyl-$\gamma_1^1$, PSAG and $\theta^1_1$ (Hinman et al. *Cancer Research* 53: 3336-3342 (1993) and Lode et al. *Cancer Research* 58: 2925-2928 (1998)). See, also, U.S. Pat. Nos. 5,714,586; 5,712,374; 5,264,586; and 5,773,001 expressly incorporated herein by reference.

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g. a ribonuclease or a DNA endonuclease such as a deoxyribonuclease; DNase).

A variety of radioactive isotopes are available for the production of radioconjugated HER2 antibodies. Examples include $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu.

Conjugates of the antibody and cytotoxic agent may be made using a variety of bifunctional protein coupling agents such as N-succinimidyl-3-(2-pyridyldithiol) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, dimethyl linker or disulfide-containing linker (Chari et al. *Cancer Research* 52: 127-131 (1992)) may be used.

Alternatively, a fusion protein comprising the HER2 antibody and cytotoxic agent may be made, e.g. by recombinant techniques or peptide synthesis.

In yet another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

(x) Other Antibody Modifications

Other modifications of the antibody are contemplated herein. For example, the antibody may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences,* 16th edition, Oslo, A., Ed., (1980).

It may be desirable to modify the antibody of the invention with respect to effector function, e.g. so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al. *Cancer Research* 53:2560-2565 (1993). Alternatively, an antibody can be engineered which has dual Fc regions and may thereby have enhanced complement lysis and ADCC capabilities. See Stevenson et al. *Anti-Cancer Drug Design* 3:219-230 (1989).

WO00/42072 (Presta, L.) describes antibodies with improved ADCC function in the presence of human effector cells, where the antibodies comprise amino acid substitutions in the Fc region thereof. Preferably, the antibody with improved ADCC comprises substitutions at positions 298, 333, and/or 334 of the Fc region. Preferably the altered Fc region is a human IgG1 Fc region comprising or consisting of substitutions at one, two or three of these positions.

Antibodies with altered C1q binding and/or complement dependent cytotoxicity (CDC) are described in WO99/51642, U.S. Pat. No. 6,194,551B1, U.S. Pat. No. 6,242,195B1, U.S. Pat. No. 6,528,624B1 and U.S. Pat. No. 6,538,124 (Idusogie et al.). The antibodies comprise an amino acid substitution at one or more of amino acid positions 270, 322, 326, 327, 329, 313, 333 and/or 334 of the Fc region thereof.

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule. Antibodies with substitutions in an Fc region thereof and increased serum half-lives are also described in WO00/42072 (Presta, L.).

Engineered antibodies with three or more (preferably four) functional antigen binding sites are also contemplated (US Appln No. US2002/0004587 A1, Miller et al.).

The HER2 antibodies disclosed herein may also be formulated as immunoliposomes. Liposomes containing the antibody are prepared by methods known in the art, such as described in Epstein et al., *Proc. Natl. Acad. Sci. USA,* 82:3688 (1985); Hwang et al., *Proc. Natl. Acad. Sci. USA,* 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine PEG-PE). Liposomes are extruded through filters of defined pore size to yield liposomes with the desired diameter. Fab' fragments of the antibody of the present invention can be conjugated to the liposomes as described in Martin et al. *J. Biol. Chem.* 257: 286-288 (1982) via a disulfide interchange reaction. A chemotherapeutic agent is optionally contained within the liposome. See Gabizon et al. *J. National Cancer Inst.* 81(19)1484 (1989).

(ix) Exemplary Antibodies

Exemplary antibodies which can be formulated according to the present invention include, but are not limited to the following:

anti-ErbB antibodies, including anti-HER2 antibodies, such as those described in more detail herein; antibodies that bind to a B-cell surface marker, such as CD19, CD20 (for example Rituximab(RITUXAN®) and humanized 2H7), CD22, CD40 or BR3;

antibodies that bind to IgE, including Omalizumab (XOLAIR®) commercially available from Genentech, E26 (FIGS. 17A-B herein), HAE1 (FIGS. 17A-B herein), IgE antibody with an amino acid substitution at position 265 of an Fc region thereof (US 2004/0191244 A1), Hu-901 (FIGS. 17A-B herein), an IgE antibody as in WO2004/070011, or an antibody (including antibody fragments and full length antibodies) comprising the variable domains of any of those IgE antibodies. See, also, Presta et al., *J. Immunol.* 151:2623-2632 (1993); International Publication No. WO 95/19181; U.S. Pat. No. 5,714,338, issued Feb. 3, 1998; U.S. Pat. No. 5,091,313, issued Feb. 25, 1992; WO 93/04173 published Mar. 4, 1993; WO 99/01556 published Jan. 14, 1999; and U.S. Pat. No. 5,714,338;

antibodies that bind to vascular endothelial growth factor (VEGF) or a receptor thereof, including Bevacizumab (AVASTIN™), commercially available from Genentech, and Ranibizumab (LUCENTIS™); anti-IL-8 antibodies (St John et al., *Chest,* 103:932 (1993), and International Publication No. WO 95/23865);

anti-PSCA antibodies (WO01/40309);

anti-CD40 antibodies, including S2C6 and humanized variants thereof (WO00/75348);

anti-CD11a antibodies, including efalizumab (RAPTIVA®) (U.S. Pat. No. 5,622,700, WO 98/23761, Steppe et al., *Transplant Intl.* 4:3-7 (1991), and Hourmant et al., *Transplantation* 58:377-380 (1994)); anti-CD18 antibodies (U.S. Pat. No. 5,622,700, issued Apr. 22, 1997, or as in WO 97/26912, published Jul. 31, 1997);

anti-Apo-2 receptor antibody (WO 98/51793 published Nov. 19, 1998);

anti-TNF-alpha antibodies including cA2 (REMICADE®), CDP571 and MAK-195 (See, U.S. Pat. No. 5,672,347 issued Sep. 30, 1997, Lorenz et al. *J. Immunol.* 156(4): 1646-1653 (1996), and Dhainaut et al. *Crit. Care Med.* 23(9):1461-1469 (1995));

anti-Tissue Factor (TF) (European Patent No. 0 420 937 B1 granted Nov. 9, 1994);
anti-human α4β7 integrin (WO 98/06248 published Feb. 19, 1998);
anti-EGFR antibodies, including chimerized or humanized 225 antibody as in WO 96/40210 published Dec. 19, 1996;
anti-CD3 antibodies, such as OKT3 (U.S. Pat. No. 4,515,893 issued May 7, 1985);
anti-CD25 or anti-tac antibodies such as CHI-621 (SIMULECT®) and (ZENAPAX®) (See U.S. Pat. No. 5,693,762 issued Dec. 2, 1997);
anti-CD4 antibodies such as the cM-7412 antibody (Choy et al. *Arthritis Rheum* 39(1):52-56 (1996));
anti-CD52 antibodies such as CAMPATH-1H (Riechmann et al. Nature 332:323-337 (1988);
anti-Fc receptor antibodies such as the M22 antibody directed against FcγRI as in Graziano et al. *J. Immunol.* 155(10): 4996-5002 (1995);
anti-carcinoembryonic antigen (CEA) antibodies such as hMN-14 (Sharkey et al. *Cancer Res.* 55(23Suppl): 5935s-5945s (1995);
antibodies directed against breast epithelial cells including huBrE-3, hu-Mc 3 and CHL6 (Ceriani et al. *Cancer Res.* 55(23): 5852s-5856s (1995); and Richman et al. *Cancer Res.* 55(23 Supp): 5916s-5920s (1995));
antibodies that bind to colon carcinoma cells such as C242 (Litton et al. *Eur J. Immunol.* 26(1):1-9 (1996));
anti-CD38 antibodies, e.g. AT 13/5 (Ellis et al. *J. Immunol.* 155(2):925-937 (1995));
anti-CD33 antibodies such as Hu M195 (Jurcic et al. *Cancer Res* 55(23 Suppl):5908s-5910s (1995) and CMA-676 or CDP771;
anti-CD22 antibodies such as LL2 or LymphoCide (Juweid et al. *Cancer Res* 55(23 Suppl):5899s-5907s (1995);
anti-EpCAM antibodies such as 17-1A (PANOREX®);
anti-GpIIb/IIIa antibodies such as abciximab or c7E3 Fab (REOPRO®);
anti-RSV antibodies such as MEDI-493 (SYNAGIS®);
anti-CMV antibodies such as PROTOVIR®;
anti-HIV antibodies such as PRO542;
anti-hepatitis antibodies such as the anti-Hep B antibody OSTAVIR®;
anti-CA 125 antibody OvaRex;
anti-idiotypic GD3 epitope antibody BEC2;
anti-αvβ3 antibody VITAXIN®;
anti-human renal cell carcinoma antibody such as ch-G250; ING-1;
anti-human 17-1A antibody (3622W94);
anti-human colorectal tumor antibody (A33);
anti-human melanoma antibody R24 directed against GD3 ganglioside;
anti-human squamous-cell carcinoma (SF-25); and
anti-human leukocyte antigen (HLA) antibodies such as Smart ID10 and the anti-HLA DR antibody Oncolym (Lym-1).

(xi) Antibody Variant Compositions

The present invention, in at least one aspect, concerns formulations comprising a composition which comprises a mixture of a main species antibody and one or more variants thereof. Where the main species antibody binds HER2, preferably the HER2 antibody (either or both of the main species HER2 antibody and antibody variant thereof) is one which binds to Domain II of HER2, inhibits HER dimerization more effectively than Trastuzamab, and/or binds to a heterodimeric binding site of HER2. The preferred embodiment herein of the main species antibody is one comprising the variable light and variable heavy amino acid sequences in SEQ ID Nos. 3 and 4, and most preferably comprising a light chain amino acid sequence selected from SEQ ID No. 15 and 23, and a heavy chain amino acid sequence selected from SEQ ID No. 16 and 24.

In one embodiment, the formulated HER2 antibody composition comprises a mixture of the main species HER2 antibody and an amino acid sequence variant thereof comprising an amino-terminal leader extension. Preferably, the amino-terminal leader extension is on a light chain of the antibody variant (e.g. on one or two light chains of the antibody variant). The main species HER2 antibody or the antibody variant may be an full length antibody or antibody fragment (e.g. Fab of F(ab')2 fragments), but preferably both are full length antibodies. The antibody variant herein may comprise an amino-terminal leader extension on any one or more of the heavy or light chains thereof. Preferably, the amino-terminal leader extension is on one or two light chains of the antibody. The amino-terminal leader extension preferably comprises or consists of VHS-. Presence of the amino-terminal leader extension in the composition can be detected by various analytical techniques including, but not limited to, N-terminal sequence analysis, assay for charge heterogeneity (for instance, cation exchange chromatography or capillary zone electrophoresis), mass spectrometry, etc. The amount of the antibody variant in the composition generally ranges from an amount that constitutes the detection limit of any assay (preferably N-terminal sequence analysis) used to detect the variant to an amount less than the amount of the main species antibody. Generally, about 20% or less (e.g. from about 1% to about 15%, for instance from 5% to about 15%) of the antibody molecules in the composition comprise an amino-terminal leader extension. Such percentage amounts are preferably determined using quantitative N-terminal sequence analysis or cation exchange analysis (preferably using a high-resolution, weak cation-exchange column, such as a PROPAC WCX-10™ cation exchange column). Aside from the amino-terminal leader extension variant, further amino acid sequence alterations of the main species antibody and/or variant are contemplated, including but not limited to an antibody comprising a C-terminal lysine residue on one or both heavy chains thereof, a deamidated antibody variant, etc.

Moreover, the main species antibody or variant may further comprise glycosylation variations, non-limiting examples of which include HER2 antibody comprising a G1 or G2 oligosaccharide structure attached to the Fc region thereof, HER2 antibody comprising a carbohydrate moiety attached to a light chain thereof (e.g. one or two carbohydrate moieties attached to one or two light chains of the antibody), HER2 antibody comprising a non-glycosylated heavy chain.

III. Preparation of the Formulation

The present invention provides, in a first aspect, a stable pharmaceutical formulation comprising a monoclonal antibody, preferably a full length human or humanized IgG1 antibody, in histidine-acetate buffer, pH 5.5 to 6.5, preferably pH 5.8 to 6.2. However, the antibody in the formulation may be an antibody fragment comprising an antigen-binding region, such as a Fab or F(ab')2 fragment.

In another embodiment, the invention concerns a pharmaceutical formulation comprising, or consisting essentially of, a full length IgG1 antibody susceptible to deamidation or aggregation in an amount from about 10 mg/mL to about 250 mg/mL; histidine-acetate buffer, pH 5.5 to 6.5; saccharide selected from the group consisting of trehalose and sucrose, in an amount from about 60 mM to about 250 mM; and polysorbate 20 in an amount from about 0.01% to about 0.1%.

In yet a further embodiment, the invention provides a pharmaceutical formulation comprising an antibody that binds to domain II of HER2 in a histidine buffer at a pH from about 5.5 to about 6.5, a saccharide and a surfactant. For example, the formulation may comprise Pertuzumab in an amount from about 20 mg/mL to about 40 mg/mL, histidine-acetate buffer, sucrose, and polysorbate 20, wherein the pH of the formulation is from about 5.5 to about 6.5

In another aspect, the invention provides a pharmaceutical formulation comprising a DR5 antibody in a histidine buffer at a pH from about 5.5 to about 6.5, a saccharide, and a surfactant. Such a formulation may, for example, comprise, Apomab in an amount from about 10 mg/mL to about 30 mg/mL, histidine-acetate buffer, trehalose, and polysorbate 20, wherein the pH of the formulation is from about 5.5 to about 6.5.

The formulation is especially useful for antibodies that are susceptible to deamidation and/or aggregation and/or fragmentation, in that the buffer retards deamidation and/or aggregation and/or fragmentation of the antibody formulated therein. In addition, unlike other histidine buffers prepared using HCl, the histidine-acetate buffer lacks the chloride ion which was found to be beneficial herein in that this buffer when combined with saccharide had the same protective effect on antibody as polysorbate 20, and was stable and compatible with storage in stainless steel tanks. Thus, in addition to the formulation per se comprising the antibody susceptible to deamidation, aggregation and/or fragmentation, the invention provides a method for reducing deamidation, aggregation and/or fragmentation of a therapeutic monoclonal antibody (for example, relative to a composition at a different pH or in a different buffer), comprising formulating the antibody in a histidine-acetate buffer, pH 5.5 to 6.5. In this embodiment, one may determine or measure deamidation, aggregation and/or fragmentation before and after the antibody is formulated, with the formulated antibody demonstrating acceptable deamidation, aggregation and/or fragmentation in the formulation and upon storage thereof.

The antibody in the formulation may bind an antigen including but not limited to: HER2, CD20, IgE, DR5, BR3 and VEGF.

Where the formulated antibody binds HER2, it preferably is one which binds to Domain II of HER2, inhibits HER dimerization more effectively than Trastuzumab, and/or binds to a heterodimeric binding site of HER2. The preferred embodiment herein of a formulated HER2 antibody is one comprising the variable light and variable heavy amino acid sequences in SEQ ID Nos. 3 and 4, and most preferably comprising the light chain and heavy chain amino acid sequences in SEQ ID Nos. 15 and 16 (Pertuzumab).

Examples of CD20 antibodies which can be formulated herein include: "C2B8" which is now called "Rituximab" ("RITUXAN®") commercially available from Genentech (see also U.S. Pat. No. 5,736,137, expressly incorporated herein by reference); the yttrium-[90]-labeled 2B8 murine antibody designated "Y2B8" or "Ibritumomab Tiuxetan" ZEVALIN® commercially available from Biogen-Idec (see also U.S. Pat. No. 5,736,137, expressly incorporated herein by reference); murine IgG2a "B1," also called "Tositumomab," optionally labeled with $^{131}$I to generate the "131I-B1" antibody (iodine I131 tositumomab, BEXXAR™) (U.S. Pat. No. 5,595,721, expressly incorporated herein by reference); murine monoclonal antibody "1F5" (Press et al. *Blood* 69(2): 584-591 (1987) and variants thereof including "framework patched" or humanized 1F5 (WO03/002607, Leung, S.); ATCC deposit HB-96450); murine 2H7 and chimeric 2H7 antibody (Clark et al. *PNAS* 82: 1766-1770 (1985); U.S. Pat. No. 5,500,362, expressly incorporated herein by reference); humanized 2H7; huMax-CD20 (WO 04/035607, Genmab, Denmark); AME-133 (Applied Molecular Evolution); A20 antibody or variants thereof such as chimeric or humanized A20 antibody (cA20, hA20, respectively) (US 2003/0219433, Immunomedics); and monoclonal antibodies L27, G28-2, 93-1B3, B-C1 or NU-B2 available from the International Leukocyte Typing Workshop (Valentine et al., In: Leukocyte Typing III (McMichael, Ed., p. 440, Oxford University Press (1987)).

In the preferred embodiment of a formulated CD20 antibody, the CD20 antibody is a humanized 2H7 antibody. Preferred humanized 2H7 antibodies herein are 2H7v16 and 2H7v511. The humanized 2H7v16 may be an intact antibody or antibody fragment comprising the variable light and variable heavy sequences in FIGS. 18A-B (SEQ ID Nos. 26 and 29). Where the humanized 2H7v16 antibody is a full length antibody, preferably it comprises the light and heavy chain amino acid sequences with SEQ ID Nos. 63 and 65.

Where the antibody binds VEGF, it preferably comprises the variable domain sequences as depicted in FIG. 19. The most preferred anti-VEGF antibody is full length humanized IgG1 antibody, Bevacizumab (AVASTIN™), commercially available from Genentech.

Where the formulated antibody binds IgE, it is preferably selected from the group consisting of: E25, Omalizumab (XOLAIR®) commercially available from Genentech (see also FIGS. 17A-B), E26 (FIGS. 17A-B herein), HAE1 (FIGS. 17A-B herein), IgE antibody with an amino acid substitution at position 265 of an Fc region thereof (US 2004/0191244 A1), Hu-901 (FIGS. 17A-B herein), an IgE antibody as in WO2004/070011, or an antibody (including antibody fragments and full length antibodies) comprising the variable domains of any of those IgE antibodies.

Where the antibody binds to a receptor in the tumor necrosis factor (TNF) superfamily or to a death receptor, it preferably binds to DR5, and preferably is an agonist antibody. Publications in this area include Sheridan et al., *Science*, 277:818-821 (1997), Pan et al., *Science*, 277:815-818 (1997), WO98/51793 published Nov. 19, 1998; WO98/41629 published Sep. 24, 1998; Screaton et al., *Curr. Biol.*, 7:693-696 (1997); Walczak et al., *EMBO J.*, 16:5386-5387 (1997); Wu et al., *Nature Genetics*, 17:141-143 (1997); WO98/35986 published Aug. 20, 1998; EP870,827 published Oct. 14, 1998; WO98/46643 published Oct. 22, 1998; WO99/02653 published Jan. 21, 1999; WO99/09165 published Feb. 25, 1999; WO99/11791 published Mar. 11, 1999; US 2002/0072091 published Aug. 13, 2002; US 2002/0098550 published Dec. 7, 2001; U.S. Pat. No. 6,313,269 issued Dec. 6, 2001; US 2001/0010924 published Aug. 2, 2001; US 2003/01255540 published Jul. 3, 2003; US 2002/0160446 published Oct. 31, 2002, US 2002/0048785 published Apr. 25, 2002; U.S. Pat. No. 6,342,369 issued February, 2002; U.S. Pat. No. 6,569, 642 issued May 27, 2003, U.S. Pat. No. 6,072,047 issued Jun. 6, 2000, U.S. Pat. No. 6,642,358 issued Nov. 4, 2003; U.S. Pat. No. 6,743,625 issued Jun. 1, 2004. The most preferred DR5 antibody is Apomab.

Each of the formulations noted above comprises a buffer, preferably a histidine buffer, and most preferably a histidine-acetate buffer with a pH of 5.5 to 6.5, preferably 5.8 to 6.2, for example approximately 6.0. The concentration of the buffer is dictated, at least in part, by the desired pH. Exemplary concentrations for the buffer are in the range from about 1 mM to about 200 mM, preferably from about 10 mM to about 40 mM, most preferably about 20 mM.

The antibody concentration in the formulation is preferably in the range from about 10 mg/mL to about 250 mg/mL. The antibody concentration may be determined based on the intended use and mode of administration of the formulation.

For example, where the formulation is for IV administration (e.g. a HER2 antibody), the antibody concentration in the formulation is preferably from about 20 mg/mL to about 40 mg/mL. In the exemplified Pertuzumab formulation intended for intravenous (IV) administration, the antibody concentration was from about 20 mg/mL to about 40 mg/mL, most preferably about 30 mg/mL.

Where the antibody is for SQ or IM administration (e.g. for an anti-IgE antibody) higher concentrations of the antibody may be desired. Such substantially high antibody concentrations may be from about 50 mg/mL to about 250 mg/mL, or from about 80 mg/mL to about 250 mg/mL, or from about 100 mg/mL to about 200 mg/mL.

Where the formulation comprises a DR5 antibody, such as Apomab, exemplary antibody concentrations are from about 10 mg/mL to about 30 mg/mL, for example about 20 mg/mL DR5 antibody; such formulation being useful for intravenous administration.

The formulation for administration is preferably an aqueous formulation (not lyophilized) and has not been subjected to prior lyophilization. While the formulation may be lyophilized, preferably it is not. However, freezing of the aqueous formulation, without simultaneous drying that occurs during freeze-drying, is specifically contemplated herein, facilitating longer term storage thereof, for instance in a stainless steel tank.

The formulation preferably further comprises a saccharide, most preferably a disaccharide, such as trehalose or sucrose. The saccharide is generally included in an amount which reduces soluble aggregate formation, such as that which occurs upon freeze/thaw. Exemplary saccharide concentrations are in the range from about 10 mM to about 1M, for example from about 60 mM to about 250 mM, and most preferably about 120 mM for a HER2 antibody formulation, and about 240 mM for a DR5 antibody formulation.

While it was found herein that a formulation comprising histidine-acetate buffer and saccharide was stable, the formulation optionally further comprises surfactant, such as polysorbate, most preferably polysorbate 20. The surfactant is generally included in an amount which reduces insoluble aggregate formation (such as that which occurs upon shaking or shipping). The surfactant concentration is preferably from about 0.0001% to about 1.0%, most preferably from about 0.01% to about 0.1%, for example about 0.02%.

Optionally, the formulation does not contain a tonicifying amount of a salt such as sodium chloride.

The formulation is generally sterile, and this can be achieved according to the procedures known to the skilled person for generating sterile pharmaceutical formulations suitable for administration to human subjects, including filtration through sterile filtration membranes, prior to, or following, preparation of the formulation.

Moreover, the formulation is desirably one which has been demonstrated to be stable upon storage. Various stability assays are available to the skilled practitioner for confirming the stability of the formulation. For example, the formulation may be one which is found to be stable upon storage: at about 40° C. for at least 4 weeks; at about 5° C. or about 15° C. for at least 3 months or at least 1 year; and/or about −20° C. for at least 3 months. Stability can be tested by evaluating physical stability, chemical stability, and/or biological activity of the antibody in the formulation around the time of formulation as well as following storage at the noted temperatures. Physical and/or stability can be evaluated qualitatively and/or quantitatively in a variety of different ways, including evaluation of aggregate formation (for example using size exclusion chromatography, by measuring turbidity, and/or by visual inspection); by assessing charge heterogeneity using cation exchange chromatography or capillary zone electrophoresis; amino-terminal or carboxy-terminal sequence analysis; mass spectrometric analysis; SDS-PAGE analysis to compare reduced and intact antibody; peptide map (for example tryptic or LYS-C) analysis; evaluating biological activity or antigen binding function of the antibody; etc. Instability may result in aggregation, deamidation (e.g. Asn deamidation), oxidation (e.g. Met oxidation), isomerization (e.g. Asp isomeriation), clipping/hydrolysis/fragmentation (e.g. hinge region fragmentation), succinimide formation, unpaired cysteine(s), N-terminal extension, C-terminal processing, glycosylation differences, etc. Biological activity or antigen binding function can be evaluated using various techniques available to the skilled practitioner.

As noted above, freezing of the formulation is specifically contemplated herein. Hence, the formulation can be tested for stability upon freezing and thawing.

According, the invention also provides a method of making a pharmaceutical formulation comprising preparing the formulation as described herein, and evaluating physical stability, chemical stability, or biological activity of the monoclonal antibody in the formulation.

In the preferred embodiment, the formulation is provided inside a vial with a stopper pierceable by a syringe, preferably in aqueous form. The vial is desirably stored at about 2-8° C. until it is administered to a subject in need thereof. The vial may for example be a 20 cc vial (for example for a 420 mg dose) or 50 cc vial (for example for a 1050 mg dose). For a DR5 antibody, such as Apomab, the formulation may be provided in a 5 cc glass vial (e.g. 5.5 ml fill).

In another embodiment, the formulation is provided inside a stainless steel tank. The formulation in the stainless steel tank is optionally frozen and not freeze-dried.

One or more other pharmaceutically acceptable carriers, excipients or stabilizers such as those described in *Remington's Pharmaceutical Sciences* 16th edition, Osol, A. Ed. (1980) may be included in the formulation provided that they do not adversely affect the desired characteristics of the formulation. Acceptable carriers, excipients or stabilizers are nontoxic to recipients at the dosages and concentrations employed and include; additional buffering agents; co-solvents; antioxidants including ascorbic acid and methionine; chelating agents such as EDTA; metal complexes (e.g. Zn-protein complexes); biodegradable polymers such as polyesters; preservatives; and/or salt-forming counterions such as sodium.

IV. Treatment with the Antibody Formulation

In one embodiment, the invention provides a method of treating a disease or disorder in a subject comprising administering the formulation described herein to a subject in an amount effective to treat the disease or disorder.

Where the antibody in the formulation binds to HER2, it is preferably used to treat cancer. The cancer will generally comprise HER2-expressing cells, such that the HER2 antibody herein is able to bind to the cancer cells. Thus, the invention in this embodiment concerns a method for treating HER2-expressing cancer in a subject, comprising administering the HER2 antibody pharmaceutical formulation to the subject in an amount effective to treat the cancer. Various cancers that can be treated with the composition are listed in the definitions section above.

It is also contemplated that the HER2 antibody formulation may be used to treat various non-malignant diseases or disorders, such a include autoimmune disease (e.g. psoriasis); endometriosis; scleroderma; restenosis; polyps such as colon polyps, nasal polyps or gastrointestinal polyps; fibroadenoma; respiratory disease (see definition above); cholecystitis; neurofibromatosis; polycystic kidney disease; inflammatory diseases; skin disorders including psoriasis and dermatitis; vascular disease (see definition above); conditions involving abnormal proliferation of vascular epithelial cells; gastrointestinal ulcers; Menetrier's disease, secreting adenomas or protein loss syndrome; renal disorders; angiogenic disorders; ocular disease such as age related macular degeneration, presumed ocular histoplasmosis syndrome, retinal neovascularization from proliferative diabetic retinopathy, retinal vascularization, diabetic retinopathy, or age related macular degeneration; bone associated pathologies such as osteoarthritis, rickets and osteoporosis; damage following a cerebral ischemic event; fibrotic or edemia diseases such as hepatic cirrhosis, lung fibrosis, carcoidosis, throiditis, hyperviscosity syndrome systemic, Osler Weber-Rendu disease, chronic occlusive pulmonary disease, or edema following burns, trauma, radiation, stroke, hypoxia or ischemia; hypersensitivity reaction of the skin; diabetic retinopathy and diabetic nephropathy; Guillain-Barre syndrome; graft versus host disease or transplant rejection; Paget's disease; bone or joint inflammation; photoaging (e.g. caused by UV radiation of human skin); benign prostatic hypertrophy; certain microbial infections including microbial pathogens selected from adenovirus, hantaviruses, *Borrelia burgdorferi, Yersinia* spp. and *Bordetella pertussis*; thrombus caused by platelet aggregation; reproductive conditions such as endometriosis, ovarian hyperstimulation syndrome, preeclampsia, dysfunctional uterine bleeding, or menometrorrhagia; synovitis; atheroma; acute and chronic nephropathies (including proliferative glomerulonephritis and diabetes-induced renal disease); eczema; hypertrophic scar formation; endotoxic shock and fungal infection; familial adenomatosis polyposis; neurodedenerative diseases (e.g. Alzheimer's disease, AIDS-related dementia, Parkinson's disease, amyotrophic lateral sclerosis, retinitis pigmentosa, spinal muscular atrophy and cerebellar degeneration); myelodysplastic syndromes; aplastic anemia; ischemic injury; fibrosis of the lung, kidney or liver; T-cell mediated hypersensitivity disease; infantile hypertrophic pyloric stenosis; urinary obstructive syndrome; psoriatic arthritis; and Hasimoto's thyroiditis. Preferred non-malignant indications for therapy herein include psoriasis, endometriosis, scleroderma, vascular disease (e.g. restenosis, artherosclerosis, coronary artery disease, or hypertension), colon polyps, fibroadenoma or respiratory disease (e.g. asthma, chronic bronchitis, bronchieactasis or cystic fibrosis)

Where the antibody in the formulation binds to a B-cell surface marker such as CD20 or BR3, the formulation may be used to treat a B-cell malignancy, such as NHL or CLL, an autoimmune disease, graft rejection, or to block an immune response to a foreign antigen, such as an antibody, a toxin, a gene therapy viral vector, a graft, an infectious agent, or an alloantigen (see WO 01/03734, Grillo-Lopez et al.).

Where the antibody in the formulation is an IgE antibody, it may be used to treat an IgE-mediated disorder (USSN 2004/0197324 A1, Liu and Shire), such as allergic asthma, allergic rhinitis, atopic dermatitis, allergic gastroenteropathy, hypersensitivity, eczema, urticaria, allergic bronchopulmonary aspergillosis, parasitic disease, hyper-IgE syndrome, ataxia-telangiectasia, Wiskott-Aldrich syndrome, thymic alymphoplasia, IgE myeloma, and graft-versus-host reaction.

Antibodies that bind to a receptor in the TNF superfamily (for instance which bind to DR5), or which bind to VEGF (or a receptor thereof), may be used to treat cancer, various forms of which are described in the definitions section above. Preferably, the cancer treated with a DR5 antibody formulation is a solid tumor or NHL.

Where the indication is cancer, the patient may be treated with a combination of the antibody formulation, and a chemotherapeutic agent. The combined administration includes coadministration or concurrent administration, using separate formulations or a single pharmaceutical formulation, and consecutive administration in either order, wherein preferably there is a time period while both (or all) active agents simultaneously exert their biological activities. Thus, the chemotherapeutic agent may be administered prior to, or following, administration of the composition. In this embodiment, the timing between at least one administration of the chemotherapeutic agent and at least one administration of the composition is preferably approximately 1 month or less, and most preferably approximately 2 weeks or less. Alternatively, the chemotherapeutic agent and the composition are administered concurrently to the patient, in a single formulation or separate formulations.

Treatment with the formulation will result in an improvement in the signs or symptoms of cancer or disease. For instance, where the disease being treated is cancer, such therapy may result in an improvement in survival (overall survival and/or progression free survival) and/or may result in an objective clinical response (partial or complete). Moreover, treatment with the combination of the chemotherapeutic agent and the antibody formulation may result in a synergistic, or greater than additive, therapeutic benefit to the patient.

Preferably, the antibody in the formulation administered is a naked antibody. However, the antibody administered may be conjugated with a cytotoxic agent. Preferably, the immunoconjugate and/or antigen to which it is bound is/are internalized by the cell, resulting in increased therapeutic efficacy of the immunoconjugate in killing the cancer cell to which it binds. In a preferred embodiment, the cytotoxic agent targets or interferes with nucleic acid in the cancer cell. Examples of such cytotoxic agents include maytansinoids, calicheamicins, ribonucleases and DNA endonucleases.

The formulation is administered to a human patient in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. Intravenous, intramuscular or subcutaneous administration of antibody composition is preferred, with intravenous administration being most preferred.

For subcutaneous delivery, the formulation may be administered via syringe; injection device (e.g. the INJECT-EASE™ and GENJECT™ device); injector pen (such as the GENPEN™); needleless device (e.g. MEDIJECTOR™ and BIOJECTOR™); or subcutaneous patch delivery system.

For the prevention or treatment of disease, the appropriate dosage of the antibody will depend on the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 50 mg/kg (e.g. 0.1-20 mg/kg) of HER2 or DR5 antibody is an initial candidate dosage for administration to the patient, whether, for example, by one or more separate administrations, or by continuous infusion. The dosage of the antibody will generally be in the range from about 0.05 mg/kg to about 10 mg/kg. If a chemotherapeutic agent is administered, it is usually administered at dosages known therefor, or optionally lowered due to combined action of the drugs or negative side effects attributable to administration of the chemotherapeutic agent. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

Other therapeutic regimens may be combined with the antibody including, but not limited to: a second (third, fourth, etc) chemotherapeutic agent(s) (i.e. "cocktails" of different chemotherapeutic agents); another monoclonal antibody; a growth inhibitory agent; a cytotoxic agent; a chemotherapeutic agent; EGFR-targeted drug; tyrosine kinase inhibitor; anti-angiogenic agent; and/or cytokine; etc.

In addition to the above therapeutic regimes, the patient may be subjected to surgical removal of cancer cells and/or radiation therapy.

V. Articles of Manufacture

In another embodiment of the invention, an article of manufacture is provided which contains the pharmaceutical formulation of the present invention and provides instructions for its use. The article of manufacture comprises a container. Suitable containers include, for example, bottles, vials (e.g. dual chamber vials), syringes (such as dual chamber syringes) and test tubes. The container may be formed from a variety of materials such as glass or plastic. The container holds the formulation and the label on, or associated with, the container may indicate directions for use. The container holding the formulation may be a multi-use vial, which allows for repeat administrations (e.g. from 2-6 administrations) of the reconstituted formulation. The article of manufacture may further include other materials desirable from a commercial and user standpoint, including other buffers, diluents, filters, needles, syringes, and package inserts with instructions for use as noted in the previous section.

The invention will be more fully understood by reference to the following examples. They should not, however, be construed as limiting the scope of the invention. All literature and patent citations are incorporated herein by reference.

EXAMPLES

Stable Pertuzumab Liquid Formulations

These examples describe the development and stability testing of stable liquid formulations comprising Pertuzumab at protein concentrations in the range from about 10 mg/mL-180 mg/mL. The selected formulations had low turbidity, and were physically and chemically stable. A chloride ion was removed from the formulation to reduce the risk of corrosion. The formulation was isotonic, and suitable for subcutaneous or intramuscular delivery. Insoluble aggregate formation upon agitation stress was prevented using histidine-acetate and sucrose formulation, without the need to include polysorbate 20.

Analytical Methods

Color, Appearance and Clarity (CAC)

The color, appearance, and clarity of the samples were determined by visual inspection of vials against a white and black background under white fluorescence light at room temperature.

UV Concentration Measurements

The liquid product aliquot was first diluted with formulation buffer so that the $A_{max}$ near 278 nm is within 0.5-1.0 absorbance unit. The UV absorbance of the diluted samples was measured in a quartz cuvette with 1 cm path length on an HP 8453 spectrophotometer. Absorbance was measured at 278 nm and 320 nm. The absorbance from 320 nm is used to correct background light scattering due to larger aggregates, bubbles and particles. The measurements were blanked against the formulation buffer. The protein concentration was determined using the absorptivity of 1.50 $(mg/mL)^{-1}cm^{-1}$.

pH Measurements

The pH was measured at room temperature using a RADIOMETER COPENHAGEN PHM82™ pH meter. The probe used was a combined glass/reference electrode with radiometer connector (Sigma, Cat# E-5759). Standard solutions of pH 4.01 and pH 7.00 (EM Science) were used for calibration of the pH meter.

Ion-Exchange Chromatography (IEX)

Cation exchange chromatography was employed to measure changes in charge variants. This assay utilizes a DIONEX PROPAC WCX-10™ column on an HP 1100™ HPLC system. Samples were diluted to 1 mg/mL with the mobile phase A containing 20 mM MES at pH 6.0. 50 mL of diluted samples were then loaded on the column that was kept at ambient temperature. The peaks were eluted with a shallow NaCl gradient using mobile B containing 20 mM MES, 250 mM NaCl, pH 6.0. The eluent was monitored at 280 nm. The data were analyzed using HP CHEMSTATION™ software (Rev A08.03).

Capillary Zone Electrophosphoresis (CZE)

The purity of Fab and F(ab')$_2$ fragments was determined by CZE. This assay was run on a BIORAD BIOFOCUS™ 3000™ capillary electrophoresis system with a BIOCAP XL™ capillary, 50 μm I.D., 44.6 cm total length and 40 cm to the detector.

Size Exclusion Chromatography (SEC)

Size exclusion chromatography was used to quantitate aggregates and fragments. This assay utilizes a TSK G3000 SWXL™, 7.8×300 mm column and runs on an HP 1100™ HPLC system. Samples were diluted to 10 mg/mL with the mobile phase and injection volume was 20 μL. The mobile phase was 100 mM K$_2$HPO$_4$ at pH 6.8 and the protein was eluted with an isocratic gradient at 0.5 mL/min for 45 minutes. The eluent absorbance was monitored at 280 nm. Integration was done using HP CHEMSTATION™ software (Rev A08.03).

Biological Activity

The biological activity of Pertuzumab was determined by measuring its ability to inhibit proliferation of the human breast cancer cell line MDA-MB-175-VII.

Example 1

Pertuzumab Fab and F(ab')$_2$ antibody fragments were formulated at protein concentration of 1.0 mg/mL in the following buffer conditions:

10 mM citrate, 140 mM NaCl, pH 4.0;

10 mM succinate, 140 mM NaCl, pH 5.0;

10 mM succinate, 140 mM NaCl, pH 6.0;

10 mM histidine, 140 mM NaCl, pH 7.0; and 10 mM glycylglycine, 140 mM NaCl, pH 8.0.

Each formulation was filtered then aliquoted into 3 cc WHEATON™ USP Type I glass vials sealed with TEFLON™ coated gray butyl stoppers. Samples were stored at 40±2° C. The stability analyses of drug product showed that the Fab and F(ab')$_2$ were most stable between pH 5.0 and 6.0.

TABLE 2

Effect of pH on degradation of Fab or F(ab')₂ stored at 40° C.

| | Fab | | F(ab')₂ | |
|---|---|---|---|---|
| Formulation pH | CZE % Main Peak | SEC % Main Peak | CZE % Main Peak | SEC % Main Peak |
| 4.0 | 74.1 | 96.7 | 43.6 | 89.4 |
| 5.0 | 83.2 | 96.4 | 65.4 | 94.0 |
| 6.0 | 82.9 | 96.2 | 69.0 | 92.3 |
| 7.0 | 83.9 | 96.4 | 62.3 | 91.3 |
| 8.0 | 72.7 | 96.4 | 49.2 | 89.8 |

Example 2

Pertuzumab was formulated into 20 mM histidine-acetate buffer with 120 mM sucrose and 0.02% polysorbate 20. The pHs of formulations were adjusted with acetic acid to final pH between 5.0 and 7.0. The protein concentration was 30 mg/mL. Each formulation was filled into 3 cc USP Type I glass vials and stored at 40° C. for stability analysis. The results showed that Pertuzumab was most stable around pH 6.0.

TABLE 3

Effect of pH on degradation of Pertuzumab stored at 40° C.

| Formulation pH | Temperature (° C.) | Storage Time (wks) | SEC % Monomer | IEX % Main Peak |
|---|---|---|---|---|
| 5.0 | 40 | 2 | 99.4 | 57.4 |
| 5.5 | 40 | 2 | 99.4 | 59.2 |
| 6.0 | 40 | 2 | 99.4 | 60.6 |
| 6.5 | 40 | 2 | 99.3 | 60.5 |
| 7.0 | 40 | 2 | 99.1 | 54.0 |
| 5.0 | 40 | 4 | 97.3 | 48.1 |
| 5.5 | 40 | 4 | 99.1 | 50.5 |
| 6.0 | 40 | 4 | 99.1 | 53.3 |
| 6.5 | 40 | 4 | 99.0 | 52.3 |
| 7.0 | 40 | 4 | 98.6 | 42.3 |

Example 3

Pertuzumab formulations at protein concentration of 100 mg/mL were prepared in the following excipients:
(1) 10 mM histidine-HCl, 240 mM sucrose, 0.02% polysorbate 20, pH 6.0;
(2) 10 mM histidine-acetate, 240 mM sucrose, 0.02% polysorbate 20, pH 6.0;
(3) 10 mM histidine-phosphate, 240 mM sucrose, 0.02% polysorbate 20, pH 6.0;
(4) 10 mM histidine-sulfate, 240 mM sucrose, 0.02% polysorbate 20 at pH 6.0.

Figure 8:
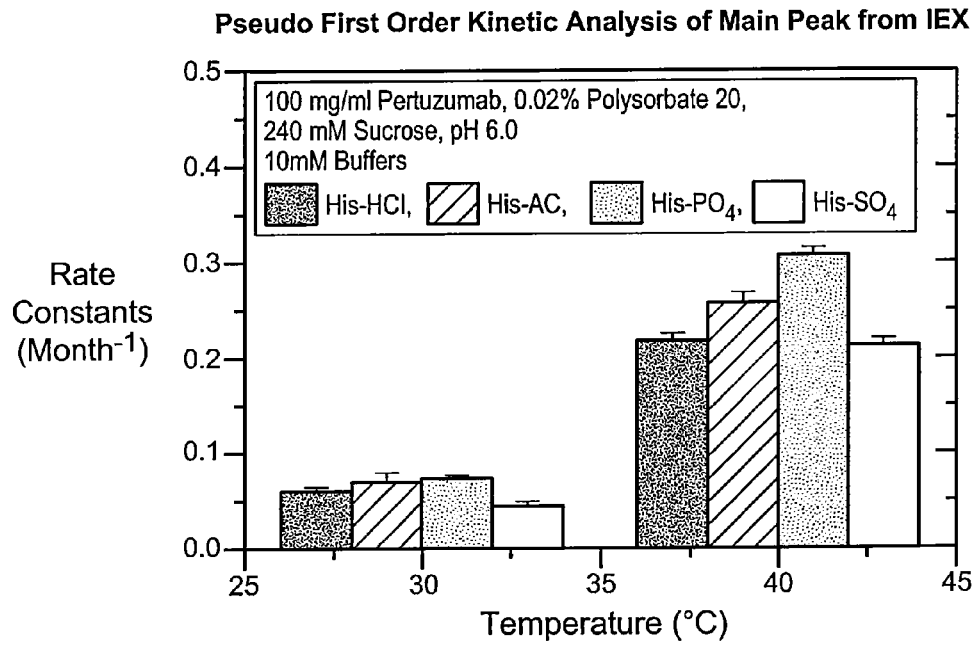
FIG. 8 depicts stability of Pertuzumab formulation by ion exchange (IEX) analyses.
Figure 9:
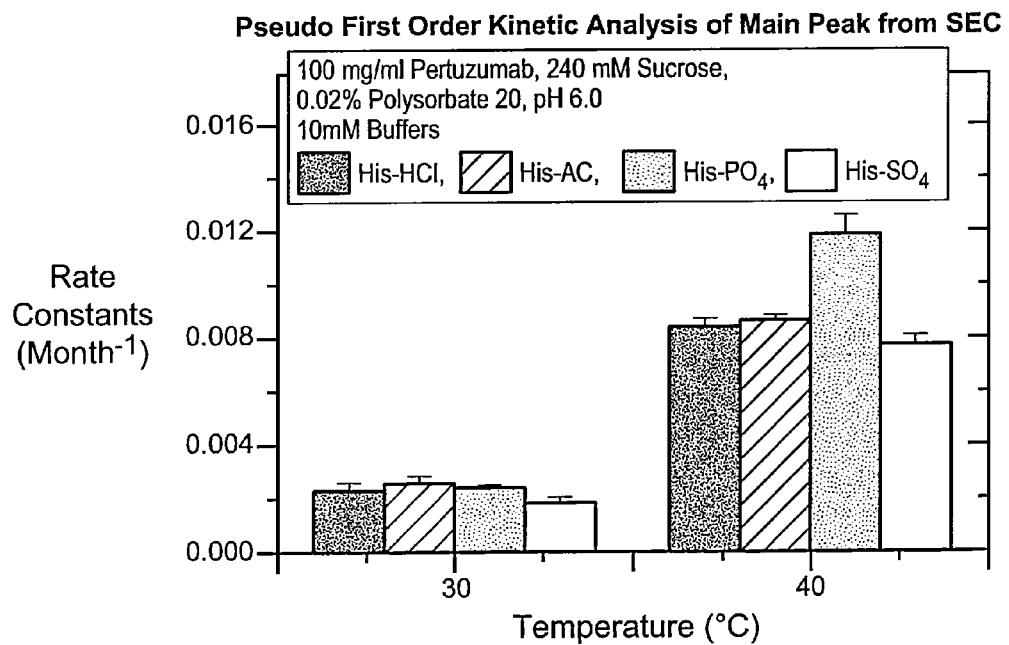
FIG. 9 shows stability of Pertuzumab formulation by size exclusion chromatography (SEC) analysis.

Each formulation was filled into 3 cc FORMA VITRUM™ USP Type I glass vial sealed with FLUROTEC™ faced butyl rubber stoppers. Samples were stored at 30° C. and 40° C. and stability was evaluated for quality (CAC) and purity (SEC, IEC). The stability results showed that Pertuzumab in histidine-phosphate buffer degraded much faster than in other histidine buffers upon storage at 40° C. (FIG. 8 and FIG. 9).

Example 4

Pertuzumab was concentrated by ultrafiltration/diafiltration to various concentrations in the following buffers:
(1) 20 mM histidine-acetate, pH 6.0;
(2) 10 mM histidine-HCl, pH 6.0, and
(3) 10 mM histidine-sulfate, pH 6.0.

Figure 10:
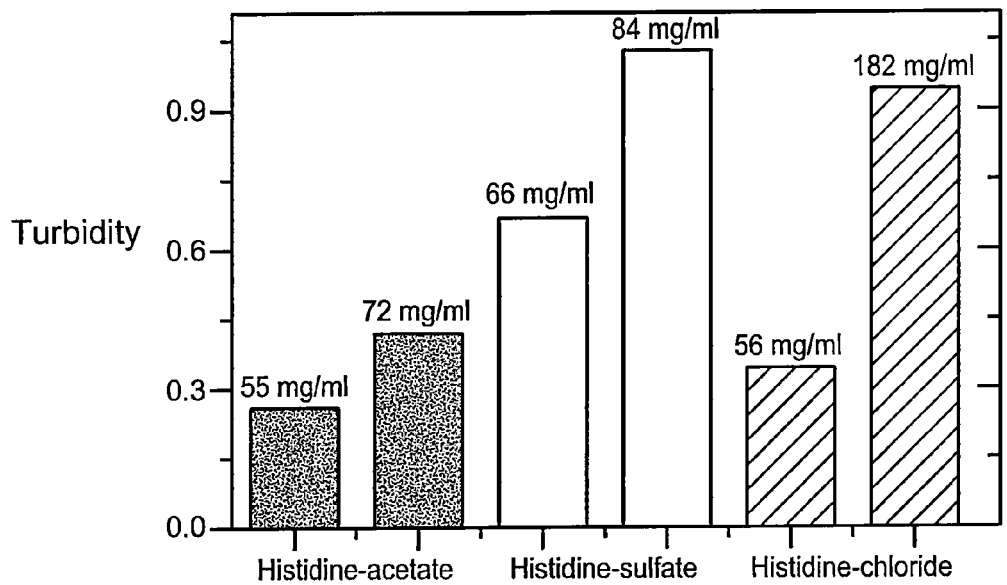
FIG. 10 reflects physical stability Pertuzumab in different formulations.

The turbidity of each formulation was measured before the filtration. The results, as shown in FIG. 10, demonstrated that Pertuzumab samples formulated in histidine-acetate and histidine-HCl had less amounts of insoluble aggregates than those in histidine-sulfate buffer.

Example 5

Pertuzumab was formulated at 30 mg/mL in 20 mM histidine-acetate, 120 mM sucrose, 0.02% polysorbate 20, pH 6.0. Pertuzumab was filled in 316L and HASTELLOY™ stainless steel miniature tanks. All samples were stored at −20° C. and 5° C. and evaluated for quality (CAC), purity (SEC, IEC) and strength (UV-Vis). The stability analyses showed that Pertuzumab was stable in this formulation upon storage at −20° C. and 5° C. for at least 3 months. The chloride free formulation is compatible with 316L and HASTELLOY™ stainless steel tank.

TABLE 4

Stability of Pertuzumab in Stainless Steel Tanks

| Tanks | Temp (° C.) | Time (Months) | CAC | UV Spec. (mg/mL) | SEC (% monomer) | IEC (% main peak) |
|---|---|---|---|---|---|---|
| 316L | | 0 | Pass[a] | 29.0 | 99.8 | 67.9 |
| | −20 | 3 | Pass | 28.9 | 99.7 | 66.8 |
| | 5 | 3 | Pass | 28.7 | 99.7 | 66.8 |
| HASTELLOY™ | −20 | 3 | Pass | 29.1 | 99.7 | 66.8 |
| | 5 | 3 | Pass | 28.8 | 99.7 | 67.7 |

[a]Pass for Color, Appearance and Clarity: Clear to slightly opalescent, colorless to pale yellow solution.

Example 6

Pertuzumab was formulated using tangential flow filtration (TFF). The final formulation contains 20 mM histidine-acetate, 120 mM sucrose, 0.02% polysorbate 20, pH 6.0 at protein concentration of 30 mg/mL. Samples were filled into a 20 Ml FORMA VITRUM™ USP Type I glass vial, capped with the 20 mm FLUROTEC™ faced butyl rubber stoppers, and sealed with aluminium flip-top caps. All samples were stored at −70° C., 5° C., 15° C., and stability was evaluated for quality (CAC), purity (SEC, IEC), strength (UV-Vis), and potency (Bioassay). The results showed that Pertuzumab is stable in this formulation upon storage at 5° C. and 15° C. for at least 3 months.

TABLE 5

Stability of Pertuzumab in glass vials

| Temp (° C.) | Time (Months) | CAC | UV Spec. (mg/mL) | SEC (% monomer) | IEC (% main peak) | Bioassay (% specific activity) |
|---|---|---|---|---|---|---|
| −70 | 0 | Pass | 29.2 | 99.8 | 64.1 | 83 |
| | 1 | Pass | 29.7 | 99.8 | 65.2 | 92 |
| | 3 | Pass | 30.7 | 99.8 | 67.0 | 93 |
| 5 | 3 | Pass | 30.4 | 99.7 | 67.2 | 90 |
| 15 | 1 | Pass | 29.7 | 99.7 | 64.4 | 78 |
| | 3 | Pass | 30.4 | 99.7 | 65.5 | 93 |

Example 7

Pertuzumab was formulated at 100 mg/mL in the following buffer conditions:
(1) 10 mM histidine-HCl, pH 6.0;
(2) 10 mM histidine-HCl, 240 mM sucrose, pH 6.0;
(3) 20 mM succinate at pH 6.0; and
(4) 20 mM succinate, 240 mM sucrose at pH 6.0.

Each formulation was added with different concentration of polysorbate 20. All samples were filled into 3 cc USP Type I glass vials and were agitated horizontally at 70 rpm at room temperature for up to 7 days. The stability of each sample was evaluated at 7 day time point for turbidity. The results demonstrated that the use of polysorbate 20 in the final formulation effectively prevented formation of insoluble aggregates. See FIG. 11.

Example 8

Pertuzumab was prepared in the following formulations:
(1) 25 mg/mL Pertuzumab, 10 mM histidine-HCl, 240 mM sucrose, pH 6.0;
(2) 50 mg/mL Pertuzumab, 10 mM histidine-HCl, 240 mM sucrose, pH 6.0;
(3) 60 mg/mL Pertuzumab, 20 mM histidine-acetate, 120 mM sucrose, pH 6.0.

Figure 12:
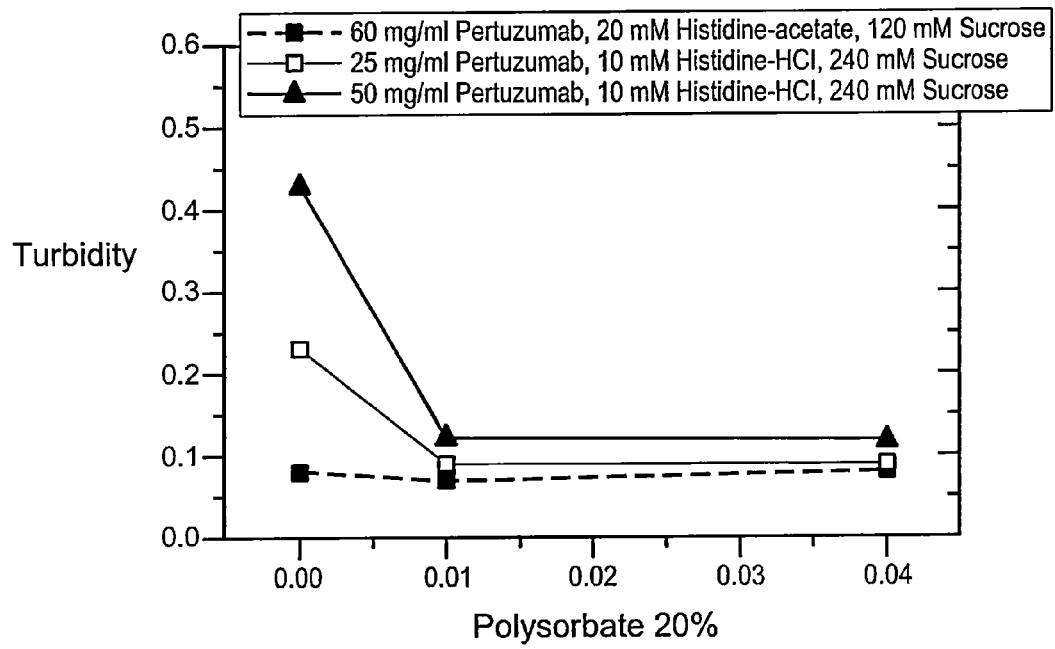
FIG. 12 is from another agitation study of Pertuzumab liquid formulations.

Various amounts of polysorbate 20 were added to each formulation. All samples were filled into 3 cc USP Type I glass vials, and agitated horizontally at 70 rpm at room temperature for up to 7 days. The physical stability of each sample was evaluated at 7 day time point for turbidity. The results demonstrated that the use of polysorbate 20 in histidine-HCl and sucrose formulation effectively prevented formation of insoluble particulates. The formulation containing histidine-acetate and sucrose appeared to have the same protective effect on protein as polysorbate 20. See FIG. 12.

Example 9

Pertuzumab was formulated as follows:
(1) 100 mg/mL protein, 10 mM histidine-HCl, pH 6.0;
(2) 100 mg/mL protein, 20 mM succinate, pH 6.0;
(3) 60 mg/mL protein, 20 mM histidine-acetate, pH 6.0.

Figure 13:
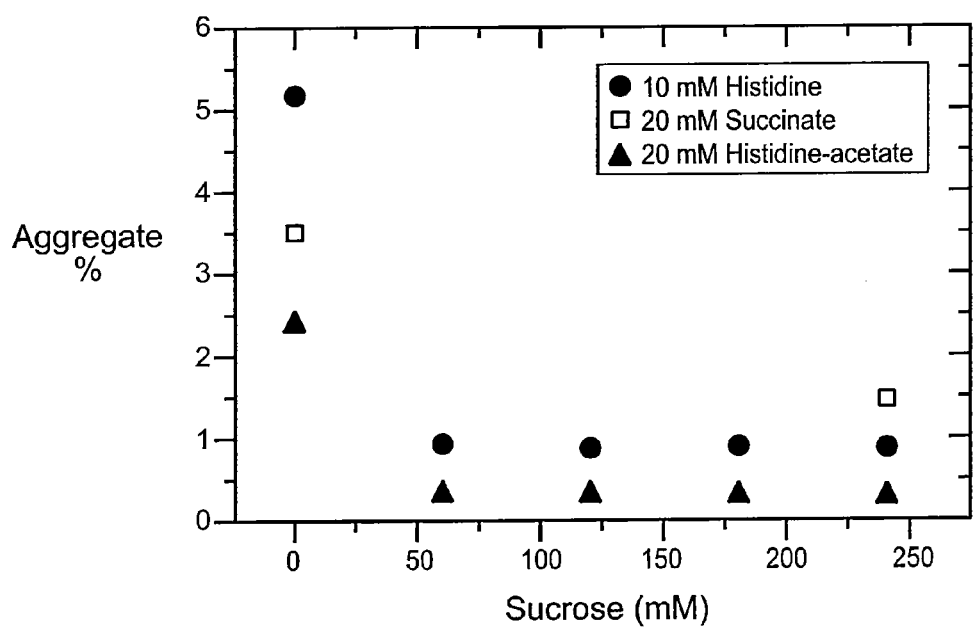
FIG. 13 is from a freeze-thawing study of Pertuzumab formulation.

Each formulation was mixed with different amounts of sucrose. All samples were sterilely filled into 3 cc USP Type I glass vials. They were then frozen at −70° C. and thawed at 5° C. three times. The physical stability of each sample was determined after the three cycles of freezing and thawing. The results demonstrated that sucrose prevents soluble aggregate formation during the freeze-thawing process. See FIG. 13.

Example 10

The preferred Pertuzumab formulation for therapeutic use consists essentially of 30 mg/mL Pertuzumab in 20 mM histidine acetate, 120 mM sucrose, 0.02% polysorbate 20, at pH 6.0.

| Compound | Concentration | Amount/L |
| --- | --- | --- |
| Pertuzumab | 30 mg/mL | 30 g |
| L-Histidine MW = 155.16 g/mol | 20 mM | 3.10 g |
| Glacial Acetic Acid MW = 60.05 g/mol Density = 1.05 g/cm³ | 11.6 mM | 0.66 mL |
| Sucrose MW = 342.3 g/mol | 120 mM | 41.1 g |
| Polysorbate 20 Density = 1.012 g/cm³ | 0.02% (w/v) | 0.2 mL |

MW: Molecular weight 420 mg dose vial configuration:
Vial: 20 cc Formal Vitrum Type I glass
Stopper: 20 mm DAIKYO GREY™, fluoro-resin laminated
Cap: 20 mm flip top aluminum
Fill volume: 14.50 mL
Delivery: 14.0 mL Pertuzumab in normal saline IV bag.
1050 mg dose vial configuration:
Vial: 50 cc Formal Vitrum Type I glass
Stopper: 20 mm DAIKYO GREY™, fluoro-resin laminated
Cap: 20 mm flip top aluminum
Fill volume: 36.0 mL
Delivery: 35.0 mL Pertuzumab in normal saline IV bag.

Example 11

This example concerns another Pertuzumab formulation which has been used in Phase I and Phase II clinical trials. The composition consists of 25 mg/ml Pertuzumab, 10 mM Histidine-HCl buffer, 240 mM sucrose, 0.02% Polysorbate 20, pH 6.0.

| Ingredient | Concentration |
| --- | --- |
| Pertuzumab | 25 mg/ml |
| L-His HCl•H₂O (MW 209.6) | 1.12 mg/ml (0.0125 M) |
| L-His (MW 155.2) | 0.72 mg/ml (0.0099 M) |
| Sucrose (MW342.3) | 82.15 mg/ml (0.240 M) |
| Polysorbate 20 | 0.2 mg/ml (0.02%) |

Example 12

Cellular apoptosis is mediated by intrinsic and extrinsic pathways. Chemotherapy can cause cell damage and may trigger apoptosis by the intrinsic pathway in response to cellular damage. However, cancer cells often develop resistance to chemotherapy through mutations in the p53 tumor suppressor gene (Ashkenazi A. Targeting Death and Decoy Receptors of the Tumour-Necrosis Factor Superfamily. *Nature Reviews* 2:420-430 (2002)). Death receptors, such as DR4 and DR5, located on the surface of cells trigger apoptosis via the extrinsic pathway that does not involve p53. Agonistic molecules, such as Apo2L, bind to DR4 and DR5 receptors and activate caspases 8 and 10 through Fas-associated death domain. Caspase 8 and 10 then activate caspases 3, 6, and 7 to induce apoptosis. Molecular signaling of death receptors on tumor cells has therapeutic potential for the elimination of cancer cells that are resistant to conventional therapies and molecules, like Apo2L, are currently undergoing clinical evaluation.

"Apomab" is a full-length CHO derived humanized IgG1 constructed with a lamda light chain. It is an agonist antibody against DR5 that has been shown to induce apoptosis of various cancer cell lines. Preclinical studies using a murine tumor implant model have shown that Apomab has similar or improved tumor reduction compared to Apo2L. Apomab is being evaluated as an anti-cancer agent in the indications of advanced solid tumors and Non-Hodgkin's Lymphoma (NHL). The heavy and light chain amino acid sequences of Apomab used in these experiments are shown in FIGS. 27 and 28.

Preparation of Antibody Formulations

Recombinantly produced Apomab had very dilute protein concentration and high pH. The material was concentrated to approximately 20 mg/mL and exchanged into 20 mM sodium acetate, pH 5.0 buffer using a Millipore Labscale tangential flow filtration (TFF) system with MILLIPORE PELLICON™ XL, PLCGC10, 50 cm membrane. Apomab samples were formulated into various buffer systems covering pH range from 4.0 to 7.0 using sodium acetate, histidine acetate, and sodium phosphate without trehalose and TWEEN 20® using dialysis with a 10,000 Da molecular weight cut off membrane (Pierce, Inc). Trehalose at 240 mM was added in the last dialysis. After dialysis, 0.02% TWEEN 20™ was added to the formulation and the samples were filtered with 0.22 μm filters (Millipore, Inc.). A 0.5 mL volume of Apomab was filled into sterile 3 cc glass vials (Form a Vitrum, Inc.) and sealed with 13 mm stoppers (Dalkyo, Inc). Protein stability was evaluated at −70° C., 5° C., 30° C., and 40° C. with storage for up to 3 months.

Stability of Apomab Formulation

For drug product stability testing, Apomab formulated bulk filled into 5 cc FORMA VITRUM® glass vials were formulated. Vials were filled with 5.5 mL of formulated antibody, fitted with 20 mm DAIKYO® stoppers, and stored at −70° C., 5° C., 30° C., and 40° C. in the upright position.

For drug substance stability testing, Apomab formulated bulk was sterile filtered through a 0.22 μm filter and 10 mL, was filled into autoclaved 20 cc 316L stainless steel mini-tanks. The tanks were placed upright at −20° C. and 5° C. A 1 mL aliquot was aseptically removed from the mini-tanks at specified time intervals to assess protein quality. The control vials were 1 mL aliquots in 3 cc glass vials stored at −20° C.

Color, Appearance, and Clarity

The clarity, appearance, and color of the samples were visually assessed under white fluorescent light using a light inspection station with black and white background. For analysis of the drug substance, mini-tank samples were transferred to a 3 cc glass vial for inspection.

pH pH was measured at room temperature with THERMO ORION SURE-FLOW ROSS™ semi-micro pH electrode for measuring buffers or THERMO ORION GLS™ combination micro pH electrode for measuring protein pH screening samples, a Beckman microelectrode probe for Toxicology stability samples. The METERLAB™ pHM240 pH/Ion meter (Radiometer Analytical) was calibrated every day with buffer standards (EM Science) at pH 7 and pH 4.

Concentration

Protein concentration was determined by ultraviolet absorption spectroscopy using an AGILENT 8453™ spectrophotometer. The samples were diluted with appropriate formulation buffer blanks to give an absorbance from 0.5 to 1.0. The instrument was blanked with the diluent solution and the spectrum was scanned from 240 to 500 nm. The absorbance value at 320 nm was subtracted from the absorbance at 279 nm to correct for offset and light scattering. The protein concentrations were calculated by the following equation:

$$\text{Conc. (mg/mL)} = \frac{(A279 - A320) \times \text{dilution factor}}{\text{absorptivity coefficient in cm}^{-1}(\text{mg/mL})^{-1}}$$

The absorptivity coefficient based on sequence was initially determined to be 1.32 cm$^{-1}$(mg/mL)$^{-1}$ and this value was used for the pH screening studies. A later value of 1.7 cm$^{-1}$(mg/mL)$^{-1}$ was determined by amino acid analysis and proteolysis methods and this value was used for the stability analysis of Apomab used in Toxicology studies.

Ion-Exchange Chromatography

Ion exchange chromatography was carried out on an 1100 series HPLC (Agilent Technologies, Inc.) equipped with a diode array detector. Chromatography was carried out on a PROPAC WCX-10™ (Dionex) column (4×250 mm) at a flow rate of 0.5 mL/min and with column temperature at 40° C. Mobile phase A was 25 mM sodium phosphate, pH 6.5. Mobile phase B was 100 mM sodium chloride in the same buffer as mobile phase A. The column was equilibrated with 100% mobile phase A. For pH screening samples an amount of 20 mg of Apomab was loaded onto the column and the absorbance was monitored at 214 nm. Protein was eluted from the column with the following gradient:

| Time (min) | % A | % B |
| --- | --- | --- |
| 0 | 100 | 0 |
| 50 | 0 | 100 |
| 51 | 100 | 0 |
| 70 | 100 | 0 |

For stability analysis of material used in the Toxicology studies an amount of 30 mg of Apomab was loaded onto the column and the absorbance was monitored at 280 nm. Protein was eluted from the column with the following gradient:

Gradient:

| Time (min) | % A | % B |
| --- | --- | --- |
| 0 | 100 | 0 |
| 40.0 | 40 | 60 |
| 41.0 | 0 | 100 |
| 45.0 | 0 | 100 |
| 45.1 | 100 | 0 |
| 60.0 | 100 | 0 |

Size-Exclusion Chromatography

Size exclusion chromatography was carried out on an 1100 series HPLC (Agilent Technologies, Inc.) equipped with a diode array detector. An amount of 50 μg Apomab was loaded onto a TSK Gel 3000SWXL™ (7.8×300 mm) column and run at a flow rate of 0.9 mL/min for 20 minutes for pH screening samples and 0.5 mL/min for 30 minutes for Toxicology stability samples with 0.20 M potassium phosphate, 0.25 M potassium chloride, pH 6.2 as a mobile phase. Absorbance was monitored at 280 nm.

Potency

The purpose of the potency bioassay was to measure the ability of Apomab to kill Colo205 cells using ALAMARBLUE™. Colo205 is a colon carcinoma cell line, which expresses both DR5 and DR4 death receptors. This assay incorporates a fluorometric/colorimetric growth indicator based on detection of metabolic activity. ALAMARBLUE™ is a redox dye that is blue and non-fluorescent in oxidized state. The intracellular metabolic reduction converts it into a red color that is also fluorescent. The changes in color and fluorescence are proportional to the metabolic activity and number of living cells. The signal decreased when cells die. Apomab was diluted in medium with anti-Fc and then Colo 205 cells were added to Apomab samples and incubate at 37° C. for 48 hours. ALAMARBLUE™ is added for the last 2-3 hours. The plate was read at 530 nm excitation and 590 nm emission to get relative fluorescence units (RFU). The data were analyzed by KALEIDAGRAPH™. A dilution curve of killing was generated.

Results

Formulation pH Screen Study

The effect of pH on antibody stability was studied using Apomab produced from an unamplified stable cell line. For this analysis, Apomab was formulated at 20 mg/mL antibody in 20 mM sodium acetate buffer at pH 4.0, 4.5, 5.0, 5.5; 20 mM histidine acetate buffer at pH 6.0 and 6.5; and 20 mM sodium phosphate buffer at pH 7.0. All of the formulations contained 240 mM trehalose and 0.02% TWEEN 20®. The formulations were stored for up to 3 months at temperatures of −70° C., 5° C., 30° C., and 40° C. and protein stability was determined by various analytical assays, including CAC, pH, concentration, SEC and IEC. No significant changes in CAC, pH or protein concentration were observed during storage of the samples.

Figure 20:
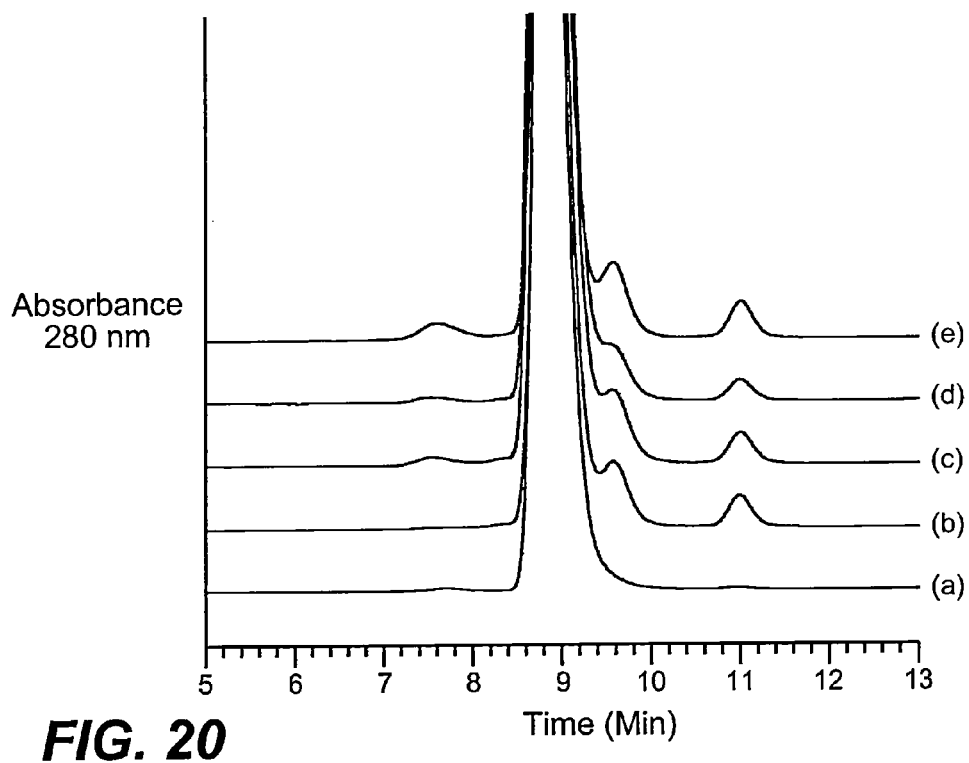
FIG. 20 shows size exclusion chromatography (SEC) elution profile of the following Apomab samples: (a) control and formulations prepared at (b) pH 4.0, (c) pH 5.0, (d) pH 6.0 and (e) pH 7.0. The formulated samples were stored at 40° C. for 2 months prior to the analysis.
Figure 21:
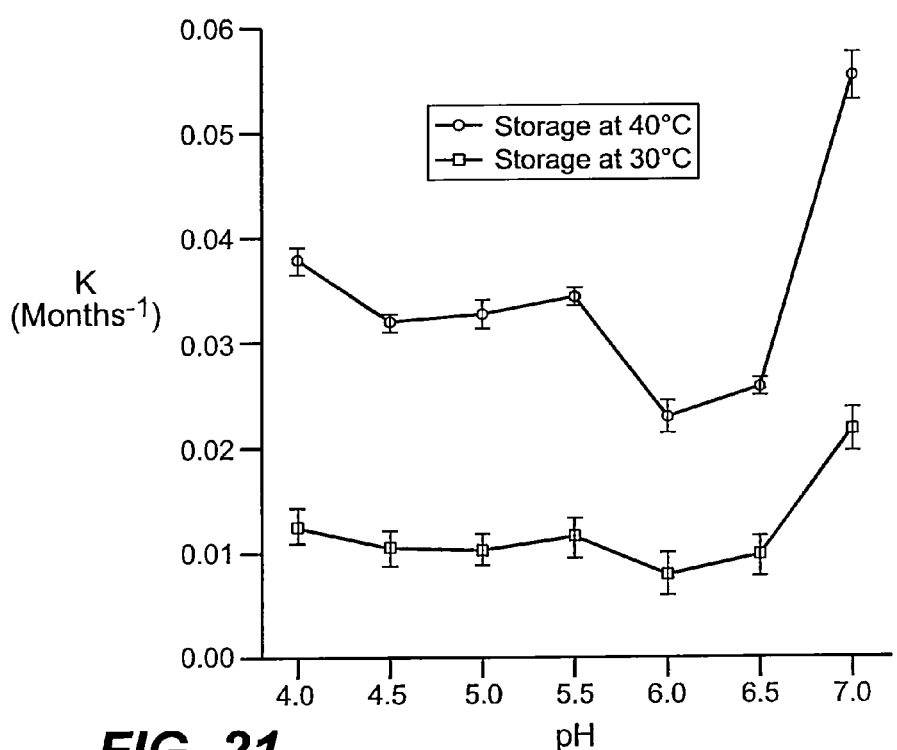
FIG. 21 depicts pH rate profile for the loss in Apomab antibody monomer during storage. Monomer kinetics by SEC was monitored during storage at 30° C. and 40° C. and the first-order rate constants were calculated.

Analysis of the samples by SEC showed that no significant changes occurred during storage at 5° C. and −70° C. However, degradation observed as the formation of antibody fragments and soluble aggregates occurred during storage at 30° C. and 40° C. (FIG. 20). To compare the formulations, antibody monomer kinetics during storage was monitored and the first-order rate constants were calculated. The obtained pH rate profile for the loss in antibody monomer is shown in FIG. 21. The optimal condition for the stability of antibody monomer was obtained by formulating in histidine acetate buffer at pH 6.0.

Figure 22:
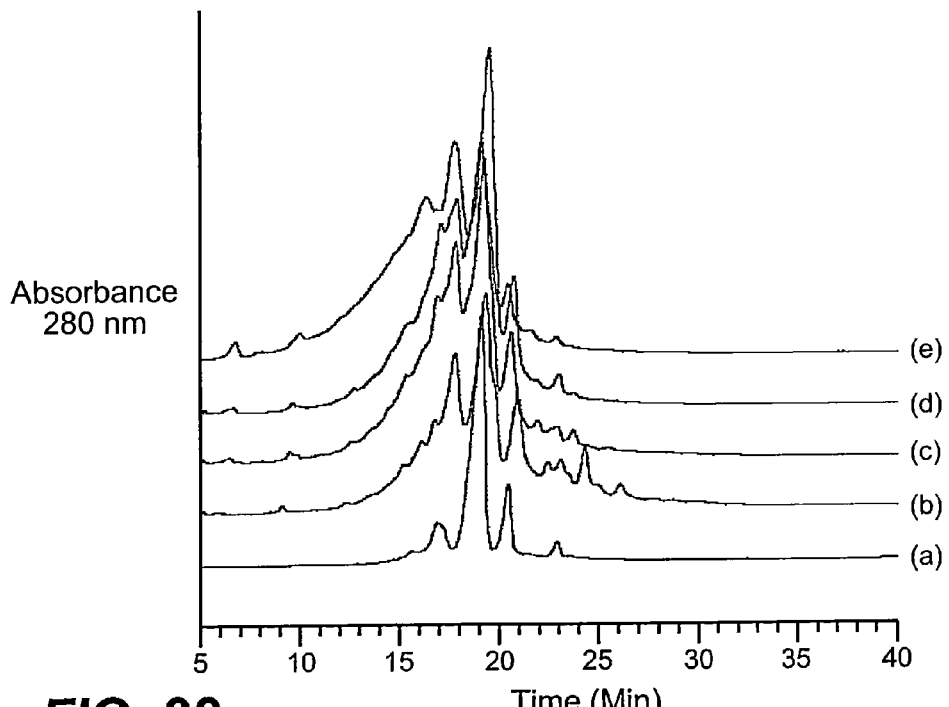
FIG. 22 provides ion exchange chromatography (IEC) elution profile of Apomab samples as follows: (a) control and formulations prepared at (b) pH 4.0, (c) pH 5.0, (d) pH 6.0 and (e) pH 7.0. The formulated samples were stored at 40° C. for 2 months prior to the analysis.
Figure 23:
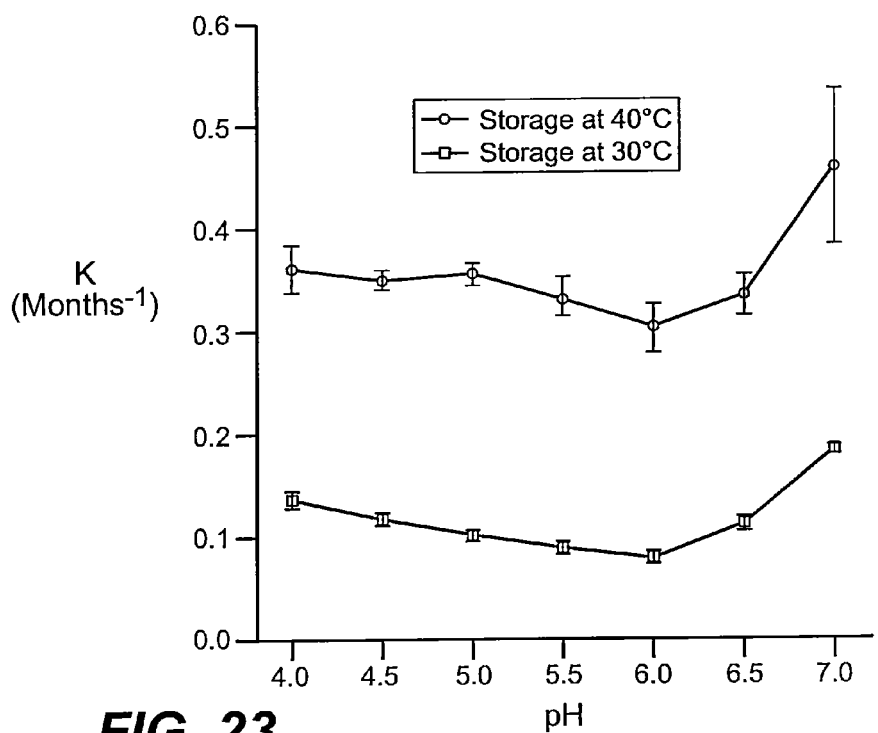
FIG. 23 shows pH rate profile for the loss in IEC main peak during storage. Main peak kinetics by IEC was monitored during storage at 30° C. and 40° C. and the first-order rate constants were calculated.

Apomab charge heterogeneity was monitored by IEC. No significant changes in the IEC profile occurred during storage at 5° C. and −70° C. However, degradation observed as the formation of acidic or basic variants occurred depending on the formulation (FIG. 22). In general, increased basic variants were formed at lower formulation pH and more acidic variants were formed at higher formulation pH. To compare the formulations, IEC main peak kinetics was monitored during storage and the first-order rate constants were calculated. The obtained pH rate profile for the loss in IEC main peak is shown in FIG. 23. The rate constants observed by IEC were approximately 10 fold higher than those from SEC (FIG. 21). Therefore, the loss in IEC main peak was the primary degradation of the antibody that will ultimately limit the product shelf life. Furthermore, as observed by SEC, optimal antibody stability to stabilize IEC main peak was obtained by formulating in histidine acetate buffer at pH 6.0.

Following the analysis of pH screening data described above, an Apomab formulation was selected that comprised 20 mg/mL antibody in 20 mM histidine acetate, 240 mM trehalose, 0.02% polysorbate 20, pH 6.0. For the drug product, the vial configuration consisted of 5.5 mL fill in a 5 cc FORMA VITRUM™ vial with a 20 mM DAIKYO™ West stopper. Apomab was stored in stainless steel tanks.

The stability of Apomab Drug Product was evaluated in the 5 cc glass vial configuration described above. Vials were stored at −70° C. (controls), 5° C., 30° C., and 40° C. Samples were pulled at specific time intervals and analyzed by the following assays: color, appearance, clarity (CAC), pH, protein concentration, SEC, IEC, and potency. The results from these assays are shown in Table 6 for samples stored at −70° C. and 5° C. and Table 7 for samples stored at 30° C. and 40° C.

TABLE 6

Stability Data for Apomab Stored at −70° C. and 5° C.

| Temp (° C.) | Time Point | Clarity | Color | pH | Concentration (mg/mL) | SEC (% monomer) | IEC (% main peak) | Potency (% Specific Activity) |
|---|---|---|---|---|---|---|---|---|
| Acceptance Criteria: | | Report | Report | 6.0 ± 0.3 | 20 ± 2 | ≥95% | Report | 60-140% |
| NA | T = 0 | Clear | Colorless | 5.9 | 20.2 | 99.8 | 63 | 94 |
| −70 | 1 month | Clear | Colorless | 6.0 | 20.5 | 99.8 | 63 | 86 |
| −70 | 2 month | Clear | Colorless | 6.0 | 20.4 | 99.7 | 64 | 91 |
| −70 | 3 month | Clear | Colorless | 6.0 | 20.5 | 99.7 | 63 | 83 |
| −70 | 6 month | Clear | Colorless | 6.0 | 20.4 | 99.7 | 64 | 85 |
| −70 | 9 month | Clear | Colorless | 6.0 | 20.4 | 99.8 | 65 | 89 |
| −70 | 12 month | Clear | Colorless | 6.0 | 20.8 | 99.7 | 63 | 107 |
| 5 | 1 month | Clear | Colorless | 6.0 | 20.5 | 99.7 | 63 | 89 |
| 5 | 2 month | Clear | Colorless | 6.0 | 20.4 | 99.7 | 64 | 99 |
| 5 | 3 month | Clear | Colorless | 6.0 | 20.6 | 99.7 | 63 | 84 |
| 5 | 6 month | Clear | Colorless | 6.0 | 20.5 | 99.7 | 64 | 93 |
| 5 | 9 month | Clear | Colorless | 6.0 | 20.6 | 99.7 | 64 | 88 |
| 5 | 12 month | Clear | Colorless | 6.0 | 20.7 | 99.6 | 64 | 106 |

TABLE 7

Stability Data for Apomab Stored at 30° C. and 40° C.

| Temp (° C.) | Time Point | Clarity | Color | pH | Concentration (mg/mL) | SEC (% monomer) | IEC (% main peak) | Potency (% Specific Activity) |
|---|---|---|---|---|---|---|---|---|
| Acceptance Criteria: | | Report | Report | 6.0 ± 0.3 | 20 ± 2 | ≥95% | Report | 60-140% |
| 30 | 1 month | Clear | Colorless | 6.0 | 20.6 | 98.2 | 59 | 91 |
| 30 | 2 month | Clear | Colorless | 6.0 | 20.3 | 97.4 | 54 | 80 |
| 30 | 3 month | Clear | Colorless | 6.0 | 20.6 | 97.2 | 49 | 74 |

TABLE 7-continued

Stability Data for Apomab Stored at 30° C. and 40° C.

| Temp (° C.) | Time Point | Clarity | Color | pH | Concentration (mg/mL) | SEC (% monomer) | IEC (% main peak) | Potency (% Specific Activity) |
|---|---|---|---|---|---|---|---|---|
| 30 | 6 month | Clear | Colorless | 6.0 | 20.2 | 94.1 | 37 | 51 |
| 30 | 9 month | Clear | Slightly yellow | 6.0 | 20.4 | 93.2 | 31 | 55 |
| 30 | 12 month | Clear | Slightly yellow | 6.0 | 20.6 | 91.6 | 25 | 59 |

TABLE 8

Freeze-Thaw Stability Data for Apomab Filled in Miniature Stainless Steel Tanks

| Temp (° C.) (Frozen/thaw) | Freeze-Thaw Cycle No. | Clarity | Color | pH | Concentration (mg/mL) | SEC (% Monomer) | | |
|---|---|---|---|---|---|---|---|---|
| Acceptance Criteria: | | Report | Report | 6.0 ± 0.3 | 20.0 ± 2.0 | ≥95% | | |
| Control (unfrozen) | 0 | Clear | Colorless | 6.0 | 20.9 | 99.6 | | |
| −20/25 | 1 | Clear | Colorless | 6.0 | 20.8 | 99.6 | | |
| −20/25 | 2 | Clear | Colorless | 6.0 | 20.8 | 99.6 | | |
| −20/25 | 3 | Clear | Colorless | 6.0 | 20.9 | 99.6 | | |
| 40 | 1 month | Clear | Colorless | 6.0 | 20.4 | 96.6 | 44 | 79 |
| 40 | 2 month | Clear | Colorless | 6.0 | 20.0 | 93.7 | 31 | 64 |
| 40 | 3 month | Clear | Slightly yellow | 5.9 | 20.3 | 91.5 | 22 | 53 |
| 40 | 6 month | Clear | Slightly yellow | 6.0 | 20.2 | 83.9 | NT | 26 |
| 40 | 9 month | Clear | Yellow | 5.9 | 20.3 | 78.8 | NT | 25 |
| 40 | 12 month | Clear | Yellow | 5.9 | 20.5 | 71.4 | NT | 31 |

NT = not quantitated

No change in protein quality was observed after twelve months storage at −70° C. and 5° C. For instance, the pH remained at 6.0±0.3, Apomab appeared as a clear and colorless liquid, the protein concentration remained at 20.0±2.0 mg/mL, and % monomer was unchanged. Furthermore, there was no significant change in % IEC main peak and % specific activity determined by the cell-killing potency assay was within the assay precision of 60% to 140% specific activity. The results showed that Apomab stored in 5 cc glass vials was stable for at least 12 months at 5° C.

Table 7 shows that changes in protein quality occurred at 30° C. and 40° C. SEC showed a decrease in % monomer with a rise primarily in fragment species. Aggregates increase as well at higher temperature, but the rate was much slower. However, the aggregates increase significantly after 6 months at 40° C. IEC % main peak decreased with a corresponding increase in acidic variants. Basic peaks decreased slightly after 2 months at 40° C. and 9 months at 30° C. After six months of storage at 40° C., degradation occurred to an extent that IEC main peak could no longer be integrated. The cell killing bioassay showed loss of % specific activity at higher temperature with longer storage time. Protein concentration and pH were unchanged. The solution becomes slightly yellow after 3 months at 40° C. and 9 months at 30° C. and becomes yellow after 9 months at 40° C.

Drug Substance Stability

Freeze-thaw stability data for drug substance are shown in Table 8.

No significant changes in the chemical characteristics of the protein were observed after being frozen at −20° C. for at least 15 hours and thawed at ambient temperature three times. For example, Apomab appeared as a clear and colorless liquid, the pH remained at 6.0±0.3, and the SEC monomer peak percentage was unchanged.

Apomab stability in stainless steel containers was evaluated at −20° C. and 5° C. (Table 9).

Samples were aseptically pulled from the mini-tanks at specific intervals and analyzed.

Apomab showed no change in protein quality at 5° C. by pH, CAC, protein concentration and % main peak by

TABLE 9

Stability Data for Apomab Filled in Miniature Stainless Steel Tanks

| Temp (° C.) | Time Point | Clarity | Color | pH | Concentration (mg/mL) | SEC (% monomer) | IEC (% main peak) | Potency (% Specific Activity) |
|---|---|---|---|---|---|---|---|---|
| Acceptance Criteria: | | Report | Report | 6.0 ± 0.3 | 20 ± 2 | ≥95% | Report | 60-140% |
| NA | T = 0 | Clear | Colorless | 5.9 | 20.0 | 99.7 | 63 | 88 |
| −20 | 1 month | Clear | Colorless | 6.0 | 20.6 | 99.7 | 63 | 107 |
| −20 | 3 month | Clear | Colorless | 6.0 | 20.6 | 99.7 | 63 | 82 |
| −20 | 6 month | Clear | Colorless | 6.0 | 20.3 | 99.7 | 64 | 92 |
| −20 | 9 month | Clear | Colorless | 6.0 | 20.6 | 99.7 | 64 | 92 |

TABLE 9-continued

Stability Data for Apomab Filled in Miniature Stainless Steel Tanks

| Temp (° C.) | Time Point | Clarity | Color | pH | Concentration (mg/mL) | SEC (% monomer) | IEC (% main peak) | Potency (% Specific Activity) |
|---|---|---|---|---|---|---|---|---|
| −20 | 12 month | Clear | Colorless | 6.0 | 21.2 | 99.7 | 65 | 94 |
| 5 | 1 month | Clear | Colorless | 6.0 | 20.5 | 99.7 | 62 | 95 |
| 5 | 3 month | Clear | Colorless | 6.0 | 20.7 | 99.6 | 62 | 71 |
| 5 | 6 month | Clear | Colorless | 6.0 | 20.4 | 99.5 | 62 | 84 |
| 5 | 9 month | Clear | Colorless | 6.0 | 20.8 | 99.4 | 61 | 84 |
| 5 | 12 month | Clear | Colorless | 6.0 | 21.3 | 99.2 | 59 | 82 |

IEC but lost 0.1% monomer by SEC every 3 months. Decreased potency was observed during storage at 5° C. for 3 months. However, the potency of the sample increased again at the 6 and 9 month timepoints. Therefore, the observed potency difference at the 3 month timepoint was attributed to assay variation. Apomab showed no change in protein quality at −20° C. by pH, CAC, protein concentration, % monomer by SEC, % main peak by IEC, and no significant change in potency. The stability data show that Apomab is stable for at least 1 year at −20° C. and three months at 5° C.

Conclusion

Formulation screening studies were performed to select a formulation for Apomab. A pH screen covering the pH range 4.0 to 7.0 using sodium acetate, histidine acetate, and sodium phosphate as buffers with 240 mM trehalose dihydrate and 0.02% polysorbate 20 showed that Apomab is most stable in solution at pH 6.0. Therefore, a formulation consisting of 20 mM histidine acetate, 240 mM trehalose, 0.02% polysorbate 2, pH 6.0 was developed and demonstrated experimentally to be stable. Using this formulation, Apomab was shown to be stable for at least 12 months at 5° C. Furthermore, Apomab was shown to be stable for at least 12 months at −20° C. and three months at 5° C. when stored in 316L stainless steel containers. Apomab was also shown to be stable when subjected to up to 3 freeze/thaw cycles.

What is claimed is:

1. A method of treating HER2-expressing cancer in a subject, comprising intravenously administering a pharmaceutical formulation to the subject in an amount effective to treat the cancer, wherein the formulation comprises an antibody that binds to domain II of HER2 in a histidine-acetate buffer at a pH from about 5.5 to about 6.5, a saccharide, and a surfactant.

2. A method of treating HER2-expressing cancer in a subject, comprising intravenously administering a pharmaceutical formulation to the subject in an amount effective to treat the cancer, wherein the formulation comprises an antibody that binds to domain II of HER2 in a histidine-acetate buffer at a pH from about 5.5 to about 6.5, a saccharide, and a surfactant, wherein the antibody concentration is from 20mg/mL to 40mg/mL, the antibody comprises the variable light and variable heavy amino acid sequences in SEQ ID Nos. 3 and 4, respectively, the saccharide is sucrose at a concentration from about 60mM to about 250mM, and the surfactant is polysorbate 20 at a concentration from about 0.01% to about 0.1%.

3. The method of claim 2 wherein the HER2 antibody comprises a light chain amino acid sequence selected from SEQ ID No. 15 and 23, and a heavy chain amino acid sequence selected from SEQ ID No. 16 and 24.

4. The method of claim 2 wherein the pH of the formulation is from about 5.8 to about 6.2.

5. The method of claim 2 wherein the antibody binds to the junction between domains I, II and III of HER2.

6. The method of claim 2 wherein the antibody is a full length antibody.

7. The method of claim 2 wherein the formulation is aqueous and has not been subjected to prior lyophilization.

8. A method of treating HER2-expressing cancer in a subject, comprising intravenously administering a pharmaceutical formulation to the subject in an amount effective to treat the cancer, wherein the formulation comprises Pertuzumab in an amount from 20mg/mL to 40mg/mL, histidine-acetate buffer, sucrose, and polysorbate 20, wherein the pH of the formulation is from about 5.5 to about 6.5.

9. The method of claim 8 wherein the formulation comprises about 30mg/mL Pertuzumab, about 20mM histidine-acetate, about 120mM sucrose, and about 0.02% polysorbate 20, wherein the pH of the formulation is about 6.0.

10. A method of treating HER2-expressing cancer in a subject, comprising intravenously administering a pharmaceutical formulation to the subject in an amount effective to treat the cancer, wherein the formulation is an aqueous pharmaceutical formulation which has not been subjected to prior lyophilization, comprising about 30mg/mL Pertuzumab, about 20mM histidine-acetate, about 120mM sucrose, and about 0.02% polysorbate 20, wherein the pH of the formulation is about 6.0.

11. A method of treating HER2-expressing cancer in a subject, comprising intravenously administering to the subject an aqueous pharmaceutical formulation which has not been subjected to prior lyophilization in an amount effective to treat the cancer, wherein the formulation comprises an antibody that binds to domain II of HER2 in a histidine-acetate buffer at a pH from about 5.5 to about 6.5, a saccharide, and a surfactant.

12. The method of claim 11 wherein the antibody is a full length IgG1 antibody.

13. A method of treating HER2-expressing cancer in a subject, comprising intravenously administering to the subject an aqueous pharmaceutical formulation which has not been subjected to prior lyophilization in an amount effective to treat the cancer, wherein the formulation comprises an antibody comprising the variable light and variable heavy amino acid sequences in SEQ ID Nos. 3 and 4, respectively, in a histidine-acetate buffer at a pH from about 5.5 to about 6.5, a saccharide, and a surfactant.

14. The method of claim 13 wherein the antibody is a full length IgG1 antibody.

* * * * *

```
SEQUENCE LISTING

<160> NUMBER OF SEQ ID NOS: 74

<210> SEQ ID NO 1
<211> LENGTH: 107
<212> TYPE: PRT
<213> ORGANISM: Mus musculus

<400> SEQUENCE: 1

Asp Thr Val Met Thr Gln Ser His Lys Ile Met Ser Thr Ser Val
 1               5                  10                  15

Gly Asp Arg Val Ser Ile Thr Cys Lys Ala Ser Gln Asp Val Ser
                20                  25                  30

Ile Gly Val Ala Trp Tyr Gln Gln Arg Pro Gly Gln Ser Pro Lys
                35                  40                  45

Leu Leu Ile Tyr Ser Ala Ser Tyr Arg Tyr Thr Gly Val Pro Asp
                50                  55                  60

Arg Phe Thr Gly Ser Gly Ser Gly Thr Asp Phe Thr Phe Thr Ile
                65                  70                  75

Ser Ser Val Gln Ala Glu Asp Leu Ala Val Tyr Tyr Cys Gln Gln
                80                  85                  90

Tyr Tyr Ile Tyr Pro Tyr Thr Phe Gly Gly Gly Thr Lys Leu Glu
                95                  100                 105

Ile Lys

<210> SEQ ID NO 2
<211> LENGTH: 119
<212> TYPE: PRT
<213> ORGANISM: Mus musculus

<400> SEQUENCE: 2

Glu Val Gln Leu Gln Gln Ser Gly Pro Glu Leu Val Lys Pro Gly
 1               5                  10                  15
```

```
Thr Ser Val Lys Ile Ser Cys Lys Ala Ser Gly Phe Thr Phe Thr
            20                  25                  30

Asp Tyr Thr Met Asp Trp Val Lys Gln Ser His Gly Lys Ser Leu
            35                  40                  45

Glu Trp Ile Gly Asp Val Asn Pro Asn Ser Gly Gly Ser Ile Tyr
            50                  55                  60

Asn Gln Arg Phe Lys Gly Lys Ala Ser Leu Thr Val Asp Arg Ser
            65                  70                  75

Ser Arg Ile Val Tyr Met Glu Leu Arg Ser Leu Thr Phe Glu Asp
            80                  85                  90

Thr Ala Val Tyr Tyr Cys Ala Arg Asn Leu Gly Pro Ser Phe Tyr
            95                 100                 105

Phe Asp Tyr Trp Gly Gln Gly Thr Thr Leu Thr Val Ser Ser
           110                 115

<210> SEQ ID NO 3
<211> LENGTH: 107
<212> TYPE: PRT
<213> ORGANISM: Artificial Sequence
<220> FEATURE:
<223> OTHER INFORMATION: sequence is synthesized

<400> SEQUENCE: 3

Asp Ile Gln Met Thr Gln Ser Pro Ser Ser Leu Ser Ala Ser Val
 1               5                  10                  15

Gly Asp Arg Val Thr Ile Thr Cys Lys Ala Ser Gln Asp Val Ser
            20                  25                  30

Ile Gly Val Ala Trp Tyr Gln Gln Lys Pro Gly Lys Ala Pro Lys
            35                  40                  45

Leu Leu Ile Tyr Ser Ala Ser Tyr Arg Tyr Thr Gly Val Pro Ser
            50                  55                  60

Arg Phe Ser Gly Ser Gly Ser Gly Thr Asp Phe Thr Leu Thr Ile
            65                  70                  75

Ser Ser Leu Gln Pro Glu Asp Phe Ala Thr Tyr Tyr Cys Gln Gln
            80                  85                  90

Tyr Tyr Ile Tyr Pro Tyr Thr Phe Gly Gln Gly Thr Lys Val Glu
            95                 100                 105

Ile Lys

<210> SEQ ID NO 4
<211> LENGTH: 119
<212> TYPE: PRT
<213> ORGANISM: Artificial Sequence
<220> FEATURE:
<223> OTHER INFORMATION: sequence is synthesized

<400> SEQUENCE: 4

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Phe Thr
            20                  25                  30

Asp Tyr Thr Met Asp Trp Val Arg Gln Ala Pro Gly Lys Gly Leu
            35                  40                  45

Glu Trp Val Ala Asp Val Asn Pro Asn Ser Gly Gly Ser Ile Tyr
            50                  55                  60

Asn Gln Arg Phe Lys Gly Arg Phe Thr Leu Ser Val Asp Arg Ser
            65                  70                  75
```

Lys Asn Thr Leu Tyr Leu Gln Met Asn Ser Leu Arg Ala Glu Asp
                80                  85                  90

Thr Ala Val Tyr Tyr Cys Ala Arg Asn Leu Gly Pro Ser Phe Tyr
                95                 100                 105

Phe Asp Tyr Trp Gly Gln Gly Thr Leu Val Thr Val Ser Ser
            110                 115

<210> SEQ ID NO 5
<211> LENGTH: 107
<212> TYPE: PRT
<213> ORGANISM: Artificial Sequence
<220> FEATURE:
<223> OTHER INFORMATION: sequence is synthesized

<400> SEQUENCE: 5

Asp Ile Gln Met Thr Gln Ser Pro Ser Ser Leu Ser Ala Ser Val
  1               5                  10                  15

Gly Asp Arg Val Thr Ile Thr Cys Arg Ala Ser Gln Ser Ile Ser
                 20                  25                  30

Asn Tyr Leu Ala Trp Tyr Gln Gln Lys Pro Gly Lys Ala Pro Lys
             35                  40                  45

Leu Leu Ile Tyr Ala Ala Ser Ser Leu Glu Ser Gly Val Pro Ser
         50                  55                  60

Arg Phe Ser Gly Ser Gly Ser Gly Thr Asp Phe Thr Leu Thr Ile
 65                  70                  75

Ser Ser Leu Gln Pro Glu Asp Phe Ala Thr Tyr Tyr Cys Gln Gln
                 80                  85                  90

Tyr Asn Ser Leu Pro Trp Thr Phe Gly Gln Gly Thr Lys Val Glu
             95                 100                 105

Ile Lys

<210> SEQ ID NO 6
<211> LENGTH: 119
<212> TYPE: PRT
<213> ORGANISM: Artificial Sequence
<220> FEATURE:
<223> OTHER INFORMATION: sequence is synthesized

<400> SEQUENCE: 6

Glu Val Gln Leu Val Glu Ser Gly Gly Gly Leu Val Gln Pro Gly
  1               5                  10                  15

Gly Ser Leu Arg Leu Ser Cys Ala Ala Ser Gly Phe Thr Phe Ser
                 20                  25                  30

Ser Tyr Ala Met Ser Trp Val Arg Gln Ala Pro Gly Lys Gly Leu
             35                  40                  45

Glu Trp Val Ala Val Ile Ser Gly Asp Gly Ser Thr Tyr Tyr
         50                  55                  60

Ala Asp Ser Val Lys Gly Arg Phe Thr Ile Ser Arg Asp Asn Ser
 65                  70                  75

Lys Asn Thr Leu Tyr Leu Gln Met Asn Ser Leu Arg Ala Glu Asp
                80                  85                  90

Thr Ala Val Tyr Tyr Cys Ala Arg Gly Arg Val Gly Tyr Ser Leu
                95                 100                 105

Tyr Asp Tyr Trp Gly Gln Gly Thr Leu Val Thr Val Ser Ser
            110                 115

<210> SEQ ID NO 7

```
<211> LENGTH: 10
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 10
<223> OTHER INFORMATION: Xaa is preferrably D or S

<400> SEQUENCE: 7

Gly Phe Thr Phe Thr Asp Tyr Thr Met Xaa
 1               5                  10

<210> SEQ ID NO 8
<211> LENGTH: 17
<212> TYPE: PRT
<213> ORGANISM: Artificial sequence
<220> FEATURE:
<223> OTHER INFORMATION: sequence is synthesized

<400> SEQUENCE: 8

Asp Val Asn Pro Asn Ser Gly Gly Ser Ile Tyr Asn Gln Arg Phe
 1               5                  10                  15

Lys Gly

<210> SEQ ID NO 9
<211> LENGTH: 10
<212> TYPE: PRT
<213> ORGANISM: Artificial sequence
<220> FEATURE:
<223> OTHER INFORMATION: sequence is synthesized

<400> SEQUENCE: 9

Asn Leu Gly Pro Ser Phe Tyr Phe Asp Tyr
 1               5                  10

<210> SEQ ID NO 10
<211> LENGTH: 11
<212> TYPE: PRT
<213> ORGANISM: Artificial sequence
<220> FEATURE:
<223> OTHER INFORMATION: sequence is synthesized

<400> SEQUENCE: 10

Lys Ala Ser Gln Asp Val Ser Ile Gly Val Ala
 1               5                  10

<210> SEQ ID NO 11
<211> LENGTH: 7
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 5
<223> OTHER INFORMATION: Xaa is preferrably R or L.
<220> FEATURE:
<221> NAME/KEY: Xaa
<222> LOCATION: 6
<223> OTHER INFORMATION: Xaa is preferrably Y or E.
<220> FEATURE:
<221> NAME/KEY: Xaa
<222> LOCATION: 7
<223> OTHER INFORMATION: Xaa is preferrably T or S.

<400> SEQUENCE: 11

Ser Ala Ser Tyr Xaa Xaa Xaa
```

```
                1               5

<210> SEQ ID NO 12
<211> LENGTH: 9
<212> TYPE: PRT
<213> ORGANISM: Artificial sequence
<220> FEATURE:
<223> OTHER INFORMATION: sequence is synthesized

<400> SEQUENCE: 12

Gln Gln Tyr Tyr Ile Tyr Pro Tyr Thr
  1               5

<210> SEQ ID NO 13
<211> LENGTH: 214
<212> TYPE: PRT
<213> ORGANISM: Artificial sequence
<220> FEATURE:
<223> OTHER INFORMATION: sequence is synthesized

<400> SEQUENCE: 13

Asp Ile Gln Met Thr Gln Ser Pro Ser Ser Leu Ser Ala Ser Val
  1               5                  10                  15

Gly Asp Arg Val Thr Ile Thr Cys Arg Ala Ser Gln Asp Val Asn
                 20                  25                  30

Thr Ala Val Ala Trp Tyr Gln Gln Lys Pro Gly Lys Ala Pro Lys
                 35                  40                  45

Leu Leu Ile Tyr Ser Ala Ser Phe Leu Tyr Ser Gly Val Pro Ser
                 50                  55                  60

Arg Phe Ser Gly Ser Arg Ser Gly Thr Asp Phe Thr Leu Thr Ile
                 65                  70                  75

Ser Ser Leu Gln Pro Glu Asp Phe Ala Thr Tyr Tyr Cys Gln Gln
                 80                  85                  90

His Tyr Thr Thr Pro Pro Thr Phe Gly Gln Gly Thr Lys Val Glu
                 95                 100                 105

Ile Lys Arg Thr Val Ala Ala Pro Ser Val Phe Ile Phe Pro Pro
                110                 115                 120

Ser Asp Glu Gln Leu Lys Ser Gly Thr Ala Ser Val Val Cys Leu
                125                 130                 135

Leu Asn Asn Phe Tyr Pro Arg Glu Ala Lys Val Gln Trp Lys Val
                140                 145                 150

Asp Asn Ala Leu Gln Ser Gly Asn Ser Gln Glu Ser Val Thr Glu
                155                 160                 165

Gln Asp Ser Lys Asp Ser Thr Tyr Ser Leu Ser Ser Thr Leu Thr
                170                 175                 180

Leu Ser Lys Ala Asp Tyr Glu Lys His Lys Val Tyr Ala Cys Glu
                185                 190                 195

Val Thr His Gln Gly Leu Ser Ser Pro Val Thr Lys Ser Phe Asn
                200                 205                 210

Arg Gly Glu Cys

<210> SEQ ID NO 14
<211> LENGTH: 449
<212> TYPE: PRT
<213> ORGANISM: Artificial sequence
<220> FEATURE:
<223> OTHER INFORMATION: sequence is synthesized

<400> SEQUENCE: 14
```

-continued

```
Glu Val Gln Leu Val Glu Ser Gly Gly Gly Leu Val Gln Pro Gly
  1               5                  10                  15

Gly Ser Leu Arg Leu Ser Cys Ala Ala Ser Gly Phe Asn Ile Lys
             20                  25                  30

Asp Thr Tyr Ile His Trp Val Arg Gln Ala Pro Gly Lys Gly Leu
             35                  40                  45

Glu Trp Val Ala Arg Ile Tyr Pro Thr Asn Gly Tyr Thr Arg Tyr
             50                  55                  60

Ala Asp Ser Val Lys Gly Arg Phe Thr Ile Ser Ala Asp Thr Ser
             65                  70                  75

Lys Asn Thr Ala Tyr Leu Gln Met Asn Ser Leu Arg Ala Glu Asp
             80                  85                  90

Thr Ala Val Tyr Tyr Cys Ser Arg Trp Gly Gly Asp Gly Phe Tyr
             95                 100                 105

Ala Met Asp Tyr Trp Gly Gln Gly Thr Leu Val Thr Val Ser Ser
            110                 115                 120

Ala Ser Thr Lys Gly Pro Ser Val Phe Pro Leu Ala Pro Ser Ser
            125                 130                 135

Lys Ser Thr Ser Gly Gly Thr Ala Ala Leu Gly Cys Leu Val Lys
            140                 145                 150

Asp Tyr Phe Pro Glu Pro Val Thr Val Ser Trp Asn Ser Gly Ala
            155                 160                 165

Leu Thr Ser Gly Val His Thr Phe Pro Ala Val Leu Gln Ser Ser
            170                 175                 180

Gly Leu Tyr Ser Leu Ser Ser Val Val Thr Val Pro Ser Ser Ser
            185                 190                 195

Leu Gly Thr Gln Thr Tyr Ile Cys Asn Val Asn His Lys Pro Ser
            200                 205                 210

Asn Thr Lys Val Asp Lys Lys Val Glu Pro Lys Ser Cys Asp Lys
            215                 220                 225

Thr His Thr Cys Pro Pro Cys Pro Ala Pro Glu Leu Leu Gly Gly
            230                 235                 240

Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn
            290                 295                 300

Ser Thr Tyr Arg Val Val Ser Val Leu Thr Val Leu His Gln Asp
            305                 310                 315

Trp Leu Asn Gly Lys Glu Tyr Lys Cys Lys Val Ser Asn Lys Ala
            320                 325                 330

Leu Pro Ala Pro Ile Glu Lys Thr Ile Ser Lys Ala Lys Gly Gln
            335                 340                 345

Pro Arg Glu Pro Gln Val Tyr Thr Leu Pro Pro Ser Arg Glu Glu
            350                 355                 360

Met Thr Lys Asn Gln Val Ser Leu Thr Cys Leu Val Lys Gly Phe
            365                 370                 375

Tyr Pro Ser Asp Ile Ala Val Glu Trp Glu Ser Asn Gly Gln Pro
            380                 385                 390

Glu Asn Asn Tyr Lys Thr Thr Pro Pro Val Leu Asp Ser Asp Gly
```

```
                395                 400                 405

Ser Phe Phe Leu Tyr Ser Lys Leu Thr Val Asp Lys Ser Arg Trp
            410                 415                 420

Gln Gln Gly Asn Val Phe Ser Cys Ser Val Met His Glu Ala Leu
            425                 430                 435

His Asn His Tyr Thr Gln Lys Ser Leu Ser Leu Ser Pro Gly
            440                 445

<210> SEQ ID NO 15
<211> LENGTH: 214
<212> TYPE: PRT
<213> ORGANISM: Artificial sequence
<220> FEATURE:
<223> OTHER INFORMATION: sequence is synthesized

<400> SEQUENCE: 15

Asp Ile Gln Met Thr Gln Ser Pro Ser Ser Leu Ser Ala Ser Val
 1               5                  10                  15

Gly Asp Arg Val Thr Ile Thr Cys Lys Ala Ser Gln Asp Val Ser
            20                  25                  30

Ile Gly Val Ala Trp Tyr Gln Gln Lys Pro Gly Lys Ala Pro Lys
            35                  40                  45

Leu Leu Ile Tyr Ser Ala Ser Tyr Arg Tyr Thr Gly Val Pro Ser
            50                  55                  60

Arg Phe Ser Gly Ser Gly Ser Gly Thr Asp Phe Thr Leu Thr Ile
            65                  70                  75

Ser Ser Leu Gln Pro Glu Asp Phe Ala Thr Tyr Tyr Cys Gln Gln
            80                  85                  90

Tyr Tyr Ile Tyr Pro Tyr Thr Phe Gly Gln Gly Thr Lys Val Glu
            95                 100                 105

Ile Lys Arg Thr Val Ala Ala Pro Ser Val Phe Ile Phe Pro Pro
           110                 115                 120

Ser Asp Glu Gln Leu Lys Ser Gly Thr Ala Ser Val Val Cys Leu
           125                 130                 135

Leu Asn Asn Phe Tyr Pro Arg Glu Ala Lys Val Gln Trp Lys Val
           140                 145                 150

Asp Asn Ala Leu Gln Ser Gly Asn Ser Gln Glu Ser Val Thr Glu
           155                 160                 165

Gln Asp Ser Lys Asp Ser Thr Tyr Ser Leu Ser Ser Thr Leu Thr
           170                 175                 180

Leu Ser Lys Ala Asp Tyr Glu Lys His Lys Val Tyr Ala Cys Glu
           185                 190                 195

Val Thr His Gln Gly Leu Ser Ser Pro Val Thr Lys Ser Phe Asn
           200                 205                 210

Arg Gly Glu Cys

<210> SEQ ID NO 16
<211> LENGTH: 448
<212> TYPE: PRT
<213> ORGANISM: Artificial sequence
<220> FEATURE:
<223> OTHER INFORMATION: sequence is synthesized

<400> SEQUENCE: 16

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Phe Thr
```

```
                        20                  25                  30
Asp Tyr Thr Met Asp Trp Val Arg Gln Ala Pro Gly Lys Gly Leu
                35                  40                  45
Glu Trp Val Ala Asp Val Asn Pro Asn Ser Gly Gly Ser Ile Tyr
                50                  55                  60
Asn Gln Arg Phe Lys Gly Arg Phe Thr Leu Ser Val Asp Arg Ser
                65                  70                  75
Lys Asn Thr Leu Tyr Leu Gln Met Asn Ser Leu Arg Ala Glu Asp
                80                  85                  90
Thr Ala Val Tyr Tyr Cys Ala Arg Asn Leu Gly Pro Ser Phe Tyr
                95                  100                 105
Phe Asp Tyr Trp Gly Gln Gly Thr Leu Val Thr Val Ser Ser Ala
                110                 115                 120
Ser Thr Lys Gly Pro Ser Val Phe Pro Leu Ala Pro Ser Ser Lys
                125                 130                 135
Ser Thr Ser Gly Gly Thr Ala Ala Leu Gly Cys Leu Val Lys Asp
                140                 145                 150
Tyr Phe Pro Glu Pro Val Thr Val Ser Trp Asn Ser Gly Ala Leu
                155                 160                 165
Thr Ser Gly Val His Thr Phe Pro Ala Val Leu Gln Ser Ser Gly
                170                 175                 180
Leu Tyr Ser Leu Ser Ser Val Val Thr Val Pro Ser Ser Ser Leu
                185                 190                 195
Gly Thr Gln Thr Tyr Ile Cys Asn Val Asn His Lys Pro Ser Asn
                200                 205                 210
Thr Lys Val Asp Lys Lys Val Glu Pro Lys Ser Cys Asp Lys Thr
                215                 220                 225
His Thr Cys Pro Pro Cys Pro Ala Pro Glu Leu Leu Gly Gly Pro
                230                 235                 240
Ser Val Phe Leu Phe Pro Pro Lys Pro Lys Asp Thr Leu Met Ile
                245                 250                 255
Ser Arg Thr Pro Glu Val Thr Cys Val Val Asp Val Ser His
                260                 265                 270
Glu Asp Pro Glu Val Lys Phe Asn Trp Tyr Val Asp Gly Val Glu
                275                 280                 285
Val His Asn Ala Lys Thr Lys Pro Arg Glu Glu Gln Tyr Asn Ser
                290                 295                 300
Thr Tyr Arg Val Val Ser Val Leu Thr Val Leu His Gln Asp Trp
                305                 310                 315
Leu Asn Gly Lys Glu Tyr Lys Cys Lys Val Ser Asn Lys Ala Leu
                320                 325                 330
Pro Ala Pro Ile Glu Lys Thr Ile Ser Lys Ala Lys Gly Gln Pro
                335                 340                 345
Arg Glu Pro Gln Val Tyr Thr Leu Pro Pro Ser Arg Glu Glu Met
                350                 355                 360
Thr Lys Asn Gln Val Ser Leu Thr Cys Leu Val Lys Gly Phe Tyr
                365                 370                 375
Pro Ser Asp Ile Ala Val Glu Trp Glu Ser Asn Gly Gln Pro Glu
                380                 385                 390
Asn Asn Tyr Lys Thr Thr Pro Pro Val Leu Asp Ser Asp Gly Ser
                395                 400                 405
Phe Phe Leu Tyr Ser Lys Leu Thr Val Asp Lys Ser Arg Trp Gln
                410                 415                 420
```

Gln Gly Asn Val Phe Ser Cys Ser Val Met His Glu Ala Leu His
                425                 430                 435

Asn His Tyr Thr Gln Lys Ser Leu Ser Leu Ser Pro Gly
                440                 445

<210> SEQ ID NO 17
<211> LENGTH: 233
<212> TYPE: PRT
<213> ORGANISM: Artificial sequence
<220> FEATURE:
<223> OTHER INFORMATION: sequence is synthesized

<400> SEQUENCE: 17

Met Gly Trp Ser Cys Ile Ile Leu Phe Leu Val Ala Thr Ala Thr
 1               5                  10                  15

Gly Val His Ser Asp Ile Gln Met Thr Gln Ser Pro Ser Ser Leu
                20                  25                  30

Ser Ala Ser Val Gly Asp Arg Val Thr Ile Thr Cys Lys Ala Ser
                35                  40                  45

Gln Asp Val Ser Ile Gly Val Ala Trp Tyr Gln Gln Lys Pro Gly
                50                  55                  60

Lys Ala Pro Lys Leu Leu Ile Tyr Ser Ala Ser Tyr Arg Tyr Thr
                65                  70                  75

Gly Val Pro Ser Arg Phe Ser Gly Ser Gly Ser Gly Thr Asp Phe
                80                  85                  90

Thr Leu Thr Ile Ser Ser Leu Gln Pro Glu Asp Phe Ala Thr Tyr
                95                  100                 105

Tyr Cys Gln Gln Tyr Tyr Ile Tyr Pro Tyr Thr Phe Gly Gln Gly
                110                 115                 120

Thr Lys Val Glu Ile Lys Arg Thr Val Ala Ala Pro Ser Val Phe
                125                 130                 135

Ile Phe Pro Pro Ser Asp Glu Gln Leu Lys Ser Gly Thr Ala Ser
                140                 145                 150

Val Val Cys Leu Leu Asn Asn Phe Tyr Pro Arg Glu Ala Lys Val
                155                 160                 165

Gln Trp Lys Val Asp Asn Ala Leu Gln Ser Gly Asn Ser Gln Glu
                170                 175                 180

Ser Val Thr Glu Gln Asp Ser Lys Asp Ser Thr Tyr Ser Leu Ser
                185                 190                 195

Ser Thr Leu Thr Leu Ser Lys Ala Asp Tyr Glu Lys His Lys Val
                200                 205                 210

Tyr Ala Cys Glu Val Thr His Gln Gly Leu Ser Ser Pro Val Thr
                215                 220                 225

Lys Ser Phe Asn Arg Gly Glu Cys
                230

<210> SEQ ID NO 18
<211> LENGTH: 467
<212> TYPE: PRT
<213> ORGANISM: Artificial sequence
<220> FEATURE:
<223> OTHER INFORMATION: sequence is synthesized

<400> SEQUENCE: 18

Met Gly Trp Ser Cys Ile Ile Leu Phe Leu Val Ala Thr Ala Thr
 1               5                  10                  15

Gly Val His Ser Glu Val Gln Leu Val Glu Ser Gly Gly Gly Leu

```
                 20                  25                  30
Val Gln Pro Gly Gly Ser Leu Arg Leu Ser Cys Ala Ala Ser Gly
             35                  40                  45
Phe Thr Phe Thr Asp Tyr Thr Met Asp Trp Val Arg Gln Ala Pro
         50                  55                  60
Gly Lys Gly Leu Glu Trp Val Ala Asp Val Asn Pro Asn Ser Gly
     65                  70                  75
Gly Ser Ile Tyr Asn Gln Arg Phe Lys Gly Arg Phe Thr Leu Ser
 80                  85                  90
Val Asp Arg Ser Lys Asn Thr Leu Tyr Leu Gln Met Asn Ser Leu
             95                 100                 105
Arg Ala Glu Asp Thr Ala Val Tyr Tyr Cys Ala Arg Asn Leu Gly
        110                 115                 120
Pro Ser Phe Tyr Phe Asp Tyr Trp Gly Gln Gly Thr Leu Val Thr
    125                 130                 135
Val Ser Ser Ala Ser Thr Lys Gly Pro Ser Val Phe Pro Leu Ala
140                 145                 150
Pro Ser Ser Lys Ser Thr Ser Gly Gly Thr Ala Ala Leu Gly Cys
            155                 160                 165
Leu Val Lys Asp Tyr Phe Pro Glu Pro Val Thr Val Ser Trp Asn
        170                 175                 180
Ser Gly Ala Leu Thr Ser Gly Val His Thr Phe Pro Ala Val Leu
    185                 190                 195
Gln Ser Ser Gly Leu Tyr Ser Leu Ser Ser Val Val Thr Val Pro
200                 205                 210
Ser Ser Ser Leu Gly Thr Gln Thr Tyr Ile Cys Asn Val Asn His
            215                 220                 225
Lys Pro Ser Asn Thr Lys Val Asp Lys Val Glu Pro Lys Ser
        230                 235                 240
Cys Asp Lys Thr His Thr Cys Pro Pro Cys Pro Ala Pro Glu Leu
    245                 250                 255
Leu Gly Gly Pro Ser Val Phe Leu Phe Pro Pro Lys Pro Lys Asp
260                 265                 270
Thr Leu Met Ile Ser Arg Thr Pro Glu Val Thr Cys Val Val Val
            275                 280                 285
Asp Val Ser His Glu Asp Pro Glu Val Lys Phe Asn Trp Tyr Val
        290                 295                 300
Asp Gly Val Glu Val His Asn Ala Lys Thr Lys Pro Arg Glu Glu
    305                 310                 315
Gln Tyr Asn Ser Thr Tyr Arg Val Val Ser Val Leu Thr Val Leu
320                 325                 330
His Gln Asp Trp Leu Asn Gly Lys Glu Tyr Lys Cys Lys Val Ser
            335                 340                 345
Asn Lys Ala Leu Pro Ala Pro Ile Glu Lys Thr Ile Ser Lys Ala
        350                 355                 360
Lys Gly Gln Pro Arg Glu Pro Gln Val Tyr Thr Leu Pro Pro Ser
    365                 370                 375
Arg Glu Glu Met Thr Lys Asn Gln Val Ser Leu Thr Cys Leu Val
380                 385                 390
Lys Gly Phe Tyr Pro Ser Asp Ile Ala Val Glu Trp Glu Ser Asn
            395                 400                 405
Gly Gln Pro Glu Asn Asn Tyr Lys Thr Thr Pro Pro Val Leu Asp
        410                 415                 420
```

```
Ser Asp Gly Ser Phe Phe Leu Tyr Ser Lys Leu Thr Val Asp Lys
                425                 430                 435

Ser Arg Trp Gln Gln Gly Asn Val Phe Ser Cys Ser Val Met His
                440                 445                 450

Glu Ala Leu His Asn His Tyr Thr Gln Lys Ser Leu Ser Leu Ser
                455                 460                 465

Pro Gly

<210> SEQ ID NO 19
<211> LENGTH: 195
<212> TYPE: PRT
<213> ORGANISM: Homo sapiens

<400> SEQUENCE: 19

Thr Gln Val Cys Thr Gly Thr Asp Met Lys Leu Arg Leu Pro Ala
 1               5                  10                  15

Ser Pro Glu Thr His Leu Asp Met Leu Arg His Leu Tyr Gln Gly
                20                  25                  30

Cys Gln Val Val Gln Gly Asn Leu Glu Leu Thr Tyr Leu Pro Thr
                35                  40                  45

Asn Ala Ser Leu Ser Phe Leu Gln Asp Ile Gln Glu Val Gln Gly
                50                  55                  60

Tyr Val Leu Ile Ala His Asn Gln Val Arg Gln Val Pro Leu Gln
                65                  70                  75

Arg Leu Arg Ile Val Arg Gly Thr Gln Leu Phe Glu Asp Asn Tyr
                80                  85                  90

Ala Leu Ala Val Leu Asp Asn Gly Asp Pro Leu Asn Asn Thr Thr
                95                  100                 105

Pro Val Thr Gly Ala Ser Pro Gly Gly Leu Arg Glu Leu Gln Leu
                110                 115                 120

Arg Ser Leu Thr Glu Ile Leu Lys Gly Gly Val Leu Ile Gln Arg
                125                 130                 135

Asn Pro Gln Leu Cys Tyr Gln Asp Thr Ile Leu Trp Lys Asp Ile
                140                 145                 150

Phe His Lys Asn Asn Gln Leu Ala Leu Thr Leu Ile Asp Thr Asn
                155                 160                 165

Arg Ser Arg Ala Cys His Pro Cys Ser Pro Met Cys Lys Gly Ser
                170                 175                 180

Arg Cys Trp Gly Glu Ser Ser Glu Asp Cys Gln Ser Leu Thr Arg
                185                 190                 195

<210> SEQ ID NO 20
<211> LENGTH: 124
<212> TYPE: PRT
<213> ORGANISM: Homo sapiens

<400> SEQUENCE: 20

Thr Val Cys Ala Gly Gly Cys Ala Arg Cys Lys Gly Pro Leu Pro
 1               5                  10                  15

Thr Asp Cys Cys His Glu Gln Cys Ala Ala Gly Cys Thr Gly Pro
                20                  25                  30

Lys His Ser Asp Cys Leu Ala Cys Leu His Phe Asn His Ser Gly
                35                  40                  45

Ile Cys Glu Leu His Cys Pro Ala Leu Val Thr Tyr Asn Thr Asp
                50                  55                  60
```

Thr Phe Glu Ser Met Pro Asn Pro Glu Gly Arg Tyr Thr Phe Gly
                65                  70                  75

Ala Ser Cys Val Thr Ala Cys Pro Tyr Asn Tyr Leu Ser Thr Asp
            80                  85                  90

Val Gly Ser Cys Thr Leu Val Cys Pro Leu His Asn Gln Glu Val
        95                 100                 105

Thr Ala Glu Asp Gly Thr Gln Arg Cys Glu Lys Cys Ser Lys Pro
    110                 115                 120

Cys Ala Arg Val

<210> SEQ ID NO 21
<211> LENGTH: 169
<212> TYPE: PRT
<213> ORGANISM: Homo sapiens

<400> SEQUENCE: 21

Cys Tyr Gly Leu Gly Met Glu His Leu Arg Glu Val Arg Ala Val
 1               5                  10                  15

Thr Ser Ala Asn Ile Gln Glu Phe Ala Gly Cys Lys Lys Ile Phe
            20                  25                  30

Gly Ser Leu Ala Phe Leu Pro Glu Ser Phe Asp Gly Asp Pro Ala
        35                  40                  45

Ser Asn Thr Ala Pro Leu Gln Pro Glu Gln Leu Gln Val Phe Glu
    50                  55                  60

Thr Leu Glu Glu Ile Thr Gly Tyr Leu Tyr Ile Ser Ala Trp Pro
65                  70                  75

Asp Ser Leu Pro Asp Leu Ser Val Phe Gln Asn Leu Gln Val Ile
                80                  85                  90

Arg Gly Arg Ile Leu His Asn Gly Ala Tyr Ser Leu Thr Leu Gln
            95                 100                 105

Gly Leu Gly Ile Ser Trp Leu Gly Leu Arg Ser Leu Arg Glu Leu
        110                 115                 120

Gly Ser Gly Leu Ala Leu Ile His His Asn Thr His Leu Cys Phe
    125                 130                 135

Val His Thr Val Pro Trp Asp Gln Leu Phe Arg Asn Pro His Gln
140                 145                 150

Ala Leu Leu His Thr Ala Asn Arg Pro Glu Asp Glu Cys Val Gly
                155                 160                 165

Glu Gly Leu Ala

<210> SEQ ID NO 22
<211> LENGTH: 142
<212> TYPE: PRT
<213> ORGANISM: Homo sapiens

<400> SEQUENCE: 22

Cys His Gln Leu Cys Ala Arg Gly His Cys Trp Gly Pro Gly Pro
 1               5                  10                  15

Thr Gln Cys Val Asn Cys Ser Gln Phe Leu Arg Gly Gln Glu Cys
            20                  25                  30

Val Glu Glu Cys Arg Val Leu Gln Gly Leu Pro Arg Glu Tyr Val
        35                  40                  45

Asn Ala Arg His Cys Leu Pro Cys His Pro Glu Cys Gln Pro Gln
    50                  55                  60

Asn Gly Ser Val Thr Cys Phe Gly Pro Glu Ala Asp Gln Cys Val
65                  70                  75

```
Ala Cys Ala His Tyr Lys Asp Pro Pro Phe Cys Val Ala Arg Cys
                80                  85                  90

Pro Ser Gly Val Lys Pro Asp Leu Ser Tyr Met Pro Ile Trp Lys
                95                 100                 105

Phe Pro Asp Glu Glu Gly Ala Cys Gln Pro Cys Pro Ile Asn Cys
               110                 115                 120

Thr His Ser Cys Val Asp Leu Asp Asp Lys Gly Cys Pro Ala Glu
               125                 130                 135

Gln Arg Ala Ser Pro Leu Thr
               140
```

<210> SEQ ID NO 23
<211> LENGTH: 217
<212> TYPE: PRT
<213> ORGANISM: Artificial sequence
<220> FEATURE:
<223> OTHER INFORMATION: sequence is synthesized

<400> SEQUENCE: 23

```
Val His Ser Asp Ile Gln Met Thr Gln Ser Pro Ser Ser Leu Ser
  1               5                  10                  15

Ala Ser Val Gly Asp Arg Val Thr Ile Thr Cys Lys Ala Ser Gln
                20                  25                  30

Asp Val Ser Ile Gly Val Ala Trp Tyr Gln Gln Lys Pro Gly Lys
                35                  40                  45

Ala Pro Lys Leu Leu Ile Tyr Ser Ala Ser Tyr Arg Tyr Thr Gly
                50                  55                  60

Val Pro Ser Arg Phe Ser Gly Ser Gly Ser Gly Thr Asp Phe Thr
                65                  70                  75

Leu Thr Ile Ser Ser Leu Gln Pro Glu Asp Phe Ala Thr Tyr Tyr
                80                  85                  90

Cys Gln Gln Tyr Tyr Ile Tyr Pro Tyr Thr Phe Gly Gln Gly Thr
                95                 100                 105

Lys Val Glu Ile Lys Arg Thr Val Ala Ala Pro Ser Val Phe Ile
               110                 115                 120

Phe Pro Pro Ser Asp Glu Gln Leu Lys Ser Gly Thr Ala Ser Val
               125                 130                 135

Val Cys Leu Leu Asn Asn Phe Tyr Pro Arg Glu Ala Lys Val Gln
               140                 145                 150

Trp Lys Val Asp Asn Ala Leu Gln Ser Gly Asn Ser Gln Glu Ser
               155                 160                 165

Val Thr Glu Gln Asp Ser Lys Asp Ser Thr Tyr Ser Leu Ser Ser
               170                 175                 180

Thr Leu Thr Leu Ser Lys Ala Asp Tyr Glu Lys His Lys Val Tyr
               185                 190                 195

Ala Cys Glu Val Thr His Gln Gly Leu Ser Ser Pro Val Thr Lys
               200                 205                 210

Ser Phe Asn Arg Gly Glu Cys
               215
```

<210> SEQ ID NO 24
<211> LENGTH: 449
<212> TYPE: PRT
<213> ORGANISM: Artificial sequence
<220> FEATURE:
<223> OTHER INFORMATION: sequence is synthesized -continued

```
<400> SEQUENCE: 24

Glu Val Gln Leu Val Glu Ser Gly Gly Gly Leu Val Gln Pro Gly
  1               5                  10                  15

Gly Ser Leu Arg Leu Ser Cys Ala Ala Ser Gly Phe Thr Phe Thr
             20                  25                  30

Asp Tyr Thr Met Asp Trp Val Arg Gln Ala Pro Gly Lys Gly Leu
         35                  40                  45

Glu Trp Val Ala Asp Val Asn Pro Asn Ser Gly Gly Ser Ile Tyr
     50                  55                  60

Asn Gln Arg Phe Lys Gly Arg Phe Thr Leu Ser Val Asp Arg Ser
 65                  70                  75

Lys Asn Thr Leu Tyr Leu Gln Met Asn Ser Leu Arg Ala Glu Asp
             80                  85                  90

Thr Ala Val Tyr Tyr Cys Ala Arg Asn Leu Gly Pro Ser Phe Tyr
         95                 100                 105

Phe Asp Tyr Trp Gly Gln Gly Thr Leu Val Thr Val Ser Ser Ala
            110                 115                 120

Ser Thr Lys Gly Pro Ser Val Phe Pro Leu Ala Pro Ser Ser Lys
            125                 130                 135

Ser Thr Ser Gly Gly Thr Ala Ala Leu Gly Cys Leu Val Lys Asp
            140                 145                 150

Tyr Phe Pro Glu Pro Val Thr Val Ser Trp Asn Ser Gly Ala Leu
            155                 160                 165

Thr Ser Gly Val His Thr Phe Pro Ala Val Leu Gln Ser Ser Gly
            170                 175                 180

Leu Tyr Ser Leu Ser Ser Val Val Thr Val Pro Ser Ser Ser Leu
            185                 190                 195

Gly Thr Gln Thr Tyr Ile Cys Asn Val Asn His Lys Pro Ser Asn
            200                 205                 210

Thr Lys Val Asp Lys Lys Val Glu Pro Lys Ser Cys Asp Lys Thr
            215                 220                 225

His Thr Cys Pro Pro Cys Pro Ala Pro Glu Leu Leu Gly Gly Pro
            230                 235                 240

Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp
            305                 310                 315

Leu Asn Gly Lys Glu Tyr Lys Cys Lys Val Ser Asn Lys Ala Leu
            320                 325                 330

Pro Ala Pro Ile Glu Lys Thr Ile Ser Lys Ala Lys Gly Gln Pro
            335                 340                 345

Arg Glu Pro Gln Val Tyr Thr Leu Pro Pro Ser Arg Glu Glu Met
            350                 355                 360

Thr Lys Asn Gln Val Ser Leu Thr Cys Leu Val Lys Gly Phe Tyr
            365                 370                 375

Pro Ser Asp Ile Ala Val Glu Trp Glu Ser Asn Gly Gln Pro Glu
            380                 385                 390
```

```
Asn Asn Tyr Lys Thr Thr Pro Pro Val Leu Asp Ser Asp Gly Ser
                395                 400                 405

Phe Phe Leu Tyr Ser Lys Leu Thr Val Asp Lys Ser Arg Trp Gln
                410                 415                 420

Gln Gly Asn Val Phe Ser Cys Ser Val Met His Glu Ala Leu His
                425                 430                 435

Asn His Tyr Thr Gln Lys Ser Leu Ser Leu Ser Pro Gly Lys
                440                 445

<210> SEQ ID NO 25
<211> LENGTH: 107
<212> TYPE: PRT
<213> ORGANISM: Mus musculus

<400> SEQUENCE: 25

Gln Ile Val Leu Ser Gln Ser Pro Ala Ile Leu Ser Ala Ser Pro
  1               5                  10                  15

Gly Glu Lys Val Thr Met Thr Cys Arg Ala Ser Ser Ser Val Ser
                 20                  25                  30

Tyr Met His Trp Tyr Gln Gln Lys Pro Gly Ser Ser Pro Lys Pro
                 35                  40                  45

Trp Ile Tyr Ala Pro Ser Asn Leu Ala Ser Gly Val Pro Ala Arg
                 50                  55                  60

Phe Ser Gly Ser Gly Ser Gly Thr Ser Tyr Ser Leu Thr Ile Ser
                 65                  70                  75

Arg Val Glu Ala Glu Asp Ala Ala Thr Tyr Tyr Cys Gln Gln Trp
                 80                  85                  90

Ser Phe Asn Pro Pro Thr Phe Gly Ala Gly Thr Lys Leu Glu Leu
                 95                 100                 105

Lys Arg

<210> SEQ ID NO 26
<211> LENGTH: 107
<212> TYPE: PRT
<213> ORGANISM: Artificial sequence
<220> FEATURE:
<223> OTHER INFORMATION: sequence is synthesized

<400> SEQUENCE: 26

Asp Ile Gln Met Thr Gln Ser Pro Ser Ser Leu Ser Ala Ser Val
  1               5                  10                  15

Gly Asp Arg Val Thr Ile Thr Cys Arg Ala Ser Ser Ser Val Ser
                 20                  25                  30

Tyr Met His Trp Tyr Gln Gln Lys Pro Gly Lys Ala Pro Lys Pro
                 35                  40                  45

Leu Ile Tyr Ala Pro Ser Asn Leu Ala Ser Gly Val Pro Ser Arg
                 50                  55                  60

Phe Ser Gly Ser Gly Ser Gly Thr Asp Phe Thr Leu Thr Ile Ser
                 65                  70                  75

Ser Leu Gln Pro Glu Asp Phe Ala Thr Tyr Tyr Cys Gln Gln Trp
                 80                  85                  90

Ser Phe Asn Pro Pro Thr Phe Gly Gln Gly Thr Lys Val Glu Ile
                 95                 100                 105

Lys Arg

<210> SEQ ID NO 27
```

<211> LENGTH: 108
<212> TYPE: PRT
<213> ORGANISM: Artificial Sequence
<220> FEATURE:
<223> OTHER INFORMATION: sequence is synthesized

<400> SEQUENCE: 27

```
Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Ser Ile Ser
                20                  25                  30

Asn Tyr Leu Ala Trp Tyr Gln Gln Lys Pro Gly Lys Ala Pro Lys
                35                  40                  45

Leu Leu Ile Tyr Ala Ala Ser Ser Leu Glu Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Tyr Asn Ser Leu Pro Trp Thr Phe Gly Gln Gly Thr Lys Val Glu
                95                  100                 105

Ile Lys Arg
```

<210> SEQ ID NO 28
<211> LENGTH: 122
<212> TYPE: PRT
<213> ORGANISM: Mus musculus

<400> SEQUENCE: 28

```
Gln Ala Tyr Leu Gln Gln Ser Gly Ala Glu Leu Val Arg Pro Gly
 1               5                  10                  15

Ala Ser Val Lys Met Ser Cys Lys Ala Ser Gly Tyr Thr Phe Thr
                20                  25                  30

Ser Tyr Asn Met His Trp Val Lys Gln Thr Pro Arg Gln Gly Leu
                35                  40                  45

Glu Trp Ile Gly Ala Ile Tyr Pro Gly Asn Gly Asp Thr Ser Tyr
                50                  55                  60

Asn Gln Lys Phe Lys Gly Lys Ala Thr Leu Thr Val Asp Lys Ser
                65                  70                  75

Ser Ser Thr Ala Tyr Met Gln Leu Ser Ser Leu Thr Ser Glu Asp
                80                  85                  90

Ser Ala Val Tyr Phe Cys Ala Arg Val Val Tyr Tyr Ser Asn Ser
                95                  100                 105

Tyr Trp Tyr Phe Asp Val Trp Gly Thr Gly Thr Thr Val Thr Val
                110                 115                 120

Ser Ser
```

<210> SEQ ID NO 29
<211> LENGTH: 122
<212> TYPE: PRT
<213> ORGANISM: Artificial sequence
<220> FEATURE:
<223> OTHER INFORMATION: sequence is synthesized

<400> SEQUENCE: 29

```
Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Thr Phe Thr
```

```
                    20                  25                  30

Ser Tyr Asn Met His Trp Val Arg Gln Ala Pro Gly Lys Gly Leu
                35                  40                  45

Glu Trp Val Gly Ala Ile Tyr Pro Gly Asn Gly Asp Thr Ser Tyr
            50                  55                  60

Asn Gln Lys Phe Lys Gly Arg Phe Thr Ile Ser Val Asp Lys Ser
        65                  70                  75

Lys Asn Thr Leu Tyr Leu Gln Met Asn Ser Leu Arg Ala Glu Asp
    80                  85                  90

Thr Ala Val Tyr Tyr Cys Ala Arg Val Val Tyr Tyr Ser Asn Ser
                95                 100                 105

Tyr Trp Tyr Phe Asp Val Trp Gly Gln Gly Thr Leu Val Thr Val
            110                 115                 120

Ser Ser

<210> SEQ ID NO 30
<211> LENGTH: 119
<212> TYPE: PRT
<213> ORGANISM: Artificial Sequence
<220> FEATURE:
<223> OTHER INFORMATION: sequence is synthesized

<400> SEQUENCE: 30

Glu Val Gln Leu Val Glu Ser Gly Gly Gly Leu Val Gln Pro Gly
  1               5                  10                  15

Gly Ser Leu Arg Leu Ser Cys Ala Ala Ser Gly Phe Thr Phe Ser
                20                  25                  30

Ser Tyr Ala Met Ser Trp Val Arg Gln Ala Pro Gly Lys Gly Leu
                35                  40                  45

Glu Trp Val Ala Val Ile Ser Gly Asp Gly Gly Ser Thr Tyr Tyr
            50                  55                  60

Ala Asp Ser Val Lys Gly Arg Phe Thr Ile Ser Arg Asp Asn Ser
        65                  70                  75

Lys Asn Thr Leu Tyr Leu Gln Met Asn Ser Leu Arg Ala Glu Asp
    80                  85                  90

Thr Ala Val Tyr Tyr Cys Ala Arg Gly Arg Val Gly Tyr Ser Leu
                95                 100                 105

Tyr Asp Tyr Trp Gly Gln Gly Thr Leu Val Thr Val Ser Ser
            110                 115

<210> SEQ ID NO 31
<211> LENGTH: 107
<212> TYPE: PRT
<213> ORGANISM: Artificial sequence
<220> FEATURE:
<223> OTHER INFORMATION: Sequence is synthesized.

<400> SEQUENCE: 31

Asp Ile Gln Met Thr Gln Thr Thr Ser Ser Leu Ser Ala Ser Leu
  1               5                  10                  15

Gly Asp Arg Val Ile Ile Ser Cys Ser Ala Ser Gln Asp Ile Ser
                20                  25                  30

Asn Tyr Leu Asn Trp Tyr Gln Gln Lys Pro Asp Gly Thr Val Lys
                35                  40                  45

Val Leu Ile Tyr Phe Thr Ser Ser Leu His Ser Gly Val Pro Ser
            50                  55                  60

Arg Phe Ser Gly Ser Gly Ser Gly Thr Asp Tyr Ser Leu Thr Ile
```

```
                 65                  70                  75
Ser Asn Leu Glu Pro Glu Asp Ile Ala Thr Tyr Tyr Cys Gln Gln
             80                  85                  90

Tyr Ser Thr Val Pro Trp Thr Phe Gly Gly Gly Thr Lys Leu Glu
             95                 100                 105

Ile Lys

<210> SEQ ID NO 32
<211> LENGTH: 123
<212> TYPE: PRT
<213> ORGANISM: Artificial sequence
<220> FEATURE:
<223> OTHER INFORMATION: Sequence is synthesized.

<400> SEQUENCE: 32

Glu Ile Gln Leu Val Gln Ser Gly Pro Glu Leu Lys Gln Pro Gly
 1               5                  10                  15

Glu Thr Val Arg Ile Ser Cys Lys Ala Ser Gly Tyr Thr Phe Thr
             20                  25                  30

Asn Tyr Gly Met Asn Trp Val Lys Gln Ala Pro Gly Lys Gly Leu
             35                  40                  45

Lys Trp Met Gly Trp Ile Asn Thr Tyr Thr Gly Glu Pro Thr Tyr
             50                  55                  60

Ala Ala Asp Phe Lys Arg Arg Phe Thr Phe Ser Leu Glu Thr Ser
             65                  70                  75

Ala Ser Thr Ala Tyr Leu Gln Ile Ser Asn Leu Lys Asn Asp Asp
             80                  85                  90

Thr Ala Thr Tyr Phe Cys Ala Lys Tyr Pro His Tyr Tyr Gly Ser
             95                 100                 105

Ser His Trp Tyr Phe Asp Val Trp Gly Ala Gly Thr Thr Val Thr
            110                 115                 120

Val Ser Ser

<210> SEQ ID NO 33
<211> LENGTH: 107
<212> TYPE: PRT
<213> ORGANISM: Artificial sequence
<220> FEATURE:
<223> OTHER INFORMATION: Sequence is synthesized.

<400> SEQUENCE: 33

Asp Ile Gln Met Thr Gln Ser Pro Ser Ser Leu Ser Ala Ser Val
 1               5                  10                  15

Gly Asp Arg Val Thr Ile Thr Cys Ser Ala Ser Gln Asp Ile Ser
             20                  25                  30

Asn Tyr Leu Asn Trp Tyr Gln Gln Lys Pro Gly Lys Ala Pro Lys
             35                  40                  45

Val Leu Ile Tyr Phe Thr Ser Ser Leu His Ser Gly Val Pro Ser
             50                  55                  60

Arg Phe Ser Gly Ser Gly Ser Gly Thr Asp Phe Thr Leu Thr Ile
             65                  70                  75

Ser Ser Leu Gln Pro Glu Asp Phe Ala Thr Tyr Tyr Cys Gln Gln
             80                  85                  90

Tyr Ser Thr Val Pro Trp Thr Phe Gly Gln Gly Thr Lys Val Glu
             95                 100                 105

Ile Lys
```

<210> SEQ ID NO 34
<211> LENGTH: 123
<212> TYPE: PRT
<213> ORGANISM: Artificial sequence
<220> FEATURE:
<223> OTHER INFORMATION: Sequence is synthesized.

<400> SEQUENCE: 34

```
Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Thr Phe Thr
                20                  25                  30

Asn Tyr Gly Met Asn Trp Val Arg Gln Ala Pro Gly Lys Gly Leu
                35                  40                  45

Glu Trp Val Gly Trp Ile Asn Thr Tyr Thr Gly Glu Pro Thr Tyr
                50                  55                  60

Ala Ala Asp Phe Lys Arg Arg Phe Thr Phe Ser Leu Asp Thr Ser
                65                  70                  75

Lys Ser Thr Ala Tyr Leu Gln Met Asn Ser Leu Arg Ala Glu Asp
                80                  85                  90

Thr Ala Val Tyr Tyr Cys Ala Lys Tyr Pro His Tyr Tyr Gly Ser
                95                 100                 105

Ser His Trp Tyr Phe Asp Val Trp Gly Gln Gly Thr Leu Val Thr
               110                 115                 120

Val Ser Ser
```

<210> SEQ ID NO 35
<211> LENGTH: 107
<212> TYPE: PRT
<213> ORGANISM: Artificial sequence
<220> FEATURE:
<223> OTHER INFORMATION: Sequence is synthesized.

<400> SEQUENCE: 35

```
Asp Ile Gln Leu Thr Gln Ser Pro Ser Ser Leu Ser Ala Ser Val
 1               5                  10                  15

Gly Asp Arg Val Thr Ile Thr Cys Ser Ala Ser Gln Asp Ile Ser
                20                  25                  30

Asn Tyr Leu Asn Trp Tyr Gln Gln Lys Pro Gly Lys Ala Pro Lys
                35                  40                  45

Val Leu Ile Tyr Phe Thr Ser Ser Leu His Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Tyr Ser Thr Val Pro Trp Thr Phe Gly Gln Gly Thr Lys Val Glu
                95                 100                 105

Ile Lys
```

<210> SEQ ID NO 36
<211> LENGTH: 123
<212> TYPE: PRT
<213> ORGANISM: Artificial sequence
<220> FEATURE:
<223> OTHER INFORMATION: Sequence is synthesized.

<400> SEQUENCE: 36

Glu Val Gln Leu Val Glu Ser Gly Gly Gly Leu Val Gln Pro Gly
1               5                  10                 15

Gly Ser Leu Arg Leu Ser Cys Ala Ala Ser Gly Tyr Asp Phe Thr
               20                  25                 30

His Tyr Gly Met Asn Trp Val Arg Gln Ala Pro Gly Lys Gly Leu
               35                  40                 45

Glu Trp Val Gly Trp Ile Asn Thr Tyr Thr Gly Glu Pro Thr Tyr
               50                  55                 60

Ala Ala Asp Phe Lys Arg Arg Phe Thr Phe Ser Leu Asp Thr Ser
               65                  70                 75

Lys Ser Thr Ala Tyr Leu Gln Met Asn Ser Leu Arg Ala Glu Asp
               80                  85                 90

Thr Ala Val Tyr Tyr Cys Ala Lys Tyr Pro Tyr Tyr Tyr Gly Thr
               95                 100                105

Ser His Trp Tyr Phe Asp Val Trp Gly Gln Gly Thr Leu Val Thr
              110                 115                120

Val Ser Ser

<210> SEQ ID NO 37
<211> LENGTH: 218
<212> TYPE: PRT
<213> ORGANISM: Artificial sequence
<220> FEATURE:
<223> OTHER INFORMATION: Sequence is synthesized.

<400> SEQUENCE: 37

Asp Ile Gln Leu Thr Gln Ser Pro Ser Ser Leu Ser Ala Ser Val
1               5                  10                 15

Gly Asp Arg Val Thr Ile Thr Cys Arg Ala Ser Gln Ser Val Asp
               20                  25                 30

Tyr Asp Gly Asp Ser Tyr Met Asn Trp Tyr Gln Gln Lys Pro Gly
               35                  40                 45

Lys Ala Pro Lys Leu Leu Ile Tyr Ala Ala Ser Tyr Leu Glu Ser
               50                  55                 60

Gly Val Pro Ser Arg Phe Ser Gly Ser Gly Ser Gly Thr Asp Phe
               65                  70                 75

Thr Leu Thr Ile Ser Ser Leu Gln Pro Glu Asp Phe Ala Thr Tyr
               80                  85                 90

Tyr Cys Gln Gln Ser His Glu Asp Pro Tyr Thr Phe Gly Gln Gly
               95                 100                105

Thr Lys Val Glu Ile Lys Arg Thr Val Ala Ala Pro Ser Val Phe
              110                 115                120

Ile Phe Pro Pro Ser Asp Glu Gln Leu Lys Ser Gly Thr Ala Ser
              125                 130                135

Val Val Cys Leu Leu Asn Asn Phe Tyr Pro Arg Glu Ala Lys Val
              140                 145                150

Gln Trp Lys Val Asp Asn Ala Leu Gln Ser Gly Asn Ser Gln Glu
              155                 160                165

Ser Val Thr Glu Gln Asp Ser Lys Asp Ser Thr Tyr Ser Leu Ser
              170                 175                180

Ser Thr Leu Thr Leu Ser Lys Ala Asp Tyr Glu Lys His Lys Val
              185                 190                195

Tyr Ala Cys Glu Val Thr His Gln Gly Leu Ser Ser Pro Val Thr
              200                 205                210

Lys Ser Phe Asn Arg Gly Glu Cys

-continued

```
                215

<210> SEQ ID NO 38
<211> LENGTH: 218
<212> TYPE: PRT
<213> ORGANISM: Artificial sequence
<220> FEATURE:
<223> OTHER INFORMATION: Sequence is synthesized.

<400> SEQUENCE: 38

Asp Ile Gln Leu Thr Gln Ser Pro Ser Ser Leu Ser Ala Ser Val
 1               5                  10                  15

Gly Asp Arg Val Thr Ile Thr Cys Arg Ala Ser Lys Pro Val Asp
                20                  25                  30

Gly Glu Gly Asp Ser Tyr Leu Asn Trp Tyr Gln Gln Lys Pro Gly
                35                  40                  45

Lys Ala Pro Lys Leu Leu Ile Tyr Ala Ala Ser Tyr Leu Glu Ser
                50                  55                  60

Gly Val Pro Ser Arg Phe Ser Gly Ser Gly Ser Gly Thr Asp Phe
                65                  70                  75

Thr Leu Thr Ile Ser Ser Leu Gln Pro Glu Asp Phe Ala Thr Tyr
                80                  85                  90

Tyr Cys Gln Gln Ser His Glu Asp Pro Tyr Thr Phe Gly Gln Gly
                95                 100                 105

Thr Lys Val Glu Ile Lys Arg Thr Val Ala Ala Pro Ser Val Phe
               110                 115                 120

Ile Phe Pro Pro Ser Ser Lys Asp Ser Thr Tyr Ser Leu Ser Ser
               125                 130                 135

Thr Leu Thr Leu Ser Lys Ala Asp Tyr Glu Lys His Lys Val Tyr
               140                 145                 150

Ala Cys Glu Val Thr His Gln Gly Leu Ser Ser Pro Val Thr Lys
               155                 160                 165

Ser Phe Asn Arg Gly Glu Cys Asp Glu Gln Leu Lys Ser Gly Thr
               170                 175                 180

Ala Ser Val Val Cys Leu Leu Asn Asn Phe Tyr Pro Arg Glu Ala
               185                 190                 195

Lys Val Gln Trp Lys Val Asp Asn Ala Leu Gln Ser Gly Asn Ser
               200                 205                 210

Gln Glu Ser Val Thr Glu Gln Asp
               215

<210> SEQ ID NO 39
<211> LENGTH: 218
<212> TYPE: PRT
<213> ORGANISM: Artificial sequence
<220> FEATURE:
<223> OTHER INFORMATION: Sequence is synthesized.

<400> SEQUENCE: 39

Asp Ile Gln Leu Thr Gln Ser Pro Ser Ser Leu Ser Ala Ser Val
 1               5                  10                  15

Gly Asp Arg Val Thr Ile Thr Cys Arg Ala Ser Lys Pro Val Asp
                20                  25                  30

Gly Glu Gly Asp Ser Tyr Leu Asn Trp Tyr Gln Gln Lys Pro Gly
                35                  40                  45

Lys Ala Pro Lys Leu Leu Ile Tyr Ala Ala Ser Tyr Leu Glu Ser
                50                  55                  60
```

```
Gly Val Pro Ser Arg Phe Ser Gly Ser Gly Ser Gly Thr Asp Phe
             65                  70                  75

Thr Leu Thr Ile Ser Ser Leu Gln Pro Glu Asp Phe Ala Thr Tyr
             80                  85                  90

Tyr Cys Gln Gln Ser His Glu Asp Pro Tyr Thr Phe Gly Gln Gly
             95                 100                 105

Thr Lys Val Glu Ile Lys Arg Thr Val Ala Ala Pro Ser Val Phe
            110                 115                 120

Ile Phe Pro Pro Ser Asp Glu Gln Leu Lys Ser Gly Thr Ala Ser
            125                 130                 135

Val Val Cys Leu Leu Asn Asn Phe Tyr Pro Arg Glu Ala Lys Val
            140                 145                 150

Gln Trp Lys Val Asp Asn Ala Leu Gln Ser Gly Asn Ser Gln Glu
            155                 160                 165

Ser Val Thr Glu Gln Asp Ser Lys Asp Ser Thr Tyr Ser Leu Ser
            170                 175                 180

Ser Thr Leu Thr Leu Ser Lys Ala Asp Tyr Glu Lys His Lys Val
            185                 190                 195

Tyr Ala Cys Glu Val Thr His Gln Gly Leu Ser Ser Pro Val Thr
            200                 205                 210

Lys Ser Phe Asn Arg Gly Glu Cys
            215

<210> SEQ ID NO 40
<211> LENGTH: 214
<212> TYPE: PRT
<213> ORGANISM: Artificial sequence
<220> FEATURE:
<223> OTHER INFORMATION: Sequence is synthesized.

<400> SEQUENCE: 40

Asp Ile Leu Leu Thr Gln Ser Pro Gly Thr Leu Ser Leu Ser Pro
  1               5                  10                  15

Gly Glu Arg Ala Thr Leu Ser Cys Arg Ala Ser Gln Ser Ile Gly
             20                  25                  30

Thr Asn Ile His Trp Tyr Gln Gln Lys Pro Gly Gln Ala Pro Arg
             35                  40                  45

Leu Leu Ile Lys Tyr Ala Ser Glu Ser Ile Ser Gly Ile Pro Ser
             50                  55                  60

Arg Phe Ser Gly Ser Gly Ser Gly Thr Asp Phe Thr Leu Thr Ile
             65                  70                  75

Ser Arg Leu Glu Pro Glu Asp Phe Ala Met Tyr Tyr Cys Gln Gln
             80                  85                  90

Ser Asp Ser Trp Pro Thr Thr Phe Gly Gln Gly Thr Lys Val Glu
             95                 100                 105

Ile Lys Arg Thr Val Ala Ala Pro Ser Val Phe Ile Phe Pro Pro
            110                 115                 120

Ser Asp Glu Gln Leu Lys Ser Gly Thr Ala Ser Val Val Cys Leu
            125                 130                 135

Leu Asn Asn Phe Tyr Pro Arg Glu Ala Lys Val Gln Trp Lys Val
            140                 145                 150

Asp Asn Ala Leu Gln Ser Gly Asn Ser Gln Glu Ser Val Thr Glu
            155                 160                 165

Gln Asp Ser Lys Asp Ser Thr Tyr Ser Leu Ser Ser Thr Leu Thr
            170                 175                 180
```

```
Leu Ser Lys Ala Asp Tyr Glu Lys His Lys Val Tyr Ala Cys Glu
            185                 190                 195

Val Thr His Gln Gly Leu Ser Ser Pro Val Thr Lys Ser Phe Asn
            200                 205                 210

Arg Gly Glu Cys

<210> SEQ ID NO 41
<211> LENGTH: 451
<212> TYPE: PRT
<213> ORGANISM: Artificial sequence
<220> FEATURE:
<223> OTHER INFORMATION: Sequence is synthesized.

<400> SEQUENCE: 41

Glu Val Gln Leu Val Glu Ser Gly Gly Gly Leu Val Gln Pro Gly
 1               5                  10                  15

Gly Ser Leu Arg Leu Ser Cys Ala Val Ser Gly Tyr Ser Ile Thr
             20                  25                  30

Ser Gly Tyr Ser Trp Asn Trp Ile Arg Gln Ala Pro Gly Lys Gly
             35                  40                  45

Leu Glu Trp Val Ala Ser Ile Thr Tyr Asp Gly Ser Thr Asn Tyr
             50                  55                  60

Asn Pro Ser Val Lys Gly Arg Ile Thr Ile Ser Arg Asp Asp Ser
             65                  70                  75

Lys Asn Thr Phe Tyr Leu Gln Met Asn Ser Leu Arg Ala Glu Asp
             80                  85                  90

Thr Ala Val Tyr Tyr Cys Ala Arg Gly Ser His Tyr Phe Gly His
             95                 100                 105

Trp His Phe Ala Val Trp Gly Gln Gly Thr Leu Val Thr Val Ser
            110                 115                 120

Ser Ala Ser Thr Lys Gly Pro Ser Val Phe Pro Leu Ala Pro Ser
            125                 130                 135

Ser Lys Ser Thr Ser Gly Gly Thr Ala Ala Leu Gly Cys Leu Val
            140                 145                 150

Lys Asp Tyr Phe Pro Glu Pro Val Thr Val Ser Trp Asn Ser Gly
            155                 160                 165

Ala Leu Thr Ser Gly Val His Thr Phe Pro Ala Val Leu Gln Ser
            170                 175                 180

Ser Gly Leu Tyr Ser Leu Ser Ser Val Val Thr Val Pro Ser Ser
            185                 190                 195

Ser Leu Gly Thr Gln Thr Tyr Ile Cys Asn Val Asn His Lys Pro
            200                 205                 210

Ser Asn Thr Lys Val Asp Lys Lys Val Glu Pro Lys Ser Cys Asp
            215                 220                 225

Lys Thr His Thr Cys Pro Pro Cys Pro Ala Pro Glu Leu Leu Gly
            230                 235                 240

Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr
            290                 295                 300

Asn Ser Thr Tyr Arg Val Val Ser Val Leu Thr Val Leu His Gln
```

```
                    305                 310                 315
Asp Trp Leu Asn Gly Lys Glu Tyr Lys Cys Lys Val Ser Asn Lys
                320                 325                 330

Ala Leu Pro Ala Pro Ile Glu Lys Thr Ile Ser Lys Ala Lys Gly
                335                 340                 345

Gln Pro Arg Glu Pro Gln Val Tyr Thr Leu Pro Pro Ser Arg Glu
                350                 355                 360

Glu Met Thr Lys Asn Gln Val Ser Leu Thr Cys Leu Val Lys Gly
                365                 370                 375

Phe Tyr Pro Ser Asp Ile Ala Val Glu Trp Glu Ser Asn Gly Gln
                380                 385                 390

Pro Glu Asn Asn Tyr Lys Thr Thr Pro Pro Val Leu Asp Ser Asp
                395                 400                 405

Gly Ser Phe Phe Leu Tyr Ser Lys Leu Thr Val Asp Lys Ser Arg
                410                 415                 420

Trp Gln Gln Gly Asn Val Phe Ser Cys Ser Val Met His Glu Ala
                425                 430                 435

Leu His Asn His Tyr Thr Gln Lys Ser Leu Ser Leu Ser Pro Gly
                440                 445                 450

Lys

<210> SEQ ID NO 42
<211> LENGTH: 451
<212> TYPE: PRT
<213> ORGANISM: Artificial sequence
<220> FEATURE:
<223> OTHER INFORMATION: Sequence is synthesized.

<400> SEQUENCE: 42

Glu Val Gln Leu Val Glu Ser Gly Gly Gly Leu Val Gln Pro Gly
  1               5                  10                  15

Gly Ser Leu Arg Leu Ser Cys Ala Val Ser Gly Tyr Ser Ile Thr
                 20                  25                  30

Ser Gly Tyr Ser Trp Asn Trp Ile Arg Gln Ala Pro Gly Lys Gly
                 35                  40                  45

Leu Glu Trp Val Ala Ser Ile Thr Tyr Asp Gly Ser Thr Asn Tyr
                 50                  55                  60

Asn Pro Ser Val Lys Gly Arg Ile Thr Ile Ser Arg Asp Asp Ser
                 65                  70                  75

Lys Asn Thr Phe Tyr Leu Gln Met Asn Ser Leu Arg Ala Glu Asp
                 80                  85                  90

Thr Ala Val Tyr Tyr Cys Ala Arg Gly Ser His Tyr Phe Gly His
                 95                 100                 105

Trp His Phe Ala Val Trp Gly Gln Gly Thr Leu Val Thr Val Ser
                110                 115                 120

Ser Ala Ser Thr Lys Gly Pro Ser Val Phe Pro Leu Ala Pro Ser
                125                 130                 135

Ser Lys Ser Thr Ser Gly Gly Thr Ala Ala Leu Gly Cys Leu Val
                140                 145                 150

Lys Asp Tyr Phe Pro Glu Pro Val Thr Val Ser Trp Asn Ser Gly
                155                 160                 165

Ala Leu Thr Ser Gly Val His Thr Phe Pro Ala Val Leu Gln Ser
                170                 175                 180

Ser Gly Leu Tyr Ser Leu Ser Ser Val Val Thr Val Pro Ser Ser
                185                 190                 195
```

```
Ser Leu Gly Thr Gln Thr Tyr Ile Cys Asn Val Asn His Lys Pro
                200                 205                 210

Ser Asn Thr Lys Val Asp Lys Lys Val Glu Pro Lys Ser Cys Asp
                215                 220                 225

Lys Thr His Thr Cys Pro Pro Cys Pro Ala Pro Glu Leu Leu Gly
                230                 235                 240

Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly
                275                 280                 285

Val Glu Val His Asn Ala Lys Thr Lys Pro Arg Glu Glu Gln Tyr
                290                 295                 300

Asn Ser Thr Tyr Arg Val Val Ser Val Leu Thr Val Leu His Gln
                305                 310                 315

Asp Trp Leu Asn Gly Lys Glu Tyr Lys Cys Lys Val Ser Asn Lys
                320                 325                 330

Ala Leu Pro Ala Pro Ile Glu Lys Thr Ile Ser Lys Ala Lys Gly
                335                 340                 345

Gln Pro Arg Glu Pro Gln Val Tyr Thr Leu Pro Pro Ser Arg Glu
                350                 355                 360

Glu Met Thr Lys Asn Gln Val Ser Leu Thr Cys Leu Val Lys Gly
                365                 370                 375

Phe Tyr Pro Ser Asp Ile Ala Val Glu Trp Glu Ser Asn Gly Gln
                380                 385                 390

Pro Glu Asn Asn Tyr Lys Thr Thr Pro Pro Val Leu Asp Ser Asp
                395                 400                 405

Gly Ser Phe Phe Leu Tyr Ser Lys Leu Thr Val Asp Lys Ser Arg
                410                 415                 420

Trp Gln Gln Gly Asn Val Phe Ser Cys Ser Val Met His Glu Ala
                425                 430                 435

Leu His Asn His Tyr Thr Gln Lys Ser Leu Ser Leu Ser Pro Gly
                440                 445                 450

Lys

<210> SEQ ID NO 43
<211> LENGTH: 451
<212> TYPE: PRT
<213> ORGANISM: Artificial sequence
<220> FEATURE:
<223> OTHER INFORMATION: Sequence is synthesized.

<400> SEQUENCE: 43

Glu Val Gln Leu Val Glu Ser Gly Gly Gly Leu Val Gln Pro Gly
  1               5                  10                  15

Gly Ser Leu Arg Leu Ser Cys Ala Val Ser Gly Tyr Ser Ile Thr
                 20                  25                  30

Ser Gly Tyr Ser Trp Asn Trp Ile Arg Gln Ala Pro Gly Lys Gly
                 35                  40                  45

Leu Glu Trp Val Ala Ser Ile Lys Tyr Ser Gly Glu Thr Lys Tyr
                 50                  55                  60

Asn Pro Ser Val Lys Gly Arg Ile Thr Ile Ser Arg Asp Asp Ser
                 65                  70                  75
```

```
Lys Asn Thr Phe Tyr Leu Gln Met Asn Ser Leu Arg Ala Glu Asp
                    80                  85                  90

Thr Ala Val Tyr Tyr Cys Ala Arg Gly Ser His Tyr Phe Gly His
                95                  100                 105

Trp His Phe Ala Val Trp Gly Gln Gly Thr Leu Val Thr Val Ser
                110                 115                 120

Ser Ala Ser Thr Lys Gly Pro Ser Val Phe Pro Leu Ala Pro Ser
                125                 130                 135

Ser Lys Ser Thr Ser Gly Gly Thr Ala Ala Leu Gly Cys Leu Val
                140                 145                 150

Lys Asp Tyr Phe Pro Glu Pro Val Thr Val Ser Trp Asn Ser Gly
                155                 160                 165

Ala Leu Thr Ser Gly Val His Thr Phe Pro Ala Val Leu Gln Ser
                170                 175                 180

Ser Gly Leu Tyr Ser Leu Ser Ser Val Val Thr Val Pro Ser Ser
                185                 190                 195

Ser Leu Gly Thr Gln Thr Tyr Ile Cys Asn Val Asn His Lys Pro
                200                 205                 210

Ser Asn Thr Lys Val Asp Lys Lys Val Glu Pro Lys Ser Cys Asp
                215                 220                 225

Lys Thr His Thr Cys Pro Pro Cys Pro Ala Pro Glu Leu Leu Gly
                230                 235                 240

Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly
                275                 280                 285

Val Glu Val His Asn Ala Lys Thr Lys Pro Arg Glu Glu Gln Tyr
                290                 295                 300

Asn Ser Thr Tyr Arg Val Val Ser Val Leu Thr Val Leu His Gln
                305                 310                 315

Asp Trp Leu Asn Gly Lys Glu Tyr Lys Cys Lys Val Ser Asn Lys
                320                 325                 330

Ala Leu Pro Ala Pro Ile Glu Lys Thr Ile Ser Lys Ala Lys Gly
                335                 340                 345

Gln Pro Arg Glu Pro Gln Val Tyr Thr Leu Pro Pro Ser Arg Glu
                350                 355                 360

Glu Met Thr Lys Asn Gln Val Ser Leu Thr Cys Leu Val Lys Gly
                365                 370                 375

Phe Tyr Pro Ser Asp Ile Ala Val Glu Trp Glu Ser Asn Gly Gln
                380                 385                 390

Pro Glu Asn Asn Tyr Lys Thr Thr Pro Pro Val Leu Asp Ser Asp
                395                 400                 405

Gly Ser Phe Phe Leu Tyr Ser Lys Leu Thr Val Asp Lys Ser Arg
                410                 415                 420

Trp Gln Gln Gly Asn Val Phe Ser Cys Ser Val Met His Glu Ala
                425                 430                 435

Leu His Asn His Tyr Thr Gln Lys Ser Leu Ser Leu Ser Pro Gly
                440                 445                 450

Lys

<210> SEQ ID NO 44
```

<211> LENGTH: 453
<212> TYPE: PRT
<213> ORGANISM: Artificial sequence
<220> FEATURE:
<223> OTHER INFORMATION: Sequence is synthesized.

<400> SEQUENCE: 44

```
Gln Val Gln Leu Val Gln Ser Gly Ala Glu Val Lys Lys Pro Gly
  1               5                  10                  15

Ala Ser Val Lys Val Ser Cys Lys Ala Ser Gly Tyr Thr Phe Ser
             20                  25                  30

Met Tyr Trp Leu Glu Trp Val Arg Gln Ala Pro Gly His Gly Leu
             35                  40                  45

Glu Trp Val Gly Glu Ile Ser Pro Gly Thr Phe Thr Thr Asn Tyr
             50                  55                  60

Asn Glu Lys Phe Lys Ala Arg Ala Thr Phe Thr Ala Asp Thr Ser
 65                  70                  75

Thr Asn Thr Ala Tyr Met Glu Leu Ser Ser Leu Arg Ser Glu Asp
             80                  85                  90

Thr Ala Val Tyr Tyr Cys Ala Arg Phe Ser His Phe Ser Gly Ser
             95                 100                 105

Asn Tyr Asp Tyr Phe Asp Tyr Trp Gly Gln Gly Thr Leu Val Thr
            110                 115                 120

Val Ser Ser Ala Ser Thr Lys Gly Pro Ser Val Phe Pro Leu Ala
            125                 130                 135

Pro Ser Ser Lys Ser Thr Ser Gly Gly Thr Ala Ala Leu Gly Cys
            140                 145                 150

Leu Val Lys Asp Tyr Phe Pro Glu Pro Val Thr Val Ser Trp Asn
            155                 160                 165

Ser Gly Ala Leu Thr Ser Gly Val His Thr Phe Pro Ala Val Leu
            170                 175                 180

Gln Ser Ser Gly Leu Tyr Ser Leu Ser Ser Val Val Thr Val Pro
            185                 190                 195

Ser Ser Ser Leu Gly Thr Gln Thr Tyr Ile Cys Asn Val Asn His
            200                 205                 210

Lys Pro Ser Asn Thr Lys Val Asp Lys Lys Val Glu Pro Lys Ser
            215                 220                 225

Cys Asp Lys Thr His Thr Cys Pro Pro Cys Pro Ala Pro Glu Leu
            230                 235                 240

Leu Gly Gly Pro Ser Val Phe Leu Phe Pro Pro Lys Pro Lys Asp
            245                 250                 255

Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val
            275                 280                 285

Asp Gly Val Glu Val His Asn Ala Lys Thr Lys Pro Arg Glu Glu
            290                 295                 300

Gln Tyr Asn Ser Thr Tyr Arg Val Val Ser Val Leu Thr Val Leu
            305                 310                 315

His Gln Asp Trp Leu Asn Gly Lys Glu Tyr Lys Cys Lys Val Ser
            320                 325                 330

Asn Lys Ala Leu Pro Ala Pro Ile Glu Lys Thr Ile Ser Lys Ala
            335                 340                 345

Lys Gly Gln Pro Arg Glu Pro Gln Val Tyr Thr Leu Pro Pro Ser
            350                 355                 360
```

```
Arg Asp Glu Leu Thr Lys Asn Gln Val Ser Leu Thr Cys Leu Val
            365                 370                 375
Lys Gly Phe Tyr Pro Ser Asp Ile Ala Val Glu Trp Glu Ser Asn
            380                 385                 390
Gly Gln Pro Glu Asn Asn Tyr Lys Thr Thr Pro Pro Val Leu Asp
            395                 400                 405
Ser Asp Gly Ser Phe Phe Leu Tyr Ser Lys Leu Thr Val Asp Lys
            410                 415                 420
Ser Arg Trp Gln Gln Gly Asn Val Phe Ser Cys Ser Val Met His
            425                 430                 435
Glu Ala Leu His Asn His Tyr Thr Gln Lys Ser Leu Ser Leu Ser
            440                 445                 450
Pro Gly Lys
```

<210> SEQ ID NO 45
<211> LENGTH: 1042
<212> TYPE: DNA
<213> ORGANISM: Homo sapiens
<220> FEATURE:
<221> NAME/KEY: Unsure
<222> LOCATION: 447
<223> OTHER INFORMATION: N is T or G

<400> SEQUENCE: 45

| | | |
|---|---|---|
| tttcctcact gactataaaa gaatagagaa ggaagggctt cagtgaccgg | 50 |
| ctgcctggct gacttacagc agtcagactc tgacaggatc atggctatga | 100 |
| tggaggtcca ggggggaccc agcctgggac agacctgcgt gctgatcgtg | 150 |
| atcttcacag tgctcctgca gtctctctgt gtggctgtaa cttacgtgta | 200 |
| ctttaccaac gagctgaagc agatgcagga caagtactcc aaaagtggca | 250 |
| ttgcttgttt cttaaaagaa gatgacagtt attgggaccc caatgacgaa | 300 |
| gagagtatga cagcccctg ctggcaagtc aagtggcaac tccgtcagct | 350 |
| cgttagaaag atgattttga gaacctctga ggaaaccatt tctacagttc | 400 |
| aagaaaagca acaaaatatt tctcccctag tgagagaaag aggtccncag | 450 |
| agagtagcag ctcacataac tgggaccaga ggaagaagca acacattgtc | 500 |
| ttctccaaac tccaagaatg aaaaggctct gggccgcaaa ataaactcct | 550 |
| gggaatcatc aaggagtggg cattcattcc tgagcaactt gcacttgagg | 600 |
| aatggtgaac tggtcatcca tgaaaaaggg ttttactaca tctattccca | 650 |
| aacatacttt cgatttcagg aggaaataaa agaaacaca aagaacgaca | 700 |
| aacaaatggt ccaatatatt tacaaataca caagttatcc tgaccctata | 750 |
| ttgttgatga aaagtgctag aaatagttgt tggtctaaag atgcagaata | 800 |
| tggactctat tccatctatc aagggggaat atttgagctt aaggaaaatg | 850 |
| acagaatttt tgtttctgta acaaatgagc acttgataga catggaccat | 900 |
| gaagccagtt ttttcggggc cttttagtt ggctaactga cctggaaaga | 950 |
| aaaagcaata acctcaaagt gactattcag ttttcaggat gatacactat | 1000 |
| gaagatgttt caaaaatct gaccaaaaca aacaaacaga aa | 1042 |

<210> SEQ ID NO 46
<211> LENGTH: 281
<212> TYPE: PRT

<213> ORGANISM: Homo sapiens

<400> SEQUENCE: 46

```
Met Ala Met Met Glu Val Gln Gly Gly Pro Ser Leu Gly Gln Thr
  1               5                  10                  15

Cys Val Leu Ile Val Ile Phe Thr Val Leu Gln Ser Leu Cys
                 20                  25                  30

Val Ala Val Thr Tyr Val Tyr Phe Thr Asn Glu Leu Lys Gln Met
                 35                  40                  45

Gln Asp Lys Tyr Ser Lys Ser Gly Ile Ala Cys Phe Leu Lys Glu
                 50                  55                  60

Asp Asp Ser Tyr Trp Asp Pro Asn Asp Glu Glu Ser Met Asn Ser
                 65                  70                  75

Pro Cys Trp Gln Val Lys Trp Gln Leu Arg Gln Leu Val Arg Lys
                 80                  85                  90

Met Ile Leu Arg Thr Ser Glu Glu Thr Ile Ser Thr Val Gln Glu
                 95                 100                 105

Lys Gln Gln Asn Ile Ser Pro Leu Val Arg Glu Arg Gly Pro Gln
                110                 115                 120

Arg Val Ala Ala His Ile Thr Gly Thr Arg Gly Arg Ser Asn Thr
                125                 130                 135

Leu Ser Ser Pro Asn Ser Lys Asn Glu Lys Ala Leu Gly Arg Lys
                140                 145                 150

Ile Asn Ser Trp Glu Ser Ser Arg Ser Gly His Ser Phe Leu Ser
                155                 160                 165

Asn Leu His Leu Arg Asn Gly Glu Leu Val Ile His Glu Lys Gly
                170                 175                 180

Phe Tyr Tyr Ile Tyr Ser Gln Thr Tyr Phe Arg Phe Gln Glu Glu
                185                 190                 195

Ile Lys Glu Asn Thr Lys Asn Asp Lys Gln Met Val Gln Tyr Ile
                200                 205                 210

Tyr Lys Tyr Thr Ser Tyr Pro Asp Pro Ile Leu Leu Met Lys Ser
                215                 220                 225

Ala Arg Asn Ser Cys Trp Ser Lys Asp Ala Glu Tyr Gly Leu Tyr
                230                 235                 240

Ser Ile Tyr Gln Gly Gly Ile Phe Glu Leu Lys Glu Asn Asp Arg
                245                 250                 255

Ile Phe Val Ser Val Thr Asn Glu His Leu Ile Asp Met Asp His
                260                 265                 270

Glu Ala Ser Phe Phe Gly Ala Phe Leu Val Gly
                275                 280
```

<210> SEQ ID NO 47
<211> LENGTH: 411
<212> TYPE: PRT
<213> ORGANISM: Homo sapiens
<220> FEATURE:
<221> NAME/KEY: Xaa
<222> LOCATION: 410
<223> OTHER INFORMATION: Xaa is L or M.

<400> SEQUENCE: 47

```
Met Glu Gln Arg Gly Gln Asn Ala Pro Ala Ala Ser Gly Ala Arg
  1               5                  10                  15

Lys Arg His Gly Pro Gly Pro Arg Glu Ala Arg Gly Ala Arg Pro
                 20                  25                  30
```

```
Gly Leu Arg Val Pro Lys Thr Leu Val Leu Val Ala Ala Val
                 35                  40                  45

Leu Leu Leu Val Ser Ala Glu Ser Ala Leu Ile Thr Gln Gln Asp
             50                  55                  60

Leu Ala Pro Gln Gln Arg Ala Ala Pro Gln Gln Lys Arg Ser Ser
                 65                  70                  75

Pro Ser Glu Gly Leu Cys Pro Pro Gly His His Ile Ser Glu Asp
                 80                  85                  90

Gly Arg Asp Cys Ile Ser Cys Lys Tyr Gly Gln Asp Tyr Ser Thr
                 95                 100                 105

His Trp Asn Asp Leu Leu Phe Cys Leu Arg Cys Thr Arg Cys Asp
                110                 115                 120

Ser Gly Glu Val Glu Leu Ser Pro Cys Thr Thr Thr Arg Asn Thr
                125                 130                 135

Val Cys Gln Cys Glu Glu Gly Thr Phe Arg Glu Asp Ser Pro
                140                 145                 150

Glu Met Cys Arg Lys Cys Arg Thr Gly Cys Pro Arg Gly Met Val
                155                 160                 165

Lys Val Gly Asp Cys Thr Pro Trp Ser Asp Ile Glu Cys Val His
                170                 175                 180

Lys Glu Ser Gly Ile Ile Ile Gly Val Thr Val Ala Ala Val Val
                185                 190                 195

Leu Ile Val Ala Val Phe Val Cys Lys Ser Leu Leu Trp Lys Lys
                200                 205                 210

Val Leu Pro Tyr Leu Lys Gly Ile Cys Ser Gly Gly Gly Gly Asp
                215                 220                 225

Pro Glu Arg Val Asp Arg Ser Ser Gln Arg Pro Gly Ala Glu Asp
                230                 235                 240

Asn Val Leu Asn Glu Ile Val Ser Ile Leu Gln Pro Thr Gln Val
                245                 250                 255

Pro Glu Gln Glu Met Glu Val Gln Glu Pro Ala Glu Pro Thr Gly
                260                 265                 270

Val Asn Met Leu Ser Pro Gly Glu Ser Glu His Leu Leu Glu Pro
                275                 280                 285

Ala Glu Ala Glu Arg Ser Gln Arg Arg Arg Leu Leu Val Pro Ala
                290                 295                 300

Asn Glu Gly Asp Pro Thr Glu Thr Leu Arg Gln Cys Phe Asp Asp
                305                 310                 315

Phe Ala Asp Leu Val Pro Phe Asp Ser Trp Glu Pro Leu Met Arg
                320                 325                 330

Lys Leu Gly Leu Met Asp Asn Glu Ile Lys Val Ala Lys Ala Glu
                335                 340                 345

Ala Ala Gly His Arg Asp Thr Leu Tyr Thr Met Leu Ile Lys Trp
                350                 355                 360

Val Asn Lys Thr Gly Arg Asp Ala Ser Val His Thr Leu Leu Asp
                365                 370                 375

Ala Leu Glu Thr Leu Gly Glu Arg Leu Ala Lys Gln Lys Ile Glu
                380                 385                 390

Asp His Leu Leu Ser Ser Gly Lys Phe Met Tyr Leu Glu Gly Asn
                395                 400                 405

Ala Asp Ser Ala Xaa Ser
                410
```

<210> SEQ ID NO 48
<211> LENGTH: 1799
<212> TYPE: DNA
<213> ORGANISM: Homo sapiens

<400> SEQUENCE: 48

| | | | | | |
|---|---|---|---|---|---|
| cccacgcgtc | cgcataaatc | agcacgcggc | cggagaaccc | cgcaatctct | 50 |
| gcgcccacaa | aatacaccga | cgatgcccga | tctactttaa | gggctgaaac | 100 |
| ccacgggcct | gagagactat | aagagcgttc | cctaccgcca | tggaacaacg | 150 |
| gggacagaac | gccccggccg | cttcggggc | ccggaaaagg | cacggcccag | 200 |
| gacccaggga | ggcgcgggga | gccaggcctg | ggctccgggt | ccccaagacc | 250 |
| cttgtgctcg | ttgtcgccgc | ggtcctgctg | ttggtctcag | ctgagtctgc | 300 |
| tctgatcacc | caacaagacc | tagctcccca | gcagagagcg | gccccacaac | 350 |
| aaaagaggtc | cagcccctca | gagggattgt | gtccacctgg | acaccatatc | 400 |
| tcagaagacg | gtagagattg | catctcctgc | aaatatggac | aggactatag | 450 |
| cactcactgg | aatgacctcc | ttttctgctt | gcgctgcacc | aggtgtgatt | 500 |
| caggtgaagt | ggagctaagt | ccctgcacca | cgaccagaaa | cacagtgtgt | 550 |
| cagtgcgaag | aaggcacctt | ccgggaagaa | gattctcctg | agatgtgccg | 600 |
| gaagtgccgc | acagggtgtc | ccagagggat | ggtcaaggtc | ggtgattgta | 650 |
| caccctggag | tgacatcgaa | tgtgtccaca | agaatcagg | catcatcata | 700 |
| ggagtcacag | ttgcagccgt | agtcttgatt | gtggctgtgt | ttgtttgcaa | 750 |
| gtctttactg | tggaagaaag | tccttcctta | cctgaaaggc | atctgctcag | 800 |
| gtggtggtgg | ggaccctgag | cgtgtggaca | gaagctcaca | acgacctggg | 850 |
| gctgaggaca | atgtcctcaa | tgagatcgtg | agtatcttgc | agcccaccca | 900 |
| ggtccctgag | caggaaatgg | aagtccagga | gccagcagag | ccaacaggtg | 950 |
| tcaacatgtt | gtccccgggg | gagtcagagc | atctgctgga | accggcagaa | 1000 |
| gctgaaaggt | ctcagaggag | gaggctgctg | gttccagcaa | atgaaggtga | 1050 |
| tcccactgag | actctgagac | agtgcttcga | tgactttgca | gacttggtgc | 1100 |
| cctttgactc | ctgggagccg | ctcatgagga | agttgggcct | catggacaat | 1150 |
| gagataaagg | tggctaaagc | tgaggcagcg | ggccacaggg | acaccttgta | 1200 |
| cacgatgctg | ataaagtggg | tcaacaaaac | cgggcgagat | gcctctgtcc | 1250 |
| acaccctgct | ggatgccttg | gagacgctgg | gagagagact | tgccaagcag | 1300 |
| aagattgagg | accacttgtt | gagctctgga | aagttcatgt | atctagaagg | 1350 |
| taatgcagac | tctgccwtgt | cctaagtgtg | attctcttca | ggaagtgaga | 1400 |
| ccttccctgg | tttaccttt | ttctggaaaa | agcccaactg | gactccagtc | 1450 |
| agtaggaaag | tgccacaatt | gtcacatgac | cggtactgga | agaaactctc | 1500 |
| ccatccaaca | tcacccagtg | gatggaacat | cctgtaactt | tcactgcac | 1550 |
| ttggcattat | ttttataagc | tgaatgtgat | aataaggaca | ctatggaaat | 1600 |
| gtctggatca | ttccgtttgt | gcgtactttg | agatttggtt | tgggatgtca | 1650 |
| ttgttttcac | agcacttttt | tatcctaatg | taaatgcttt | atttatttat | 1700 |
| ttgggctaca | ttgtaagatc | catctacaaa | aaaaaaaaa | aaaaaaaag | 1750 |
| ggcggccgcg | actctagagt | cgacctgcag | aagcttggcc | gccatggcc | 1799 |

<210> SEQ ID NO 49
<211> LENGTH: 440
<212> TYPE: PRT
<213> ORGANISM: Homo sapiens

<400> SEQUENCE: 49

```
Met Glu Gln Arg Gly Gln Asn Ala Pro Ala Ser Gly Ala Arg
  1               5                  10                  15

Lys Arg His Gly Pro Gly Pro Arg Glu Ala Arg Gly Ala Arg Pro
                 20                  25                  30

Gly Pro Arg Val Pro Lys Thr Leu Val Leu Val Val Ala Ala Val
                 35                  40                  45

Leu Leu Leu Val Ser Ala Glu Ser Ala Leu Ile Thr Gln Gln Asp
                 50                  55                  60

Leu Ala Pro Gln Gln Arg Ala Ala Pro Gln Gln Lys Arg Ser Ser
                 65                  70                  75

Pro Ser Glu Gly Leu Cys Pro Pro Gly His His Ile Ser Glu Asp
                 80                  85                  90

Gly Arg Asp Cys Ile Ser Cys Lys Tyr Gly Gln Asp Tyr Ser Thr
                 95                 100                 105

His Trp Asn Asp Leu Leu Phe Cys Leu Arg Cys Thr Arg Cys Asp
                110                 115                 120

Ser Gly Glu Val Glu Leu Ser Pro Cys Thr Thr Thr Arg Asn Thr
                125                 130                 135

Val Cys Gln Cys Glu Glu Gly Thr Phe Arg Glu Glu Asp Ser Pro
                140                 145                 150

Glu Met Cys Arg Lys Cys Arg Thr Gly Cys Pro Arg Gly Met Val
                155                 160                 165

Lys Val Gly Asp Cys Thr Pro Trp Ser Asp Ile Glu Cys Val His
                170                 175                 180

Lys Glu Ser Gly Thr Lys His Ser Gly Glu Ala Pro Ala Val Glu
                185                 190                 195

Glu Thr Val Thr Ser Ser Pro Gly Thr Pro Ala Ser Pro Cys Ser
                200                 205                 210

Leu Ser Gly Ile Ile Ile Gly Val Thr Val Ala Ala Val Val Leu
                215                 220                 225

Ile Val Ala Val Phe Val Cys Lys Ser Leu Leu Trp Lys Lys Val
                230                 235                 240

Leu Pro Tyr Leu Lys Gly Ile Cys Ser Gly Gly Gly Asp Pro
                245                 250                 255

Glu Arg Val Asp Arg Ser Ser Gln Arg Pro Gly Ala Glu Asp Asn
                260                 265                 270

Val Leu Asn Glu Ile Val Ser Ile Leu Gln Pro Thr Gln Val Pro
                275                 280                 285

Glu Gln Glu Met Glu Val Gln Glu Pro Ala Glu Pro Thr Gly Val
                290                 295                 300

Asn Met Leu Ser Pro Gly Glu Ser Glu His Leu Leu Glu Pro Ala
                305                 310                 315

Glu Ala Glu Arg Ser Gln Arg Arg Arg Leu Leu Val Pro Ala Asn
                320                 325                 330

Glu Gly Asp Pro Thr Glu Thr Leu Arg Gln Cys Phe Asp Asp Phe
                335                 340                 345

Ala Asp Leu Val Pro Phe Asp Ser Trp Glu Pro Leu Met Arg Lys
                350                 355                 360
```

```
Leu Gly Leu Met Asp Asn Glu Ile Lys Val Ala Lys Ala Glu Ala
            365                 370                 375

Ala Gly His Arg Asp Thr Leu Tyr Thr Met Leu Ile Lys Trp Val
            380                 385                 390

Asn Lys Thr Gly Arg Asp Ala Ser Val His Thr Leu Leu Asp Ala
            395                 400                 405

Leu Glu Thr Leu Gly Glu Arg Leu Ala Lys Gln Lys Ile Glu Asp
            410                 415                 420

His Leu Leu Ser Ser Gly Lys Phe Met Tyr Leu Glu Gly Asn Ala
            425                 430                 435

Asp Ser Ala Met Ser
            440

<210> SEQ ID NO 50
<211> LENGTH: 1323
<212> TYPE: DNA
<213> ORGANISM: Homo sapiens

<400> SEQUENCE: 50
atggaacaac gggacagaa cgccccggcc gcttcggggg cccggaaaag        50
gcacggccca ggacccaggg aggcgcgggg agccaggcct gggccccggg       100
tccccaagac ccttgtgctc gttgtcgccg cggtcctgct gttggtctca       150
gctgagtctg ctctgatcac ccaacaagac ctagctcccc agcagagagc       200
ggccccacaa caaagaggt ccagcccctc agagggattg tgtccacctg        250
gacaccatat ctcagaagac ggtagagatt gcatctcctg caaatatgga       300
caggactata gcactcactg gaatgacctc cttttctgct gcgctgcac        350 caggtgtgat tcaggtgaag tggagctaag tccgtgcacc acgaccagaa       400
acacagtgtg tcagtgcgaa gaaggcacct tccgggaaga agattctcct       450
gagatgtgcc ggaagtgccg cacagggtgt cccagaggga tggtcaaggt       500
cggtgattgt acaccctgga gtgacatcga atgtgtccac aaagaatcag       550
gtacaaagca cagtggggaa gccccagctg tggaggagac ggtgacctcc       600
agcccaggga ctcctgcctc tccctgttct ctctcaggca tcatcatagg       650
agtcacagtt gcagccgtag tcttgattgt ggctgtgttt gtttgcaagt       700
ctttactgtg gaagaaagtc cttccttacc tgaaaggcat ctgctcaggt       750
ggtggtgggg accctgagcg tgtggacaga agctcacaac gacctggggc       800
tgaggacaat gtcctcaatg agatcgtgag tatcttgcag cccacccagg       850
tccctgagca ggaaatggaa gtccaggagc agcagagcc aacaggtgtc        900 aacatgttgt cccccgggga gtcagagcat ctgctggaac cggcagaagc       950
tgaaaggtct cagaggagga ggctgctggt tccagcaaat gaaggtgatc      1000
ccactgagac tctgagacag tgcttcgatg actttgcaga cttggtgccc      1050
tttgactcct gggagccgct catgaggaag ttgggcctca tggacaatga      1100
gataaaggtg gctaaagctg aggcagcggg ccacaggac accttgtaca      1150 cgatgctgat aaagtgggtc aacaaaaccg gcgagatgc ctctgtccac       1200 accctgctgg atgccttgga gacgctggga gagagacttg ccaagcagaa      1250
gattgaggac cacttgttga gctctggaaa gttcatgtat ctagaaggta      1300
```
atgcagactc tgccatgtcc taa                                    1323

<210> SEQ ID NO 51
<211> LENGTH: 451
<212> TYPE: PRT
<213> ORGANISM: Artificial sequence
<220> FEATURE:
<223> OTHER INFORMATION: Sequence is synthesized.

<400> SEQUENCE: 51

Glu Val Gln Leu Val Gln Ser Gly Gly Gly Val Glu Arg Pro Gly
 1               5                  10                  15

Gly Ser Leu Arg Leu Ser Cys Ala Ala Ser Gly Phe Thr Phe Asp
                20                  25                  30

Asp Tyr Ala Met Ser Trp Val Arg Gln Ala Pro Gly Lys Gly Leu
                35                  40                  45

Glu Trp Val Ser Gly Ile Asn Trp Gln Gly Gly Ser Thr Gly Tyr
            50                  55                  60

Ala Asp Ser Val Lys Gly Arg Val Thr Ile Ser Arg Asp Asn Ala
65                  70                  75

Lys Asn Ser Leu Tyr Leu Gln Met Asn Ser Leu Arg Ala Glu Asp
                80                  85                  90

Thr Ala Val Tyr Tyr Cys Ala Lys Ile Leu Gly Ala Gly Arg Gly
                95                  100                 105

Trp Tyr Phe Asp Tyr Trp Gly Lys Gly Thr Thr Val Thr Val Ser
                110                 115                 120

Ser Ala Ser Thr Lys Gly Pro Ser Val Phe Pro Leu Ala Pro Ser
                125                 130                 135

Ser Lys Ser Thr Ser Gly Gly Thr Ala Ala Leu Gly Cys Leu Val
                140                 145                 150

Lys Asp Tyr Phe Pro Glu Pro Val Thr Val Ser Trp Asn Ser Gly
                155                 160                 165

Ala Leu Thr Ser Gly Val His Thr Phe Pro Ala Val Leu Gln Ser
                170                 175                 180

Ser Gly Leu Tyr Ser Leu Ser Ser Val Val Thr Val Pro Ser Ser
                185                 190                 195

Ser Leu Gly Thr Gln Thr Tyr Ile Cys Asn Val Asn His Lys Pro
                200                 205                 210

Ser Asn Thr Lys Val Asp Lys Lys Val Glu Pro Lys Ser Cys Asp
                215                 220                 225

Lys Thr His Thr Cys Pro Pro Cys Pro Ala Pro Glu Leu Leu Gly
                230                 235                 240

Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly
                275                 280                 285

Val Glu Val His Asn Ala Lys Thr Lys Pro Arg Glu Glu Gln Tyr
                290                 295                 300

Asn Ser Thr Tyr Arg Val Val Ser Val Leu Thr Val Leu His Gln
                305                 310                 315

Asp Trp Leu Asn Gly Lys Glu Tyr Lys Cys Lys Val Ser Asn Lys
                320                 325                 330

Ala Leu Pro Ala Pro Ile Glu Lys Thr Ile Ser Lys Ala Lys Gly

```
                    335                 340                 345
Gln Pro Arg Glu Pro Gln Val Tyr Thr Leu Pro Pro Ser Arg Glu
                350                 355                 360
Glu Met Thr Lys Asn Gln Val Ser Leu Thr Cys Leu Val Lys Gly
            365                 370                 375
Phe Tyr Pro Ser Asp Ile Ala Val Glu Trp Glu Ser Asn Gly Gln
        380                 385                 390
Pro Glu Asn Asn Tyr Lys Thr Thr Pro Pro Val Leu Asp Ser Asp
    395                 400                 405
Gly Ser Phe Phe Leu Tyr Ser Lys Leu Thr Val Asp Lys Ser Arg
            410                 415                 420
Trp Gln Gln Gly Asn Val Phe Ser Cys Ser Val Met His Glu Ala
                425                 430                 435
Leu His Asn His Tyr Thr Gln Lys Ser Leu Ser Leu Ser Pro Gly
                    440                 445                 450
Lys

<210> SEQ ID NO 52
<211> LENGTH: 213
<212> TYPE: PRT
<213> ORGANISM: Artificial sequence
<220> FEATURE:
<223> OTHER INFORMATION: Sequence is synthesized.

<400> SEQUENCE: 52

Ser Glu Leu Thr Gln Asp Pro Ala Val Ser Val Ala Leu Gly Gln
  1               5                  10                  15
Thr Val Arg Ile Thr Cys Ser Gly Asp Ser Leu Arg Ser Tyr Tyr
                 20                  25                  30
Ala Ser Trp Tyr Gln Gln Lys Pro Gly Gln Ala Pro Val Leu Val
                 35                  40                  45
Ile Tyr Gly Ala Asn Asn Arg Pro Ser Gly Ile Pro Asp Arg Phe
             50                  55                  60
Ser Gly Ser Ser Ser Gly Asn Thr Ala Ser Leu Thr Ile Thr Gly
         65                  70                  75
Ala Gln Ala Glu Asp Glu Ala Asp Tyr Tyr Cys Asn Ser Ala Asp
                 80                  85                  90
Ser Ser Gly Asn His Val Val Phe Gly Gly Gly Thr Lys Leu Thr
                 95                 100                 105
Val Leu Gly Gln Pro Lys Ala Ala Pro Ser Val Thr Leu Phe Pro
            110                 115                 120
Pro Ser Ser Glu Glu Leu Gln Ala Asn Lys Ala Thr Leu Val Cys
        125                 130                 135
Leu Ile Ser Asp Phe Tyr Pro Gly Ala Val Thr Val Ala Trp Lys
    140                 145                 150
Ala Asp Ser Ser Pro Val Lys Ala Gly Val Glu Thr Thr Thr Pro
            155                 160                 165
Ser Lys Gln Ser Asn Asn Lys Tyr Ala Ala Ser Ser Tyr Leu Ser
        170                 175                 180
Leu Thr Pro Glu Gln Trp Lys Ser His Lys Ser Tyr Ser Cys Gln
    185                 190                 195
Val Thr His Glu Gly Ser Thr Val Glu Lys Thr Val Ala Pro Thr
            200                 205                 210
Glu Cys Ser
```

<210> SEQ ID NO 53
<211> LENGTH: 451
<212> TYPE: PRT
<213> ORGANISM: Artificial sequence
<220> FEATURE:
<223> OTHER INFORMATION: Sequence is synthesized.

<400> SEQUENCE: 53

```
Glu Val Gln Leu Val Gln Ser Gly Gly Gly Val Glu Arg Pro Gly
 1               5                  10                  15

Gly Ser Leu Arg Leu Ser Cys Ala Ala Ser Gly Phe Thr Phe Asp
                20                  25                  30

Asp Tyr Gly Met Ser Trp Val Arg Gln Ala Pro Gly Lys Gly Leu
            35                  40                  45

Glu Trp Val Ser Gly Ile Asn Trp Asn Gly Ser Thr Gly Tyr
        50                  55                  60

Ala Asp Ser Val Lys Gly Arg Val Thr Ile Ser Arg Asp Asn Ala
65                  70                  75

Lys Asn Ser Leu Tyr Leu Gln Met Asn Ser Leu Arg Ala Glu Asp
                80                  85                  90

Thr Ala Val Tyr Tyr Cys Ala Lys Ile Leu Gly Ala Gly Arg Gly
            95                 100                 105

Trp Tyr Phe Asp Leu Trp Gly Lys Gly Thr Thr Val Thr Val Ser
           110                 115                 120

Ser Ala Ser Thr Lys Gly Pro Ser Val Phe Pro Leu Ala Pro Ser
           125                 130                 135

Ser Lys Ser Thr Ser Gly Gly Thr Ala Ala Leu Gly Cys Leu Val
           140                 145                 150

Lys Asp Tyr Phe Pro Glu Pro Val Thr Val Ser Trp Asn Ser Gly
           155                 160                 165

Ala Leu Thr Ser Gly Val His Thr Phe Pro Ala Val Leu Gln Ser
           170                 175                 180

Ser Gly Leu Tyr Ser Leu Ser Ser Val Val Thr Val Pro Ser Ser
           185                 190                 195

Ser Leu Gly Thr Gln Thr Tyr Ile Cys Asn Val Asn His Lys Pro
           200                 205                 210

Ser Asn Thr Lys Val Asp Lys Lys Val Glu Pro Lys Ser Cys Asp
           215                 220                 225

Lys Thr His Thr Cys Pro Pro Cys Pro Ala Pro Glu Leu Leu Gly
           230                 235                 240

Gly Pro Ser Val Phe Leu Phe Pro Pro Lys Pro Lys Asp Thr Leu
           245                 250                 255

Met Ile Ser Arg Thr Pro Glu Val Thr Cys Val Val Val Asp Val
           260                 265                 270

Ser His Glu Asp Pro Glu Val Lys Phe Asn Trp Tyr Val Asp Gly
           275                 280                 285

Val Glu Val His Asn Ala Lys Thr Lys Pro Arg Glu Glu Gln Tyr
           290                 295                 300

Asn Ser Thr Tyr Arg Val Val Ser Val Leu Thr Val Leu His Gln
           305                 310                 315

Asp Trp Leu Asn Gly Lys Glu Tyr Lys Cys Lys Val Ser Asn Lys
           320                 325                 330

Ala Leu Pro Ala Pro Ile Glu Lys Thr Ile Ser Lys Ala Lys Gly
           335                 340                 345
```

```
Gln Pro Arg Glu Pro Gln Val Tyr Thr Leu Pro Pro Ser Arg Glu
                350                 355                 360

Glu Met Thr Lys Asn Gln Val Ser Leu Thr Cys Leu Val Lys Gly
            365                 370                 375

Phe Tyr Pro Ser Asp Ile Ala Val Glu Trp Glu Ser Asn Gly Gln
        380                 385                 390

Pro Glu Asn Asn Tyr Lys Thr Thr Pro Pro Val Leu Asp Ser Asp
    395                 400                 405

Gly Ser Phe Phe Leu Tyr Ser Lys Leu Thr Val Asp Lys Ser Arg
410                 415                 420

Trp Gln Gln Gly Asn Val Phe Ser Cys Ser Val Met His Glu Ala
                425                 430                 435

Leu His Asn His Tyr Thr Gln Lys Ser Leu Ser Leu Ser Pro Gly
            440                 445                 450

Lys
```

<210> SEQ ID NO 54
<211> LENGTH: 213
<212> TYPE: PRT
<213> ORGANISM: Artificial sequence
<220> FEATURE:
<223> OTHER INFORMATION: Sequence is synthesized.

<400> SEQUENCE: 54

```
Ser Glu Leu Thr Gln Asp Pro Ala Val Ser Val Ala Leu Gly Gln
  1               5                  10                  15

Thr Val Arg Ile Thr Cys Gln Gly Asp Ser Leu Arg Ser Tyr Tyr
             20                  25                  30

Ala Ser Trp Tyr Gln Gln Lys Pro Gly Gln Ala Pro Val Leu Val
         35                  40                  45

Ile Tyr Gly Lys Asn Asn Arg Pro Ser Gly Ile Pro Asp Arg Phe
     50                  55                  60

Ser Gly Ser Ser Ser Gly Asn Thr Ala Ser Leu Thr Ile Thr Gly
 65                  70                  75

Ala Gln Ala Glu Asp Glu Ala Asp Tyr Tyr Cys Asn Ser Arg Asp
             80                  85                  90

Ser Ser Gly Asn His Val Val Phe Gly Gly Gly Thr Lys Leu Thr
         95                 100                 105

Val Leu Gly Gln Pro Lys Ala Ala Pro Ser Val Thr Leu Phe Pro
    110                 115                 120

Pro Ser Ser Glu Glu Leu Gln Ala Asn Lys Ala Thr Leu Val Cys
    125                 130                 135

Leu Ile Ser Asp Phe Tyr Pro Gly Ala Val Thr Val Ala Trp Lys
        140                 145                 150

Ala Asp Ser Ser Pro Val Lys Ala Gly Val Glu Thr Thr Thr Pro
            155                 160                 165

Ser Lys Gln Ser Asn Asn Lys Tyr Ala Ala Ser Ser Tyr Leu Ser
        170                 175                 180

Leu Thr Pro Glu Gln Trp Lys Ser His Lys Ser Tyr Ser Cys Gln
        185                 190                 195

Val Thr His Glu Gly Ser Thr Val Glu Lys Thr Val Ala Pro Thr
            200                 205                 210

Glu Cys Ser
```

<210> SEQ ID NO 55

```
<211> LENGTH: 126
<212> TYPE: PRT
<213> ORGANISM: Artificial sequence
<220> FEATURE:
<223> OTHER INFORMATION: Sequence is synthesized.

<400> SEQUENCE: 55

Glu Val Gln Leu Val Gln Ser Gly Gly Gly Val Glu Arg Pro Gly
 1               5                  10                  15

Gly Ser Leu Arg Leu Ser Cys Ala Ala Ser Gly Phe Thr Phe Asp
                20                  25                  30

Asp Tyr Ala Met Trp Val Arg Gln Ala Pro Gly Lys Gly Leu Glu
                35                  40                  45

Trp Val Ser Gly Ile Asn Trp Gln Gly Gly Ser Thr Gly Tyr Ala
                50                  55                  60

Asp Ser Val Lys Gly Arg Val Thr Ile Ser Arg Asp Asn Ala Lys
                65                  70                  75

Asn Ser Leu Tyr Leu Gln Met Asn Ser Leu Arg Ala Glu Asp Thr
                80                  85                  90

Ala Val Tyr Tyr Cys Ala Lys Ile Leu Gly Ala Gly Arg Gly Trp
                95                  100                 105

Tyr Phe Asp Tyr Trp Gly Lys Gly Thr Thr Val Thr Val Ser Ser
                110                 115                 120

Ala Ser Thr Lys Gly Pro
                125

<210> SEQ ID NO 56
<211> LENGTH: 108
<212> TYPE: PRT
<213> ORGANISM: Artificial sequence
<220> FEATURE:
<223> OTHER INFORMATION: Sequence is synthesized.

<400> SEQUENCE: 56

Ser Glu Leu Thr Gln Asp Pro Ala Val Ser Val Ala Leu Gly Gln
 1               5                  10                  15

Thr Val Arg Ile Thr Cys Ser Gly Asp Ser Leu Arg Ser Tyr Tyr
                20                  25                  30

Ala Ser Trp Tyr Gln Gln Lys Pro Gly Gln Ala Pro Val Leu Val
                35                  40                  45

Ile Tyr Gly Ala Asn Asn Arg Pro Ser Gly Ile Pro Asp Arg Phe
                50                  55                  60

Ser Gly Ser Ser Ser Gly Asn Thr Ala Ser Leu Thr Ile Thr Gly
                65                  70                  75

Ala Gln Ala Glu Asp Glu Ala Asp Tyr Tyr Cys Asn Ser Ala Asp
                80                  85                  90

Ser Ser Gly Asn His Val Val Phe Gly Gly Gly Thr Lys Leu Thr
                95                  100                 105

Val Leu Gly

<210> SEQ ID NO 57
<211> LENGTH: 10
<212> TYPE: PRT
<213> ORGANISM: Artificial sequence
<220> FEATURE:
<223> OTHER INFORMATION: Sequence is synthesized.

<400> SEQUENCE: 57

Arg Ala Ser Ser Ser Val Ser Tyr Met His
```

```
1               5                  10
```

<210> SEQ ID NO 58
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 58

```
Ala Pro Ser Asn Leu Ala Ser
 1               5
```

<210> SEQ ID NO 59
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 59

```
Gln Gln Trp Ser Phe Asn Pro Pro Thr
 1               5
```

<210> SEQ ID NO 60
<211> LENGTH: 10
<212> TYPE: PRT
<213> ORGANISM: Artificial sequence
<220> FEATURE:
<223> OTHER INFORMATION: Sequence is synthesized.

<400> SEQUENCE: 60

```
Gly Tyr Thr Phe Thr Ser Tyr Asn Met His
 1               5                  10
```

<210> SEQ ID NO 61
<211> LENGTH: 17
<212> TYPE: PRT
<213> ORGANISM: Artificial sequence
<220> FEATURE:
<223> OTHER INFORMATION: Sequence is synthesized.

<400> SEQUENCE: 61

```
Ala Ile Tyr Pro Gly Asn Gly Asp Thr Ser Tyr Asn Gln Lys Phe
 1               5                  10                  15

Lys Gly
```

<210> SEQ ID NO 62
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 62

```
Val Val Tyr Tyr Ser Asn Ser Tyr Trp Tyr Phe Asp Val
 1               5                  10
```

<210> SEQ ID NO 63
<211> LENGTH: 213
<212> TYPE: PRT
<213> ORGANISM: Artificial sequence
<220> FEATURE:
<223> OTHER INFORMATION: Sequence is synthesized.

<400> SEQUENCE: 63

```
Asp Ile Gln Met Thr Gln Ser Pro Ser Ser Leu Ser Ala Ser Val
1               5                   10                  15

Gly Asp Arg Val Thr Ile Thr Cys Arg Ala Ser Ser Ser Val Ser
            20                  25                  30

Tyr Met His Trp Tyr Gln Gln Lys Pro Gly Lys Ala Pro Lys Pro
        35                  40                  45

Leu Ile Tyr Ala Pro Ser Asn Leu Ala Ser Gly Val Pro Ser Arg
            50                  55                  60

Phe Ser Gly Ser Gly Ser Gly Thr Asp Phe Thr Leu Thr Ile Ser
65                  70                  75

Ser Leu Gln Pro Glu Asp Phe Ala Thr Tyr Tyr Cys Gln Gln Trp
            80                  85                  90

Ser Phe Asn Pro Pro Thr Phe Gly Gln Gly Thr Lys Val Glu Ile
            95                  100                 105

Lys Arg Thr Val Ala Ala Pro Ser Val Phe Ile Phe Pro Pro Ser
            110                 115                 120

Asp Glu Gln Leu Lys Ser Gly Thr Ala Ser Val Val Cys Leu Leu
            125                 130                 135

Asn Asn Phe Tyr Pro Arg Glu Ala Lys Val Gln Trp Lys Val Asp
            140                 145                 150

Asn Ala Leu Gln Ser Gly Asn Ser Gln Glu Ser Val Thr Glu Gln
            155                 160                 165

Asp Ser Lys Asp Ser Thr Tyr Ser Leu Ser Ser Thr Leu Thr Leu
            170                 175                 180

Ser Lys Ala Asp Tyr Glu Lys His Lys Val Tyr Ala Cys Glu Val
            185                 190                 195

Thr His Gln Gly Leu Ser Ser Pro Val Thr Lys Ser Phe Asn Arg
            200                 205                 210

Gly Glu Cys

<210> SEQ ID NO 64
<211> LENGTH: 213
<212> TYPE: PRT
<213> ORGANISM: Artificial sequence
<220> FEATURE:
<223> OTHER INFORMATION: Sequence is synthesized.

<400> SEQUENCE: 64

Asp Ile Gln Met Thr Gln Ser Pro Ser Ser Leu Ser Ala Ser Val
1               5                   10                  15

Gly Asp Arg Val Thr Ile Thr Cys Arg Ala Ser Ser Ser Val Ser
            20                  25                  30

Tyr Leu His Trp Tyr Gln Gln Lys Pro Gly Lys Ala Pro Lys Pro
        35                  40                  45

Leu Ile Tyr Ala Pro Ser Asn Leu Ala Ser Gly Val Pro Ser Arg
            50                  55                  60

Phe Ser Gly Ser Gly Ser Gly Thr Asp Phe Thr Leu Thr Ile Ser
65                  70                  75

Ser Leu Gln Pro Glu Asp Phe Ala Thr Tyr Tyr Cys Gln Gln Trp
            80                  85                  90

Ala Phe Asn Pro Pro Thr Phe Gly Gln Gly Thr Lys Val Glu Ile
            95                  100                 105

Lys Arg Thr Val Ala Ala Pro Ser Val Phe Ile Phe Pro Pro Ser
            110                 115                 120

Asp Glu Gln Leu Lys Ser Gly Thr Ala Ser Val Val Cys Leu Leu
```

```
                    125                 130                 135

Asn Asn Phe Tyr Pro Arg Glu Ala Lys Val Gln Trp Lys Val Asp
                140                 145                 150

Asn Ala Leu Gln Ser Gly Asn Ser Gln Glu Ser Val Thr Glu Gln
            155                 160                 165

Asp Ser Lys Asp Ser Thr Tyr Ser Leu Ser Ser Thr Leu Thr Leu
        170                 175                 180

Ser Lys Ala Asp Tyr Glu Lys His Lys Val Tyr Ala Cys Glu Val
    185                 190                 195

Thr His Gln Gly Leu Ser Ser Pro Val Thr Lys Ser Phe Asn Arg
                200                 205                 210

Gly Glu Cys

<210> SEQ ID NO 65
<211> LENGTH: 452
<212> TYPE: PRT
<213> ORGANISM: Artificial sequence
<220> FEATURE:
<223> OTHER INFORMATION: Sequence is synthesized.

<400> SEQUENCE: 65

Glu Val Gln Leu Val Glu Ser Gly Gly Gly Leu Val Gln Pro Gly
  1               5                  10                  15

Gly Ser Leu Arg Leu Ser Cys Ala Ala Ser Gly Tyr Thr Phe Thr
                 20                  25                  30

Ser Tyr Asn Met His Trp Val Arg Gln Ala Pro Gly Lys Gly Leu
             35                  40                  45

Glu Trp Val Gly Ala Ile Tyr Pro Gly Asn Gly Asp Thr Ser Tyr
         50                  55                  60

Asn Gln Lys Phe Lys Gly Arg Phe Thr Ile Ser Val Asp Lys Ser
     65                  70                  75

Lys Asn Thr Leu Tyr Leu Gln Met Asn Ser Leu Arg Ala Glu Asp
 80                  85                  90

Thr Ala Val Tyr Tyr Cys Ala Arg Val Val Tyr Tyr Ser Asn Ser
                 95                 100                 105

Tyr Trp Tyr Phe Asp Val Trp Gly Gln Gly Thr Leu Val Thr Val
                110                 115                 120

Ser Ser Ala Ser Thr Lys Gly Pro Ser Val Phe Pro Leu Ala Pro
                125                 130                 135

Ser Ser Lys Ser Thr Ser Gly Gly Thr Ala Ala Leu Gly Cys Leu
                140                 145                 150

Val Lys Asp Tyr Phe Pro Glu Pro Val Thr Val Ser Trp Asn Ser
                155                 160                 165

Gly Ala Leu Thr Ser Gly Val His Thr Phe Pro Ala Val Leu Gln
                170                 175                 180

Ser Ser Gly Leu Tyr Ser Leu Ser Ser Val Val Thr Val Pro Ser
                185                 190                 195

Ser Ser Leu Gly Thr Gln Thr Tyr Ile Cys Asn Val Asn His Lys
                200                 205                 210

Pro Ser Asn Thr Lys Val Asp Lys Lys Val Glu Pro Lys Ser Cys
                215                 220                 225

Asp Lys Thr His Thr Cys Pro Pro Cys Pro Ala Pro Glu Leu Leu
                230                 235                 240

Gly Gly Pro Ser Val Phe Leu Phe Pro Pro Lys Pro Lys Asp Thr
                245                 250                 255
```

```
Leu Met Ile Ser Arg Thr Pro Glu Val Thr Cys Val Val Asp
            260                 265                 270

Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln
            290                 295                 300

Tyr Asn Ser Thr Tyr Arg Val Val Ser Val Leu Thr Val Leu His
            305                 310                 315

Gln Asp Trp Leu Asn Gly Lys Glu Tyr Lys Cys Lys Val Ser Asn
            320                 325                 330

Lys Ala Leu Pro Ala Pro Ile Glu Lys Thr Ile Ser Lys Ala Lys
            335                 340                 345

Gly Gln Pro Arg Glu Pro Gln Val Tyr Thr Leu Pro Pro Ser Arg
            350                 355                 360

Glu Glu Met Thr Lys Asn Gln Val Ser Leu Thr Cys Leu Val Lys
            365                 370                 375

Gly Phe Tyr Pro Ser Asp Ile Ala Val Glu Trp Glu Ser Asn Gly
            380                 385                 390

Gln Pro Glu Asn Asn Tyr Lys Thr Thr Pro Pro Val Leu Asp Ser
            395                 400                 405

Asp Gly Ser Phe Phe Leu Tyr Ser Lys Leu Thr Val Asp Lys Ser
            410                 415                 420

Arg Trp Gln Gln Gly Asn Val Phe Ser Cys Ser Val Met His Glu
            425                 430                 435

Ala Leu His Asn His Tyr Thr Gln Lys Ser Leu Ser Leu Ser Pro
            440                 445                 450

Gly Lys

<210> SEQ ID NO 66
<211> LENGTH: 452
<212> TYPE: PRT
<213> ORGANISM: Artificial sequence
<220> FEATURE:
<223> OTHER INFORMATION: Sequence is synthesized.

<400> SEQUENCE: 66

Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Thr Phe Thr
            20                  25                  30

Ser Tyr Asn Met His Trp Val Arg Gln Ala Pro Gly Lys Gly Leu
            35                  40                  45

Glu Trp Val Gly Ala Ile Tyr Pro Gly Asn Gly Ala Thr Ser Tyr
            50                  55                  60

Asn Gln Lys Phe Lys Gly Arg Phe Thr Ile Ser Val Asp Lys Ser
            65                  70                  75

Lys Asn Thr Leu Tyr Leu Gln Met Asn Ser Leu Arg Ala Glu Asp
            80                  85                  90

Thr Ala Val Tyr Tyr Cys Ala Arg Val Val Tyr Tyr Ser Tyr Arg
            95                 100                 105

Tyr Trp Tyr Phe Asp Val Trp Gly Gln Gly Thr Leu Val Thr Val
           110                 115                 120

Ser Ser Ala Ser Thr Lys Gly Pro Ser Val Phe Pro Leu Ala Pro
           125                 130                 135
```

```
Ser Ser Lys Ser Thr Ser Gly Gly Thr Ala Ala Leu Gly Cys Leu
            140                 145                 150

Val Lys Asp Tyr Phe Pro Glu Pro Val Thr Val Ser Trp Asn Ser
            155                 160                 165

Gly Ala Leu Thr Ser Gly Val His Thr Phe Pro Ala Val Leu Gln
            170                 175                 180

Ser Ser Gly Leu Tyr Ser Leu Ser Ser Val Val Thr Val Pro Ser
            185                 190                 195

Ser Ser Leu Gly Thr Gln Thr Tyr Ile Cys Asn Val Asn His Lys
            200                 205                 210

Pro Ser Asn Thr Lys Val Asp Lys Lys Val Glu Pro Lys Ser Cys
            215                 220                 225

Asp Lys Thr His Thr Cys Pro Pro Cys Pro Ala Pro Glu Leu Leu
            230                 235                 240

Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln
            290                 295                 300

Tyr Asn Ala Thr Tyr Arg Val Val Ser Val Leu Thr Val Leu His
            305                 310                 315

Gln Asp Trp Leu Asn Gly Lys Glu Tyr Lys Cys Lys Val Ser Asn
            320                 325                 330

Ala Ala Leu Pro Ala Pro Ile Ala Ala Thr Ile Ser Lys Ala Lys
            335                 340                 345

Gly Gln Pro Arg Glu Pro Gln Val Tyr Thr Leu Pro Pro Ser Arg
            350                 355                 360

Glu Glu Met Thr Lys Asn Gln Val Ser Leu Thr Cys Leu Val Lys
            365                 370                 375

Gly Phe Tyr Pro Ser Asp Ile Ala Val Glu Trp Glu Ser Asn Gly
            380                 385                 390

Gln Pro Glu Asn Asn Tyr Lys Thr Thr Pro Pro Val Leu Asp Ser
            395                 400                 405

Asp Gly Ser Phe Phe Leu Tyr Ser Lys Leu Thr Val Asp Lys Ser
            410                 415                 420

Arg Trp Gln Gln Gly Asn Val Phe Ser Cys Ser Val Met His Glu
            425                 430                 435

Ala Leu His Asn His Tyr Thr Gln Lys Ser Leu Ser Leu Ser Pro
            440                 445                 450

Gly Lys

<210> SEQ ID NO 67
<211> LENGTH: 10
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 9
<223> OTHER INFORMATION: Xaa is M or L.

<400> SEQUENCE: 67
```

Arg Ala Ser Ser Ser Val Ser Tyr Xaa His
1               5                   10

<210> SEQ ID NO 68
<211> LENGTH: 9
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 4
<223> OTHER INFORMATION: Xaa is S or A.

<400> SEQUENCE: 68

Gln Gln Trp Xaa Phe Asn Pro Pro Thr
1               5

<210> SEQ ID NO 69
<211> LENGTH: 17
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 8
<223> OTHER INFORMATION: Xaa is D or A.

<400> SEQUENCE: 69

Ala Ile Tyr Pro Gly Asn Gly Xaa Thr Ser Tyr Asn Gln Lys Phe
1               5                   10                  15

Lys Gly

<210> SEQ ID NO 70
<211> LENGTH: 13
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 6
<223> OTHER INFORMATION: Xaa is N, A, Y, W or D.
<220> FEATURE:
<221> NAME/KEY: Xaa
<222> LOCATION: 7
<223> OTHER INFORMATION: Xaa is S or R.

<400> SEQUENCE: 70

Val Val Tyr Tyr Ser Xaa Xaa Tyr Trp Tyr Phe Asp Val
1               5                   10

<210> SEQ ID NO 71
<211> LENGTH: 451
<212> TYPE: PRT
<213> ORGANISM: Artificial sequence
<220> FEATURE:
<223> OTHER INFORMATION: Sequence is synthesized.

<400> SEQUENCE: 71

Glu Val Gln Leu Val Glu Ser Gly Gly Gly Leu Val Gln Pro Gly
1               5                   10                  15

Gly Ser Leu Arg Leu Ser Cys Ala Ala Ser Gly Tyr Thr Phe Thr
                20                  25                  30

Ser Tyr Asn Met His Trp Val Arg Gln Ala Pro Gly Lys Gly Leu
                35                  40                  45

Glu Trp Val Gly Ala Ile Tyr Pro Gly Asn Gly Asp Thr Ser Tyr
                50                  55                  60

Asn Gln Lys Phe Lys Gly Arg Phe Thr Ile Ser Val Asp Lys Ser
                65                  70                  75

Lys Asn Thr Leu Tyr Leu Gln Met Asn Ser Leu Arg Ala Glu Asp
                80                  85                  90

Thr Ala Val Tyr Tyr Cys Ala Arg Val Val Tyr Tyr Ser Asn Ser
                95                 100                 105

Tyr Trp Tyr Phe Asp Val Trp Gly Gln Gly Thr Leu Val Thr Val
               110                 115                 120

Ser Ser Ala Ser Thr Lys Gly Pro Ser Val Phe Pro Leu Ala Pro
               125                 130                 135

Ser Ser Lys Ser Thr Ser Gly Gly Thr Ala Ala Leu Gly Cys Leu
               140                 145                 150

Val Lys Asp Tyr Phe Pro Glu Pro Val Thr Val Ser Trp Asn Ser
               155                 160                 165

Gly Ala Leu Thr Ser Gly Val His Thr Phe Pro Ala Val Leu Gln
               170                 175                 180

Ser Ser Gly Leu Tyr Ser Leu Ser Ser Val Val Thr Val Pro Ser
               185                 190                 195

Ser Ser Leu Gly Thr Gln Thr Tyr Ile Cys Asn Val Asn His Lys
               200                 205                 210

Pro Ser Asn Thr Lys Val Asp Lys Lys Val Glu Pro Lys Ser Cys
               215                 220                 225

Asp Lys Thr His Thr Cys Pro Pro Cys Pro Ala Pro Glu Leu Leu
               230                 235                 240

Gly Gly Pro Ser Val Phe Leu Phe Pro Pro Lys Pro Lys Asp Thr
               245                 250                 255

Leu Met Ile Ser Arg Thr Pro Glu Val Thr Cys Val Val Val Asp
               260                 265                 270

Val Ser His Glu Asp Pro Glu Val Lys Phe Asn Trp Tyr Val Asp
               275                 280                 285

Gly Val Glu Val His Asn Ala Lys Thr Lys Pro Arg Glu Glu Gln
               290                 295                 300

Tyr Asn Ser Thr Tyr Arg Val Val Ser Val Leu Thr Val Leu His
               305                 310                 315

Gln Asp Trp Leu Asn Gly Lys Glu Tyr Lys Cys Lys Val Ser Asn
               320                 325                 330

Lys Ala Leu Pro Ala Pro Ile Glu Lys Thr Ile Ser Lys Ala Lys
               335                 340                 345

Gly Gln Pro Arg Glu Pro Gln Val Tyr Thr Leu Pro Pro Ser Arg
               350                 355                 360

Glu Glu Met Thr Lys Asn Gln Val Ser Leu Thr Cys Leu Val Lys
               365                 370                 375

Gly Phe Tyr Pro Ser Asp Ile Ala Val Glu Trp Glu Ser Asn Gly
               380                 385                 390

Gln Pro Glu Asn Asn Tyr Lys Thr Thr Pro Pro Val Leu Asp Ser
               395                 400                 405

Asp Gly Ser Phe Phe Leu Tyr Ser Lys Leu Thr Val Asp Lys Ser
               410                 415                 420

Arg Trp Gln Gln Gly Asn Val Phe Ser Cys Ser Val Met His Glu
               425                 430                 435

Ala Leu His Asn His Tyr Thr Gln Lys Ser Leu Ser Leu Ser Pro

Gly

<210> SEQ ID NO 72
<211> LENGTH: 451
<212> TYPE: PRT
<213> ORGANISM: Artificial sequence
<220> FEATURE:
<223> OTHER INFORMATION: Sequence is synthesized.

<400> SEQUENCE: 72

```
Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Thr Phe Thr
                20                  25                  30

Ser Tyr Asn Met His Trp Val Arg Gln Ala Pro Gly Lys Gly Leu
                35                  40                  45

Glu Trp Val Gly Ala Ile Tyr Pro Gly Asn Gly Ala Thr Ser Tyr
                50                  55                  60

Asn Gln Lys Phe Lys Gly Arg Phe Thr Ile Ser Val Asp Lys Ser
                65                  70                  75

Lys Asn Thr Leu Tyr Leu Gln Met Asn Ser Leu Arg Ala Glu Asp
                80                  85                  90

Thr Ala Val Tyr Tyr Cys Ala Arg Val Val Tyr Tyr Ser Tyr Arg
                95                  100                 105

Tyr Trp Tyr Phe Asp Val Trp Gly Gln Gly Thr Leu Val Thr Val
                110                 115                 120

Ser Ser Ala Ser Thr Lys Gly Pro Ser Val Phe Pro Leu Ala Pro
                125                 130                 135

Ser Ser Lys Ser Thr Ser Gly Gly Thr Ala Ala Leu Gly Cys Leu
                140                 145                 150

Val Lys Asp Tyr Phe Pro Glu Pro Val Thr Val Ser Trp Asn Ser
                155                 160                 165

Gly Ala Leu Thr Ser Gly Val His Thr Phe Pro Ala Val Leu Gln
                170                 175                 180

Ser Ser Gly Leu Tyr Ser Leu Ser Ser Val Val Thr Val Pro Ser
                185                 190                 195

Ser Ser Leu Gly Thr Gln Thr Tyr Ile Cys Asn Val Asn His Lys
                200                 205                 210

Pro Ser Asn Thr Lys Val Asp Lys Lys Val Glu Pro Lys Ser Cys
                215                 220                 225

Asp Lys Thr His Thr Cys Pro Pro Cys Pro Ala Pro Glu Leu Leu
                230                 235                 240

Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp
                275                 280                 285

Gly Val Glu Val His Asn Ala Lys Thr Lys Pro Arg Glu Glu Gln
                290                 295                 300

Tyr Asn Ala Thr Tyr Arg Val Val Ser Val Leu Thr Val Leu His
                305                 310                 315

Gln Asp Trp Leu Asn Gly Lys Glu Tyr Lys Cys Lys Val Ser Asn
                320                 325                 330
```

```
Ala Ala Leu Pro Ala Pro Ile Ala Ala Thr Ile Ser Lys Ala Lys
            335                 340                 345

Gly Gln Pro Arg Glu Pro Gln Val Tyr Thr Leu Pro Pro Ser Arg
        350                 355                 360

Glu Glu Met Thr Lys Asn Gln Val Ser Leu Thr Cys Leu Val Lys
    365                 370                 375

Gly Phe Tyr Pro Ser Asp Ile Ala Val Glu Trp Glu Ser Asn Gly
380                 385                 390

Gln Pro Glu Asn Asn Tyr Lys Thr Thr Pro Pro Val Leu Asp Ser
            395                 400                 405

Asp Gly Ser Phe Phe Leu Tyr Ser Lys Leu Thr Val Asp Lys Ser
        410                 415                 420

Arg Trp Gln Gln Gly Asn Val Phe Ser Cys Ser Val Met His Glu
    425                 430                 435

Ala Leu His Asn His Tyr Thr Gln Lys Ser Leu Ser Leu Ser Pro
440                 445                 450

Gly

<210> SEQ ID NO 73
<211> LENGTH: 107
<212> TYPE: PRT
<213> ORGANISM: Artificial sequence
<220> FEATURE:
<223> OTHER INFORMATION: Sequence is synthesized.

<400> SEQUENCE: 73

Asp Ile Gln Met Thr Gln Ser Pro Ser Ser Leu Ser Ala Ser Val
 1               5                  10                  15

Gly Asp Arg Val Thr Ile Thr Cys Arg Ala Ser Ser Ser Val Ser
                20                  25                  30

Tyr Leu His Trp Tyr Gln Gln Lys Pro Gly Lys Ala Pro Lys Pro
            35                  40                  45

Leu Ile Tyr Ala Pro Ser Asn Leu Ala Ser Gly Val Pro Ser Arg
        50                  55                  60

Phe Ser Gly Ser Gly Ser Gly Thr Asp Phe Thr Leu Thr Ile Ser
    65                  70                  75

Ser Leu Gln Pro Glu Asp Phe Ala Thr Tyr Tyr Cys Gln Gln Trp
80                  85                  90

Ala Phe Asn Pro Pro Thr Phe Gly Gln Gly Thr Lys Val Glu Ile
            95                  100                 105

Lys Arg

<210> SEQ ID NO 74
<211> LENGTH: 122
<212> TYPE: PRT
<213> ORGANISM: Artificial sequence
<220> FEATURE:
<223> OTHER INFORMATION: Sequence is synthesized.

<400> SEQUENCE: 74

Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Thr Phe Thr
                20                  25                  30

Ser Tyr Asn Met His Trp Val Arg Gln Ala Pro Gly Lys Gly Leu
            35                  40                  45
```

-continued

```
Glu Trp Val Gly Ala Ile Tyr Pro Gly Asn Gly Ala Thr Ser Tyr
                50                  55                  60

Asn Gln Lys Phe Lys Gly Arg Phe Thr Ile Ser Val Asp Lys Ser
                65                  70                  75

Lys Asn Thr Leu Tyr Leu Gln Met Asn Ser Leu Arg Ala Glu Asp
                80                  85                  90

Thr Ala Val Tyr Tyr Cys Ala Arg Val Val Tyr Tyr Ser Tyr Arg
                95                  100                 105

Tyr Trp Tyr Phe Asp Val Trp Gly Gln Gly Thr Leu Val Thr Val
                110                 115                 120

Ser Ser
```